(12) United States Patent
Mazzaferro et al.

(10) Patent No.: US 10,183,940 B2
(45) Date of Patent: Jan. 22, 2019

(54) ARYL AND HETEROARYL-FUSED TETRAHYDRO-1,4-OXAZEPINE AMIDES AS SOMATOSTATIN RECEPTOR SUBTYPE 4 (SSTR4) AGONISTS

(71) Applicant: Boehringer Ingelheim International GmbH, Ingelheim am Rhein (DE)

(72) Inventors: Rocco Mazzaferro, San Giuliano Milanese (IT); Marco Ferrara, San Donato Milanese (IT); Riccardo Giovannini, Biberach an der Riss (DE); Iain Lingard, Monza (IT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 73 days.

(21) Appl. No.: 15/526,360

(22) PCT Filed: Nov. 12, 2015

(86) PCT No.: PCT/EP2015/076439
§ 371 (c)(1),
(2) Date: May 12, 2017

(87) PCT Pub. No.: WO2016/075239
PCT Pub. Date: May 19, 2016

(65) Prior Publication Data
US 2018/0291018 A1    Oct. 11, 2018

(30) Foreign Application Priority Data

Nov. 14, 2014 (EP) .................................. 14193182

(51) Int. Cl.
| | | |
|---|---|---|
| *C07D 267/14* | (2006.01) | |
| *C07D 413/12* | (2006.01) | |
| *C07D 471/04* | (2006.01) | |
| *C07D 498/04* | (2006.01) | |
| *C07D 519/00* | (2006.01) | |
| *A61K 31/553* | (2006.01) | |
| *A61P 19/02* | (2006.01) | |
| *A61P 23/00* | (2006.01) | |

(52) U.S. Cl.
CPC ......... *C07D 471/04* (2013.01); *C07D 267/14* (2013.01); *C07D 413/12* (2013.01); *C07D 498/04* (2013.01); *C07D 519/00* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,693,636 A | * | 12/1997 | Bondinell | ............ C07D 223/16 |
| | | | | 514/13.6 |
| 2014/0343065 A1 | | 11/2014 | Giovannini et al. | |
| 2015/0353533 A1 | * | 12/2015 | Bandyopadhyay | .. C07D 403/12 |
| | | | | 514/211.06 |
| 2016/0229848 A1 | * | 8/2016 | Zhang | .................. A61K 31/553 |

FOREIGN PATENT DOCUMENTS

| | | |
|---|---|---|
| EP | 2123644 A1 | 11/2009 |
| WO | 9847882 A1 | 10/1998 |
| WO | 2010059922 A1 | 5/2010 |
| WO | 2014184275 A1 | 11/2014 |

OTHER PUBLICATIONS

International Search Report and Written Opinion for corresponding application PCT/EP2015/076439, dated Dec. 22, 2015.

* cited by examiner

*Primary Examiner* — Amanda L Aguirre
(74) *Attorney, Agent, or Firm* — David L. Kershner

(57) ABSTRACT

The invention relates to aryl and heteroaryl-fused tetrahydro-1,4-oxazepine amide derivatives of general formula (1), which are agonists of somatostatin receptor subtype 4 (SSTR4), useful for preventing or treating medical disorders related to SSTR4. In addition, the invention relates processes for manufacture of the compounds according to the invention.

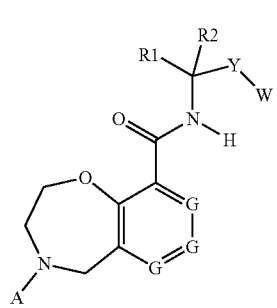

15 Claims, No Drawings

ARYL AND HETEROARYL-FUSED TETRAHYDRO-1,4-OXAZEPINE AMIDES AS SOMATOSTATIN RECEPTOR SUBTYPE 4 (SSTR4) AGONISTS

FIELD OF THE INVENTION

The invention relates to aryl and heteroaryl-fused tetrahydro-1,4-oxazepine amide derivatives of general formula (I), which are agonists of somatostatin receptor subtype 4 (SSTR4), useful for preventing or treating medical disorders related to SSTR4. In addition, the invention processes for the manufacture of the compounds according to the invention.

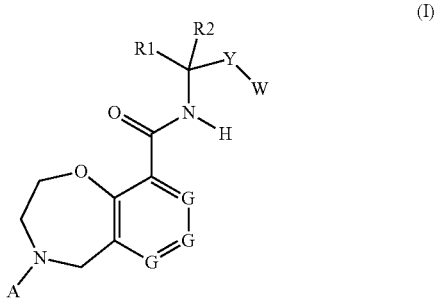

BACKGROUND OF THE INVENTION

Somatostatin, or somatotropin-release inhibitory factor (SRIF), is a cyclic peptide found in humans. It is produced widely in the human body and acts both systemically and locally to inhibit the secretion of various hormones, growth factors and neurotransmitters. The effects of somatostatin are mediated by a family of G protein-coupled receptors, of which five subtypes are known. These subtypes are divided into two subfamilies, the first comprising SSTR2, SSTR3 and SSTR5 and the second SSTR1 and SSTR4.

Somatostatin is involved in the regulation of processes such as for example cellular proliferation, glucose homeostasis, inflammation and pain.

In this aspect somatostatin or other members of the somatostatin peptide familiy are believed to inhibit nociceptive and inflammatory processes via the SSTR4 pathway.

A number of further therapeutic areas for SSTR4 agonists have been discussed (see e.g. Crider, A; *Mini Rev. Med. Chem.* 2002, 7, 213 (and references therein); WO 2010/059922 (and references therein).

Selective SSTR4 agonists have been disclosed, for instance, in *J. Am. Chem. Soc.* 1998, 120, 1368-1373.

WO 2010/059922 provides pyrrolidine carboxamide agonists of SSTR4.

U.S. Ser. No. 14/275,879 relates to 3-aza-bicyclo[3.1.0] hexane-6-carboxylic acid amide derivatives as SSTR4 agonists.

However, there is further need for selective SSTR4 agonists, especially for non-peptidic agonists, which show high stability, permeability and other advantageous properties, such as oral efficacy and metabolic stability.

AIM OF THE INVENTION

It has now been found that compounds of the present invention according to general formula (I) are effective agonists of somatostatin receptor 4 (SSTR4).

Besides the agonistic property toward somatostatin receptor 4, the compounds of the present invention provide advantageous pharmacokinetic properties. For example the compounds of the present invention show high metabolic stability.

Furthermore, the compounds according to the present invention show high selectivity for the SSTR4 receptor with respect to the other subtypes of the same subfamily including the SSTR1 receptor. As a consequence the probability of side effects is reduced.

Accordingly, one aspect of the invention refers to compounds according to formula (I) and salts, hydrates or solvates thereof as agonists of somatostatin receptor 4.

Another aspect of the invention refers to compounds according to formula (I) and salts, hydrates or solvates thereof as selective agonists of SSTR4 over other subtypes of the same family, including selectivity over the other subtype of the same subfamily (SSTR1).

A further aspect of the invention relates to the physiologically acceptable salts of the compounds of general formula (I) according to this invention with inorganic or organic acids.

In a further aspect this invention relates to pharmaceutical compositions, containing at least one compound according to formula (I) or a physiologically acceptable salt, hydrate or solvate thereof, optionally together with one or more inert carriers and/or diluents.

A further aspect of the present invention relates to compounds according to formula (I) or a physiologically acceptable salt thereof or pharmaceutical compositions comprising compounds according to formula (I) or physiologically acceptable salts thereof for the use in the prevention and/or treatment of disorders related to SSTR4.

Another aspect of the invention relates to processes of manufacture of the compounds of the present invention.

A further aspect of the present invention relates to compounds according to formula (I) or a physiologically acceptable salt thereof or pharmaceutical compositions comprising compounds according to formula (I) or physiologically acceptable salts thereof for the use in the prevention and/or treatment of diseases or conditions which can be influenced by activation of SSTR4. In this aspect the present invention relates to compounds according to formula (I) or a physiologically acceptable salt thereof for the treatment of pain of various origins and/or inflammation.

Other aims of the present invention will become apparent to the skilled man directly from the foregoing and following remarks.

DETAILED DESCRIPTION

In a first aspect the present invention relates to compounds of general formula (I)

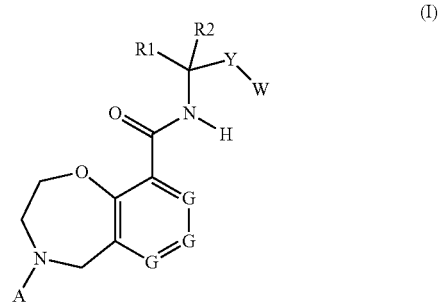

wherein

A is selected from the group $A^1$ consisting of
 H and $C_{1-6}$-alkyl;

G is selected from the group $G^1$ consisting of CH and N, wherein up to two G are N, the other(s) being CH;

$R^1$ and $R^2$ are independently selected from the group $R^{1.1}$, $R^{2.1}$ consisting of
 H, $C_{1-6}$-alkyl and $C_{3-6}$-cycloalkyl, wherein at least one of $R^1$ or $R^2$ is $C_{1-6}$-alkyl or $C_{3-6}$-cycloalkyl, or wherein $R^1$ and $R^2$ together form a 2- to 5-membered alkylene-bridge incorporating 0 to 2 heteroatoms independently selected from the group consisting of N, O or S wherein the $C_{1-6}$-alkyl, the $C_{3-6}$-cycloalkyl or the alkylene-bridge is optionally substituted with halogens;

W is selected from the group $W^1$ consisting of a
 mono- or bicyclic aryl, mono- or bicyclic heteroaryl, mono- or bicyclic heterocyclyl and mono- or bicyclic cycloalkyl.
  wherein each of these ring systems are optionally substituted with one or more $R^3$, and wherein the heteroaryl comprises up to 4 heteroatoms and one or two 5- or 6-membered ring(s);

$R^3$ is independently selected from the group $R^{31}$ consisting of
 $C_{1-6}$alkyl, $C_{3-8}$-cycloalkyl, $C_{1-6}$-alkyl-O—, benzyl, halogen, HO—, NC—, mono- or bicyclic heteroaryl, and 5- or 6-membered monocyclic heterocyclyl containing one heteroatom selected from the group consisting of N, O or $S(O)_r$, wherein the heteroaryl contains up to 4 heteroatoms and one or two 5- or 6-membered ring(s), and r is 0, 1 or 2,
  wherein the $C_{1-6}$-alkyl, $C_{3-8}$-cycloalkyl, $C_{1-6}$-alkyl-O—, benzyl, heteroaryl and the heterocyclyl are optionally substituted with halogens, HO—, acetyl, $C_{1-6}$-alkyl-O—, oxo, $R^4$—$S(O)_2$—, with $R^4$ being aryl, $C_{3-6}$-cycloalkyl and/or $C_{1-6}$-alkyl;

Y is selected from the group $Y^1$ consisting of a bond and —$CH_2O$—; or a salt of any of the above compounds.

Unless otherwise stated, the groups, residues, and substituents, particularly $R^1$, $R^2$, $R^3$, $R^4$, A, G, W and Y are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
A is selected from the group $A^2$ consisting of H or $C_{1-3}$-alkyl.

In a further embodiment of the present invention
A is selected from the group $A^3$ consisting of H or $H_3C$—.

In a further embodiment of the present invention
A is selected from the group $A^4$ consisting of H.

In a further embodiment of the present invention
G is selected from the group $G^2$ consisting of CH and N, wherein up to one G is N, the others being CH;

In a further embodiment of the present invention
G is selected from the group $G^3$ consisting of CH;

In a further embodiment of the present invention
$R^1$ and $R^2$ are independently selected from the group $R^{1.2}$, $R^{2.2}$ consisting of $C_{1-6}$-alkyl and $C_{3-6}$-cycloalkyl, or wherein $R^1$ and $R^2$ together form a 2- to 5-membered alkylene-bridge incorporating 0 to 2 heteroatoms independently selected from the group consisting of N, O or S, wherein the $C_{1-6}$-alkyl, the $C_{3-6}$-cycloalkyl or the alkylene-bridge is optionally substituted with halogens.

In a further embodiment of the present invention
$R^1$ and $R^2$ are independently selected from the group $R^{1.3}$, $R^{2.3}$ consisting of H, $C_{1-3}$-alkyl and $C_{3-4}$-cycloalkyl or wherein $R^1$ and $R^2$ together form a 2- to 5-membered alkylene-bridge incorporating 0 to 2 heteroatoms independently selected from the group consisting of N, O or S, wherein the $C_{1-3}$-alkyl, the $C_{3-4}$-cycloalkyl or the alkylene-bridge is optionally substituted with halogens.

In a further embodiment of the present invention
$R^1$ and $R^2$ are selected from the group $R^{1.4}$ and $R^{2.4}$ consisting of $C_{1-3}$-alkyl or, wherein $R^1$ and $R^2$ together form a 2- to 5-membered alkylene-bridge incorporating 0 to 2 heteroatoms independently selected from the group consisting of N, O and S.

In a further embodiment of the present invention
$R^1$ and $R^2$ are selected from the group $R^{1.5}$ and $R^{2.5}$ consisting of $H_3C$— or wherein $R^1$ and $R^2$ together form a 2- or 3-membered alkylene-bridge.

In a further embodiment of the present invention
$R^1$ and $R^2$ are selected from the group $R^{1.6}$ and $R^{2.6}$ consisting of $H_3C$—.

In a further embodiment of the present invention
W is selected from the group $W^2$ consisting of a mono- or bicyclic aryl, a mono- or bicyclic heteroaryl and a mono- or bicyclic heterocyclyl, wherein each of these ring systems are optionally substituted with one or more $R^3$, and wherein the heteroaryl comprises up to 4 heteroatoms and one or two 5- or 6-membered ring(s).

In a further embodiment of the present invention
W is selected from the group $W^3$ consisting of a monocyclic aryl, a monocyclic heteroaryl and a monocyclic heterocyclyl,
 wherein each of these ring systems are optionally substituted with one or more $R^3$, and wherein the heteroaryl comprises up to 4 heteroatoms and one 5- or 6-membered ring.

In a further embodiment of the present invention
W is selected from the group $W^4$ consisting of a bicyclic aryl, a bicyclic heteroaryl and a bicyclic heterocyclyl,
 wherein each of these ring systems are optionally substituted with one or more $R^3$, and wherein the heteroaryl comprises up to 4 heteroatoms and two 5- or 6-membered rings.

In a further embodiment of the present invention
W is a selected from the group $W^5$ consisting of

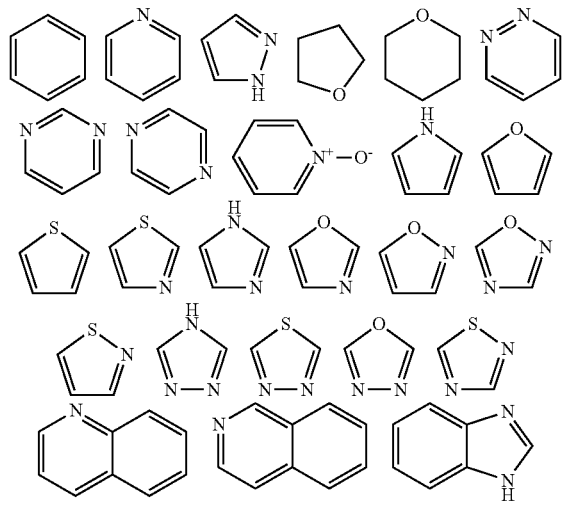

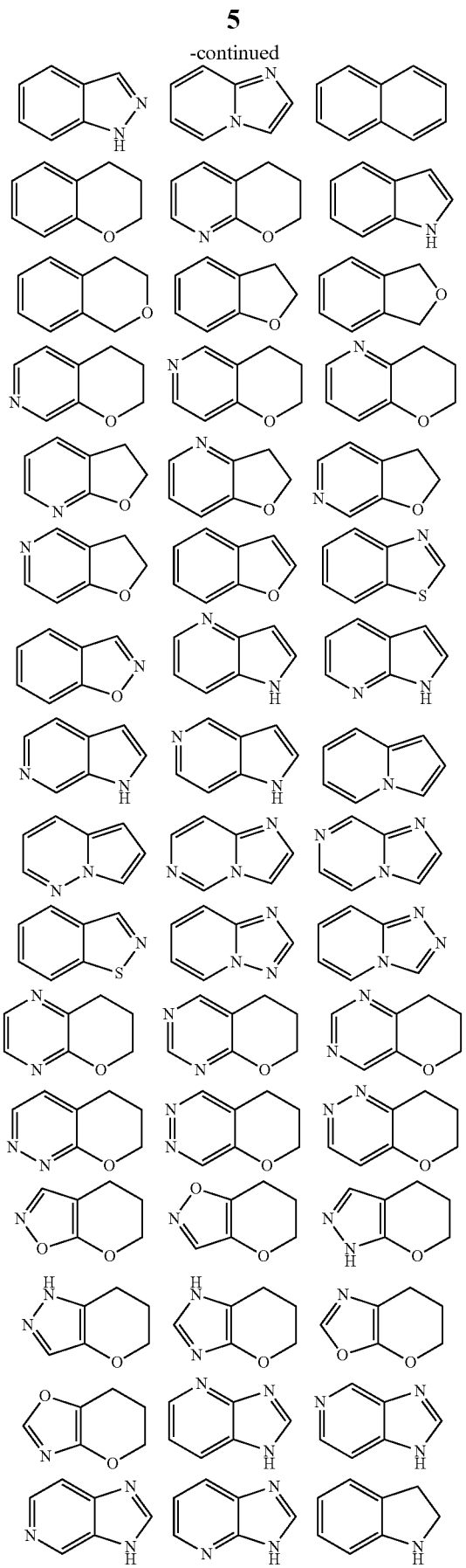
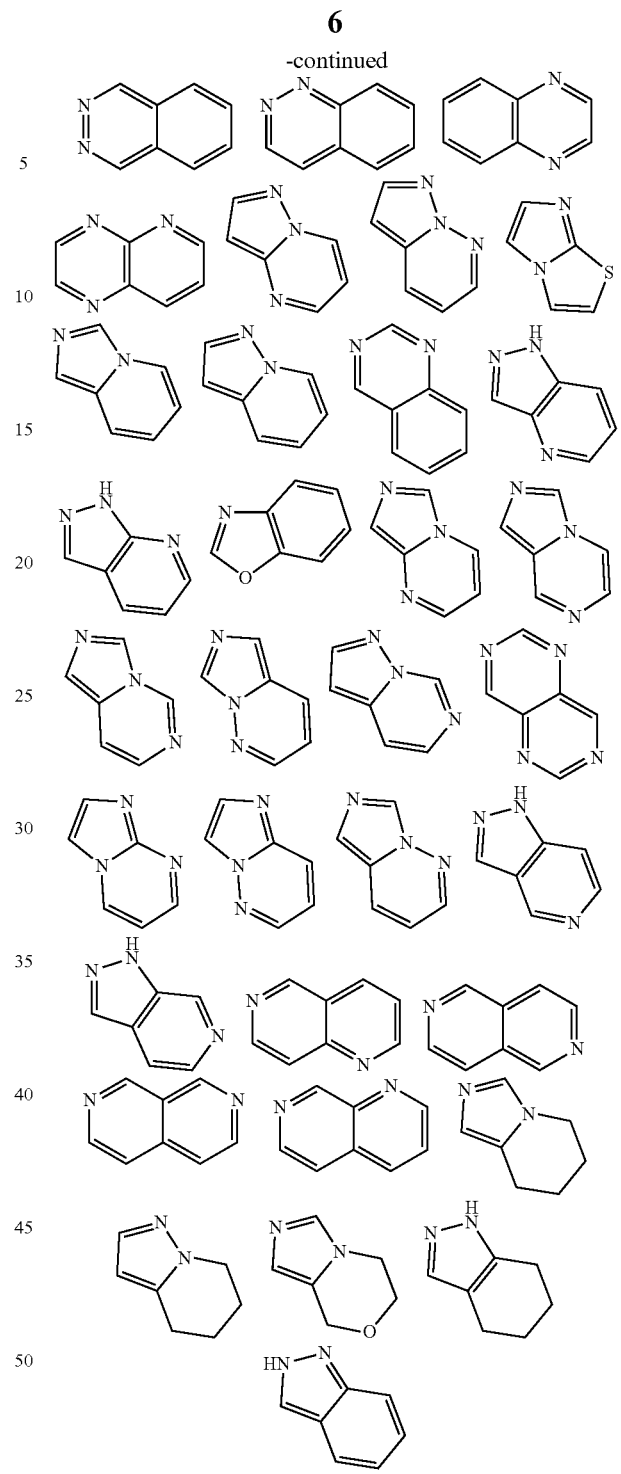
wherein each of these ring systems are optionally substituted with one or more $R^3$.
In a further embodiment of the present invention W is a selected from the group $W^6$ consisting of
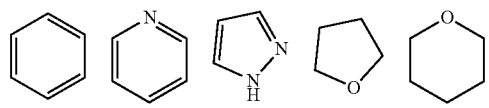

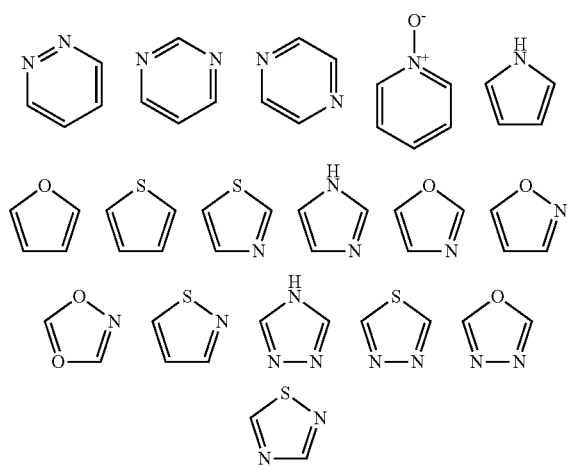
wherein each of these ring systems are optionally substituted with one or more $R^3$.
In a further embodiment of the present invention W is a selected from the group $W^7$ consisting of
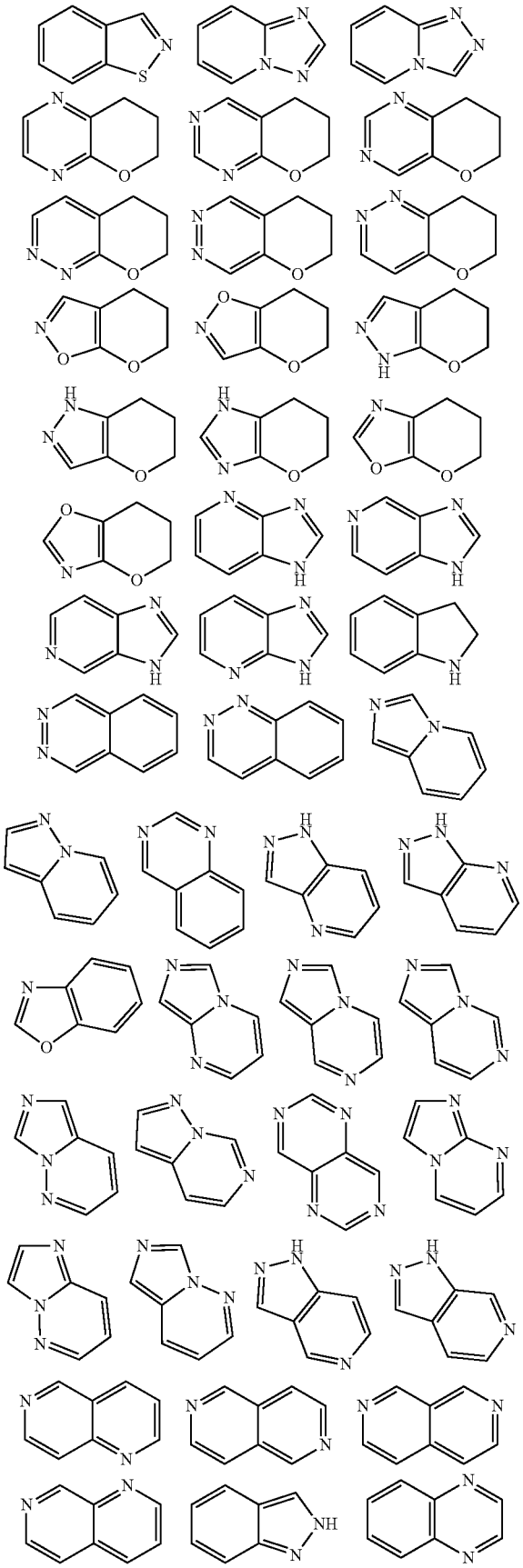

-continued

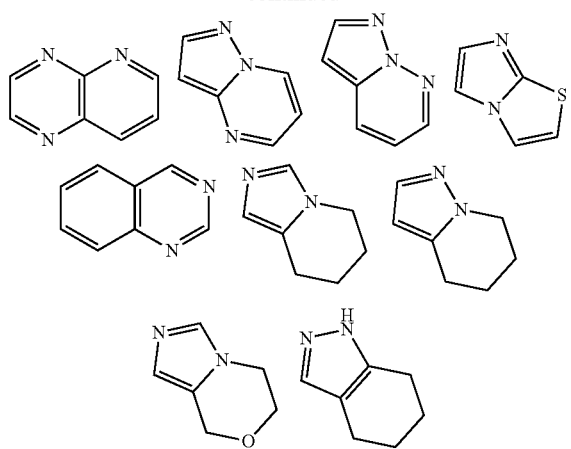

wherein each of these ring systems are optionally substituted with one or more $R^3$.

In a further embodiment of the present invention W is selected from the group $W^8$ consisting of

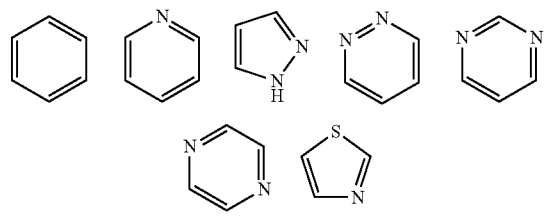

wherein each of these ring systems are optionally substituted with one to three $R^3$.

In a further embodiment of the present invention W is selected from the group $W^9$ consisting of

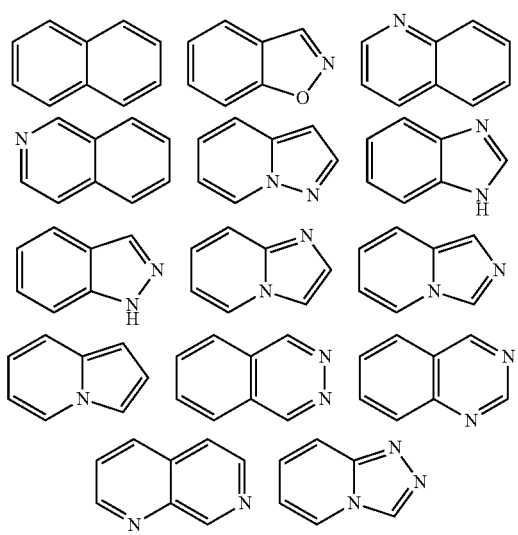

wherein each of these ring systems are optionally substituted with one to three $R^3$.

In a further embodiment of the present invention W is selected from the group $W^{10}$ consisting of

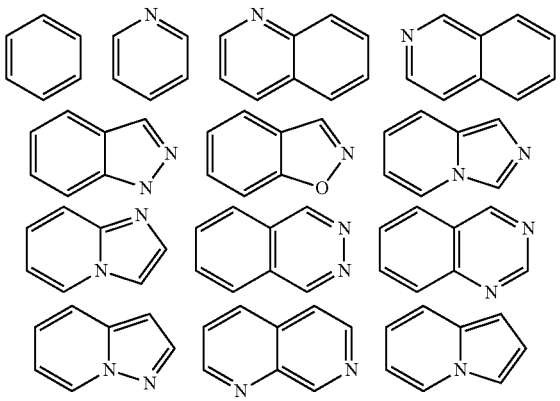

wherein each of these ring systems are optionally substituted with one to three $R^3$.

In a further embodiment of the present invention W is selected from the group $W^{11}$ consisting of

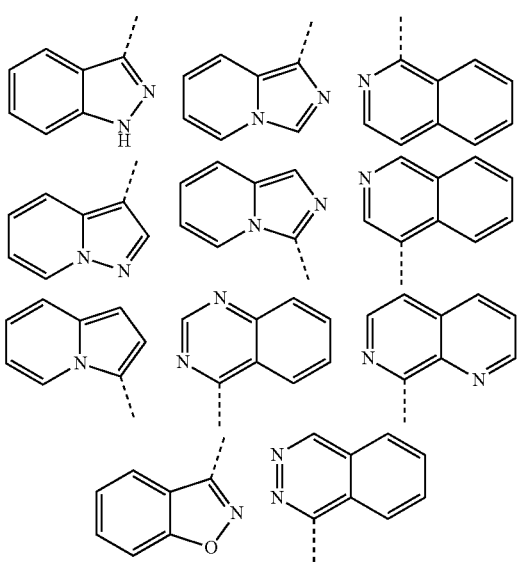

wherein each of these ring systems is attached to Y as indicated by a dotted line and optionally substituted with one to three $R^3$.

In a further embodiment of the present invention $R^3$ is independently selected from the group $R^{3.2}$ consisting of
$C_{1-6}$alkyl, $C_{3-8}$-cycloalkyl, benzyl, halogen, HO—, and NC—, wherein the $C_{1-6}$-alkyl, $C_{3-8}$-cycloalkyl, $C_{1-6}$-alkyl-O—, and the benzyl-substituents are optionally substituted with halogens and/or HO—;

In a further embodiment of the present invention $R^3$ is independently selected from the group $R^{3.3}$ consisting of
$C_{1-3}$-alkyl, $C_{3-6}$-cycloalkyl, $C_{1-3}$-alkyl-O—, halogen, NC—, wherein, in case $R^3$ is connected to N-atoms of W, $R^3$ is selected from the group consisting of $C_{1-3}$-alkyl and $C_{3-6}$-cycloalkyl, wherein the $C_{1-3}$-alkyl, $C_{3-6}$-cycloalkyl and $C_{1-3}$-alkyl-O-substituents are optionally substituted with halogens.

In a further embodiment of the present invention
$R^3$ is independently selected from the group $R^{3.4}$ consisting of
  $H_3C$—, cyclopropyl, $H_3CO$—, F—, Cl—, NC— and $F_3C$—, wherein, in case $R^3$ is connected to N-atoms of W, $R^3$ is selected from $H_3C$— and cyclopropyl.
In a further embodiment of the present invention
$R^3$ is independently selected from the group $R^{3.5}$ consisting of
  $H_3C$—, cyclopropyl, $F_3C$—, Cl and F—, wherein, in case $R^3$ is connected to N-atoms of W, $R^3$ is $H_3C$—.
In a further embodiment of the present invention
$R^3$ is selected from the group $R^{3.6}$ consisting of $H_3C$—, Cl and F.
In a further embodiment of the present invention
Y is selected from the group $Y^2$ consisting of —$CH_2O$—.
In a further embodiment of the present invention
Y is selected from the group $Y^3$ consisting of a bond.
In a further embodiment, if W is a monocyclic ring, at least one of $R^3$ is preferably attached at the ortho-position or neighbouring position with respect to the attachment point of W to Y.
In a further embodiment, if W is a monocyclic ring, Y is preferably selected from $Y^2$. In a further embodiment, if W is a bicyclic ring, Y is preferably selected from $Y^3$.

In a further aspect the present invention relates to pharmaceutically acceptable salts, hydrates or solvates, more specifically to pharmarceutically acceptable salts, hydrates or solvates for use as a medicament.

In a further aspect, the present invention relates to pharmaceutical compositions containing at least one compound according to the specifications above or a pharmaceutically acceptable salt, hydrate or solvate thereof together with one or more pharmaceutically acceptable carrier.

In a further aspect, the present invention relates compounds according to the specifications above for use in the treatment or prevention of diseases or conditions which can be influenced by modulation of SSTR4, for example for the treatment of pain, e.g. of acute pain, neuropathic peripheral pain, chronic pain or osteoarthritis.

In a further aspect, the present invention relates a pharmaceutically acceptable salt, hydrate or solvate of the compounds according to the specifications above for use in the treatment or prevention of diseases or conditions which can be influenced by modulation of SSTR4, for example for the treatment of pain, e.g. of acute pain, neuropathic peripheral pain, chronic pain or osteoarthritis.

In a further aspect, the present invention relates to a pharmaceutical composition containing at least one compound according to the specifications above or a pharmaceutically acceptable salt, hydrate or solvate thereof together with one or more pharmaceutically acceptable carrier for use in the treatment or prevention of diseases or conditions which can be influenced by modulation of SSTR4, for example for the treatment of pain, e.g. of acute pain, neuropathic peripheral pain, chronic pain or osteoarthritis.

Each $R^{1.x}$, $R^{2.x}$, $R^{3.x}$, $A^x$, $G^x$, $W^x$, and $Y^x$ represents a characterized, individual embodiment for the corresponding substituent as described above. Thus given the above definitions, substituents $R^1$, $R^2$, $R^3$, A, G, W, and Y are fully characterized by the term ($R^{1.x}$, $R^{2.x}$, $R^{3.x}$, $A^x$, $G^x$, $W^x$, and $Y^x$), wherein for each index x an individual FIGURE is given that ranges from "1" to the highest number given above. All individual embodiments described by the term in parentheses with full permutation of the indices x, referring to the definitions above, shall be comprised by the present invention.

The following Table 1 shows, exemplarily and generally in the order of increasing preference from the first line to the last line, such embodiments E-1 to E-21 of the invention that are considered preferred. This means that, for example, embodiments E-15 to E-21 are preferred over earlier entries, such as E-1 to E-7.

TABLE 1

Preferred embodiments E-1 to E- 21 of the invention.

| | A | G | W | $R^1/R^2$ | $R^3$ | Y |
|---|---|---|---|---|---|---|
| E-1 | $A^1$ | $G^1$ | $W^1$ | $R^{1.1}/R^{2.1}$ | $R^{3.1}$ | $Y^1$ |
| E-2 | $A^1$ | $G^1$ | $W^2$ | $R^{1.1}/R^{2.1}$ | $R^{3.1}$ | $Y^1$ |
| E-3 | $A^1$ | $G^1$ | $W^3$ | $R^{1.1}/R^{2.1}$ | $R^{3.1}$ | $Y^2$ |
| E-4 | $A^1$ | $G^1$ | $W^4$ | $R^{1.1}/R^{2.1}$ | $R^{3.1}$ | $Y^3$ |
| E-5 | $A^1$ | $G^2$ | $W^2$ | $R^{1.2}/R^{2.2}$ | $R^{3.2}$ | $Y^1$ |
| E-6 | $A^2$ | $G^2$ | $W^2$ | $R^{1.2}/R^{2.2}$ | $R^{3.1}$ | $Y^1$ |
| E-7 | $A^3$ | $G^2$ | $W^2$ | $R^{1.2}/R^{2.2}$ | $R^{3.2}$ | $Y^1$ |
| E-8 | $A^4$ | $G^2$ | $W^2$ | $R^{1.2}/R^{2.2}$ | $R^{3.2}$ | $Y^1$ |
| E-9 | $A^4$ | $G^2$ | $W^5$ | $R^{1.3}/R^{2.3}$ | $R^{3.2}$ | $Y^1$ |
| E-10 | $A^4$ | $G^2$ | $W^5$ | $R^{1.4}/R^{2.4}$ | $R^{3.2}$ | $Y^1$ |
| E-11 | $A^4$ | $G^3$ | $W^5$ | $R^{1.4}/R^{2.4}$ | $R^{3.2}$ | $Y^1$ |
| E-12 | $A^4$ | $G^2$ | $W^6$ | $R^{1.3}/R^{2.3}$ | $R^{3.2}$ | $Y^2$ |
| E-13 | $A^4$ | $G^2$ | $W^7$ | $R^{1.3}/R^{2.3}$ | $R^{3.2}$ | $Y^3$ |
| E-14 | $A^4$ | $G^2$ | $W^8$ | $R^{1.3}/R^{2.3}$ | $R^{3.2}$ | $Y^2$ |
| E-15 | $A^4$ | $G^2$ | $W^9$ | $R^{1.3}/R^{2.3}$ | $R^{3.2}$ | $Y^3$ |
| E-16 | $A^4$ | $G^3$ | $W^8$ | $R^{1.5}/R^{2.5}$ | $R^{3.3}$ | $Y^2$ |
| E-17 | $A^4$ | $G^3$ | $W^9$ | $R^{1.5}/R^{2.5}$ | $R^{3.3}$ | $Y^3$ |
| E-18 | $A^4$ | $G^3$ | $W^{10}$ | $R^{1.5}/R^{2.5}$ | $R^{3.3}$ | $Y^1$ |
| E-19 | $A^4$ | $G^3$ | $W^{10}$ | $R^{1.5}/R^{2.5}$ | $R^{3.4}$ | $Y^1$ |
| E-20 | $A^4$ | $G^3$ | $W^{10}$ | $R^{1.6}/R^{2.6}$ | $R^{3.5}$ | $Y^3$ |
| E-21 | $A^4$ | $G^3$ | $W^{11}$ | $R^{1.6}/R^{2.6}$ | $R^{3.6}$ | $Y^3$ | the tautomers thereof, the stereoisomers thereof, the mixtures thereof, the salts thereof, the hydrates thereof and the solvates thereof.

Accordingly, for example E-5 covers compounds of formula (I), wherein
  A is selected from the group consisting of H and $C_{1-6}$-alkyl;
  G is selected from the group consisting of CH and N, wherein up to one G is N, the others being CH;
  W is selected from the group consisting of a mono- or bicyclic aryl, a mono- or bicyclic heteroaryl and a mono- or bicyclic heterocyclyl, wherein each of these ring systems are optionally substituted with one or more $R^3$, and wherein the heteroaryl comprises up to 4 heteroatoms and one or two 5- or 6-membered ring(s).
  $R^1$ and $R^2$ are independently selected from the group consisting of $C_{1-6}$-alkyl and $C_{3-6}$-cycloalkyl, or wherein $R^1$ and $R^2$ together form a 2- to 5-membered alkylene-bridge incorporating 0 to 2 heteroatoms independently selected from the group consisting of N, O or S, wherein the $C_{1-6}$-alkyl, the $C_{3-6}$-cycloalkyl or the alkylene-bridge is optionally substituted with halogens or MeO—.
  $R^3$ is independently selected from the group consisting of $C_{1-6}$-alkyl, $C_{3-8}$-cycloalkyl, $C_{1-6}$-alkyl-O—, benzyl, halogen, HO—, and NC—, wherein the $C_{1-6}$-alkyl, $C_{3-8}$-cycloalkyl, $C_{1-6}$-alkyl-O—, and the benzyl-substituents are optionally substituted with halogens and/or HO—;
  Y is selected from the group consisting of a bond and —$CH_2O$—;
  the tautomers thereof, the stereoisomers thereof, the mixtures thereof, the salts thereof, the hydrates thereof and the solvates thereof.

Accordingly, for example E-18 covers compounds of formula (I), wherein

A is H,

G is selected from the group consisting of CH and N, wherein up to one G is N, the others being CH, W is selected from the group $W^{10}$ consisting of

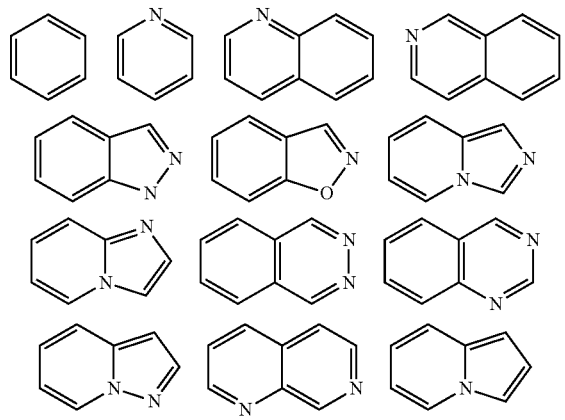

wherein each of these ring systems are optionally substituted with one to three $R^3$, $R^1$ and $R^2$ are selected from the group consisting of $H_3C$— or wherein $R^1$ and $R^2$ together form a 2- or 3-membered alkylene-bridge.

$R^3$ is independently selected from the group consisting of $C_{1-3}$-alkyl, $C_{3-6}$-cycloalkyl, $C_{1-3}$-alkyl-O—, halogen, NC—, wherein, in case $R^3$ is connected to N-atoms of W, $R^3$ is selected from the group consisting of $C_{1-3}$-alkyl and $C_{3-6}$-cycloalkyl, wherein the $C_{1-3}$-alkyl, $C_{3-6}$-cycloalkyl and $C_{1-3}$-alkyl-O-substituents are optionally substituted with halogens.

Y is selected from the group consisting of a bond and —$CH_2O$—, the tautomers thereof, the stereoisomers thereof, the mixtures thereof, the salts thereof, the hydrates thereof and the solvates thereof.

The present invention preferrably relates to the following compounds:

| Comp. | Structure |
|---|---|
| I | |
| II | 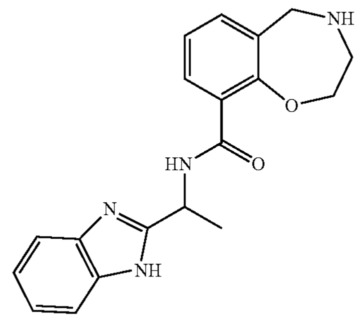 [SMILES: CC(NC(=O)c1cccc2c1OCCNC2)c1nc2ccccc2[nH]1] |
| III | 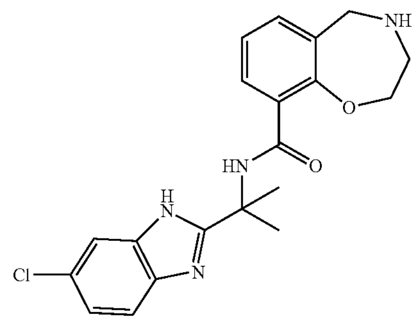 [SMILES: CC(C)(NC(=O)c1cccc2c1OCCNC2)c1nc2ccc(Cl)cc2[nH]1] |
| IV | 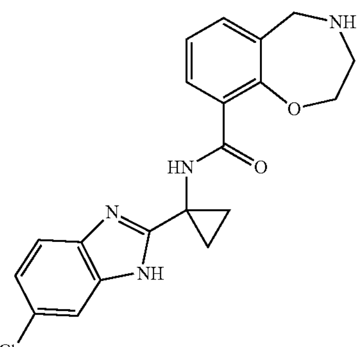 |
| V | 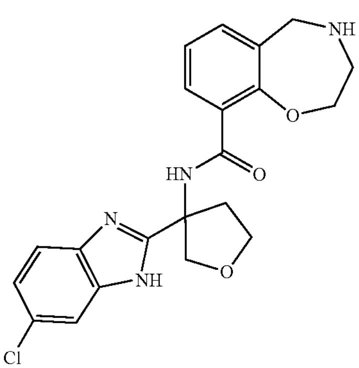 [SMILES: O=C(NC1(c2nc3ccc(Cl)cc3[nH]2)CCOC1)c1cccc2c1OCCNC2] |

-continued
| Comp. | Structure |
|---|---|
| VI | 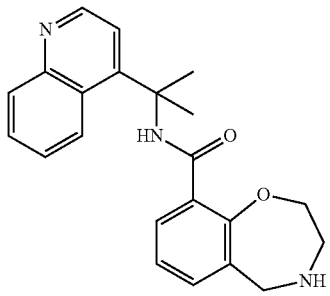 [SMILES: CC(C)(NC(=O)c1cccc2c1OCCNC2)c1ccnc2ccccc12] |
| VII | 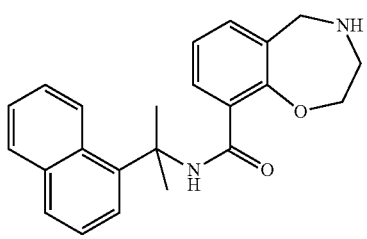 [SMILES: CC(C)(NC(=O)c1cccc2c1OCCNC2)c1cccc2ccccc12] |
| VIII | 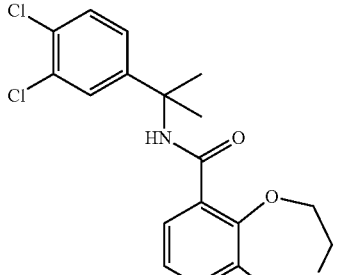 |
| IX | 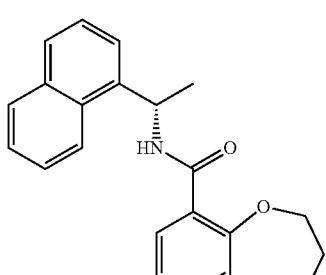 |
| X | 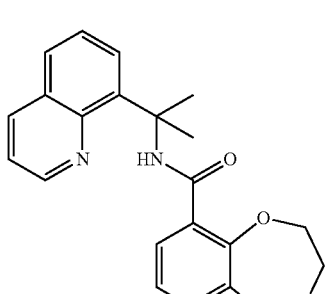 |
-continued
| Comp. | Structure |
|---|---|
| XI | 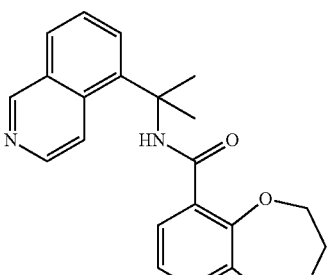 |
| XII | 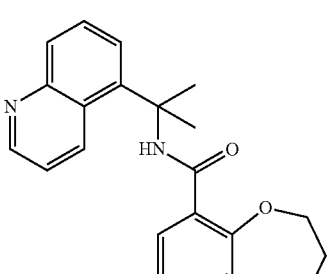 |
| XIII | 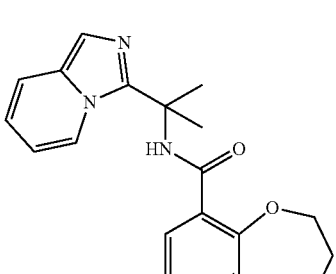 |
| XIV | 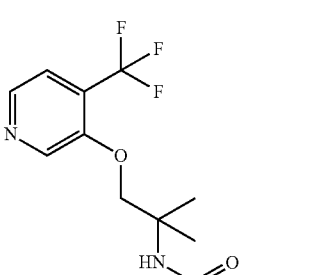 |

| Comp. | Structure |
|---|---|
| XV | 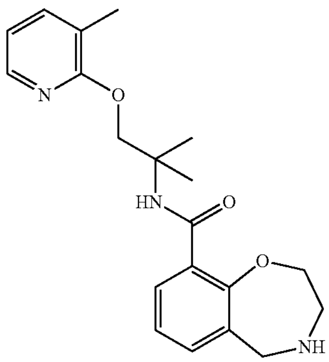 [SMILES: Cc1cccnc1OCC(C)(C)NC(=O)c1cccc2c1OCCNC2] |
| XVI | 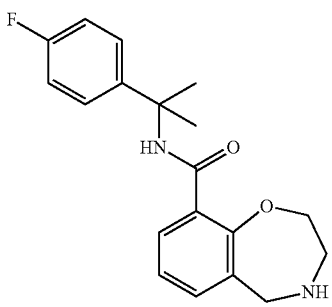 [SMILES: CC(C)(NC(=O)c1cccc2c1OCCNC2)c1ccc(F)cc1] |
| XVII | 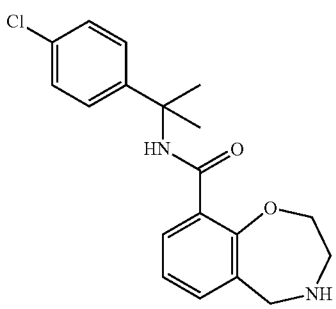 [SMILES: CC(C)(NC(=O)c1cccc2c1OCCNC2)c1ccc(Cl)cc1] |
| XVIII | 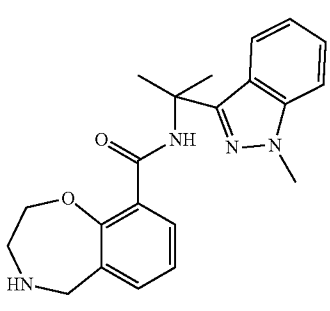 [SMILES: Cn1nc(C(C)(C)NC(=O)c2cccc3c2OCCNC3)c2ccccc21] |
| XIX | 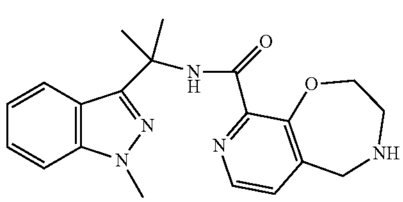 [SMILES: Cn1nc(C(C)(C)NC(=O)c2nccc3c2OCCNC3)c2ccccc21] |
| XX | 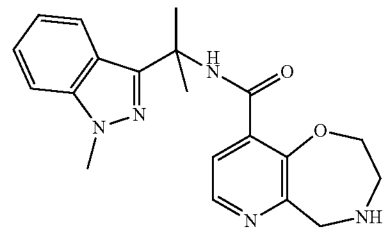 [SMILES: Cn1nc(C(C)(C)NC(=O)c2ccnc3c2OCCNC3)c2ccccc21] |
| XXI | 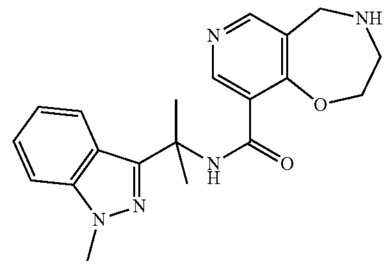 [SMILES: Cn1nc(C(C)(C)NC(=O)c2cncc3c2OCCNC3)c2ccccc21] |
| XXII | 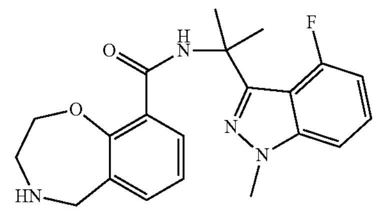 [SMILES: Cn1nc(C(C)(C)NC(=O)c2cccc3c2OCCNC3)c2c(F)cccc21] |
| XXIII | 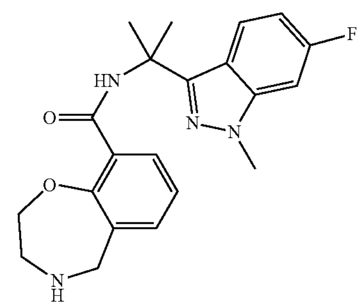 [SMILES: Cn1nc(C(C)(C)NC(=O)c2cccc3c2OCCNC3)c2ccc(F)cc21] |
| XXIV | 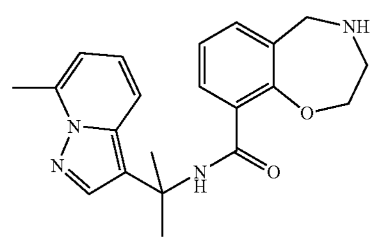 [SMILES: Cc1cccc2c(C(C)(C)NC(=O)c3cccc4c3OCCNC4)cnn12] |
| XXV | 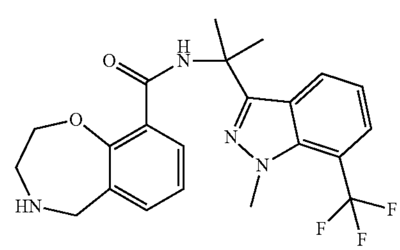 [SMILES: Cn1nc(C(C)(C)NC(=O)c2cccc3c2OCCNC3)c2cccc(C(F)(F)F)c21] |

-continued

| Comp. | Structure |
|---|---|
| XXVI | 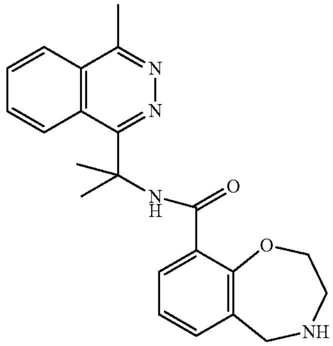 [SMILES: Cc1nnc(C(C)(C)NC(=O)c2cccc3c2OCCNC3)c2ccccc12] |
| XXVII | 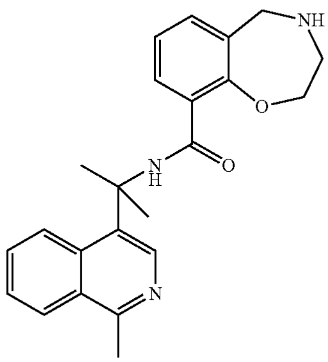 [SMILES: Cc1ncc(C(C)(C)NC(=O)c2cccc3c2OCCNC3)c2ccccc12] |
| XXVIII | 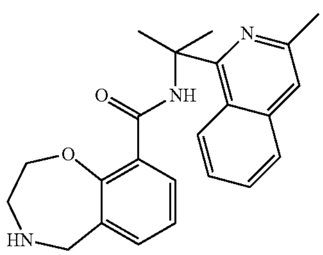 [SMILES: Cc1cc2ccccc2c(C(C)(C)NC(=O)c2cccc3c2OCCNC3)n1] |
| XXIX | 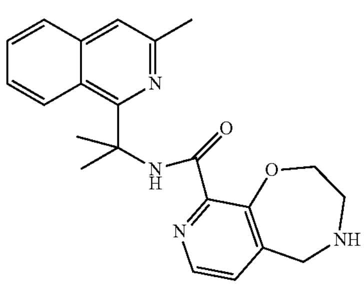 [SMILES: Cc1cc2ccccc2c(C(C)(C)NC(=O)c2nccc3c2OCCNC3)n1] |
| XXX | 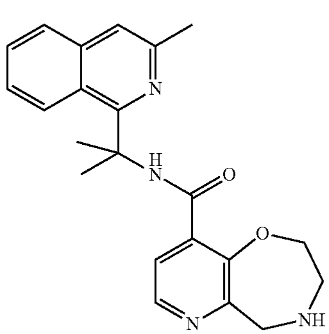 [SMILES: Cc1cc2ccccc2c(C(C)(C)NC(=O)c2ccnc3c2OCCNC3)n1] |

-continued

| Comp. | Structure |
|---|---|
| XXXI | 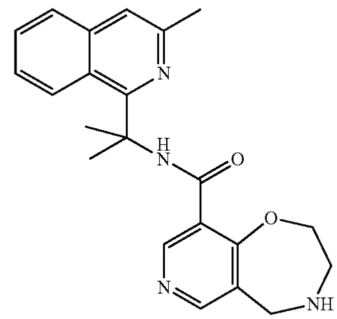 [SMILES: Cc1cc2ccccc2c(C(C)(C)NC(=O)c2cncc3c2OCCNC3)n1] |
| XXXII | 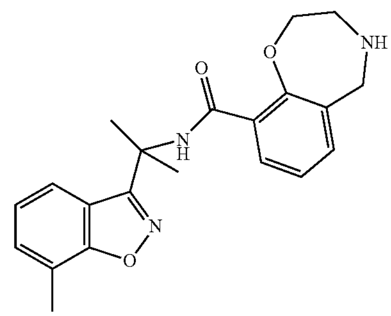 [SMILES: Cc1cccc2c(C(C)(C)NC(=O)c3cccc4c3OCCNC4)noc12] |
| XXXIII | 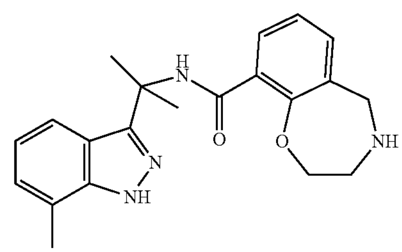 [SMILES: Cc1cccc2c(C(C)(C)NC(=O)c3cccc4c3OCCNC4)n[nH]c12] |
| XXXIV | 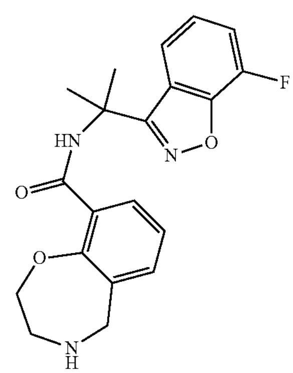 [SMILES: CC(C)(NC(=O)c1cccc2c1OCCNC2)c1noc2c(F)cccc12] |
| XXXV | 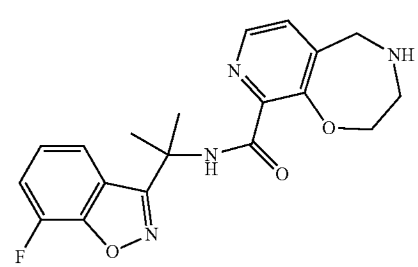 [SMILES: CC(C)(NC(=O)c1nccc2c1OCCNC2)c1noc2c(F)cccc12] |

-continued
| Comp. | Structure |
|---|---|
| XXXVI | 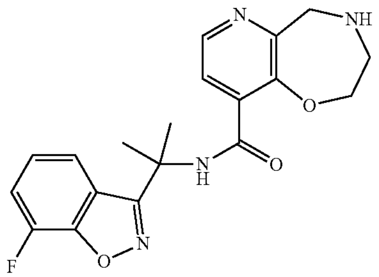 [SMILES: CC(C)(NC(=O)c1ccnc2c1OCCNC2)c1noc2c(F)cccc12] |
| XXXVII | 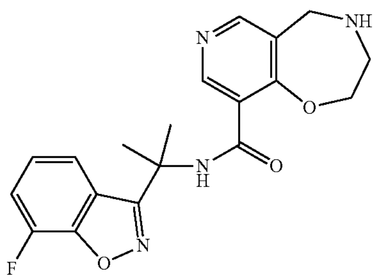 [SMILES: CC(C)(NC(=O)c1cncc2c1OCCNC2)c1noc2c(F)cccc12] |
| XXXVIII | 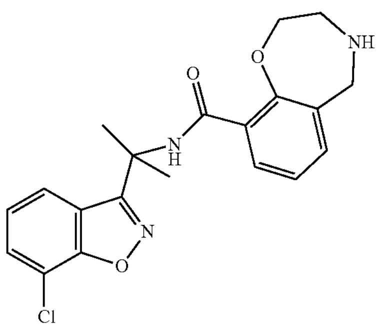 [SMILES: CC(C)(NC(=O)c1cccc2c1OCCNC2)c1noc2c(Cl)cccc12] |
| XXXIX | 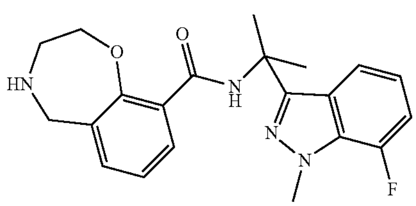 |
| XL | 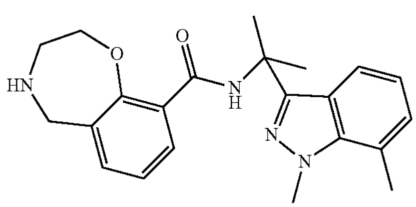 [SMILES: Cc1cccc2c(C(C)(C)NC(=O)c3cccc4c3OCCNC4)nn(C)c12] |
| XLI | 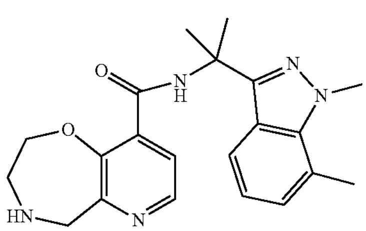 [SMILES: Cc1cccc2c(C(C)(C)NC(=O)c3ccnc4c3OCCNC4)nn(C)c12] |
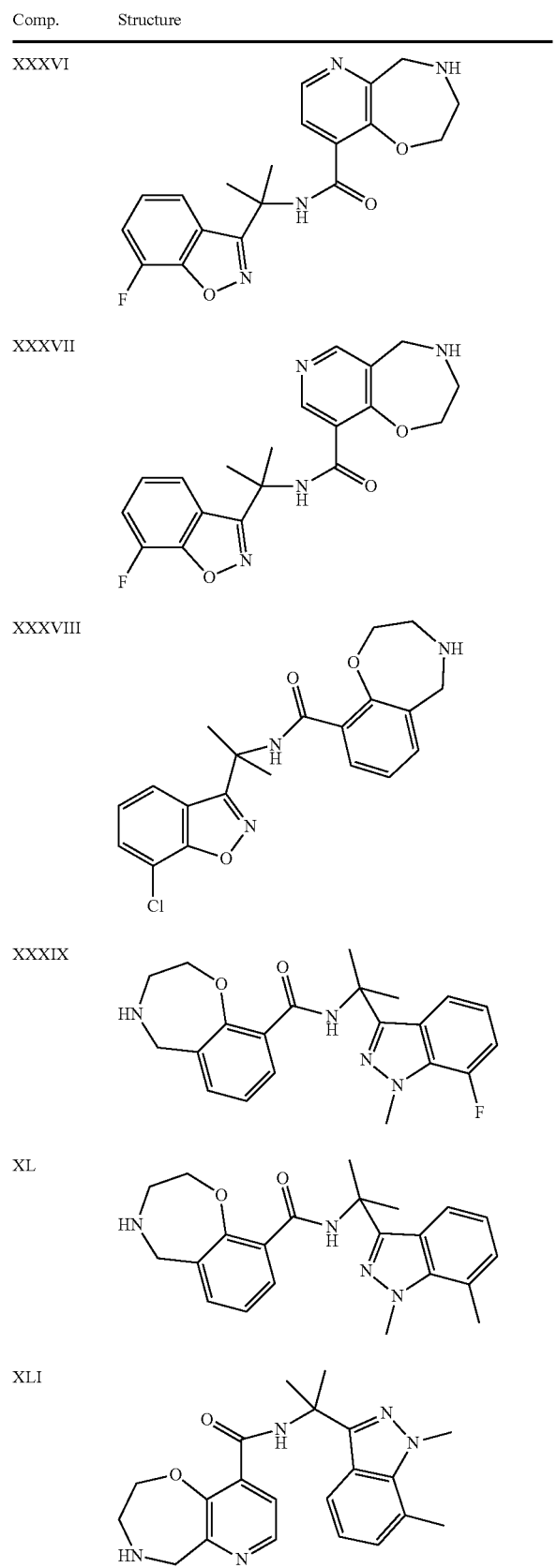
-continued
| Comp. | Structure |
|---|---|
| XLII | 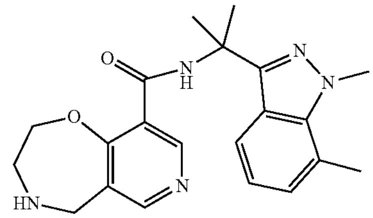 [SMILES: Cc1cccc2c(C(C)(C)NC(=O)c3cncc4c3OCCNC4)nn(C)c12] |
| XLIII | 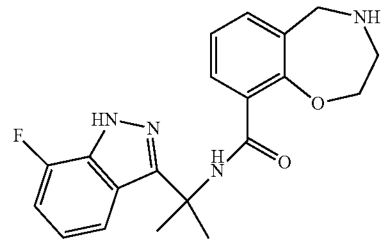 [SMILES: CC(C)(NC(=O)c1cccc2c1OCCNC2)c1n[nH]c2c(F)cccc12] |
| XLIV | 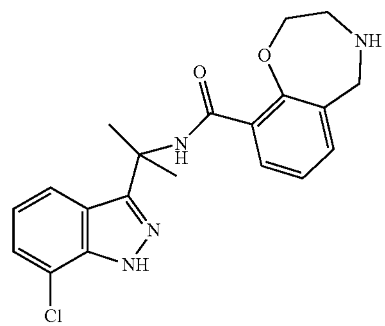 [SMILES: CC(C)(NC(=O)c1cccc2c1OCCNC2)c1n[nH]c2c(Cl)cccc12] |
| XLV | 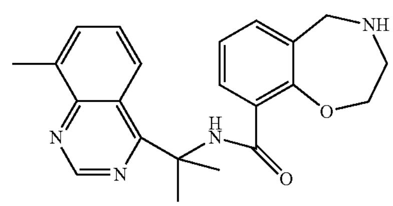 [SMILES: Cc1cccc2c(C(C)(C)NC(=O)c3cccc4c3OCCNC4)ncnc12] |
| XLVI | 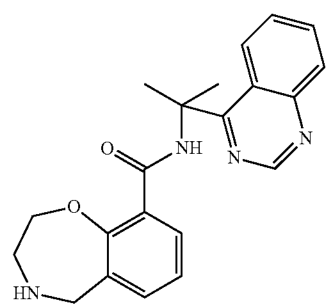 [SMILES: CC(C)(NC(=O)c1cccc2c1OCCNC2)c1ncnc2ccccc12] |
| XLVII | 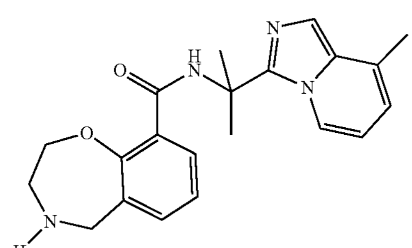 |
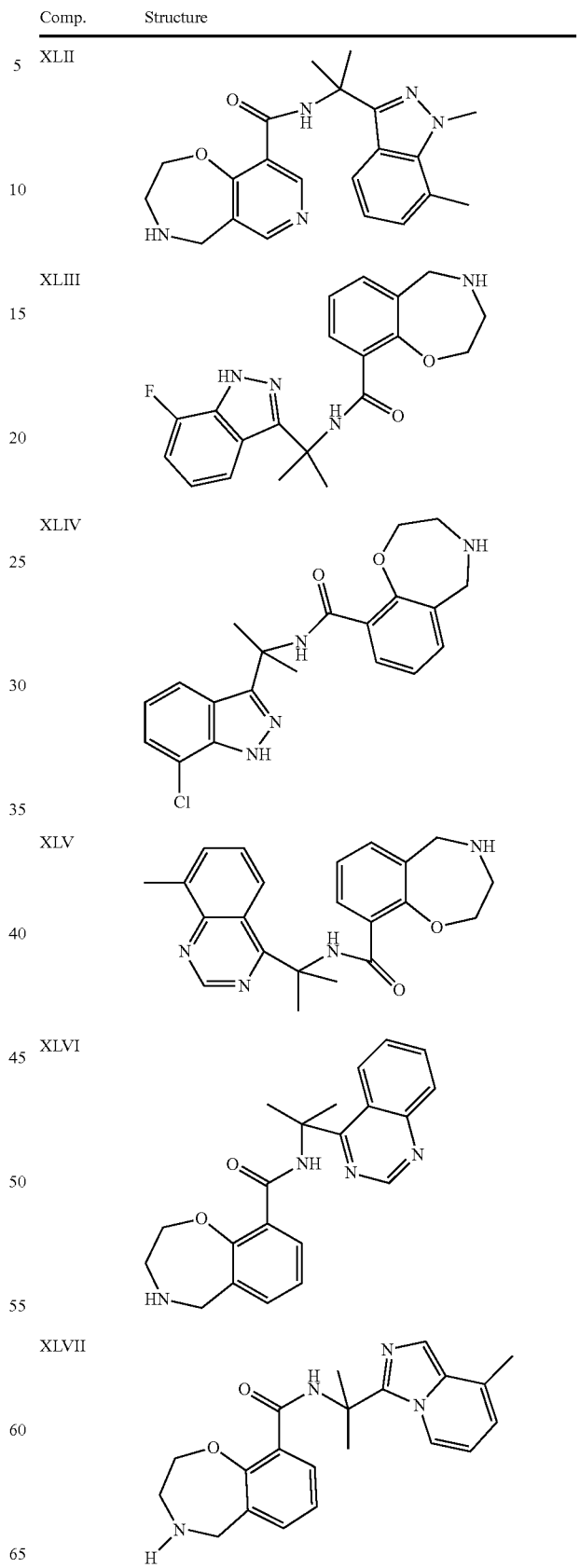

-continued
| Comp. | Structure |
|---|---|
| XLVIII | 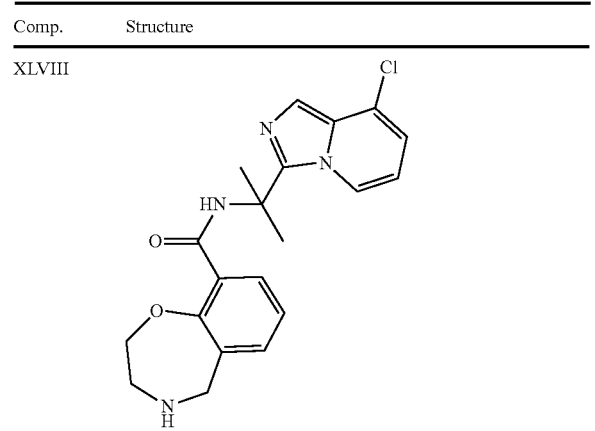 |
| XLIX | 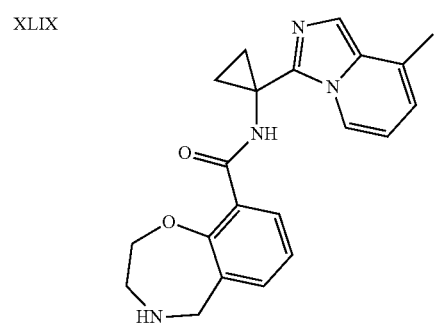 |
| L | 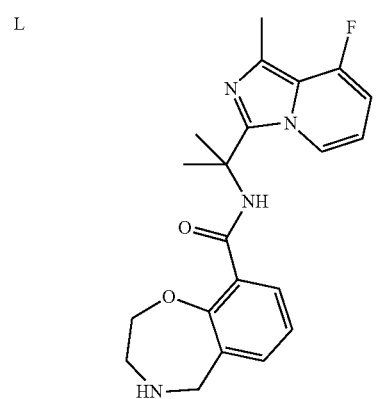 |
| LI | 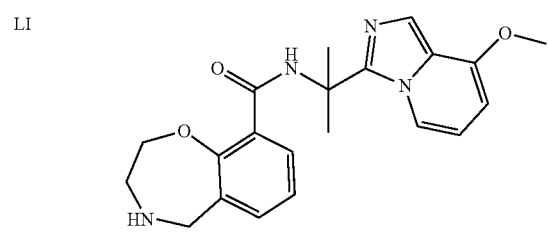 |
| LII | 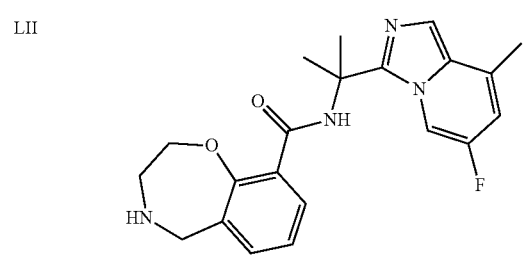 |
-continued
| Comp. | Structure |
|---|---|
| LIII | 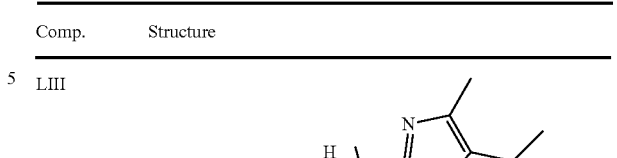 |
| LIV | 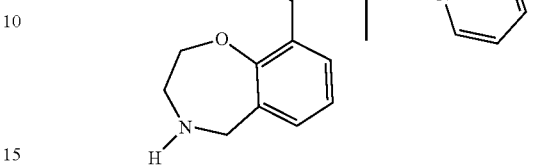 |
| LV | 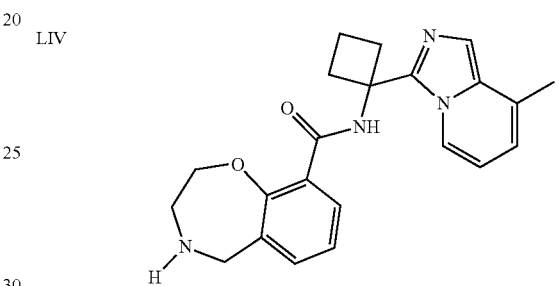 |
| LVI | 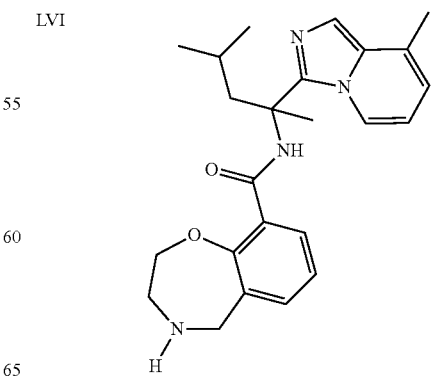 |

-continued
| Comp. | Structure |
|---|---|
| LVII | 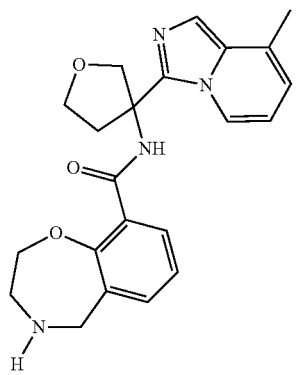 [SMILES: Cc1cccn2c(C3(NC(=O)c4cccc5c4OCCNC5)CCOC3)ncc12] |
| LVIII | 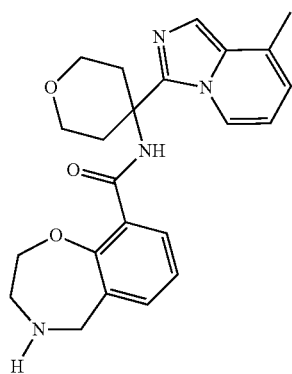 [SMILES: Cc1cccn2c(C3(NC(=O)c4cccc5c4OCCNC5)CCOCC3)ncc12] |
| LIX | 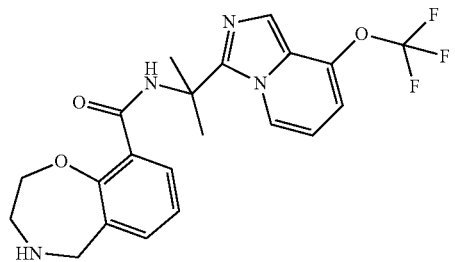 [SMILES: CC(C)(NC(=O)c1cccc2c1OCCNC2)c1ncc2c(OC(F)(F)F)cccn12] |
| LX | 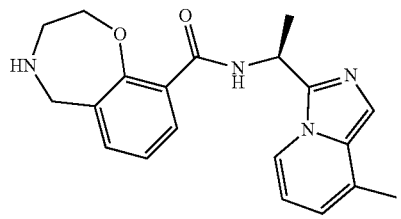 [SMILES: Cc1cccn2c([C@H](C)NC(=O)c3cccc4c3OCCNC4)ncc12] |
| LXI | 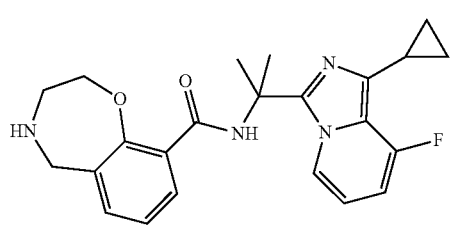 [SMILES: CC(C)(NC(=O)c1cccc2c1OCCNC2)c1nc(C2CC2)c2c(F)cccn12] |
-continued
| Comp. | Structure |
|---|---|
| LXII | 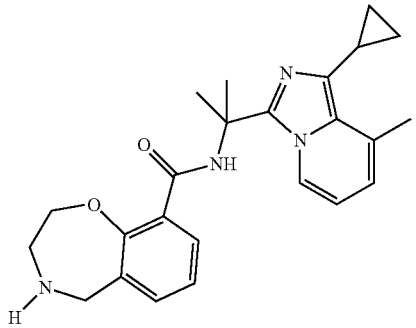 [SMILES: Cc1cccn2c(C(C)(C)NC(=O)c3cccc4c3OCCNC4)nc(C3CC3)c12] |
| LXIII | 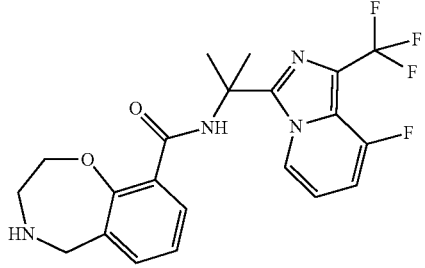 [SMILES: CC(C)(NC(=O)c1cccc2c1OCCNC2)c1nc(C(F)(F)F)c2c(F)cccn12] |
| LXIV | 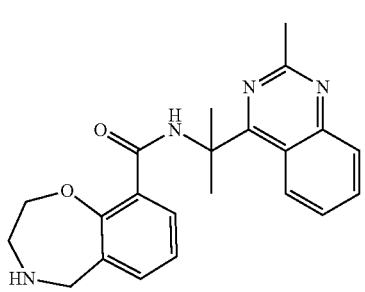 [SMILES: Cc1nc(C(C)(C)NC(=O)c2cccc3c2OCCNC3)c2ccccc2n1] |
| LXV | 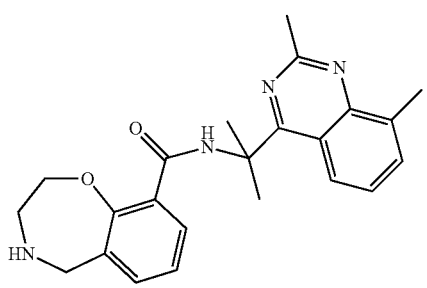 [SMILES: Cc1nc(C(C)(C)NC(=O)c2cccc3c2OCCNC3)c2cccc(C)c2n1] |
| LXVI | 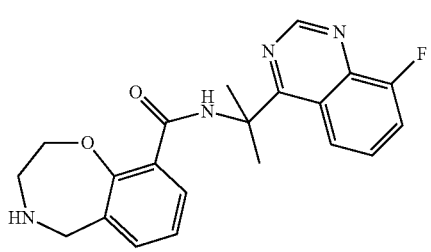 [SMILES: CC(C)(NC(=O)c1cccc2c1OCCNC2)c1ncnc2c(F)cccc12] |

| Comp. | Structure |
|---|---|
| LXVII | 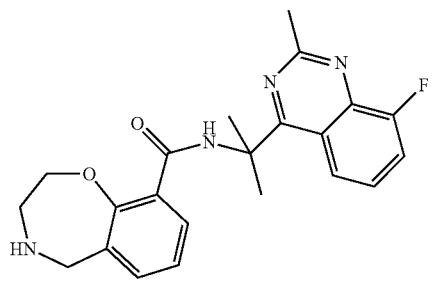 [SMILES: Cc1nc(C(C)(C)NC(=O)c2cccc3c2OCCNC3)c2cccc(F)c2n1] |
| LXVIII | 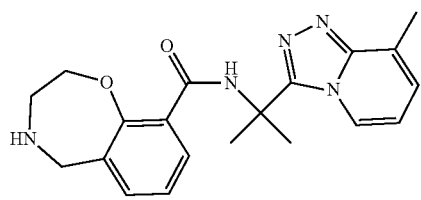 [SMILES: Cc1cccn2c(C(C)(C)NC(=O)c3cccc4c3OCCNC4)nnc12] |
| LXIX | 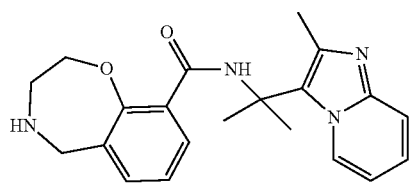 [SMILES: Cc1nc2ccccn2c1C(C)(C)NC(=O)c1cccc2c1OCCNC2] |
| LXX | 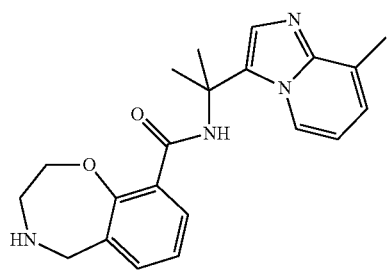 [SMILES: Cc1cccn2c(C(C)(C)NC(=O)c3cccc4c3OCCNC4)cnc12] |
| LXXI | 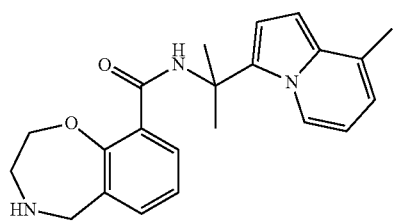 [SMILES: Cc1cccn2c(C(C)(C)NC(=O)c3cccc4c3OCCNC4)ccc12] |
| LXXII | 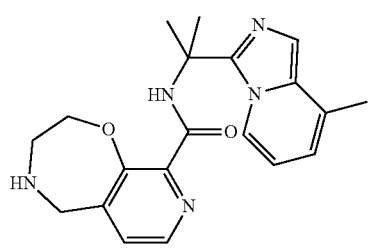 [SMILES: Cc1cccn2c(C(C)(C)NC(=O)c3nccc4c3OCCNC4)ncc12] |
| LXXIII | 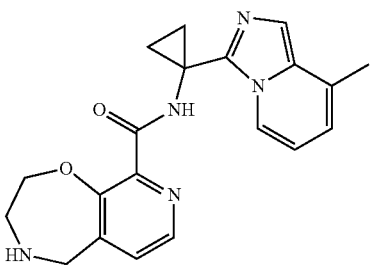 [SMILES: Cc1cccn2c(C3(NC(=O)c4nccc5c4OCCNC5)CC3)ncc12] |
| LXXIV | 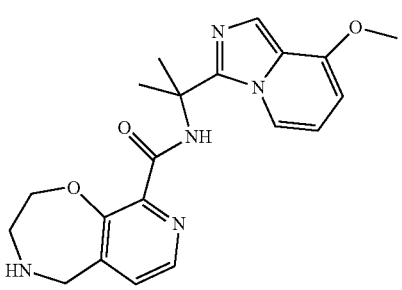 [SMILES: COc1cccn2c(C(C)(C)NC(=O)c3nccc4c3OCCNC4)ncc12] |
| LXXV | 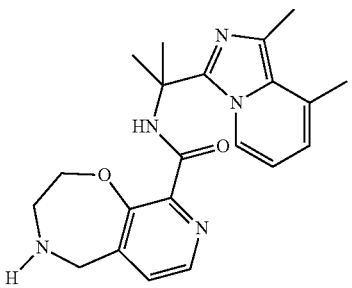 [SMILES: Cc1cccn2c(C(C)(C)NC(=O)c3nccc4c3OCCNC4)nc(C)c12] |
| LXXVI | 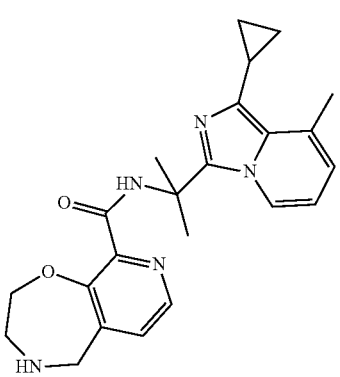 [SMILES: Cc1cccn2c(C(C)(C)NC(=O)c3nccc4c3OCCNC4)nc(C3CC3)c12] |
| LXXVII | 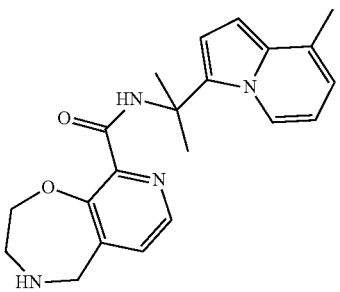 [SMILES: Cc1cccn2c(C(C)(C)NC(=O)c3nccc4c3OCCNC4)ccc12] |

| Comp. | Structure |
|---|---|
| LXXVIII | (structure) |
| LXXIX | (structure) |

Terms and Definitions Used

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

The number of substituents $R^3$ of W is preferably from 0 to 3, more preferably from 0 to 2, most preferably 1 or 2.

For the instances where Y is —CH$_2$O— this to be interpreted such that the oxygen atom of —CH$_2$O— is connected to W.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The prefix "meso" indicates the presence of a symmetry element of the second kind (mirror plane, centre of inversion, rotation-reflection axis) in a chemical species.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2''-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamidobenzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

Halogen:

The term "halogen" generally denotes fluorine, chlorine, bromine and iodine.

Alkyl:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Alkylene:

The term "$C_{1-n}$-alkylene" wherein n is an integer 2 to n, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

Alkenyl:

The term "$C_{2-n}$-alkenyl" is used for a group as defined in the definition for "$C_{1-n}$-alkyl" with at least two carbon atoms, if at least two of those carbon atoms of said group are bonded to each other by a double bond.

Alkynyl:

The term "$C_{2-n}$-alkynyl" is used for a group as defined in the definition for "$C_{1-n}$-alkyl" with at least two carbon atoms, if at least two of those carbon atoms of said group are bonded to each other by a triple bond.

Cycloalkyl:

The term "$C_{3-n}$-cycloalkyl" wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Heterocyclyl:

The term "heterocyclyl" means a saturated or unsaturated mono- or polycyclic-ring systems including aromatic ring system containing one or more heteroatoms selected from N, O or S(O)r, wherein r=0, 1 or 2, consisting of 5 to 11 ring atoms wherein none of the heteroatoms is part of the aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

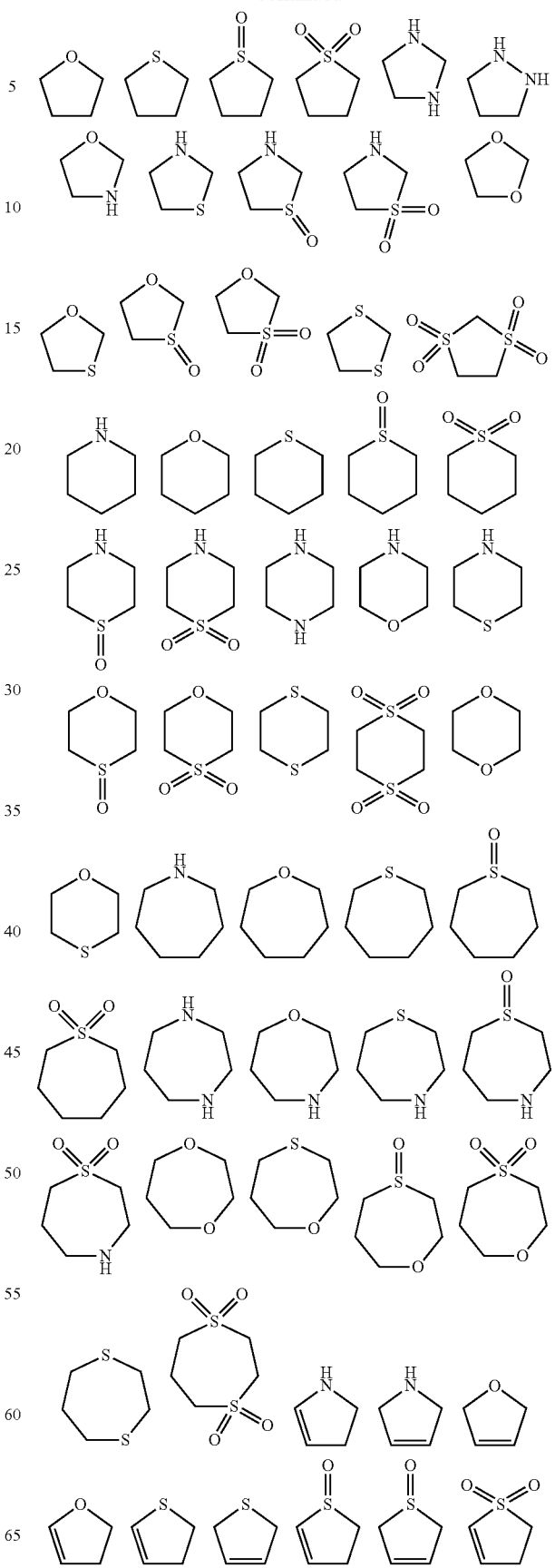

33
-continued
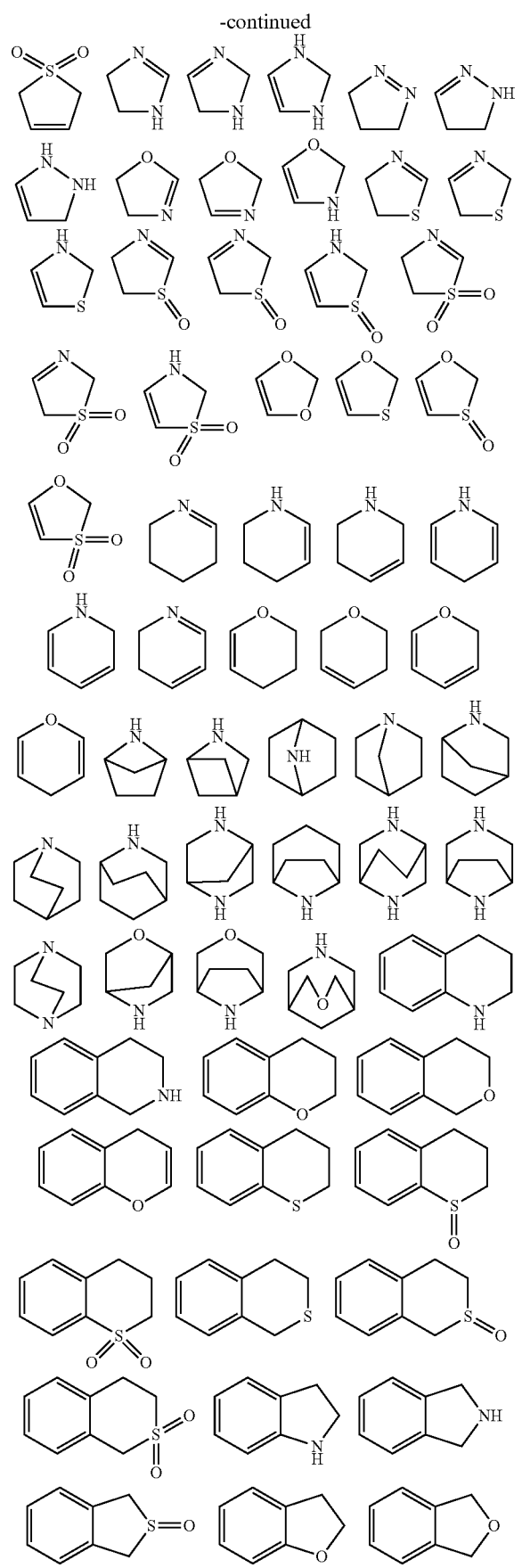
34
-continued
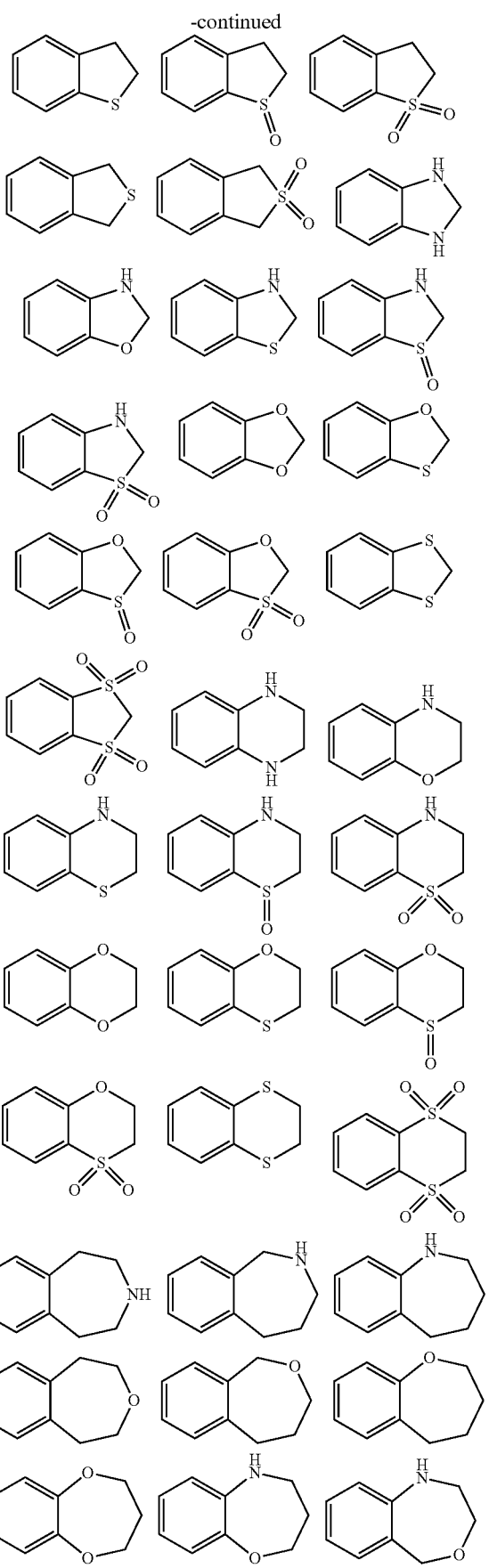

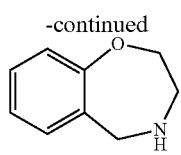

Aryl:

The term "aryl" as used herein, either alone or in combination with another radical, denotes a carbocyclic aromatic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heteroaryl:

The term "heteroaryl" means a mono- or bicyclic-ring systems containing one or more heteroatoms selected from N, O or S(O)$_r$, wherein r=0, 1 or 2, consisting of 5 to 10 ring atoms, wherein at least one of the heteroatoms is part of an aromatic ring. The term "heteroaryl" is intended to include all the possible isomeric forms. Preferred heteroaryls for the present invention comprise up to 4 heteroatoms and at least one 5- or 6-membered ring, more preferably at least one 6-membered ring.

Thus, the term "heteroaryl" includes the following exemplary structures which are not depicted as radicals as each form may be attached through a covalent bond to any atom so long as appropriate valences are maintained:

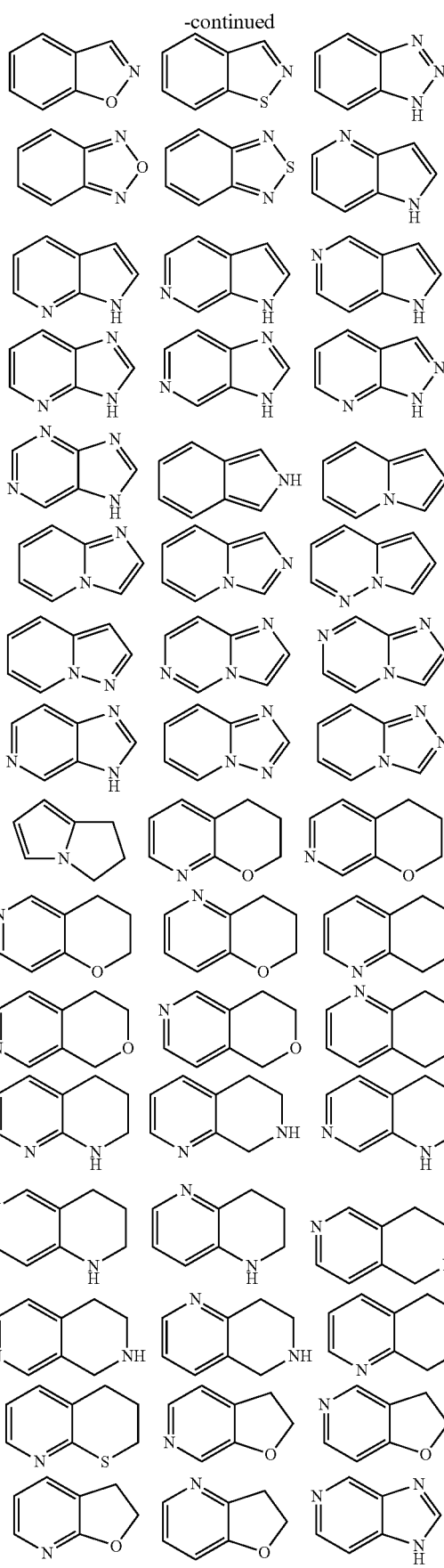

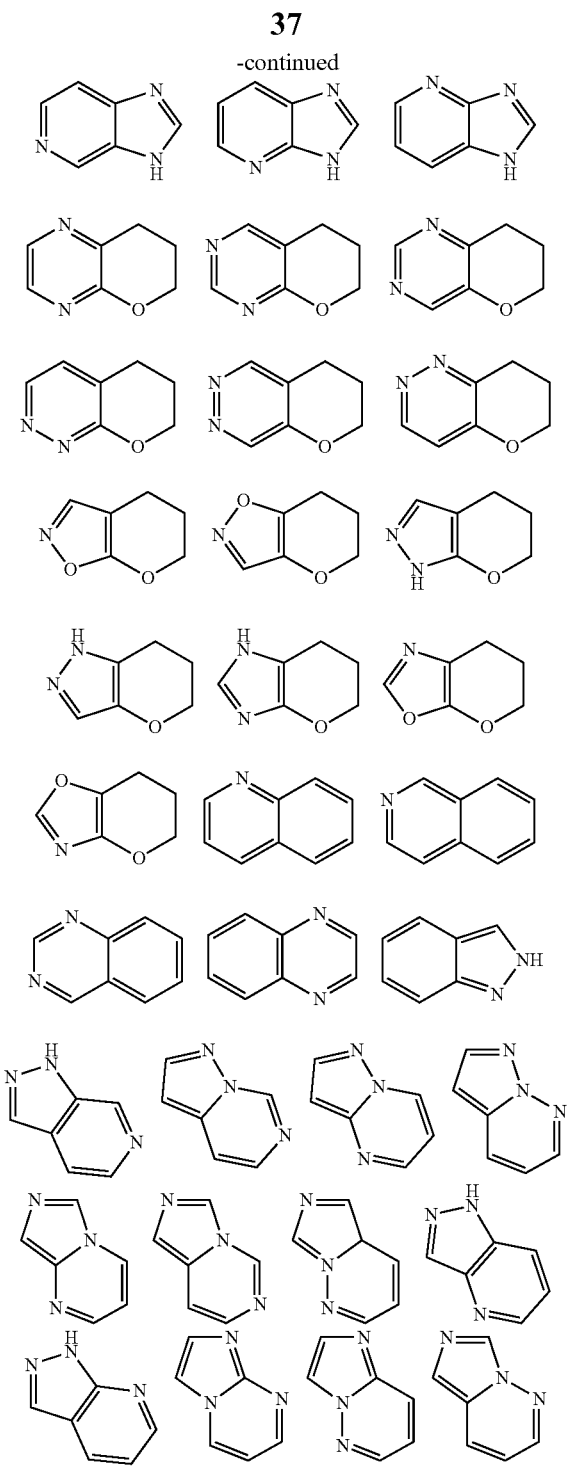

Many of the terms given above may be used repeatedly in the definition of a formula or group and in each case have one of the meanings given above, independently of one another.

Methods of Preparation

The compounds according to the invention may be obtained using methods of synthesis known in principle. Preferably, the compounds are obtained by the following methods according to the invention which are described in more detail hereinafter.

The following schemes shall illustrate generally how to manufacture the compounds according to general formula (I) and the corresponding intermediate compounds by way of example. The abbreviated substituents may be as defined above if not defined otherwise within the context of the schemes. For a list of abbreviations, see below.

Scheme 1

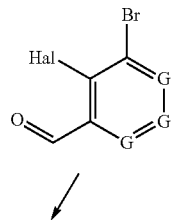

-continued

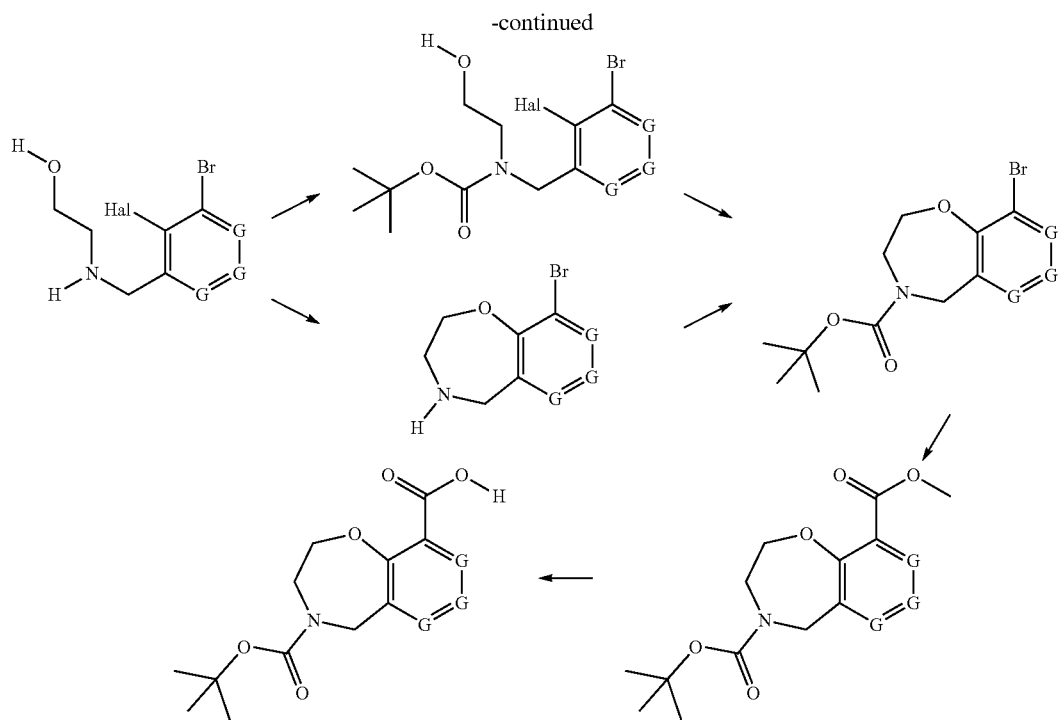

In scheme 1, Hal=halogen.

Scheme 1:

In a first step an aldehyde undergoes reductive amination with 2-aminoethanol in the presence of an appropriate reducing agent such as sodium triacetoxyborohydride in an appropriate solvent such as 1,2-dichloroethane. The resulting amine is Boc-protected using di-tert-butyl dicarbonate in the presence of a base (e.g. TEA) in an appropriate solvent such as 1,2-dichloroethane. Intramolecular ether formation is accomplished by treatment with a base such as sodium hydride in an appropriate solvent such as DMF. Alternatively, the order of the steps may be reverted performing the ether formation before Boc protection. The bromide is converted into an ester under high carbon dioxide pressure and high temperatures in the presence of a catalyst (e.g. [1,1'-Bis(diphenylphosphino)ferrocene]-dichloropalladium (II)), a base (e.g. TEA) in an appropriate alcoholic solvent (e.g. MeOH). Ester hydrolisys is carried using Lithium hydroxide in THF/water. 2,3-Dihydro-5H-benzo[f][1,4]oxazepine-4,9-dicarboxylic acid 4-tert-butyl ester can be prepared as described in WO2008108445.

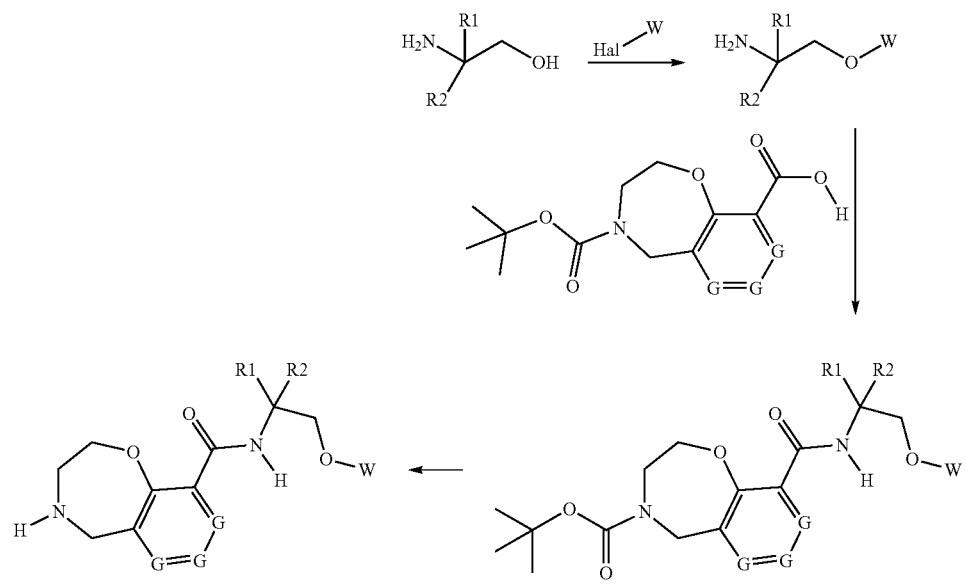

Scheme 2

In scheme 2, Hal=halogen.

Scheme 2:

In a first step an amino ether is prepared reacting an amino alcohol with an halide in the presence of an appropriate base such as sodium hydride in an appropriate solvent such as dioxane. The amino ether is coupled with an appropriate carboxylic acid in an appropriate solvent such as DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

phine (e.g. 1,1'-bis(diphenylphosphino)ferrocene), optionally Zinc, in appropriate solvents such as DMF or N,N-dimethyl-acetamide at elevated temperatures. Nitriles are reacted with Cerium (III) chloride and alkyllithiums (see *J. Org. Chem.* 1992, 57, 4521-452) in an appropriate solvent such as THF or alternatively with Grignard reagents in an appropriate solvent such as toluene at elevated temperatures. The resulting amine is coupled with an appropriate carboxylic acid in an appropriate solvent such as DCM or DMF and in the presence of a coupling agent (e.g. HATU or TBTU) and a base (e.g. TEA or DIPEA). In case W is substituted with $R^3$=halogen, such group can be substituted upon treatment with a stannane or a boronic acid or a trifluoroborate or a boroxine in the presence of a Palladium source (e.g. 1,1'-Bis(diphenylphosphino)ferrocene-palladium(II)dichlo-

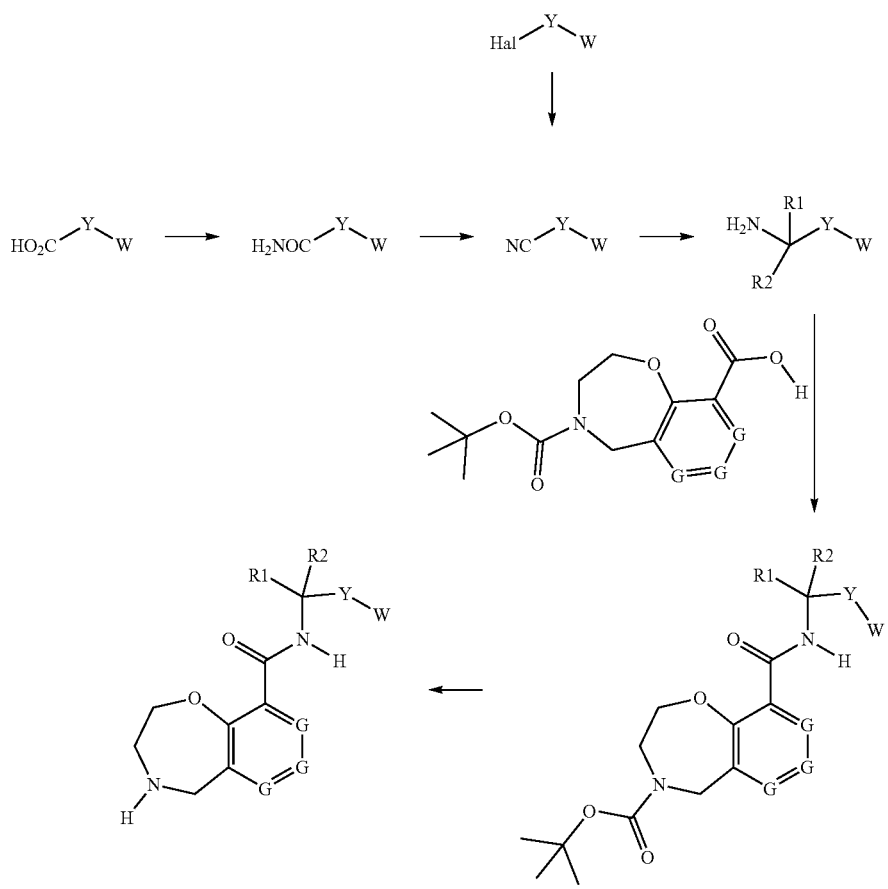

In scheme 3, Hal=halogen.

Scheme 3:

In a first step a carboxylic acid is coupled with ammonium hydroxide in the presence of 1,1'-carbonyldiimidazole in an appropriate solvent such as THF. The primary amide functional group is converted into a nitrile functional group using Burgess reagent in an appropriate solvent such as DCM or using trifluoroacetic anhydride and pyridine in an appropriate solvent such as DCM. Alternatively, a halogen-substituted derivative is converted into a nitrile upon treatment with Zinc cyanide in the presence of a Palladium source (e.g. tris(dibenzylideneacetone)dipalladium(0) or 1,1-bis(diphenylphosphino)ferrocene-dichloro palladium(II)), a phosride dichloromethane complex), in appropriate solvents such as DMF at elevated temperatures.

The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol. Alternatively, Boc removal is accomplished by treatment with a silylating agent (e.g. tert-butyldimethylsilyl trifluoromethanesulfonate) in the presence of a base (e.g. 2,6-lutidine) in appropriate solvents such as DCM followed by reaction with a fluoride source (e.g. tetrabutylammonium fluoride) in appropriate solvents such as THF.

Scheme 4

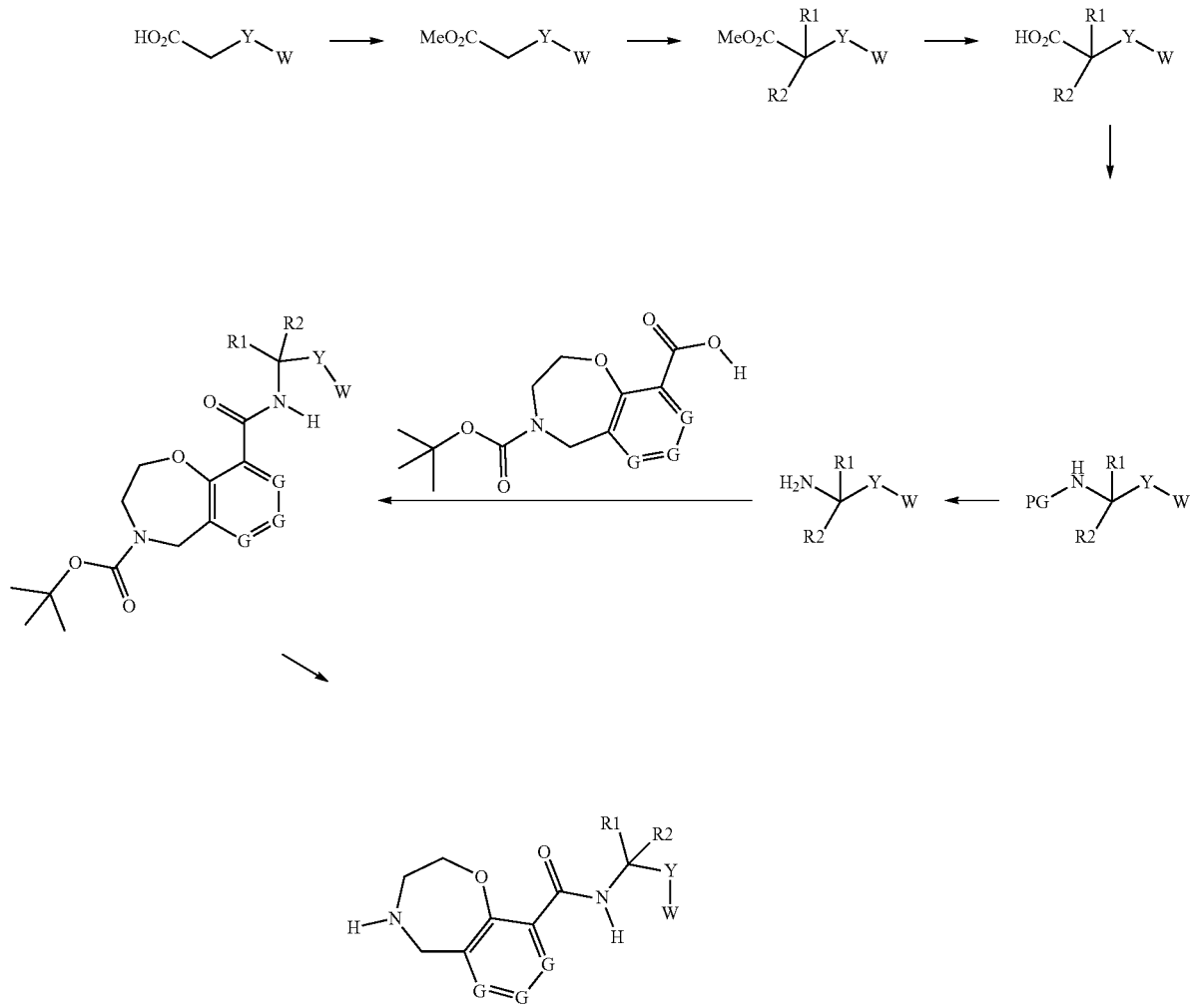

In scheme 4, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting group is 4-methoxy-benzyloxycarbonyl-.

Scheme 4:

In a first step a carboxylic is converted into the corresponding ester (e.g. with trimethylsilyldiazomethane in DCM/MeOH). The ester is bis-alkylated by treatment with a base (e.g. Lithium bis(trimethylsilyl)amide) in an appropriate solvent such as THF followed by treatment with with alkylating agent(s) (e.g. iodomethane). The bis-alkylated ester is hydrolysed to the carboxylic acid with a base (e.g. lithium hydroxyde) in appropriate solvent such as THF and water. The carboxylic acid is treated with diphenylphosphoryl azide, a base (e.g. TEA) and an alcohol (e.g. 4-methoxy-benzyl alcohol) in an appropriate solvent such as toluene at high temperatures. The 4-methoxy-benzyloxycarbonyl protecting group is deprotected with TFA in an appropriate solvent such as DCM. The amine is coupled with an appropriate carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 5

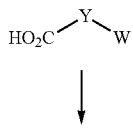

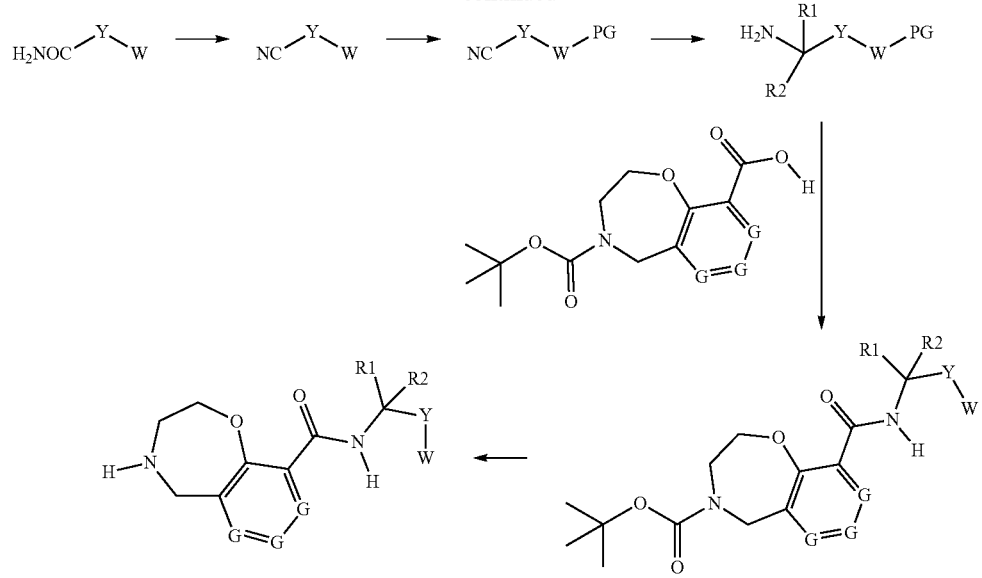

In scheme 5, PG=protecting group for a heteroaryl or heterocyclyl Nitrogen such as outlined in: Peter G. M. Wuts, Theodora W. Greene, Greene's Protective Groups in Organic Synthesis, Wiley-Interscience; 4 edition (Oct. 30, 2006). Preferred protecting group is trimethylsilylethoxymethyl-.

Scheme 5:

in a first step a carboxylic acid is coupled with ammonium hydroxide in the presence of 1,1'-carbonyldiimidazole in an appropriate solvent such as THF. The primary amide functional group is converted into a nitrile functional group using Burgess reagent in an appropriate solvent such as DCM. The trimethylsilylethoxymethyl-protecting group is installed by reaction with 2-(trimethylsilyl)ethoxymethyl chloride, a base (e.g. Sodium hydride) in an appropriate solvent such as DMF. Protected nitriles compounds are reacted with Cerium (III) chloride and alkyllithiums (see *J. Org. Chem.* 1992, 57, 4521-452) in an appropriate solvent such as THF or alternatively with Grignard reagents in an appropriate solvent such as toluene at elevated temperatures. The resulting amine is coupled with an appropriate acid in an appropriate solvent such as DCM or DMF and in the presence of a coupling agent (e.g. HATU or TBTU) and a base (e.g. TEA or DIPEA). The trimethylsilylethoxymethyl-protecting group is removed with tetrabutylammonium fluoride and ethylenediamine. The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 6

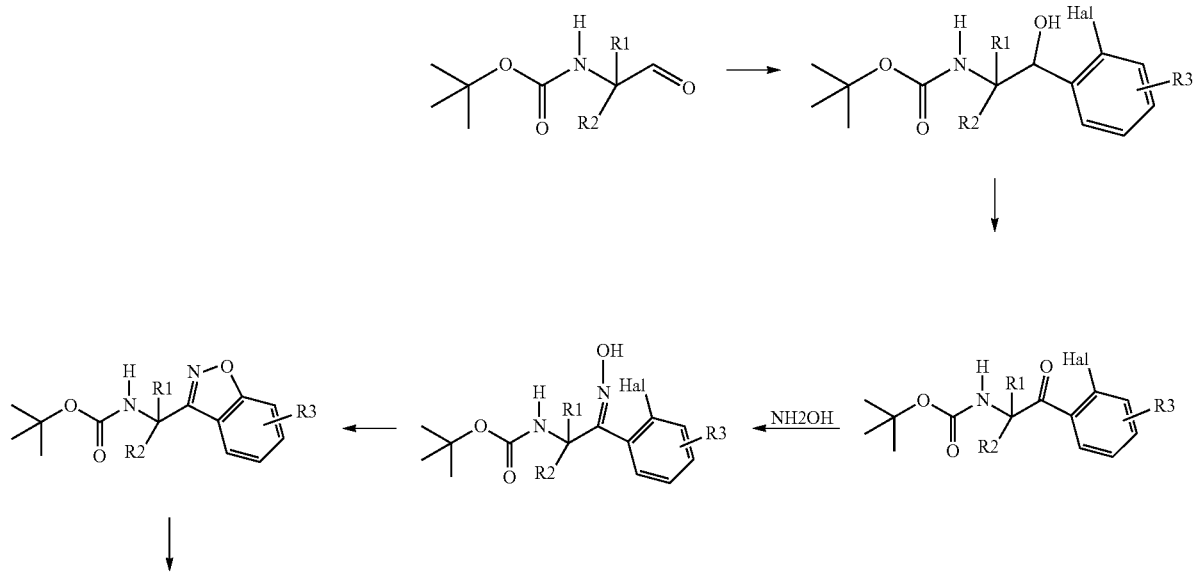

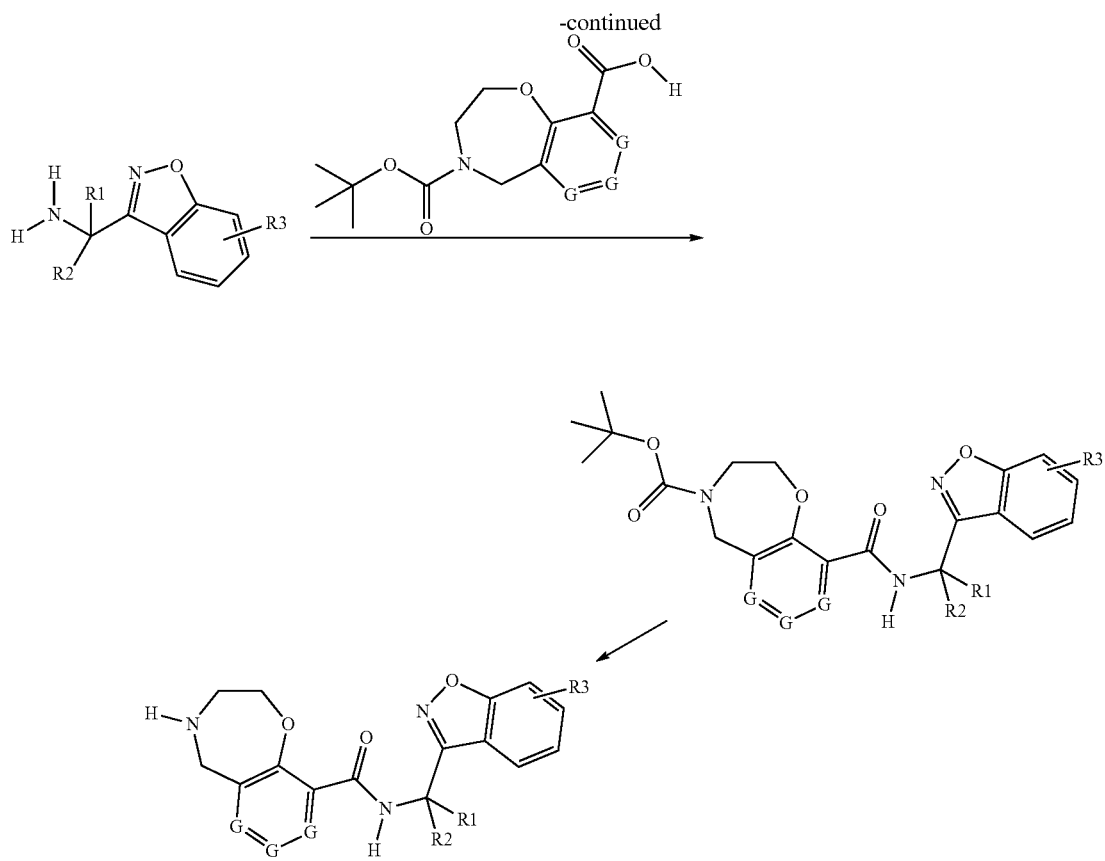

In scheme 6, Hal=halogen.

Scheme 6:

in a first step an aldehyde is reacted with an ortho-metallated halide in an appropriate solvent such as THF at low temperatures to afford an alcohol, which in turn is oxidized to the ketone with Dess-Martin periodinane in DCM. The ketone is converted to the oxime upon treatment with hydroxylamine hydrochloride in an appropriate solvent such as pyridine. Reaction with a base (e.g. potassium tert-butoxide) in an appropriate solvent such as THF gives rise to a benzoisoxazole optionally substituted with one or more $R^3$. The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol. The resulting amine is coupled with an acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 7

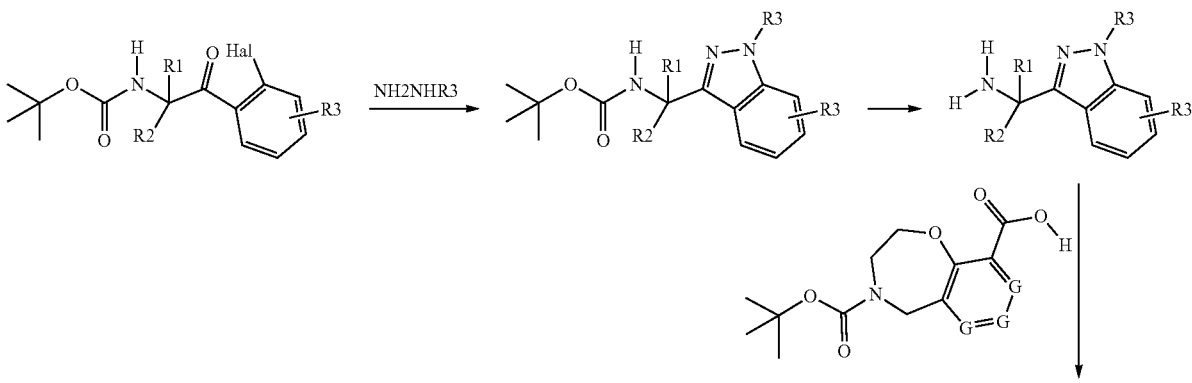

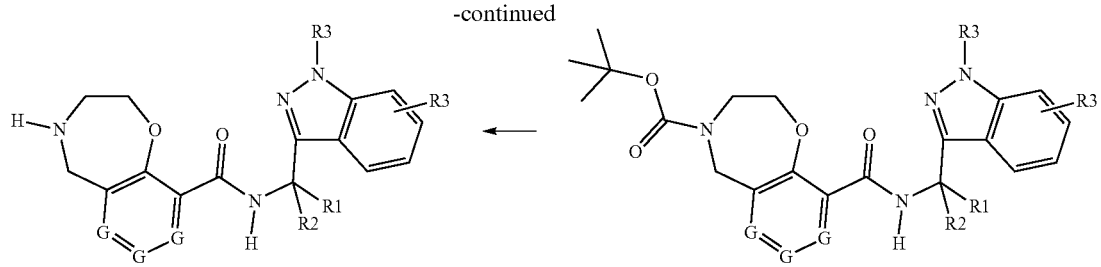

In scheme 7, Hal=halogen; $R^3$=substituent as defined for W.

Scheme 7:

the previously described ketone is converted to the 1H-indazole optionally substituted with one or more $R^3$ upon treatment with optionally substituted hydrazine in an appropriate solvent such as ethanol at high temperatures. In case $R^3$=halogen, such group can be substituted upon treatment with a boronic acid in the presence of a Palladium source (e.g. 1,1'-Bis(diphenylphosphino)ferrocenepalladium(ii) dichloride), a base (e.g. potassium carbonate) in appropriate solvents such as DMF at elevated temperatures. The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol. The resulting amine is coupled with an acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

Scheme 8

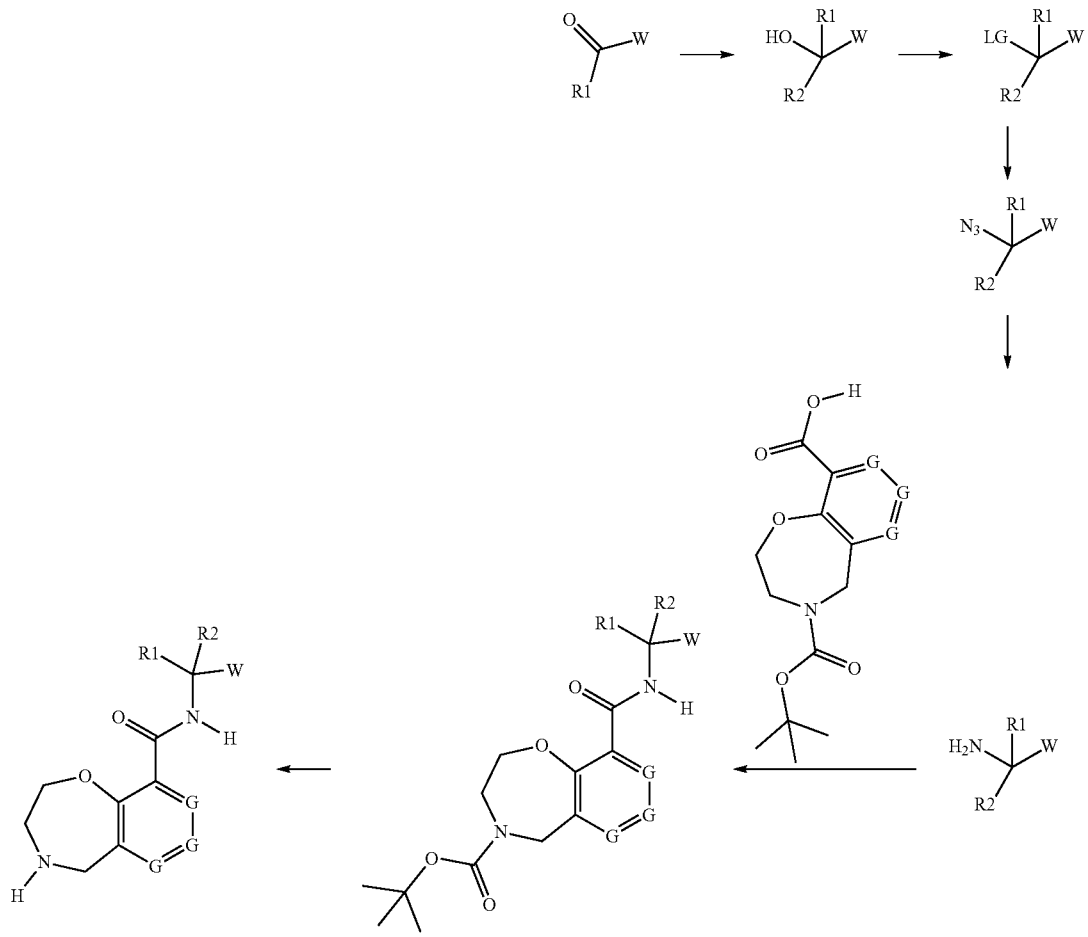

In scheme 8, Hal=halogen; LG=sulfonic ester or halogen

Scheme 8:

In a first step a ketone is reacted with an appropriate organometallic reagent such as a Grignard reagent in an appropriate solvent such as THF to afford an alcohol, which in turn is converted to a leaving group, such as a sulfonic ester by treatment with a sulfonyl chloride (e.g. methane-sulfonyl chloride), a base (e.g. triethylamine) in an appropriate solvent such as THF. The leaving group is displaced with Sodium azide in DMF to afford an azide. Azide reduction is carried out by hydrogenation in the presence of palladium in an appropriate solvent such as EtOAc. The resulting amine is coupled with an appropriate carboxylic acid in an appropriate solvent such as THF or DMF or DCM and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

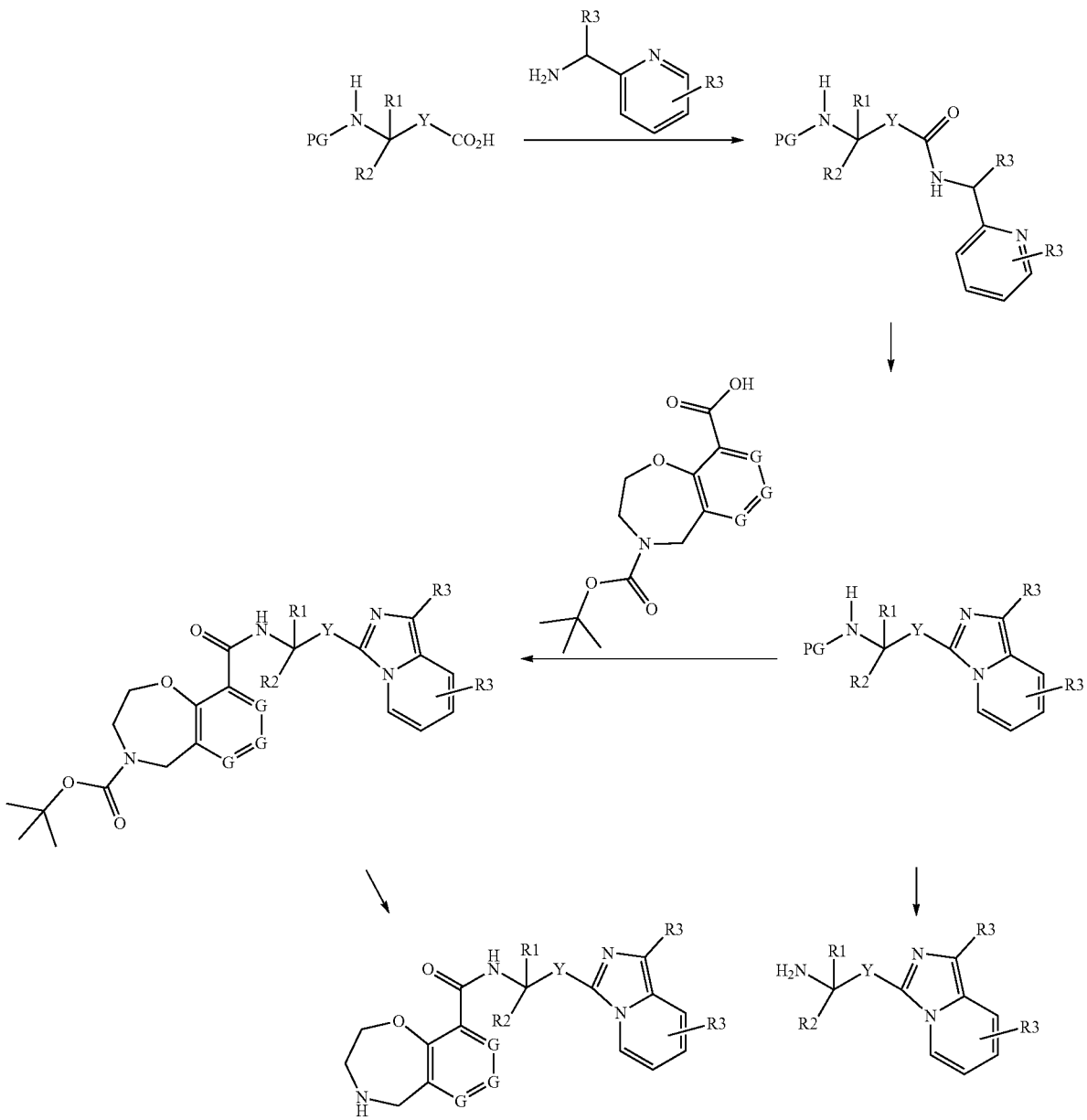

Scheme 9

In scheme 9, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting groups are tert-butoxycarbonyl-, benzyloxycarbonyl- and 9-fluorenylmethoxycarbonyl-. R3=substituents as defined for W.

Scheme 9:

In a first step a carboxylic acid is coupled with 2-(aminomethyl)-substituted pyridine in an appropriate solvent such as THF or DCM and in the presence of a coupling agent (e.g. TBTU or HATU) and a base (e.g. TEA). Condensation is achieved using Burgess reagent in an appropriate solvent such as DCM or using phosphorus oxychloride and DMF at elevated temperatures. The tert-butoxycarbonyl-protecting group is removed with hydrochloric acid in an appropriate solvent such as ethyl ether while the benzyloxycarbonyl- is removed by hydrogenation in the presence of a catalyst (e.g. palladium on carbon) in appropriate solvents such as MeOH and water. The resulting amine is coupled with a suitable carboxylic acid in an appropriate solvent such as THF or DCM and in the presence of a coupling agent (e.g. HATU) and a base (e.g. TEA). The Boc protecting group is deprotected with hydrochloric acid in an appropriate solvent such as dioxane, methanol or ethyl ether or with trifluoroacetic acid in appropriate solvent such as dichlorometane. Alternatively, Boc cleavage is carried out upon heating at elevated temperatures in appropriate solvents such as water and methanol.

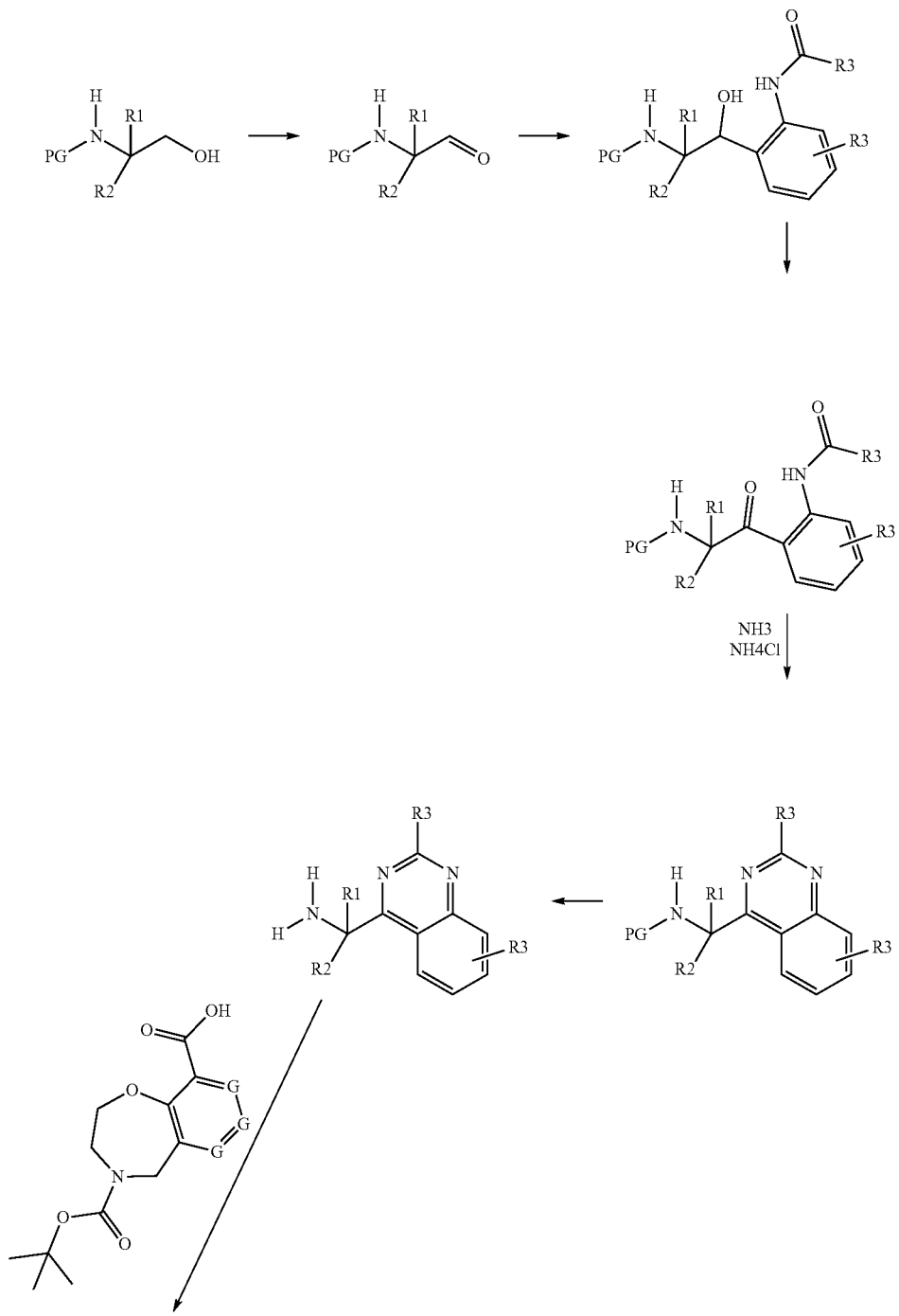

Scheme 10

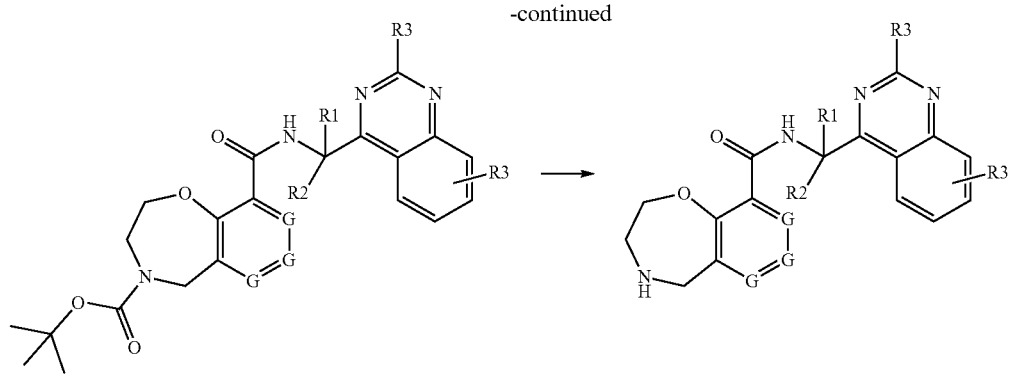

In scheme 10, PG=protecting group for an amino function such as outlined in: Peter G. M. Wuts, Theodora W. Greene, Greene's Protective Groups in Organic Synthesis, Wiley-Interscience; 4 edition (Oct. 30, 2006).

Preferred protecting group is tert-butoxycarbonyl-.

R3=substituents as defined above.

Scheme 10:

in a first step an alcohol is oxidized to the aldehyde with Dess-Martin periodinane in DCM. The aldehyde is reacted with an ortho-metallated acetanilide prepared from a corresponding 2-halo acetanilide by halogen-metal exchange in an appropriate solvent such as THF at low temperatures to afford an alcohol, which in turn is oxidized to the ketone with Dess-Martin periodinane in DCM. The ketone is converted to the quinazoline optionally substituted with one or more R3 upon treatment with ammonia and ammonium chloride in an appropriate solvent such as methanol at high temperatures. When the resulting product is Boc-protected, deprotection is accomplished with hydrochloric acid in an appropriate solvent such as dioxane, methanol or ethyl ether. Alternatively, Boc cleavage is carried out upon heating at elevated temperatures in appropriate solvents such as water and methanol. The resulting amine is coupled with a suitable carboxylic acid in an appropriate solvent such as DCM or DMF and in the presence of a coupling agent (e.g. HATU or TBTU) and a base (e.g. TEA or DIPEA). The Boc protecting group is deprotected with hydrochloric acid in an appropriate solvent such as dioxane, methanol or ethyl ether or with trifluoroacetic acid in appropriate solvent such as dichloromethane. Alternatively, Boc cleavage is carried out upon heating at elevated temperatures in appropriate solvents such as water and methanol.

Method of Treatment

Indications

The present invention relates to the use of a compound of formula (I) for the treatment and/or prevention of a disease or medical condition.

The present invention relates to compounds of formula (I) or pharmaceutically acceptable salts thereof, which are useful in the prevention and/or treatment of a disease and/or condition in which the activation of SSTR4 receptors is of therapeutic benefit, including improvement of symptoms, including but not limited to the treatment and/or prevention of pain of any kind and/or inflammatory diseases and/or associated conditions.

In a further aspect the present invention encompasses the compounds of the above-mentioned general formula (I) or pharmaceutically acceptable salts thereof, according to the invention for use as medicaments.

In view of their pharmacological effect the substances are suitable for the treatment of (1) acute pain such as for example toothache, peri- and post-operative pain, traumatic pain, muscle pain, the pain caused by burns, sunburn, trigeminal neuralgia, pain caused by colic, as well as spasms of the gastro-intestinal tract or uterus; sprains (2) visceral pain such as for example chronic pelvic pain, gynaecological pain, pain before and during menstruation, pain caused by pancreatitis, peptic ulcers, interstitial cystitis, renal colic, cholecystitis, prostatitis, angina pectoris, pain caused by irritable bowel, non-ulcerative dyspepsia and gastritis, prostatitis, non-cardiac thoracic pain and pain caused by myocardial ischaemia and cardiac infarct;

(3) neuropathic pain such as lumbosacral radiculopathy, low back pain, hip pain, leg pain, non-herpetic neuralgia, post herpetic neuralgia, diabetic neuropathy, nerve injury-induced pain, acquired immune deficiency syndrome (AIDS) related neuropathic pain, head trauma, toxin and chemotherapy caused nerve injuries, phantom limb pain, multiple sclerosis, root avulsions, painful traumatic mononeuropathy, painful polyneuropathy, thalamic pain syndrome, post-stroke pain, central nervous system injury, post surgical pain, carpal tunnel syndrome, trigeminal neuralgia, post mastectomy syndrome, postthoracotomy syndrome, stump pain, repetitive motion pain, neuropathic pain associated hyperalgesia and allodynia, alcoholism and other drug-induced pain;

(4) inflammatory pain/receptor-mediated pain in connection with diseases such as for example osteoarthritis, rheumatoid arthritis, inflammatory arthropathy, rheumatic fever, tendo-synovitis, bursitis, tendonitis, gout and gout-arthritis, traumatic arthritis, vulvodynia, damage to and diseases of the muscles and fascia, juvenile arthritis, spondylitis, psoriasis-arthritis, myositides, dental disease, influenza and other viral infections such as colds, systemic lupus erythematodes or pain caused by burns;

(5) tumour pain associated with cancers such as for example lymphatic or myeloid leukaemia, Hodgkin's disease, non-Hodgkin's lymphomas, lymphogranulomatosis, lymphosarcomas, solid malignant tumours and extensive metastases;

(6) headache diseases of various origins, such as for example cluster headaches, migraine (with or without aura) and tension headaches;

(7) sympathetically maintained pain like complex regional pain syndrome Type I and II;

(8) painful conditions of mixed origin, such as for example chronic back pain including lumbago, or fibromyalgia, sciatica, endometriosis, kidney stones.

The compounds are also suitable for treating (9) inflammatory and/or oedematous diseases of the skin and mucous membranes, such as for example allergic and non-allergic dermatitis, atopic dermatitis, psoriasis, burns, sunburn, bacterial inflammations, irritations and inflammations triggered by chemical or natural substances (plants, insects, insect bites), itching; inflammation of the gums, oedema following trauma caused by burns, angiooedema or uveitis;

(10) Vascular and heart diseases which are inflammation-related like artheriosclerosis including cardiac transplant atherosclerosis, panarteritis nodosa, periarteritis nodosa, arteritis temporalis, Wegner granulomatosis, giant cell arthritis, reperfusion injury and erythema nodosum, thrombosis (e.g. deep vein thrombosis, renal, hepatic, portal vein thrombosis); coronary artery disease, aneurysm, vascular rejection, myocardial infarction, embolism, stroke, thrombosis including venous thrombosis, angina including unstable angina, coronary plaque inflammation, bacterial-induced inflammation including Chlamydia-induced inflammation, viral induced inflammation, and inflammation associated with surgical procedures such as vascular grafting including coronary artery bypass surgery, revascularization procedures including angioplasty, stent placement, endarterectomy, or other invasive procedures involving arteries, veins and capillaries, artery restenosis;

(11) inflammatory changes connected with diseases of the airways and lungs such as bronchial asthma, including allergic asthma (atopic and non-atopic) as well as bronchospasm on exertion, occupationally induced asthma, viral or bacterial exacerbation of an existing asthma and other non-allergically induced asthmatic diseases; chronic bronchitis and chronic obstructive pulmonary disease (COPD) including pulmonary emphysema, viral or bacterial exacerbation of chronic bronchitis or chronic obstructive bronchitis, acute adult respiratory distress syndrome (ARDS), bronchitis, lung inflammation, allergic rhinitis (seasonal and all year round) vasomotor rhinitis and diseases caused by dust in the lungs such as aluminosis, anthracosis, asbestosis, chalicosis, siderosis, silicosis, tabacosis and byssinosis, exogenous allergic alveolitis, pulmonary fibrosis, bronchiectasis, pulmonary diseases in alpha1-antitrypsin deficiency and cough;

(12) inflammatory diseases of the gastrointestinal tract including Crohn's disease and ulcerative colitis, irritable bowel syndrome, pancreatitis;

(13) inflammation associated diseases of ear, nose, mouth and throat like influenza and viral/bacterial infections such as the common cold, allergic rhinitis (seasonal and perennial), pharyngitis, tonsillitis, gingivitis, larhyngitis, sinusitis, and vasomotor rhinitis, fever, hay fever, thyroiditis, otitis, dental conditions like toothache, perioperative and post-operative conditions, trigeminal neuralgia, uveitis; iritis, allergic keratitis, conjunctivitis, blepharitis, neuritis nervi optici, choroiditis, glaucoma and sympathetic opthalmia, as well as pain thereof;

(14) diabetes mellitus and its effects (such as e.g. diabetic vasculopathy, diabetic neuropathy, diabetic retinopathy, diabetic nephropathy) and diabetic symptoms in insulitis (for example hyperglycaemia, diuresis, proteinuria and increased renal excretion of nitrite and kallikrein); Doan syndrome and orthostatic hypotension;

(15) sepsis and septic shock after bacterial infections or after trauma;

(16) inflammatory diseases of the joints and connective tissue such as vascular diseases of the connective tissue, sprains and fractures, and musculoskeletal diseases with inflammatory symptoms such as acute rheumatic fever, polymyalgia rheumatica, reactive arthritis, rheumatoid arthritis, spondylarthritis, and also osteoarthritis, and inflammation of the connective tissue of other origins, and collagenoses of all origins such as systemic lupus erythematodes, scleroderma, polymyositis, dermatomyositis, Sjögren syndrome, Still's disease or Felty syndrome; as well as vascular diseases such as panarteriitis nodosa, polyarthritis nodosa, periarteriitis nodosa, arteriitis temporalis, Wegner's granulomatosis, giant cell arteriitis, arteriosclerosis and erythema nodosum;

(17) diseases of and damage to the central nervous system such as for example cerebral oedema and the treatment and prevention of psychiatric diseases such as depression, for example, and for the treatment and prevention of epilepsy;

(18) disorders of the motility or spasms of respiratory, genito-urinary, gastro-intestinal including biliary or vascular structures and organs;

(19) post-operative fever;

(20) for the treatment and prevention of arteriosclerosis and related complaints;

(21) for the treatment and prevention of diseases of the genito-urinary tract such as for example urinary incontinence and related complaints, benign prostatic hyperplasia and hyperactive bladder, nephritis, cystitis (interstitial cystitis);

(22) for the treatment and prevention of morbid obesity and related complaints;

(23) neurological diseases such as cerebral oedema and angioedema, cerebral dementia like e.g. Parkinson's and Alzheimers disease, senile dementia; multiple sclerosis, epilepsy, temporal lobe epilepsy, drug resistant epilepsy, stroke, myasthenia gravis, brain and meningeal infections like encephalomyelitis, meningitis, HIV as well as schizophrenia, delusional disorders, autism, affective disorders and tic disorders;

(24) cognitive impairments associated with schizophrenia, Alzheimer's Disease and other neurological and psychiatric disorders. With respect to Alzheimer's disease, the compounds of general formula (I) may also be useful as disease modifying agent;

(25) work-related diseases like pneumoconiosis, including aluminosis, anthracosis, asbestosis, chalicosis, ptilosis, siderosis, silicosis, tabacosis and byssinosis;

(26) benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, large bowel cancer, small bowel cancer, stomach cancer, colon cancer, gastroenteropancreatic tumours, gastric carcinomas, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers effecting epithelial cells throughout the body; neoplasias like gastrointestinal cancer, Barrett's esophagus, liver cancer, bladder cancer, pancreatic cancer, ovarian cancer, prostate cancer, cervical cancer, lung cancer, breast cancer and skin cancer; the proliferation of adenoma cells, thyroid cancer, GI tumours, cholan-giocarcinoma, hepatic cancer, vesical cancer, chondrosarcoma, malignant pheochromocytoma, neuroblastoma, thymoma, paragangliomas, phaeochromocytomas, ependymomas, leukemia e.g., leukemia of basophilic leukemia, chronic lymphocytic leukemia, chronic myeloid leukemia, Hodgkin disease and non-Hodgkin lymphoma; adenomatous polyps, including familial adenomatous polyposis (FAP) as well preventing polyps from forming in patients at risk of FAP. Suitable uses may include use in the treatment of acromegaly, cancer, arthritis, carcinoid tumours, and vasoactive intestinal peptide tumours;

(27) various other disease states and conditions like epilepsy, septic shock e.g. as antihypovolemic and/or antihypotensive agents, sepsis, osteoporosis, benign prostatic hyperplasia and hyperactive bladder, nephritis, pruritis, vitiligo, disturbances of visceral motility at respiratory, genitourinary, gastrointestinal or vascular regions, wounds, allergic skin reactions, mixed-vascular and non-vascular syndromes, septic shock associated with bacterial infections or with trauma, central nervous system injury, tissue damage and postoperative fever, syndromes associated with itching;

(28) anxiety, depression, schizophrenia, epilepsy, attention deficit and hyperactive disorders and neurodegenerative diseases such as dementia, Alzheimer's disease and Parkinson's disease. The treatment of affective disorders includes bipolar disorders, e.g. manic-depressive psychoses, extreme psychotic states, e.g. mania and excessive mood swings for which a behavioural stabilization is being sought. The treatment of anxiety states includes generalized anxiety as well as social anxiety, agoraphobia and those behavioural states characterized by social withdrawal, e.g. negative symptoms;

(29) diseases involving pathological vascular proliferation, e.g. angiogenesis, restenosis, smooth muscle proliferation, endothelial cell proliferation and new blood vessel sprouting or conditions requiring the activation of neovascularization. The angiogenic disease may for example be age-related macular degeneration or vascular proliferation associated with surgical procedures, e.g. angioplasty and AV shunts. Other possible uses are the treatments of arteriosclerosis, plaque neovascularization, hypertrophic cardiomyopathy, myocardial angiogenesis, valvular disease, myo-cardiac infarction, coronary collaterals, cerebral collaterals and ischemic limb angiogenesis;

(30) pathological condition in the retina and/or iris-ciliary body of mammals. Such conditions may be high intraocular pressure (IOP) and/or deep ocular infections. Treatable diseases may e.g. be glaucoma, stromal keratitis, iritis, retinitis, cataract and conjunctivitis. Other diseases connected to the eye may be ocular and corneal angiogenic conditions, for example, corneal graft rejection, retrolental fibroplasia, Osier-Webber Syndrome or rubeosis.

(31) compounds of the invention, after incorporation of a label (e.g. 35-S, 123-I, 125-I, 111-In, 11-C, etc.) either directly in the compound or via a suitable spacer, can also be used for the imaging of healthy or diseased tissues and/or organs, such as prostate, lung, brain, blood vessels or tumours possessing ssti and/or SSTR4 receptors.

Preferred according to the present invention is the use of a compound of formula (I) for the treatment and/or prevention of pain; in particular pain that is associated with any one of the diseases or conditions listed above.

Another aspect of the present invention is a method for the treatment and/or prevention of above mentioned diseases and conditions, which method comprises the administration of an effective amount of a compound of formula (I) to a human being.

Dosage:

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions:

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

A further aspect of the invention is a pharmaceutical formulation including a compound of formula (I) in admixture with a pharmaceutically acceptable adjuvant, diluent or carrier.

Combination Therapy

The compounds according to the present invention can be combined with other treatment options known to be used in the art in connection with a treatment of any of the indications the treatment of which is in the focus of the present invention.

Among such treatment options that are considered suitable for combination with the treatment according to the present inventions are:

non-steroidal antiinflammatory drugs (NSAIDs) including COX-2 inhibitors;
opiate receptor agonists;
Cannabionoid agonists or inhibitors of the endocannabinoid pathway
Sodium channel blockers;
N-type calcium channel blockers;
serotonergic and noradrenergic modulators;
corticosteroids;
histamine H1, H2, H3 and H4 receptor antagonists;
proton pump inhibitors;
leukotriene antagonists and 5-lipoxygenase inhibitors;
local anesthetics;
VR1 agonists and antagonists;
Nicotinic acetylcholine receptor agonists;
P2X3 receptor antagonists;
NGF agonists and antagonists or anti-NGF antibodies;
NK1 and NK2 antagonists;
Bradykinin B1 antagonists
CCR2 antagonists
iNOS or nNOS or eNOS inhibitors NMDA antagonist;
potassium channel modulators;
GABA modulators;
serotonergic and noradrenergic modulators;
anti-migraine drugs;
neuropathic pain drugs such as pregabaline or duloxetine.
Said list is not considered to have a limiting character.

In the following representative examples of such treatment options shall be given:

Non-steroidal antiinflammatory drugs (NSAIDs) including COX-2 inhibitors: propionic acid derivatives (alminoprofen, benoxaprofen, bucloxic acid, carprofen, fenhufen, fenoprofen, flubiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (meclofenamic acid, mefenamic acid, and tolfenamic acid), biphenylcarboxylic acid derivatives, oxicams (isoxicam, meloxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone), and the coxibs (celecoxib, valecoxib, rofecoxib and etoricoxib) and the like;

Antiviral drugs like acyclovir, tenovir, pleconaril, peramivir, pocosanol and the like.

Antibiotic drugs like gentamicin, streptomycin, geldanamycin, doripenem, cephalexin, cefaclor, ceftazichine, cefepime, erythromycin, vancomycin, aztreonam, amoxicillin, bacitracin, enoxacin, mafenide, doxycycline, chloramphenicol and the like;

Opiate receptor agonists: morphine, propoxyphene (Darvon), tramadol, buprenorphin and the like;

Glucocorticosteroids such as bethamethasone, budesonide, dexamethasone, hydrocortisone, methylprednisolone, prednisolone, prednisone, triamcinolone and deflazacort; immunosuppressive, immunomodulatory, or cytsostatic drugs inlcuding but not limited to hydroxychlorquine, D-penicillamine, sulfasalizine, auranofin, gold mercaptopurine, tacrolimus, sirolimus, mycophenolate mofetil, cyclosporine, leflunomide, methotrexate, azathioprine, cyclophosphamide and glatiramer acetate and novantrone, fingolimod (FTY720), minocycline and thalidomide and the like;

anti-TNF antibodies or TNF-receptor antagonists such as but not limited to Etanercept, Infliximab, Adalimumab (D2E7), CDP 571, and Ro 45-2081 (Lenercept), or biologic agents directed against targets such as but not limited to CD-4, CTLA-4, LFA-1, IL-6, ICAM-1, C5 and Natalizumab and the like;

IL-1 receptor antagonists such as but not limited to Kineret;

Sodium channel blockers: carbamazepine, mexiletine, lamotrigine, tectin, lacosamide and the like.

N-type calcium channel blockers: Ziconotide and the like;

Serotonergic and noradrenergic modulators: paroxetine, duloxetine, clonidine, amitriptyline, citalopram;

Histamine H1 receptor antagonists: bromophtniramint, chlorpheniramine, dexchlorpheniramine, triprolidine, clemastine, diphenhydramine, diphenylpyraline, tripelennamine, hydroxyzine, methdiJazine, promethazine, trimeprazine, azatadine, cyproheptadine, antazoline, pheniramine pyrilamine, astemizole, terfenadine, loratadine, cetirizine, deslo-ratadine, fexofenadine and levocetirizine and the like;

Histamine H2 receptor antagonists: cimetidine, famotidine and ranitidine and the like;

Histamine H3 receptor antagonists: ciproxifan and the like

Histamine H4 receptor antagonists: thioperamide and the like

Proton pump inhibitors: omeprazole, pantoprazole and esomeprazole and the like;

Leukotriene antagonists and 5-lipoxygenase inhibitors: zafirlukast, montelukast, pranlukast and zileuton and the like;

Local anesthetics such as ambroxol, lidocaine and the like;

Potassium channel modulators, like retigabine;

GABA modulators: lacosamide, pregabalin, gabapentin and the like;

Anti-migraine drugs: sumatriptan, zolmitriptan, naratriptan, eletriptan, telcegepant and the like;

NGF antibodies such as RI-724 and the like.

Combination therapy is also possible with new principles for the treatment of pain e.g. P2X3 antagonists, VR1 antagonists, NK1 and NK2 antagonists, NMDA antagonists, mGluR antagonists and the like.

The combination of compounds is preferably a synergistic combination. Synergy, as described for example by Chou and Talalay, Adv. Enzyme Regul. 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased pharmacological effect, or some other beneficial effect of the combination compared with the individual components.

Chemical Manufacture

Abbreviations:

Ac Acetyl
ACN acetonitrile
APCI Atmospheric pressure chemical ionization
Boc tert-butyloxycarbony
Burgess reagent: methoxycarbonylsulfamoyl-triethyl ammonium hydroxide inner salt
CDI 1,1'-carbonyldiimidazole
d day
dba dibenzylideneacetone
DCE dichloroethane
DCM dichloromethane
DIPEA diisopropylethylamine
DME 1,2-dimethoxyethane
DMF dimethylformamide
DMSO dimethyl sulfoxide
ESI electrospray ionization (in MS)
EtOAc ethylacetate
EtOH ethanol
Exp. example
GC gas chromathography
GC-MS coupled gas chromatography-mass spectrometry
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
LC liquid chromatography LC-MS coupled liquid chromatography-mass spectrometry
M molar (mol/L)
MeOH methanol
min minute(s)
MS mass spectrometry
NMP 1-methyl-2-pyrrolidinone
RP reverse phase
rt room temperature
$R_t$ retention time (in HPLC/LC)
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
UPLC-MS ultra performance liquid chromatography-mass spectrometry Methods:

UPLC-MS and HPLC-MS Methods:

Method 1

Instrument: LC/MS Waters Acquity UPLC System DAD, SQD single quadrupole; column: HSS C18 1.7 μm 2.1×50 mm, Temp 35° C.; mobile phase: A=$H_2O$ 90%+10% $CH_3CN$+$CF_3COOH$ 0.1%, B=$CH_3CN$ 90%+$H_2O$ 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ESI+/ESI−; scan range: 90-900 amu Method 2

Instrument: LC/MS Waters Acquity UPLC System DAD, SQD single quadrupole; column: BEH C18 1.7 μm 2.1×50 mm, Temp 35° C.; mobile phase: A=$H_2O$ 90%+10% $CH_3CN$+$NH_4COOH$ 5 mmol, B=$CH_3CN$ 90%+$H_2O$ 10%; gradient: 0.0 min 0% B→1.20 min 100% B→1.45 min 100% B→1.55 min 0% B→1.75 min 0% B; flow rate: 0.70 mL/min; detection: UV 254 nm; detection: SQD, single quadrupole; ion source: ESI+/ESI−; scan range: 90-900 amu Method 3

Instrument: LC/MS Waters Acquity UPLC System DAD, ELSD detector, SQD single quadrupole; column: HSS C18 1.8 μm 2.1×50 mm, Temp 35° C.; mobile phase: A=$H_2O$ 90%+10% $CH_3CN$+$CF_3COOH$ 0.1%, B=$CH_3CN$ 90%+$H_2O$ 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ESI+/ESI−; scan range: 90-900 amu Method 4

Instrument: LC/MS Waters Acquity UPLC System DAD, ELSD detector, SQD single quadrupole; column: BEH C18 1.7 μm 2.1×50 mm; mobile phase: A=$H_2O$ 90%+$CH_3CN$ 10%+$NH_4COOH$ 5 mM, B=$CH_3CN$ 90%+$H_2O$ 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ESI+/ESI−; scan range: 90-900 amu Method 4a Instrument: LC/MS Waters Acquity UPLC System DAD, ELSD detector, SQD single quadrupole; column: BEH C18 1.7 μm 2.1×50 mm, Temp 35° C.; mobile phase: A=$H_2O$ 90%+$CH_3CN$ 10%+$NH_4HCO_3$ 5 mM, B=$CH_3CN$ 90%+$H_2O$ 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ESI+/ESI−; scan range: 90-900 amu Method 5

Instrument: LC/MS Waters Acquity UPLC System DAD, ELSD detector, SQD single quadrupole; column: HSS C18 1.8 μm 2.1×50 mm, Temp 35° C.; mobile phase: A=$H_2O$ 90%+$CH_3CN$ 10%+$CF_3COOH$ 0.1%, B=$CH_3CN$ 90%+$H_2O$ 10%; gradient: 0.0 min 0% B→2.40 min 100% B→2.70 min 100% B→2.80 min 0% B→3.00 min 0% B; flow rate: 0.70 mL/min; detection: UV 254 nm; detection: ELSD detector; detection: SQD, single quadrupole; ion source: ESI+; scan range: 90-900 amu Method 6

Instrument: LC/MS ThermoFinnigan HPLC Surveyor DAD, LCQ Fleet Ion Trap; column: Simmetry Shield RP8, 5 μm, 4.6×150 mm; eluent A: 90% water+10% ACN+HCOOH 0.1%; eluent B=ACN 90%+10% $H_2O$+HCOOH 0.1%; gradient: 0.0 min 5% B→1.5 min 5% B→11.5 min 95% B→13.0 min 95% B→13.3 min 5% B→15.0 min 5% B; flow rate: 1.0 mL/min; UV Detection: 254 nm; Detection: Finnigan Fleet, Ion Trap; ion source: ESI+; scan range: 100-900 amu Method 7

Instrument: LC/MS ThermoFinnigan. HPLC Surveyor DAD, MSQ Quadrupole; column: Synergi Hydro RP100A, 2.5 um, 3×50 mm; eluent A: 90% water+10% ACN+ammonium formate 10 mM; eluent B=ACN 90%+10% $H_2O$+$NH_4COOH$ 10 mM; gradient: 0.0 min 0% B→1.50 min 0% B→8.00 min 100% B→10.00 min 100% B→11.00 min 0% B→12.00 min 0% B; flow rate: 0.7 mL/min; UV Detection: 254 nm; Ion source: APCI+/APCI−.

Method 7a

Instrument: LC/MS ThermoFinnigan. HPLC Surveyor DAD, MSQ Quadrupole; column: Synergi Hydro RP100A, 2.5 um, 3×50 mm; eluent A: 90% water+10% ACN+ammonium formate 10 mM; eluent B=ACN 90%+10% $H_2O$+$NH_4COOH$ 10 mM; gradient: 0.0 min 0% B→0.50 min 0% B→6.50 min 100% B→7.50 min 100% B→8.00 min 0% B→9.00 min 0% B; flow rate: 1.2 mL/min; UV Detection: 254 nm; Ion source: APCI+/APCI−.

Method 7b

Instrument: LC/MS ThermoFinnigan. HPLC Surveyor DAD, MSQ Quadrupole; column: Synergi Hydro RP100A, 2.5 um, 3×50 mm; eluent A: 90% water+10% ACN+ammonium formate 5 mM; eluent B=ACN 90%+10% $H_2O$; gradient: 0.0 min 0% B→4.00 min 100% B→5.30 min 100% B→5.50 min 0% B→6.00 min 0% B; flow rate: 1.2 mL/min; UV Detection: 254 nm; Ion source: APCI+/APCI−.

Method 8

Instrument: LC/MS ThermoFinnigan. HPLC Surveyor DAD, MSQ Quadrupole; column: Synergi Hydro RP100A, 2.5 um, 3×50 mm; eluent A: 90% water+10% ACN+ammonium formate 10 mM; eluent B=ACN 90%+10% $H_2O$+$NH_4COOH$ 10 mM; gradient: 0.0 min 0% B→4.00 min 100% B→5.30 min 100% B→5.50 min 0% B→6.00 min 0% B; flow rate: 1.2 mL/min; UV Detection: 254 nm; Ion source: APCI+/APCI−.

Method 9

Instrument: LC/MS Waters Alliance 2695 HPLC System DAD, Quattro Micro Triple quadrupole; column: SunFire C18 3.5 μm 4.6×50 mm; eluent A: $H_2O$ 90%+10% $CH_3CN$+$CF_3COOH$ 0.05%; eluent B=$CH_3CN$ 90%+10% $H_2O$; gradient: 0.0 min 0% B→4.50 min 100% B→5.80 min 100% B→6.00 min 0% B; flow rate: 1.3 mL/min; UV Detection: 254 nm; Ion source: ESI+.

Method 10

Instrument: LC/MS Waters Alliance 2695 HPLC System DAD, Quattro Micro Triple quadrupole; column: Atlantis dC18 5 μm 4.6×50 mm; eluent A: H$_2$O 90%+10% CH$_3$CN+CF$_3$COOH 0.05%; eluent B=CH$_3$CN 90%+10% H$_2$O; gradient: 0.0 min 0% B→0.70 min 0% B→4.50 min 100% B→5.80 min 100% B→6.00 min 0% B; flow rate: 1.3 mL/min; UV Detection: 254 nm; Ion source: ESI+.

Method 11

Instrument: LC/MS Waters Alliance 2695 HPLC System DAD, Quattro Micro Triple quadrupole; column: Xbridge Phenyl 3.5 μm 3×30 mm; eluent A: H$_2$O 90%+10% CH$_3$CN+NH$_4$HCO$_3$ 5 mM; eluent B=CH$_3$CN 90%+10% H$_2$O; gradient: 0.0 min 0% B→4.50 min 100% B→5.80 min 100% B→6.00 min 0% B; flow rate: 1.3 mL/min; UV Detection: 254 nm; Ion source: ESI+/ESI−

Method 12

Instrument: LC/MS ThermoFinnigan HPLC Surveyor DAD, LCQFleet Ion Trap; column: Xselect CSH, 2.5 μm, 4.6×50 mm; eluent A: H$_2$O 90%+10% CH$_3$CN+HCOOH 0.1%; eluent B=CH$_3$CN 90%+H$_2$O 10%+HCOOH 0.1%; gradient: 0.0 min 0% B→4.00 min 100% B→5.30 min 100% B→5.50 min 0% B→6.00 min 0% B; flow rate: 1.4 mL/min; UV Detection: 254 nm; Ion source: ESI+/ESI−

Method 12a

Instrument: LC/MS Waters Alliance 2695 HPLC System DAD, Quattro Micro Triple quadrupole; column: Zorbax Eclipse XDB-C18 3.5 μm 4.6×50 mm, Temp 35° C.; eluent A: H$_2$O 90%+10% CH$_3$CN+NH$_4$COOH 5 mM; eluent B=CH$_3$CN 90%+10% H$_2$O; gradient: 0.0 min 0% B→4.50 min 100% B→5.80 min 100% B→6.00 min 0% B; flow rate: 1.3 mL/min; UV Detection: 254 nm; Ion source: ESI+/ESI−

Method 12b

Instrument: Agilent6110MS, Agilent6110MS, Agilent1200, DAD200-400 nm; MS: Pos 100-1000 70V; column: Chromolith Flash RP-18e 25-2 mm; Temp: 40° C.; flow rate: 1.5 ml/min; eluent A: H$_2$O containing 0.0375% TFA; eluent B: CH$_3$CN containing 0.018% TFA; gradient: 0.00:95% A→0.70:5% A→1.15:5% A→1.16:95% A→1.60: 5% A; UV Detection: 254 nm; Ion source: ESI+/ESI−

Method 12c

Instrument: Agilent6110MS, Agilent1200, DAD200-400 nm; MS: Pos 100-1000 50V; column: Venusil XBP-C18, 2.1×50 mm, 5 μm; Temp: 50° C.; flow rate: 1.0 ml/min; eluent A: H$_2$O containing 0.0375% TFA; eluent B: CH$_3$CN containing 0.018% TFA; gradient: 0.00:90% A→2.00:20% A→2.48:20% A→2.50:90% A→3.00:90% A; UV Detection: 254 nm; Ion source: ESI+/ESI−

Method 12d

Instrument: Agilent6110MS, Agilent1200, DAD200-400 nm; MS: Pos 100-1000 50V; column: Venusil XBP-C18, 2.1×50 mm, 5 μm; Temp: 50° C.; flow rate: 0.8 ml/min; eluent A: H$_2$O containing 0.0375% TFA; eluent B: CH$_3$CN containing 0.018% TFA; gradient: 0.00:90% A→0.40:90% A→3.40:0% A→3.85:0% A→3.86:90% A→4.50:90% A; UV Detection: 254 nm; Ion source: ESI+/ESI−

Method 12e

Instrument: Agilent6110MS, Agilent1200, DAD200-400 nm; MS: Pos 100-1000 50V; column: Xbridge Shield RPC18, 2.1×50 mm, 5 μm; Temp: 50° C.; flow rate: 1.0 ml/min; eluent A: H$_2$O containing 10 mmol NH$_4$CO$_3$; eluent B: CH$_3$CN; gradient: 0.00:100% A→0.70:70% A→1.10: 70% A→1.11:100% A→2.00:100% A; UV Detection: 254 nm; Ion source: ESI+/ESI−

GC-MS Methods:

Method 13

Instrument: GC/MS Thermo Scientific TRACE GC ULTRA, DSQ II MS single quadrupole; column: Agilent DB-5MS, 25 m×0.2 5 mmol×0.25 μm; carrier gas: Helium, 1 mL/min costant flow; oven program: 50° C., to 100° C. in 10° C./min, to 200° C. in 20° C./min, to 320° C. in 30° C./min (hold 10 min); detection: DSQ II MS single quadrupole; ion source: El; scan range: 50-450 amu Microwave Heating:

Discover® OEM instruments, equipped with 10 and 35 mL vessels

NMR Equipment:

The $^1$H NMR spectra were recorded on a Bruker Avance III (500 MHz) or a Varian 400 (400 MHz) or Varian Mercury (300 MHz) instrument using deuterated dimethylsulfoxide (DMSO-d6) as the solvent with tetramethylsilane (TMS) and residual solvent peak as an internal standard. Chemical shifts are reported in δ values (ppm) relative to TMS.

Experimental:

Example 1A

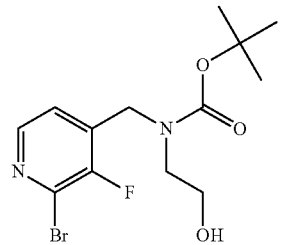 [SMILES: CC(C)(C)OC(=O)N(CCO)Cc1ccnc(Br)c1F]

To a solution of 2-Bromo-3-fluoroisonicotinaldehyde hydrate (11.4 g, 46.1 mmol) in DCE (230 mL) is added AcOH (5.6 g; 92.103 mmol) and 2-aminoethanol (5.7 g; 92.103 mmol), and the mixture is stirred for 10 min. And then is added Sodium triacetoxyborohydride (29.5 g; 138.155 mmol), and the mixture is stirred at room temperature overnight. 1,2-Dichloroethane (230 mL), TEA (14.1 g; 139 mmol) and di-tert-butyl dicarbonate (30.5 g; 139 mmol) are added and the mixture is stirred at room temperature for 2 h. The mixture is diluted with DCM, and washed with water and brine. The organic layers is dried over Na$_2$SO$_4$ and concentrated under reduced pressure to furnish a residue that is purified by flash chromatography (eluent 10% EtOAc/cyclohexane) to furnish the title compound (18 g, 80% content, 89%).

HPLC-MS (Method 12b): R$_t$=0.87 min

MS (ESI+): m/z=349 (M+H)$^+$

Example 1b

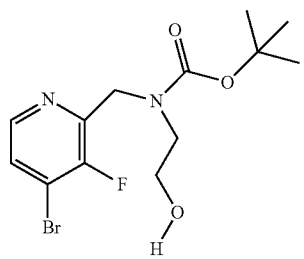 [SMILES: CC(C)(C)OC(=O)N(CCO)Cc1nccc(Br)c1F]

To a solution of 4-Bromo-3-fluoropyridine (4.5 g; 25.3 mmol) in THF (200 mL) is added Lithium diisopropylamide (25 mL; 50.6 mmol) at −70° C., and stirred at this temperature for 2 h. Then is added DMF (1.9 g; 25.3 mmol) and stirred for 2 h. To the mixture is added saturated NH$_4$Cl at low temperature and extracted with ethyl acetate. The combined organic extracts are dried over Na$_2$SO$_4$ and concentrated under reduced pressure to afford a residue that is redissolved in DCE (100 mL). To the mixture are added AcOH (1.5 g, 24.510 mmol) and 2-aminoethanol (1.5 g, 24.510 mmol), and the mixture is stirred for 10 min. And then is added Sodium triacetoxyborohydride (7.9 g, 36.765 mmol), and the mixture is stirred at room temperature overnight. 1,2-Dichloroethane (100 mL), TEA (0.65 g, 6.347 mmol) and di-tert-butyl dicarbonate (2.3 g, 6.347 mmol) are added and the mixture is stirred at room temperature for 2 h. The mixture is diluted with DCM, and washed with water and brine. The organic layers are dried over Na$_2$SO$_4$ and concentrated under reduced pressure to furnish a residue that is purified by flash chromatography (eluent 9% EtOAc/cyclohexane) to furnish the title compound (2.5 g, 85% content, 24%). TLC Rf=0.4 (eluent 17% EtOAc/cyclohexane)

Example 2a

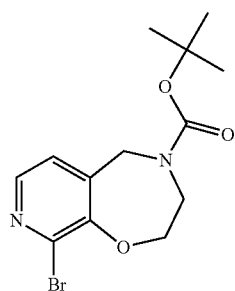 [SMILES: CC(C)(C)OC(=O)N1CCOc2c(ccnc2Br)C1]

A solution of example 1a (2.0 g, 85% content, 4.868 mmol) in THF (200 mL) and DMF (50 mL) is treated with sodium hydride (234 mg, 60% content, 5.842 mmol) at 0° C. and the mixture is stirred at room temperature overnight. The mixture is concentrated under reduced pressure and washed with water and brine. The organic layers are dried over Na$_2$SO$_4$ and concentrated under reduce pressure to furnish a residue that is purified by flash chromatography (eluent 0.5-1% MeOH/DCM) to furnish the title compound (1.5 g, 90% content, 84%).

HPLC-MS (Method 12b): R$_t$=0.99 min
MS (ESI+): m/z=329 (M+H)$^+$

The following example is synthesized in analogy to the preparation of example 2a:

| Example | Structure | Reactant(s) | TLC (eluent 33% EtOAc/petroleum ether), Rf |
|---|---|---|---|
| 2b | 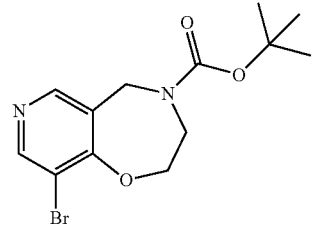 [SMILES: CC(C)(C)OC(=O)N1CCOc2c(Br)cncc2C1] | 1b (2.5 g, 85% content, 6.085 mmol) | 0.3 |

Example 2c

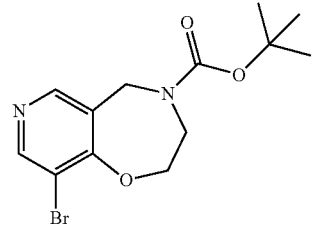 [SMILES: CC(C)(C)OC(=O)N1CCOc2c(Br)cncc2C1]

To a solution of 5-Bromo-4-chloronicotinaldehyde (11.0 g, 70% content, 34.928 mmol) in DCE (200 mL) is added AcOH (4.2 g, 69.857 mmol) and 2-aminoethanol (4.3 g, 69.857 mmol), and the mixture is stirred for 10 min. And then is added Sodium triacetoxyborohydride (22.3 g, 104.785 mmol), and the mixture is stirred at room temperature overnight. The mixture is washed with water and concentrated to afford a residue that is purified by preparative HPLC (stationary phase: Luna C18 250*50 mm i.d. 10

μm. Mobile phase: H₂O+0.09% TFA/ACN). Fractions containing the title compound are combined and lyophilised to furnish 2-[(5-bromo-4-chloro-pyridin-3-ylmethyl)-amino]-ethanol (7 g), that is redissolved in DMF (300 mL) and treated with sodium hydride (4.0 g; 100.175 mmol) and the mixture is stirred at room temperature overnight. The mixture is diluted with EtOAc, and washed with water and brine. The organic layers are dried over Na₂SO₄ and concentrated under reduced pressure to furnish a residue that is redissolved in DMF (300 mL) and treated with di-tert-butyl dicarbonate (8.8 g; 39.812 mmol) and the mixture is stirred at room temperature for 2 h. The mixture is diluted with EtOAc, and washed with water. The organic layers are dried over Na₂SO₄ and concentrated under reduce pressure to furnish a residue that is purified by flash chromatography (eluent 17-25% EtOAc/cyclohexane) to furnish the title compound (4.8 g, 90% content, 38%).

HPLC-MS (Method 12b): R$_t$=0.75 min

MS (ESI+): m/z=329 (M+H)⁺

Example 3a

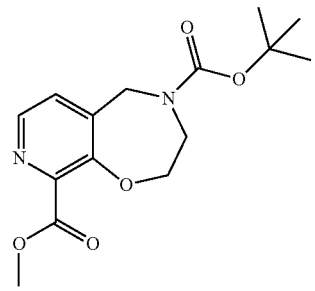 [SMILES: COC(=O)c1nccc2c1OCCN(C(=O)OC(C)(C)C)C2]

TEA (2.231 g; 21.872 mmol and) and [1,1'-bis(diphenylphosphino)ferrocene]dichloropalladium(II) (0.794 g; 1.094 mmol) are added to a solution of example 2a (4.0 g, 90% content, 10.936 mmol) in MeOH (60 mL) and the reaction mixture is stirred at 105° C. for 40 h under 28 bar of CO. Undissolved materials are filtered away and volatiles are concentrated under reduced pressure to furnish a residue that is purified by flash chromatography (eluent 0-2% MeOH/DCM) to furnish the title compound (2.5 g, 88% content, 65%).

HPLC-MS (Method 12b): R$_t$=0.76 min

MS (ESI+): m/z=309 (M+H)⁺

The following example is synthesized in analogy to the preparation of example 3a:

| Example | Structure | Reactant(s) | HPLC-MS R$_t$ [min], method, MS (ESI+ or APCI+, m/z) (M + H)⁺ |
|---|---|---|---|
| 3b | 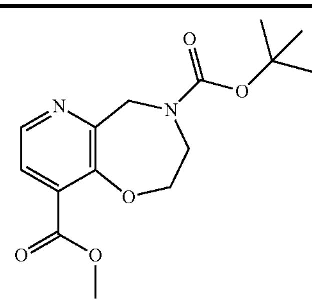 | 2b (2.3 g, 90.5 content, 6.29 mmol) | 1.29 12c 309 |

The following example is synthesized in analogy to the preparation of example 3a:

| Example | Structure | Reactant(s) | TLC (eluent 25% EtOAc/petroleum ether), Rf |
|---|---|---|---|
| 3c | 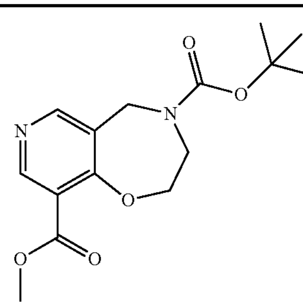 | 2c (0.8 g, 90% content, 2.187 mmol) | 0.5 |

Example 4a

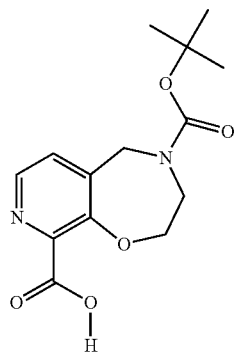 [SMILES: CC(C)(C)OC(=O)N1CCOc2c(ccnc2C(=O)O)C1]

Lithium hydroxide monohydrate (1.189 g; 28.022 mmol) in water (20 mL) is added to example 3a in THF (40 mL). After 4 h HCl is added until pH=5-6. Volatiles are evaporated under reduced pressure to furnish a residue that is purified by preparative HPLC (stationary phase: Gemini C18 250*50 mm i.d. 10 μm. Mobile phase: H₂O+0.09% TFA/ACN). Fractions containing the title compound are combined and lyophilised to furnish the title compound (2.0 g, 98% content, 71%)

HPLC-MS (Method 12d): $R_t$=1.83 min
MS (ESI+): m/z=295 (M+H)⁺

The following examples are synthesized in analogy to the preparation of example 4a:

Example 5a

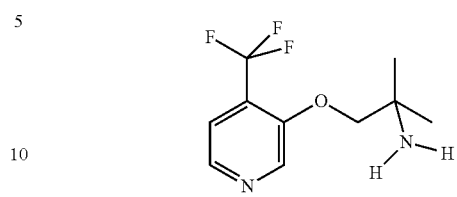

2-Amino-2-methyl-propan-1-ol (19 mL, 194 mmol) is dissolved in dioxane (50 mL) and sodium hydride (60% suspension in mineral oil, 8.1 g, 204 mmol) is added portionwise at 0° C. and after 15 minutes 3-fluoro-4-(trifluoromethyl)-pyridine (8 g, 48.46 mmol) is added. The resulting mixture is heated at 100° C. for 1 h. The reaction is diluted with DCM and washed with water. The organic layer is separated, dried and evaporated under reduced pressure to furnish a residue that dissolved in MeOH and washed with n-heptane. Volatiles are removed under reduced pressure to give the title compound (9.5 g, 84%).

HPLC-MS (Method 11): $R_t$=1.97 min
MS (ESI+): m/z=235 (M+H)⁺

| Example | Structure | Reactant(s) | HPLC-MS $R_t$ [min], method, MS (ESI+ or APCI+, m/z) (M + H)⁺ |
|---|---|---|---|
| 4b | 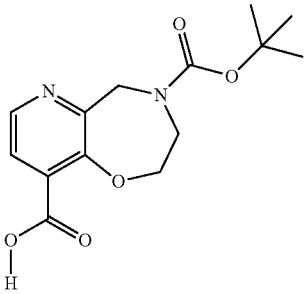 [SMILES: CC(C)(C)OC(=O)N1CCOc2c(C(=O)O)ccnc2C1] | 3b (0.9 g, 2.62 mmol) | 1.89<br>12d<br>295 |
| 4c | 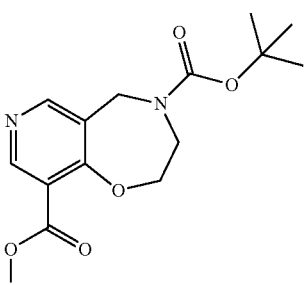 | 2c (2.3 g, 90% content, 6.29 mmol) | 1.10<br>12e<br>295 |

Example 5b

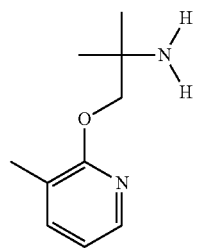

2-Amino-2-methyl-propan-1-ol (11 mL, 118.8 mmol) is dissolved in dioxane (20 mL) and sodium hydride (60% suspension in mineral oil, 5.0 g, 124.7 mmol) is added portionwise at 0° C. and after 15 minutes 2-fluoro-3-methyl-pyridine (3 mL, 29.7 mmol) is added. The resulting mixture is heated at 100° C. for 1 h. The reaction is diluted with DCM and washed with water. The organic layer is separated, dried and evaporated under reduced pressure to furnish the title compound (5.1 g, 95%) that is used as such.

HPLC-MS (Method 8): $R_t$=1.78 min
MS (APCI+): m/z=181 (M+H)$^+$

Example 6a

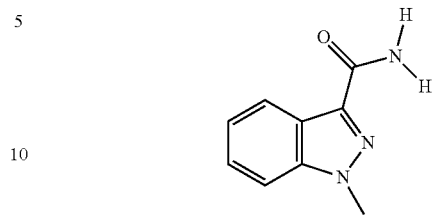

To a solution of 1-methylindazole-3-carboxylic acid (1 g, 5.67 mmol) in dry THF (15 mL), CDI (1 g, 6.24 mmol) is added. The mixture is stirred at rt for 1.5 h, then ammonium hydroxide (13 mL of a 30% solution in water) is added and the mixture stirred for additional 15 min. Solvents are evaporated, the crude dissolved in EtOAc, washed with 0.1 N hydrochloric acid, sat. NaHCO$_3$ and brine. The organic layer is separated, dried and evaporated under vacuum to obtain the title compound (840 mg, 83%) used in the next step without any further purification.

$^1$H NMR (300 MHz, DMSO-d$_6$): δ 4.12 (s, 3H), 7.26 (ddd, J=1.0, 6.7, 7.6 Hz, 1H), 7.33 (br, s, 1H), 7.46 (ddd, J=1.0, 6.8, 8.0 Hz, 1H), 7.65 (br, s, 1H), 7.71 (dd, J=8.2 Hz, 1H), 8.16 (dd, J=8.2 Hz, 1H)

The following examples are synthesized in analogy to the preparation of example 6a:

| Example | Structure | Reactant(s) | HPLC-MS $R_t$ [min], method, MS (ESI+ or APCI+, m/z) (M + H)$^+$ |
|---|---|---|---|
| 6b | 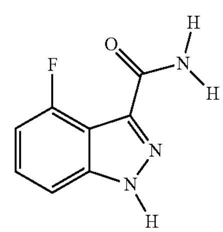 [SMILES: NC(=O)c1n[nH]c2cccc(F)c12] | 4-fluoro-1H-indazole-3-carboxylic acid (1.1 g, 5.80 mmol) | 0.62 2 180 |
| 6c | 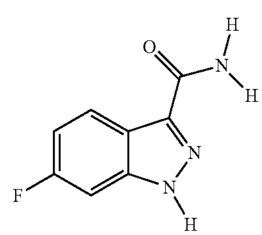 [SMILES: NC(=O)c1n[nH]c2cc(F)ccc12] | 6-fluoro-1H-indazole-3-carboxylic acid (3.0 g, 16.65 mmol) | 0.69 1 180 |
| 6d | 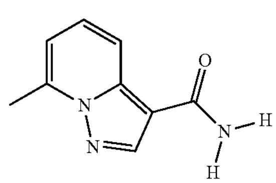 | 7-Methyl-pyrazolo[1,5-a]pyridine-3-carboxylic acid (synthesised as described in J. Comb. Chem., 2005, 7, 309-316; 160 mg, 0.91 mmol) | 0.59 2 176 |

| Example | Structure | Reactant(s) | HPLC-MS $R_t$ [min], method, MS (ESI+ or APCI+, m/z) $(M + H)^+$ |
|---|---|---|---|
| 6e | 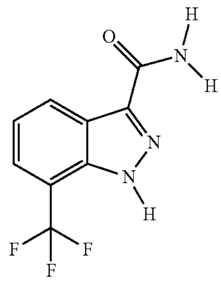 [SMILES: Cn1nc(C(N)=O)c2cccc(C(F)(F)F)c21] | 7-(trifluoromethyl)-1H-indazole-3-carboxylic acid (2.0 g, 6.08 mmol) | 0.77 2 230 |

Example 6f

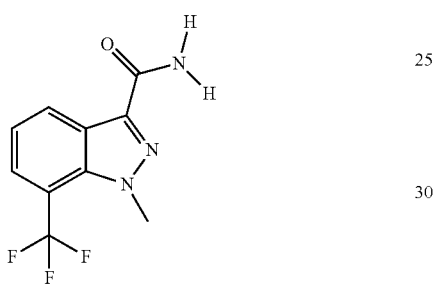

Cesium carbonate (1.37 g, 4.19 mmol) is added to a solution of 6e (800 mg, 3.49 mmol) in DMF (10 mL). After 15 min, Iodomethane (215 µl, 3.49 mmol) is added dropwise to the reaction mixture. After 5 min the reaction is diluted with EtOAc, washed with saturated ammonium chloride and water. The organic layer is separated and dried with a Phase separator cartridge and evaporated under vacuum to obtain a the title compound (800 mg, 85% content, 80%), that is used as such.

UPLC-MS (Method 2): $R_t$=0.93
MS (ESI+): m/z=244 (M+H)$^+$

Example 7a

Burgess reagent (1.7 g, 7.19 mmol) is added to a solution of 6a (840 mg, 4.79 mmol) in DCM (15 mL), and the mixture is heated for 3 h at 35° C. The reaction is diluted with DCM, washed with 0.2N hydrochloric acid and brine. The organic layer is separated and dried with a Phase separator cartridge and evaporated under vacuum to obtain a crude that is purified by flash chromatography (eluent 0-20% EtOAc/cyclohexane) to furnish the title compound (680 mg, 90%).

GC-MS (Method 13): $R_t$=9.74 min
MS (ESI+): m/z=157 [M]$^+$

Example 7b

Trifluoroacetic anhydride (1.16 mL, 8.37 mmol) is added to a solution of 6b (600 mg, 3.35 mmol) in pyridine (6 mL) and DCM (15 mL). After 30 min the reaction is diluted with EtOAc, washed with saturated NaHCO$_3$, saturated NH$_4$Cl, water and brine. The organic layer is separated and dried with a Phase separator cartridge and evaporated under vacuum to furnish the title compound (500 mg, 93%), that is used as such.

UPLC-MS (Method 2): $R_t$=0.91
MS (ESI+): m/z=162 (M+H)$^+$

The following examples are synthesized in analogy to the preparation of example 7b:

| Example | Structure | Reactant(s) | HPLC-MS or UPLC-MS $R_t$ [min], method | MS (ESI+, m/z) $(M + H)^+$ |
|---|---|---|---|---|
| 7c | 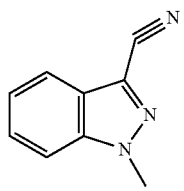 | Example 6c (1.20 g, 6.70 mmol) | 0.85 2 | 162 |

| Example | Structure | Reactant(s) | HPLC-MS or UPLC-MS $R_t$ [min], method | MS (ESI+, m/z) (M + H)+ |
|---|---|---|---|---|
| 7d | 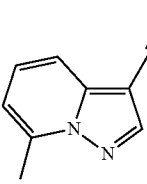 | Example 6d (109 mg, 0.62 mmol) | 0.89 2 | 159 |

| Example | Structure | Reactant(s) | ¹H NMR |
|---|---|---|---|
| 7e | 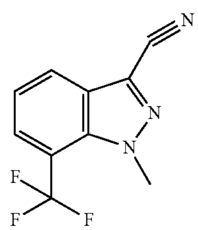 [SMILES: Cn1nc(C#N)c2cccc(C(F)(F)F)c21] | Example 6f (800 mg, 90% content, 2.96 mmol) | ¹H NMR (500 MHz, DMSO-$d_6$): δ 4.26-4.28 (3H, m), 7.59 (1H, dd, J = 7.8, 7.8 Hz), 8.08 (1H, d, J = 7.5 Hz), 8.28 (1H, d, J = 8.2 Hz) |

Example 7f

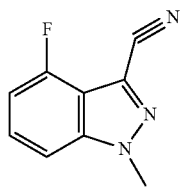

Cesium carbonate (1.31 g, 4.03 mmol) is added to a solution of 7b (500 mg, 3.10 mmol) in DMF (10 mL). After 15 min, iodomethane (192 µl, 3.10 mmol) is added dropwise to the reaction mixture. After stirring overnight the reaction is diluted with EtOAc, washed with saturated ammonium chloride and water. The organic layer is separated and dried with a Phase separator cartridge and evaporated under vacuum to obtain a crude that is purified by flash chromatography (eluent 0-20% EtOAc/cyclohexane) to furnish the title compound (340 mg, 63%).

UPLC-MS (Method 2): $R_t$=0.99

MS (ESI+): m/z=176 (M+H)+

The following example is synthesized in analogy to the preparation of example 7f:

| Example | Structure | Reactant(s) | HPLC-MS or UPLC-MS $R_t$ [min], method | MS (ESI+, m/z) (M + H)+ |
|---|---|---|---|---|
| 7g | 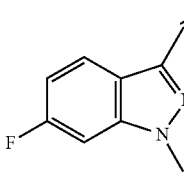 | Example 7c (600 mg, 3.72 mmol) | 1.09 1 | 176 |

Example 7h

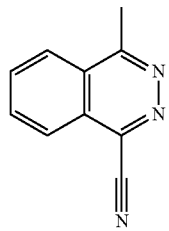

1-Chloro-4-methylphthalazine (5.00 g, 28.00 mmol), Zinc cyanide (3.62 g, 30.79 mmol), 1,1'-Bis(diphenylphosphino)ferrocene (1.40 g, 2.52 mmol), Tris(dibenzylideneacetone)dipalladium(0) (1.03 g, 1.12 mmol) in DMF (50 mL) were heated at 100° C. for 3 h. The reaction is diluted with EtOAc/water. The organic layer is separated, washed with brine, dried and evaporated under reduced pressure to give a residue that is purified by flash chromatography (eluent 0-60% EtOAc/cyclohexane) to furnish the title compound (4.17 g, 88%).

GC-MS (Method 13): $R_t$=10.85 min

MS (EI+): m/z=169 [M]+

The following example is synthesized in analogy to the preparation of example 7h:

| Example | Structure | Reactant(s) | HPLC-MS or UPLC-MS $R_t$ [min], method | MS (ESI+, m/z) (M + H)+ |
|---|---|---|---|---|
| 7i | 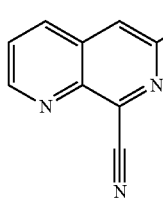 | 8-Chloro-6-methyl-1,7-naphthyridine (700 mg, 3.92 mmol) | 3.26 10 | 170 |

Example 8a

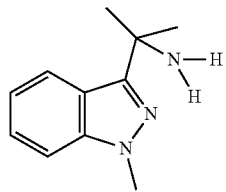

Under nitrogen atmosphere, dry THF (22 mL) is added to anhydrous Cerium (III) chloride (3.2 g, 13 mmol) at 0° C. The reaction is allowed to reach rt and stirred for 2 h. At −78° C. methyllithium as a complex with Lithium Iodide (1.6M in ethyl ether, 8.1 mL, 13.1 mmol) is added and stirring is continued for 30 minutes at −78° C. A solution of 7a (680 mg, 4.32 mmol) in THF dry (3 mL) is added to the mixture and stirring is continued for 30 minutes at −78° C. and then overnight at rt. Saturated NH$_4$Cl and NaOH (50% in water) are added to the mixture until a precipitate forms. Undissolved material is filtered away on a celite pad. The filtrate is washed with water, separated and dried with a phase separator cartridge. The solvent is evaporated under reduced pressure to obtain a crude (350 mg, 30%) used in the next step without any further purification.

GC-MS (Method 13): R$_t$=9.85 min
MS (ESI+): m/z=189 [M]$^+$

The following examples are synthesized in analogy to the preparation of example 8a:

| Example | Structure | Reactant(s) | UPLC-MS R$_t$ [min], method | MS (ESI+, m/z) (M + H)$^+$ |
|---|---|---|---|---|
| 8b | 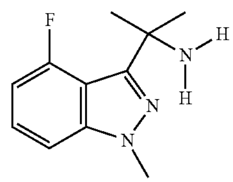 | Example 7f (300 mg, 1.71 mmol) | 0.64 2 | 191 (M − NH$_2$)$^+$ |
| 8c | 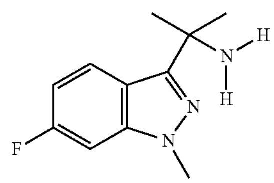 | Example 7g (300 mg, 1.71 mmol) | 0.68 1 | 191 (M − NH$_2$)$^+$ |
| 8d | 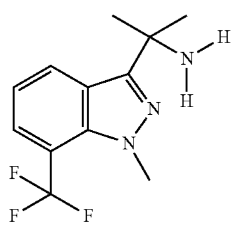 [SMILES: Cn1nc(C(C)(C)N)c2cccc(C(F)(F)F)c21] | Example 7e (400 mg, 1.78 mmol) | 0.77 2 | 241 (M − NH$_2$)$^+$ |
| 8e | 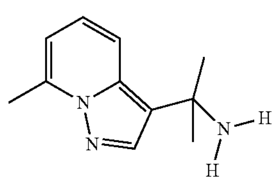 | Example 7d 97 mg, 0.62 mmol) | 0.61 2 | 173 (M − NH$_2$)$^+$ |
| 8f | 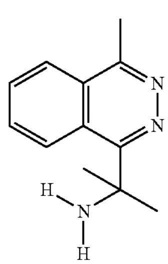 | Example 7h (2.80 g, 16.6 mmol) | 0.57 2 | 202 |

| Example | Structure | Reactant(s) | UPLC-MS $R_t$ [min], method | MS (ESI+, m/z) $(M + H)^+$ |
|---|---|---|---|---|
| 8g | 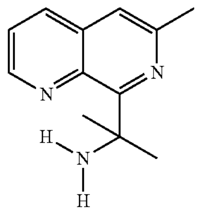 | Example 7i (300 mg, 1.77 mmol) | 0.62 2 | 202 |
| 8h | 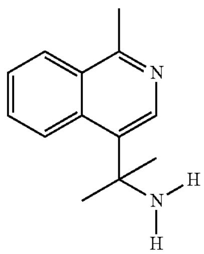 | 1-Methyl-4-Isoquinoline-carbonitrile (500 mg, 2.97 mmol) | 0.60 2 | 201 |
| 8i | 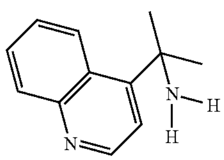 | 4-cyanoquinoline (400 mg, 2.595 mmol) | 0.62 2 | 187 |

Example 8j

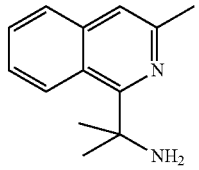

Example 8j is prepared as described for example 8a using 3-methylisoquinoline-1-carbonitrile (350 mg, 2.08 mmol) as starting material. Following work-up, the resulting residue is purified by flash chromatography (eluent 100% DCM to 95:5:0.5 DCM/MeOH/NH$_4$OH) to furnish the title compound (162 mg, 39%).

GC-MS (Method 13): $R_t$=10.28
MS (EI+): m/z=200 [M]$^+$

Example 9a

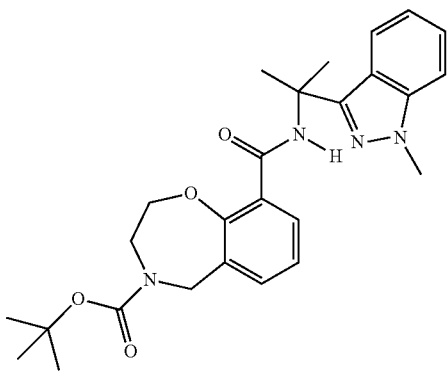 [SMILES: Cn1nc(C(C)(C)NC(=O)c2cccc3c2OCCN(C(=O)OC(C)(C)C)C3)c2ccccc21]

HATU (133 mg, 0.350 mmol) is added to 2,3-dihydro-5H-benzo[f][1,4]oxazepine-4,9-dicarboxylic acid 4-tert-butyl ester (for the preparation, see WO2008108445) (79 mg, 0.269 mmol), example 8a (170 mg, 30% content, 0.269 mmol) and DIPEA (141 µl, 0.808 mmol) in dry DMF (2 mL) and stirring is continued overnight. Volatiles are evaporated under reduced pressure to furnish a residue that is diluted with ethyl acetate and washed with saturated NaHCO$_3$ and brine. The organic layers is separated, dried on a Phase separator cartridge and evaporated under reduced pressure to give a residue that is purified by preparative HPLC (stationary phase XTerra C18 OBD 5 µM 30×100 mm. Mobile phase: ACN/H$_2$O+NH$_4$COOH 5 mM). Fractions containing the title compound are combined and ACN is evaporated under reduced pressure. The aqueous layer is extracted with DCM, separated and the organic layer dried on a Phase separator cartridge and evaporated under reduced pressure to furnish the title compound (113 mg, 98% content, 89%)

UPLC-MS (Method 2): $R_t$=1.30

MS (ESI+): m/z=465 (M+H)$^+$

The following examples are synthesized in analogy to the preparation of example 9a:

| Example | Structure | Reactant(s) | HPLC-MS or UPLC-MS $R_t$ [min], method | MS (ESI+ or APCI+, m/z) $(M + H)^+$ |
|---|---|---|---|---|
| 9b | 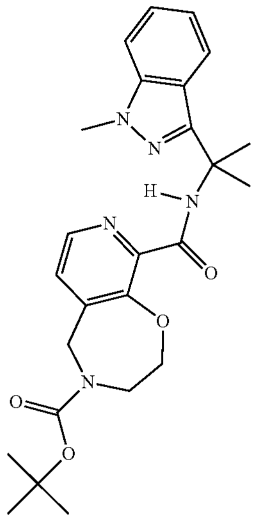 [SMILES: Cn1nc(C(C)(C)NC(=O)c2nccc3c2OCCN(C(=O)OC(C)(C)C)C3)c2ccccc21] | Example 8a (177 mg, 80% content, 0.748 mmol), example 4a (200 mg, 0.680 mmol) | 1.13 2 | 466 |
| 9c | 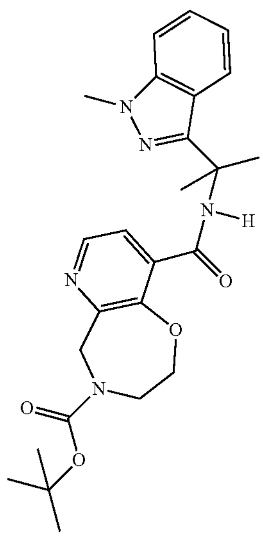 [SMILES: Cn1nc(C(C)(C)NC(=O)c2ccnc3c2OCCN(C(=O)OC(C)(C)C)C3)c2ccccc21] | Example 8a (150 mg, 60% content, 0.476 mmol), example 4b (140 mg, 0.476 mmol) | 1.13 2 | 466 |
| 9d | 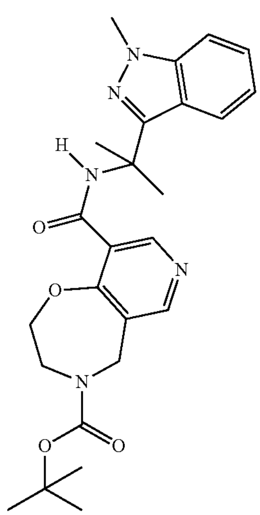 [SMILES: Cn1nc(C(C)(C)NC(=O)c2cncc3c2OCCN(C(=O)OC(C)(C)C)C3)c2ccccc21] | Example 8a (150 mg, 60% content, 0.476 mmol), example 4c (140 mg, 0.476 mmol) | 1.11 2 | 466 |

-continued

| Example | Structure | Reactant(s) | HPLC-MS or UPLC-MS $R_t$ [min], method | MS (ESI+ or APCI+, m/z) (M + H)+ |
|---|---|---|---|---|
| 9e | 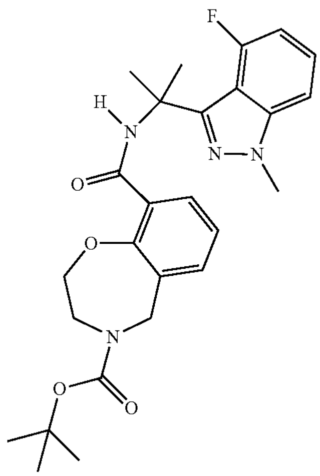 [SMILES: Cn1nc(C(C)(C)NC(=O)c2cccc3c2OCCN(C(=O)OC(C)(C)C)C3)c2c(F)cccc21] | Example 8b (70 mg, 40% content, 0.135 mmol) | 1.33 2 | 483 |
| 9f | 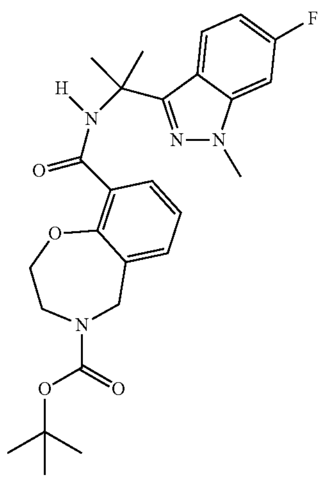 [SMILES: Cn1nc(C(C)(C)NC(=O)c2cccc3c2OCCN(C(=O)OC(C)(C)C)C3)c2ccc(F)cc21] | Example 8c (90 mg, 40% content, 0.174 mmol) | 2.05 4 | 483 |
| 9g | 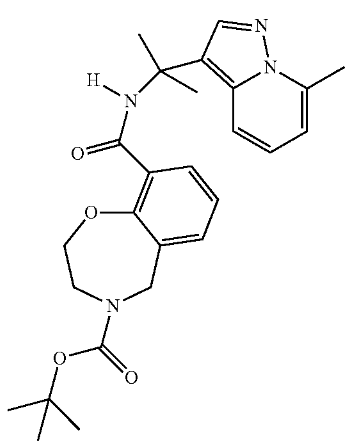 [SMILES: Cc1cccc2c(C(C)(C)NC(=O)c3cccc4c3OCCN(C(=O)OC(C)(C)C)C4)cnn12] | Example 8e (90 mg, 40% content, 0.174 mmol) | 1.27 2 | 465 |

-continued

| Example | Structure | Reactant(s) | HPLC-MS or UPLC-MS $R_t$ [min], method | MS (ESI+ or APCI+, m/z) $(M + H)^+$ |
|---|---|---|---|---|
| 9h | 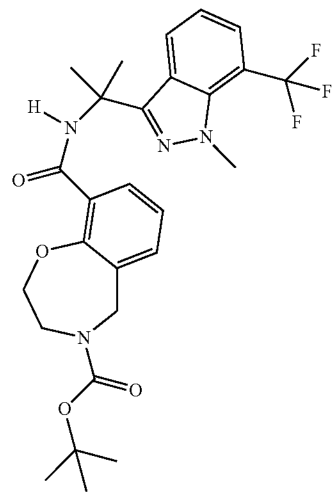 [SMILES: Cn1nc(C(C)(C)NC(=O)c2cccc3c2OCCN(C(=O)OC(C)(C)C)C3)c2cccc(C(F)(F)F)c21] | Example 8d (100 mg, 72% content, 0.280 mmol) | 1.48 2 | 533 |
| 9i | 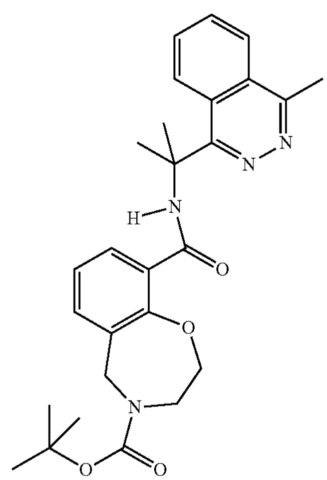 [SMILES: Cc1nnc(C(C)(C)NC(=O)c2cccc3c2OCCN(C(=O)OC(C)(C)C)C3)c2ccccc12] | Example 8f (1.4 g, 26% content, 1.809 mmol) | 1.13 2 | 477 |
| 9j | 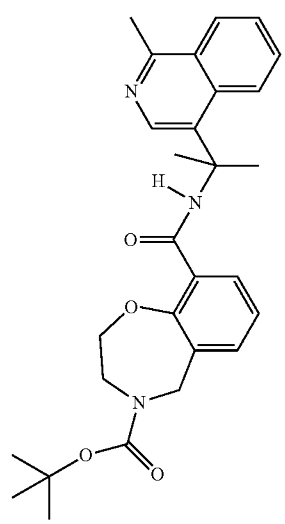 [SMILES: Cc1ncc(C(C)(C)NC(=O)c2cccc3c2OCCN(C(=O)OC(C)(C)C)C3)c2ccccc12] | Example 8h (30 mg, 60% content, 0.090 mmol) | 1.21 2 | 476 |

-continued
| Example | Structure | Reactant(s) | HPLC-MS or UPLC-MS $R_t$ [min], method | MS (ESI+ or APCI+, m/z) (M + H)+ |
|---|---|---|---|---|
| 9k | 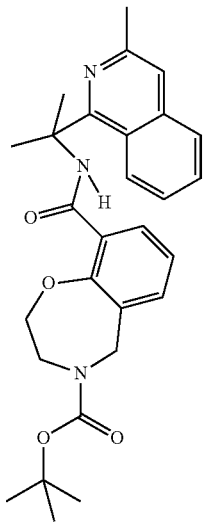 [SMILES: Cc1cc2ccccc2c(C(C)(C)NC(=O)c2cccc3c2OCCN(C(=O)OC(C)(C)C)C3)n1] | Example 8j (113 mg, 40% content, 0.226 mmol) | 1.49 2 | 476 |
| 91 | 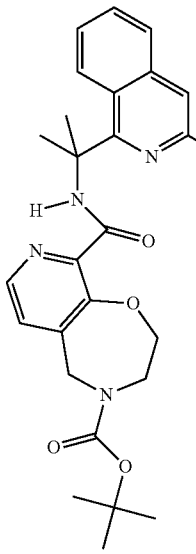 | Example 8j (110 mg, 76% content, 0.379 mmol), example 4a (117 mg, 0.379 mmol) | 1.35 2 | 477 |

| Example | Structure | Reactant(s) | HPLC-MS or UPLC-MS $R_t$ [min], method | MS (ESI+ or APCI+, m/z) (M + H)+ |
|---|---|---|---|---|
| 9m | 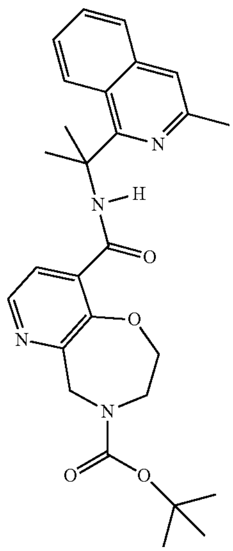 [SMILES: Cc1cc2ccccc2c(C(C)(C)NC(=O)c2ccnc3c2OCCN(C(=O)OC(C)(C)C)C3)n1] | Example 8j (65 mg, 76% content, 0.245 mmol), example 4b (60 mg, 0.204 mmol) | 1.33 2 | 477 |
| 9n | 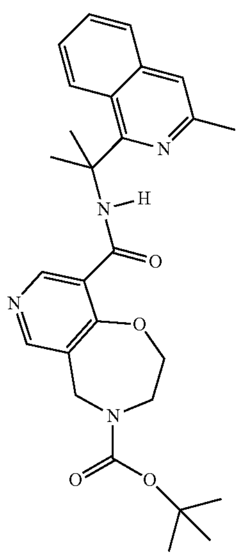 [SMILES: Cc1cc2ccccc2c(C(C)(C)NC(=O)c2cncc3c2OCCN(C(=O)OC(C)(C)C)C3)n1] | Example 8j (150 mg, 76% content, 0.569 mmol), example 4c (223 mg, 0.569 mmol) | 1.30 2 | 477 |

Example 10a

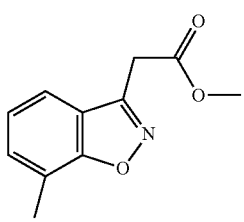

Hydroxylamine hydrochloride (4.4 g, 62.582 mmol) is added to a solution of 4-hydroxy-8-methyl-2H-1-benzopyran-2-one (3.15 g, 17.88 mmol) in MeOH (30 mL) at rt. Sodium acetate (5.1 g, 62.582 mmol) is added portionwise in 1.5 h. The reaction is stirred for 1.5 h at rt and then is heated at reflux overnight. Hydroxylamine hydrochloride (1.9 g, 26.821 mmol) and sodium acetate (2.2 g, 26.821 mmol) are added. The reaction is stirred for 3 h at reflux. Volatiles are evaporated, water is added and the mixture is cooled with ice-water bath. The aqueous layer is acidified to pH=3 with 4N HCl. A precipitate is filtered out and washed several times with water. The precipitate is dried under reduced pressure at 50° C. to (7-methyl-benzo[d]isoxazol-3-yl)-acetic acid (1.4 g, 42%).

HPLC-MS (Method 11): $R_t$=3.49 min
MS (ESI+): m/z=146 (M−CO$_2$H)+

Trimethylsilydiazomethane (3.8 mL, 7.517 mmol) is added dropwise to (7-methyl-benzo[d]isoxazol-3-yl)-acetic acid (1.42 g, 6.833 mmol) in DCM/MeOH 10:1 (8.5 mL/0.85 mL) at 0° C. and stirring is continued for 1 h at 0° C. Volatiles are evaporated to give the title compound (1.39 g, 95% content, 94%).

UPLC-MS (Method 2): $R_t$=1.02 min
MS (ESI+): m/z=206 (M+H)$^+$

Example 11a

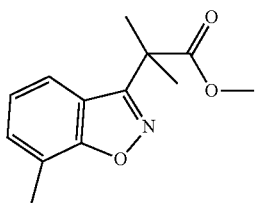 [SMILES: COC(=O)C(C)(C)c1noc2c(C)cccc12]

Sodium hydride (60% suspension in mineral oil, 973 mg, 24.32 mmol) is added portionwise to example 10a (1.42 g, 95% content, 6.57 mmol) in DMF (12 mL) at 0° C. The reaction is allowed to reach rt and stirred for 30 min. Iodomethane (2.1 mL, 33.20 mmol) is added dropwise to the reaction mixture cooled at 0° C. and the reaction is stirred at rt overnight.

Water is added and the reaction is extracted with EtOAc. Organic phase is washed with brine, dried and evaporated to give a residue that is purified by flash chromatography (eluent 0-40% EtOAc/Cyclohexane) to furnish the title compound (1.47 g, 96%).

GC-MS (Method 13): $R_t$=10.32 min
MS (EI+): m/z=233 [M]$^+$

Example 12a

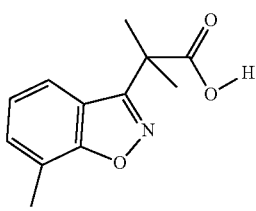 [SMILES: Cc1cccc2c(C(C)(C)C(=O)O)noc12]

Lithium hydroxide monohydrate (793 mg, 18.91 mmol) is added to example 11a (1.47 g, 6.30 mmol) in water/THF 1:1 (28 mL) and the reaction is stirred at rt overnight. THF is evaporated evaporated, the mixture is cooled with ice-water bath. The aqueous layer is acidified to pH=4-5 with 1N HCl and extracted with DCM. Organic layer is dried on a phase separator cartridge and evaporated to give the title compound (1.28 g, 93%)

HPLC-MS (Method 7a): $R_t$=2.22 min
MS (APCI+): m/z=220 (M+H)$^+$

Example 13a

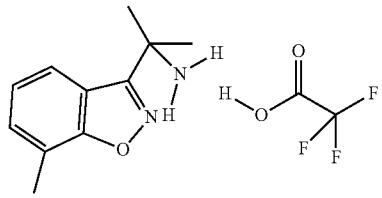

Diphenylphosphoryl azide (0.596 mL, 2.773 mmol) is added to example 12a (640 mg, 2.919 mmol) and TEA (0.386 mL, 2.773 mmol) in toluene (5.4 mL) and the mixture is stirred at rt for 1 h and at 80° C. for 2 h. 4-Methoxybenzyl alcohol (0.364 mL, 2.919 mmol) and TEA (0.386 mL, 2.773 mmol) are added and stirring is continued overnight at 80° C. The mixture is diluted with EtOAc, washed with 10% citric acid, washed with brine, dried and evaporated to give a residue that is purified by flash chromatography (eluent 0-20% EtOAc/cyclohexane) to furnish [1-methyl-1-(7-methyl-benzo[d]isoxazol-3-yl)ethyl]-carbamic acid 4-methoxy-benzyl ester (794 mg, 77%).

HPLC-MS (Method 12): $R_t$=3.73 min
MS (ESI+): m/z=377 (M+Na)$^+$

TFA (4.3 mL) is added to [1-methyl-1-(7-methyl-benzo[d]isoxazol-3-yl)-ethyl]-carbamic acid 4-methoxy-benzyl ester (350 mg, 0.988 mmol) in DCM (4.4 mL) at 0° C. After stirring for 30 min at rt, volatiles are evaporated under reduced pressure to afford the title compound (300 mg, 98% content, 98%) that is used as such.

UPLC-MS (Method 2): $R_t$=0.66 min
MS (ESI+): m/z=191 (M+H)$^+$

Example 14a

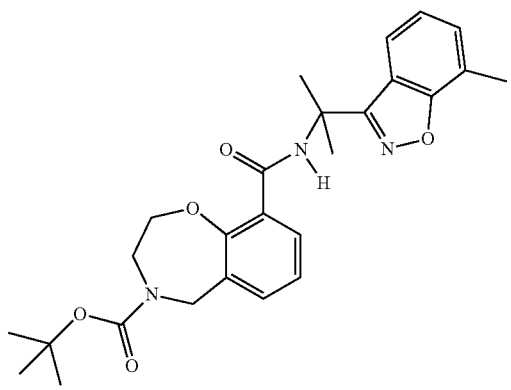 [SMILES: Cc1cccc2c(C(C)(C)NC(=O)c3cccc4c3OCCN(C(=O)OC(C)(C)C)C4)noc12]

HATU (133 mg, 0.350 mmol) is added to 2,3-dihydro-5H-benzo[f][1,4]oxazepine-4,9-dicarboxylic acid 4-tert-butyl ester (for the preparation, see WO2008108445) (79 mg, 0.269 mmol), example 13a (82 mg, 90% content, 0.243 mmol) and DIPEA (140 µl, 0.804 mmol) in dry DMF (2 mL) and stirring is continued for overnight. The reaction mixture is diluted with DCM and water. The organic layers is separated, dried on a Phase separator cartridge and evaporated under reduced pressure to give a residue that is purified by flash chromatography (eluent 10-40% EtOAc/cyclohexane) to furnish the title compound (131 mg, 85% content, 99%).

UPLC-MS (Method 2): $R_t$=1.40 min
MS (ESI+): m/z=466 (M+H)$^+$

Example 15a

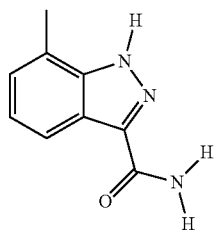

Example 15a is prepared from 7-methyl-1H-indazole-3-carboxylic acid (13.1 mmol) in analogy to example 8a to give the title compound (730 mg, 77% content, 25%)

UPLC-MS (Method 2): $R_t$=0.69 min
MS (ESI+): m/z=176 (M+H)$^+$

Example 16a

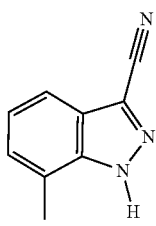

Example 16a is prepared from example 15a (650 mg, 77% content, 2.86 mmol) in analogy to example 7b to give the title compound (109 mg, 91% content, 22%)

UPLC-MS (Method 2): $R_t$=0.96 min
MS (ESI+): m/z=158 (M+H)$^+$

Example 17a

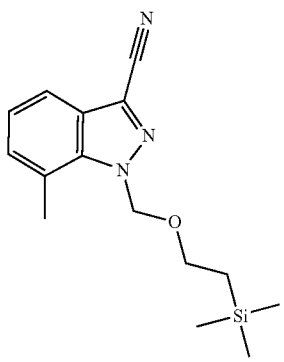 [SMILES: Cc1cccc2c(C#N)nn(COCC[Si](C)(C)C)c12]

Sodium hydride (60% suspension in mineral oil, 31 mg, 0.76 mmol) is added to a solution of 16a (109 mg, 91% content, 0.63 mmol) in DMF (1 mL) at 0° C. After 20 min, 2-(trimethylsilyl)ethoxymethyl chloride (157 µl, 0.88 mmol) is added dropwise to the reaction mixture. After stirring for 1 h at rt, the reaction is diluted with EtOAc, washed with NaHCO$_3$ satured solution and brine. The organic layer is separated and dried with a Phase separator cartridge and evaporated under vacuum to give a residue that is purified by flash chromatography (eluent 0-10% EtOAc/cyclohexane) to furnish the title compound (182 mg).

UPLC-MS (Method 2): $R_t$=1.61
MS (ESI+): m/z=288 (M+H)$^+$

The following example is synthesized in analogy to the preparation of example 8a:

| Example | Structure | Reactant(s) | UPLC-MS $R_t$ [min], method | MS (ESI+, m/z) (M + H)$^+$ |
|---|---|---|---|---|
| 18a | 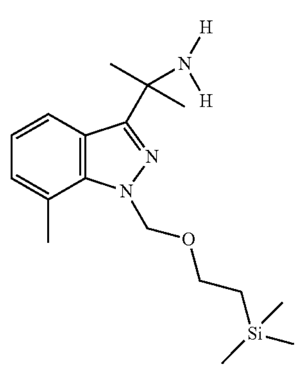 [SMILES: Cc1cccc2c(C(C)(C)N)nn(COCC[Si](C)(C)C)c12] | Example 17a (500 mg, 80% content, 1.392 mmol) | 1.13 2 | 303 (M − NH$_2$)$^+$ |

The following examples are synthesized in analogy to the preparation of example 9a:

NH$_4$OH) to furnish the title compound (77 mg, 80% content, 98%).

| Example | Structure | Reactant(s) | HPLC-MS or UPLC-MS R$_t$ [min], method | MS (ESI+ or APCI+, m/z) (M + H)$^+$ |
|---|---|---|---|---|
| 19a | 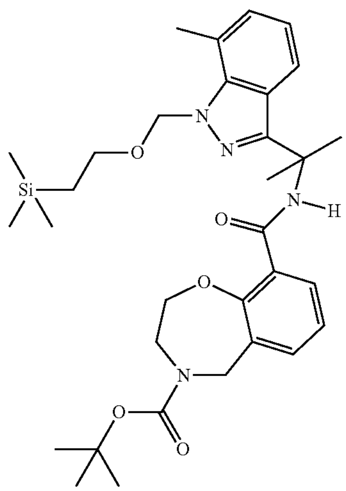 [SMILES: Cc1cccc2c(C(C)(C)NC(=O)c3cccc4c3OCCN(C(=O)OC(C)(C)C)C4)nn(COCC[Si](C)(C)C)c12] | Example 18a (177 mg, 80% content, 0.748 mmol) | 1.13 2 | 466 |

Example 19b

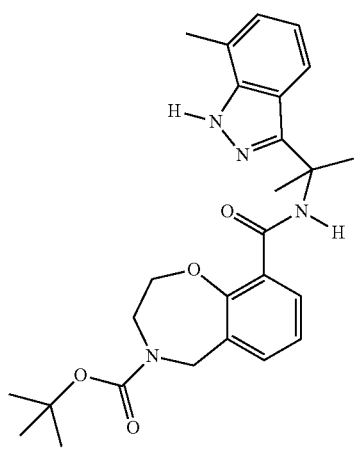 [SMILES: Cc1cccc2c(C(C)(C)NC(=O)c3cccc4c3OCCN(C(=O)OC(C)(C)C)C4)n[nH]c12]

Example 19a (100 mg, 80% content, 0.134 mmol), tetrabutylammonium fluoride (1.0 M in THF, 2.0 mL, 2.0 mmol) and ethylenediamine (55 µl, 0.823 mmol) are heated at 65° C. overnight. Tetrabutylammonium fluoride (1.0 M in THF, 0.5 mL, 0.5 mmol) is added and the reaction mixture is heated at 65° C. overnight. Volatiles are evaporated under reduced pressure and the resulting residue is partitioned between DCM and water. The organic layers is separated, dried on a Phase separator cartridge and evaporated under reduced pressure to give a residue purified by flash chromatography (eluent 100% DCM to 95:5:0.5 DCM/MeOH/

UPLC-MS (Method 2): R$_t$=1.28 min
MS (ESI+): m/z=465 (M+H)$^+$

Example 20A (Racemic Mixture)

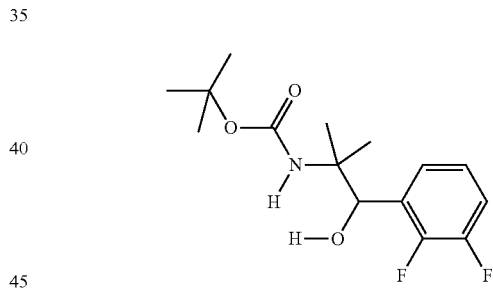

n-Butyllithium (2.5 M in hexanes, 150 mL, 374 mmol) is added to 1,2-difluorobenzene (32 mL, 321 mmol) in THF (301 mL) at −78° C. Stirring is continued for 2 h. Tert-butyl 2-formylpropan-2-ylcarbamate (20.0 g, 107 mmol) in THF (50 mL) is added to the reaction mixture at −78° C. and stirring is continued for 1 h at that temperature. Saturated NH$_4$Cl is added to the reaction mixture at −78° C. The reaction mixture is warmed to rt. The organic layer is separated, washed with brine, dried with a Phase separator cartridge and evaporated under vacuum to give a residue that is washed several times with pentane to furnish the title compound (16.2 g, 50%).

HPLC-MS (Method 11): R$_t$=2.92 min
MS (ESI+): m/z=302 (M+H)$^+$

The following example is synthesized in analogy to the preparation of example 20a:

| Example | Structure | Reactant(s) | UPLC-MS $R_t$ [min], method | MS (ESI+, m/z) (M + H)+ |
|---|---|---|---|---|
| 20b | 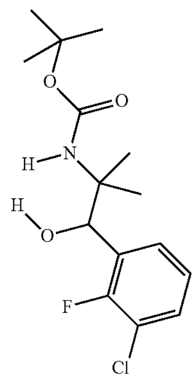 [SMILES: CC(C)(C)OC(=O)NC(C)(C)C(O)c1cccc(Cl)c1F] | Tert-butyl 2-formylpropan-2-ylcarbamate (12.0 g, 64.1 mmol); 1-chloro-2-fluorobenzene (20 mL, 190 mmol) | 1.31 2 | 318 |

Example 21A

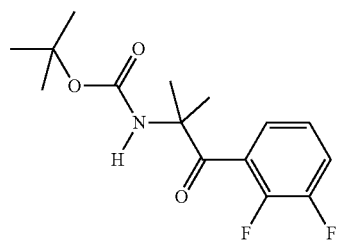 [SMILES: CC(C)(C)OC(=O)NC(C)(C)C(=O)c1cccc(F)c1F]

Dess-Martin periodinane (25.0 g, 59.1 mmol) is added portionwise to example 20a (16.2 g, 53.8 mmol) in DCM (159 mL) cooled to 0° C. and stirring is continued at rt overnight. 10% sodium thiosulfate solution is added and stirring is continued for 30 min. The organic layers is separated, washed with saturated NaHCO₃ solution, dried on a Phase separator cartridge and evaporated under reduced pressure to furnish the title compound (16.0 g, 99%), that is used as such.

HPLC-MS (Method 7a): $R_t$=4.82 min
MS (APCI+): m/z=200 (M+H-Boc)+

The following example is synthesized in analogy to the preparation of example 21a:

| Example | Structure | Reactant(s) | UPLC-MS $R_t$ [min], method | MS (ESI+, m/z) (M + H)+ |
|---|---|---|---|---|
| 21b | 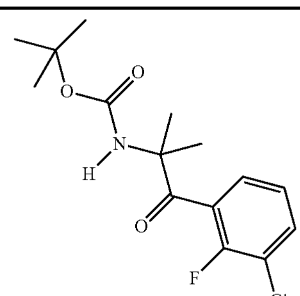 | Example 20b (12.6 g, 39.6 mmol) | 1.31 2 | 316 |

Example 22a

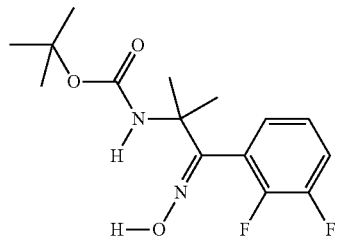 [SMILES: CC(C)(C)OC(=O)NC(C)(C)C(=NO)c1cccc(F)c1F]

Hydroxylamine hydrochloride (4.64 g, 66.8 mmol) is added to example 21a (8.00 g, 26.7 mmol) in pyridine (35 mL) and stirring is continued at 50° C. overnight. Volatiles are evaporated under reduced pressure, DCM and water are added. The organic layers is separated, washed with brine, dried on a Phase separator cartridge and evaporated under reduced pressure to furnish the title compound (8.20 g, 98%), that is used as such.

¹H NMR (500 MHz, DMSO-d₆): δ 1.27 ppm (s, br, 3H), 1.37 ppm (s, 9H), 1.53 ppm (s, br, 3H), 6.87 (s, br, 1H), 6.91 (m, 1H), 7.21 (m, 1H), 7.39 (m, 1H), 10.95 (s, 1H).

The following examples is synthesized in analogy to the preparation of example 22a:

| Example | Structure | Reactant(s) | UPLC-MS $R_t$ [min], method | MS (ESI+, m/z) (M + H)+ |
|---|---|---|---|---|
| 22b | 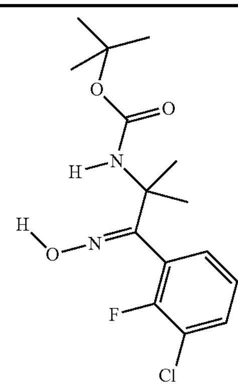 | Example 21b (5.00 g, 15.8 mmol) | 1.21 2 | 331 |

Example 23a

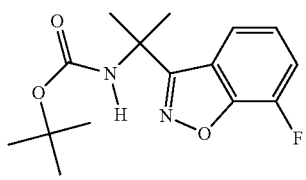 [SMILES: CC(C)(C)OC(=O)NC(C)(C)c1noc2c(F)cccc12]

Potassium tert-butoxide (3.51 g, 31.3 mmol) is added to example 22a (8.20 g, 26.1 mmol) in THF (80 mL) and the reaction mixture is stirred at rt for 3 h. The reaction is diluted with EtOAc, washed with water and brine. The organic layer is separated and dried with a Phase separator cartridge and evaporated under vacuum to furnish the title compound (340 mg, 60%), that is used as such.

UPLC-MS (Method 2): $R_t$=1.23 min
MS (ESI+): m/z=295 (M+H)$^+$

The following example is synthesized in analogy to the preparation of example 23a:

| Example | Structure | Reactant(s) | UPLC-MS $R_t$ [min], method | MS (ESI+, m/z) (M + H)$^+$ |
|---|---|---|---|---|
| 23b | 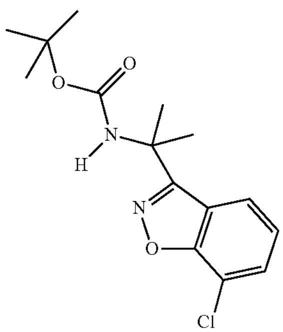 [SMILES: CC(C)(C)OC(=O)NC(C)(C)c1noc2c(Cl)cccc12] | Example 22b (5.79 g, 80% content, 14.0 mmol) | 1.30 2 | 311 |

Example 23A

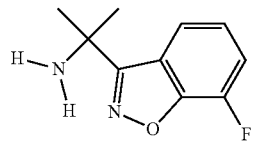

Example 23a (1.00 g, 3.40 mmol) is dissolved in MeOH (3 mL) and then hydrogen chloride 4M in dioxane (6.0 mL, 24 mmol) is added dropwise. Stirring is continued overnight at rt. The reaction mixture is basified with with metanolic ammonia and water and DCM are added. The organic layer is separated, dried and evaporated under reduced pressure to afford the title compound (0.58 g, 88%), that is used as such.

UPLC-MS (Method 2): $R_t$=0.67 min
MS (ESI+): m/z=195 (M+H)$^+$

Example 23b

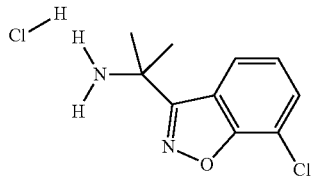

Example 23b (500 mg, 1.609 mmol) is dissolved in dioxane and then hydrogen chloride 4M in dioxane (4.0 mL, 16 mmol) is added dropwise. Stirring is continued overnight at rt. Volatiles are evaporated under reduced pressure to give a residue that is washed several times with ethyl ether afford the title compound (374 mg, 94%), that is used as such.

UPLC-MS (Method 2): $R_t$=0.70 min
MS (ESI+): m/z=211 (M+H)$^+$

The following examples are synthesized in analogy to the preparation of example 9a:

| Example | Structure | Reactant(s) | UPLC-MS $R_t$ [min], method | MS (ESI+, m/z) (M + H)$^+$ |
|---|---|---|---|---|
| 24a | 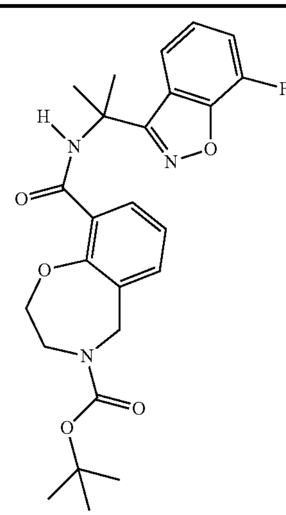 | Example 23a (160 mg, 80% content, 0.659 mmol) | 1.36 2 | 470 |

| Example | Structure | Reactant(s) | UPLC-MS R$_t$ [min], method | MS (ESI+, m/z) (M + H)$^+$ |
|---|---|---|---|---|
| 24b | 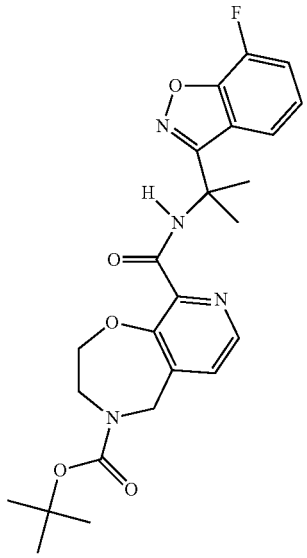 [SMILES: CC(C)(C)OC(=O)N1CCOc2c(ccnc2C(=O)NC(C)(C)c2noc3c(F)cccc23)C1] | Example 23a (48 mg, 0.245 mmol), example 4a (60 mg, 0.204 mmol) | 1.19 2 | 471 |
| 24c | 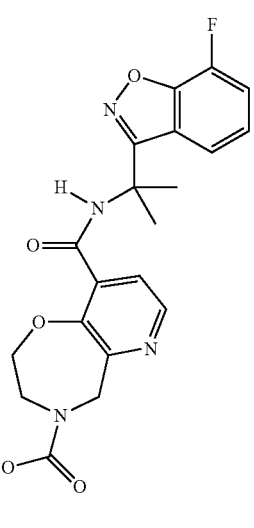 | Example 23a (79 mg, 0.408 mmol), example 4b (100 mg, 0.340 mmol) | 1.18 2 | 471 |

-continued

| Example | Structure | Reactant(s) | UPLC-MS R$_t$ [min], method | MS (ESI+, m/z) (M + H)$^+$ |
|---|---|---|---|---|
| 24d | 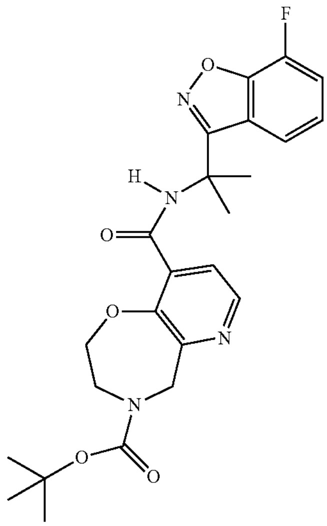 [SMILES: CC(C)(C)OC(=O)N1CCOc2c(C(=O)NC(C)(C)c3noc4c(F)cccc34)ccnc2C1] | Example 23a (48 mg, 0.245 mmol), example 4c (80 mg, 0.272 mmol) | 1.18 2 | 471 |
| 24e | 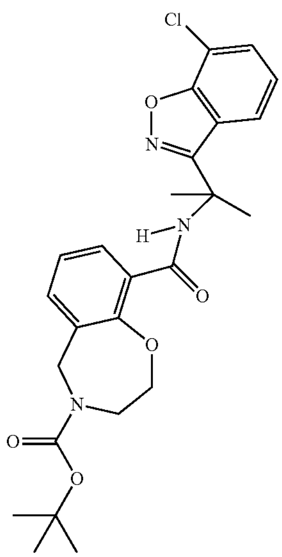 [SMILES: CC(C)(C)OC(=O)N1CCOc2c(cccc2C(=O)NC(C)(C)c2noc3c(Cl)cccc23)C1] | Example 23b (80 mg, 0.324 mmol) | 1.41 2 | 486 |

Example 25A

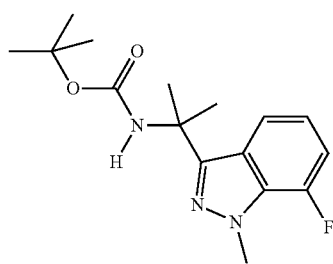 [SMILES: Cn1nc(C(C)(C)NC(=O)OC(C)(C)C)c2cccc(F)c21]

Example 21a (3.50 g, 11.7 mmol) and methylhydrazine (7.4 mL, 140 mmol) in EtOH (14 mL) are heated at 80° C. for 6 h and at rt over weekend. Volatiles are evaporated under reduced pressure to give a residue that is purified by flash chromatography (eluent 5% EtOAc/cyclohexane) to furnish the title compound (2.60 g, 72%).

$^1$H NMR (500 MHz, DMSO-d$_6$): δ 0.86 (s, br, 2H), 1.25 (s, br, 7H), 1.59 (s, 6H), 4.09 (d, J=1.0 Hz, 3H), 7.00 (ddd, J=4.3, 7.9, 12.3 Hz, 1H), 7.13 (dd, J=7.6, 12.4 Hz, 1H), 7.44 (s, br, 1H), 7.13 (d, J=8.1 Hz, 1H)

The following examples are synthesized in analogy to the preparation of example 25a:

| Example | Structure | Reactant | UPLC-MS $R_t$ [min], method | MS (ESI+, m/z) (M + H)+ |
|---|---|---|---|---|
| 25b | 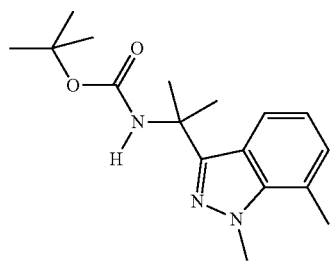 [SMILES: Cc1cccc2c(C(C)(C)NC(=O)OC(C)(C)C)nn(C)c12] | Example 21b (1.86 g, 6.18 mmol) | 1.37 2 | 324 |

Example 25c

Trimethylboroxine (1.2 mL, 8.5 mmol) is added to example 25b (1.00 g, 92% content, 2.841 mmol), potassium carbonate 1.96 g, 14.206 mmol) and 1,1'-bis(diphenylphosphino)ferrocene-palladium(II)dichloride dichloromethane complex (232 mg, 0.284 mmol) in DMF (14 mL) and the reaction mixture is heated at 100° C. overnight. Trimethylboroxine (542 µl, 3.87 mmol), potassium carbonate (892 mg, 6.46 mmol) and 1,1'-bis(diphenylphosphino)ferrocene-palladium(II)dichloride dichloromethane complex (105 mg, 0.129 mmol) are added to the reaction mixture cooled to rt and) and the reaction mixture is heated at 100° C. overnight. Volatiles are evaporated under reduced pressure and the residue dissolved with EtOAc/water. The organic layer is separated, dried and evaporated under reduced pressure to give a residue that is purified by flash chromatography (eluent 0-20% EtOAc/cyclohexane) to furnish the title compound (700 mg, 81%).

UPLC-MS (Method 2): $R_t$=1.23 min
MS (ESI+): m/z=304 (M+H)+

Example 25d

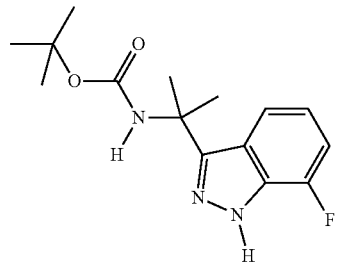 [SMILES: CC(C)(C)OC(=O)NC(C)(C)c1n[nH]c2c(F)cccc12]

Example 21a (1.86 g, 6.18 mmol) and hydrazine hydrate (65% content, 1.6 mL, 21.633 mmol) in EtOH (20 mL) are split in two equal batches and heated under microwaves irradation (140° C.) for 35 min. EtOAc and water are added to the reaction mixture. The organic layer is separated, washed with brine, dried and evaporated under reduced pressure to give a residue that is purified by flash chromatography (eluent 0-10% EtOAc/DCM) to furnish the title compound (1.72 g, 95%).

UPLC-MS (Method 2): $R_t$=1.06 min
MS (ESI+): m/z=294 (M+H)+

The following examples are synthesized in analogy to the preparation of example 25d:

| Example | Structure | Reactant(s) | UPLC-MS $R_t$ [min], method | MS (ESI+ or APCI+, m/z) (M + H)+ |
|---|---|---|---|---|
| 25e | (structure) | Example 25a (1.00 g, 3.17 mmol) | 1.13 2 | 310 |

The following examples are synthesized in analogy to the preparation of example 23b:

| Example | Structure | Reactant(s) | UPLC-MS $R_t$ [min], method | MS (ESI+ or APCI+, m/z) (M + H)+ |
|---|---|---|---|---|
| 26a | (structure) | Example 25a (600 mg, 1.952 mmol) | 0.67 2 | 191 (M − NH$_2$)+ |

Example 26b

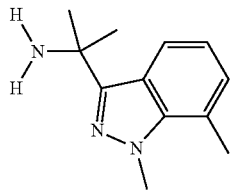

Example 25c (150 mg, 0.494 mmol) is suspended in MeOH/Water 1:1 (1 mL/1 mL) and heated under microwaves irradation (150° C.) for 35 min. The reaction mixture is purified on a SCX cartridge, which is washed with MeOH and DCM, and then eluted with $NH_3$ in MeOH to give the title compound (50 mg, 48%).

UPLC-MS (Method 2): $R_t$=0.70 min
MS (ESI+): m/z=187 $(M-NH_2)^+$

The following examples are synthesized in analogy to the preparation of example 26b:

| Example | Structure | Reactant(s) | HPLC-MS or UPLC-MS $R_t$ [min], method | MS (ESI+ or APCI+, m/z) $(M + H)^+$ |
|---|---|---|---|---|
| 26c | 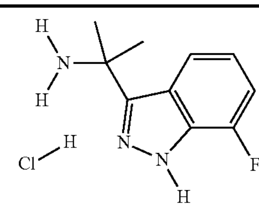 | Example 25d (608 mg, 2.073 mmol) | 0.63 2 | 177 $(M - NH_2)^+$ |
| 26d | 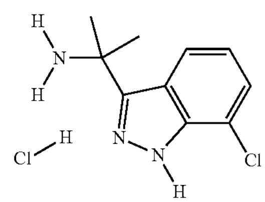 | Example 25e (555 mg, 1.792 mmol) | 0.66 2 | 1.93 $(M - NH_2)^+$ |

The following examples are synthesized in analogy to the preparation of example 9a:

| Example | Structure | Reactant(s) | HPLC-MS or UPLC-MS $R_t$ [min], method | MS (ESI+ or APCI+, m/z) $(M + H)^+$ |
|---|---|---|---|---|
| 27a | 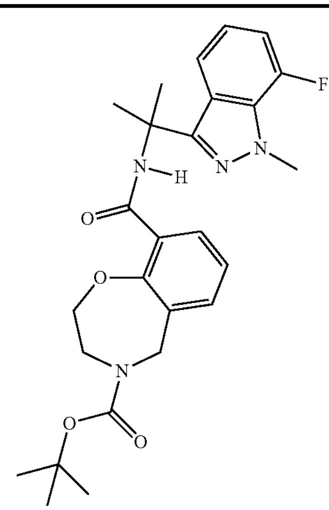 | Example 26a (92 mg, 0.375 mmol) | 1.41 2 | 483 |

-continued

| Example | Structure | Reactant(s) | HPLC-MS or UPLC-MS $R_t$ [min], method | MS (ESI+ or APCI+, m/z) (M + H)+ |
|---|---|---|---|---|
| 27b | 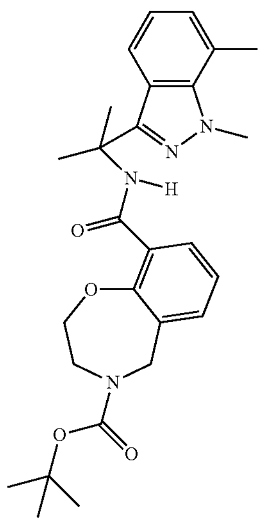 [SMILES: Cc1cccc2c(C(C)(C)NC(=O)c3cccc4c3OCCN(C(=O)OC(C)(C)C)C4)nn(C)c12] | Example 26b (40 mg, 75% content, 0.148 mmol) | 1.38 2 | 479 |
| 27c | 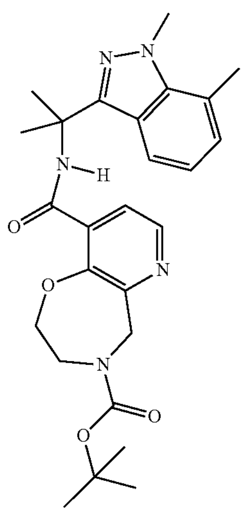 [SMILES: Cc1cccc2c(C(C)(C)NC(=O)c3ccnc4c3OCCN(C(=O)OC(C)(C)C)C4)nn(C)c12] | Example 26b (40 mg, 100% content, 0.197 mmol), example 4b (58 mg, 0.197 mmol) | 1.21 2 | 480 |
| 27d | 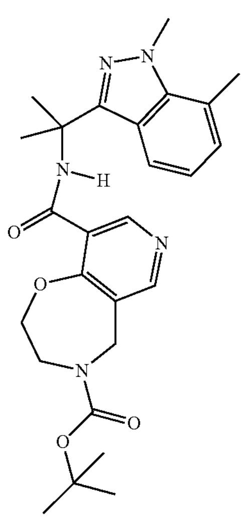 [SMILES: Cc1cccc2c(C(C)(C)NC(=O)c3cncc4c3OCCN(C(=O)OC(C)(C)C)C4)nn(C)c12] | Example 26b (40 mg, 100% content, 0.197 mmol), example 4c (58 mg, 0.197 mmol) | 1.19 2 | 480 |

| Example | Structure | Reactant(s) | HPLC-MS or UPLC-MS $R_t$ [min], method | MS (ESI+ or APCI+, m/z) $(M + H)^+$ |
|---|---|---|---|---|
| 27e | 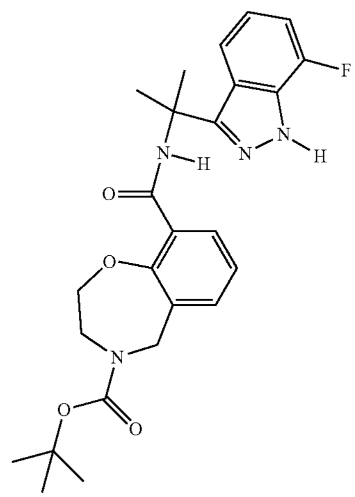 [SMILES: CC(C)(C)OC(=O)N1CCOc2c(cccc2C(=O)NC(C)(C)c2n[nH]c3c(F)cccc23)C1] | Example 26c (80 mg, 0.348 mmol) | 1.26 2 | 469 |
| 27f | 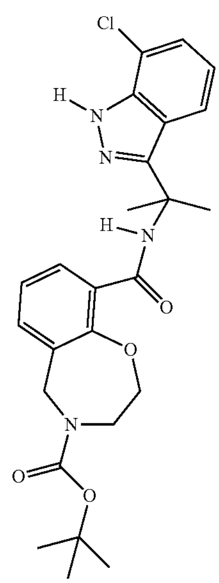 [SMILES: CC(C)(C)OC(=O)N1CCOc2c(cccc2C(=O)NC(C)(C)c2n[nH]c3c(Cl)cccc23)C1] | Example 26d (50 mg, 0.203 mmol) | 1.32 2 | 485 |

Example 28A

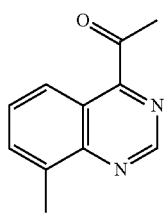

4-Chloro-8-methylquinazoline (5.10 g, 25.13 mmol) is dissolved in toluene (50 mL) and tributyl(1-ethoxyvinyl)tin (9.98 g, 27.64 mmol) and tetrakis(triphenylphosphine) palladium(0) (1.45 g, 1.26 mmol) are added to the solution and the reaction is refluxed for 3 h. Volatiles are evaporated under reduced pressure and the resulting mixture is diluted with brine and ethyl acetate. The phases separated and the organic phase washed with brine, dried and volatiles evaporated under reduced pressure. The residue is purified by flash chromatography (0-30% EtOAc in cyclohexane) to give 4-(1-ethoxy-vinyl)-8-methyl-quinazoline (4.80 g, 89%).

UPLC-MS (Method 2): $R_t$=1.15 min

MS (ESI+): m/z=215 (M+H)$^+$ 4-(1-Ethoxy-vinyl)-8-methyl-quinazoline (4.80 g, 22.40 mmol) is suspended in aqueous 1M HCl (100 mL) and stirring is continued for 3 h. The reaction mixture is basified with Na$_2$CO$_3$ saturated solution, and extracted with ethyl acetate. The organic layer is dried, evaporated to give the title compound (4.02 g, 96%) that is used as such.

UPLC-MS (Method 2): $R_t$=1.07 min

MS (ESI+): m/z=187 (M+H)$^+$

Example 29A

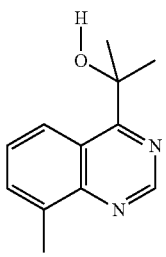

Methylmagnesium bromide (1.4M in THF, 23 mL, 32 mmol) is added to example 28a (4.02 g, 21.59 mmol) in THF (80 mL) at 0° C. The mixture is stirred at 0° C. for 30 min and at rt overnight. Methylmagnesium bromide (1.4M in THF, 11 mL, 15 mmol) is added to the reaction mixture. After 4 h saturated NH$_4$Cl is added to the reaction mixture cooled to 0° C. followed by EtOAc. The organic layer is dried, filtered and evaporated to give a residue that is purified by flash chromatography (0-50% EtOAc in cyclohexane) to furnish the title compound (1.6 g, 80% content, 29%).

$^1$H NMR (300 MHz, DMSO-d$_6$): δ 1.66 (s, 6H), δ 2.67 (s, 3H), 5.80 (s, 1H), 7.55 (dd, J=6.9, 8.7 Hz, 1H), 7.78 (ddd, J=1.1, 2.2, 7.1 Hz, 1H), 8.93 (dd, J=1.1, 8.7 Hz, 1H), 9.19 (s, 1H)

Example 30A

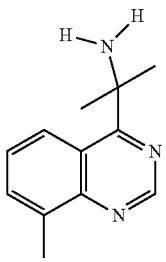

Methanesulfonyl chloride (0.61 mL, 7.91 mmol) is added dropwise to 29a (500 mg, 80% content, 1.98 mmol) and triethylamine (1.4 mL, 7.9 mmol) in THF (20 mL) at −78° C. Stirring is continued for 1.5 h at rt. The reaction mixture is diluted with water and ethyl acetate. The phases are separated and the organic phase is dried and volatiles are evaporated to give methanesulfonic acid 1-methyl-1-(8-methyl-quinazolin-4-yl)-ethyl ester (680 mg, 78% content, 96%) that is used as such.

UPLC-MS (Method 2): R$_t$=1.08 min

MS (ESI+): m/z=281 (M+H)$^+$

Sodium azide (492 mg, 7.57 mmol) is added to methanesulfonic acid 1-methyl-1-(8-methyl-quinazolin-4-yl)-ethyl ester (680 mg, 78% content, 1.89 mmol) in DMF (1.5 mL, 19.56 mmol) and stirring is continued for 4 d. The reaction mixture is diluted with saturated Na$_2$CO$_3$ and EtOAc. The organic layer is washed with brine, dried and filtered to give 4-(1-azido-1-methyl-ethyl)-8-methyl-quinazoline (as a solution in EtOAc).

UPLC-MS (Method 2): R$_t$=1.39 min

MS (ESI+): m/z=228 (M+H)$^+$ 4-(1-Azido-1-methyl-ethyl)-8-methyl-quinazoline (solution in ethyl acetate) is hydrogenated (1.5 bar) in presence of palladium (10% on carbon, 14 mg, 0.013 mmol) for 2 h.

The solids are removed by filtration through a celite pad and the resulting solution is evaporated to give the title compound (250 mg, 80% content) that is used as such.

UPLC-MS (Method 2): R$_t$=0.87 min

MS (ESI+): m/z=202 (M+H)$^+$

The following examples are synthesized in analogy to the preparation of example 9a:

| Example | Structure | Reactant(s) | HPLC-MS or UPLC-MS R$_t$ [min], method | MS (ESI+ or APCI+, m/z) (M + H)$^+$ |
|---|---|---|---|---|
| 31a | 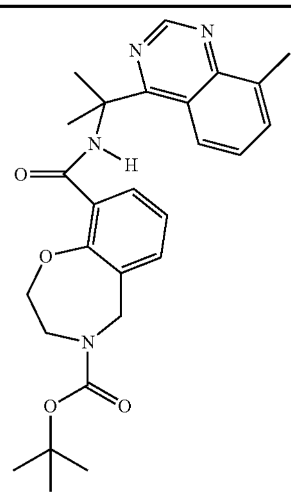 | Example 30a (100 mg, 80% content, 0.397 mmol) | 1.34<br>2 | 477 |

-continued

| Example | Structure | Reactant(s) | HPLC-MS or UPLC-MS $R_t$ [min], method | MS (ESI+ or APCI+, m/z) $(M + H)^+$ |
|---|---|---|---|---|
| 31b | 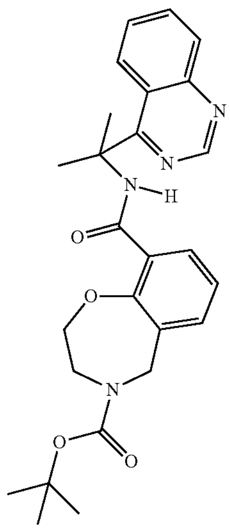 [SMILES: CC(C)(C)OC(=O)N1CCOc2c(cccc2C(=O)NC(C)(C)c2ncnc3ccccc23)C1] | 2-Quinazolin-4-ylpropan-2-amine (64 mg, 82% content, 0.280 mmol) | 2.97 11 | 463 |

Example 32A

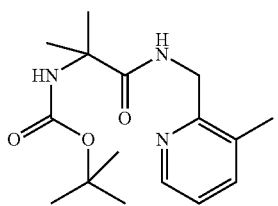 [SMILES: Cc1cccnc1CNC(=O)C(C)(C)NC(=O)OC(C)(C)C]

3-methyl-2-(aminomethyl)pyridine (13.5 g, 110 mmol), is suspended in dry THF and 2-tert-butoxycarbonylamino-2-methylpropionic acid (22.4 g, 110 mmol) is added followed by TEA (46.1 mL, 331 mmol) and TBTU (35.4 g, 110 mmol). The mixture is stirred overnight at room temperature then the solvent is evaporated, the residue is diluted with dichloromethane and washed with 1N NaOH solution and brine. The organic layer is dried, filtered and evaporated under reduced pressure to give a residue that is purified by flash chromatography (eluent 50-100% EtOAc/cyclohexane) to furnish the title compound (28.5 g, 84%).

UPLC-MS (Method 2): $R_t$=0.98 min
MS (ESI+): m/z=308 (M+H)$^+$

The following examples are synthesized in analogy to the preparation of example 32a (using HATU as the coupling agent where specified). Products are purified where appropriate by flash chromatography (eluent: gradient of EtOAc in cyclohexame):

| Example | Structure | Reactant(s) Conditions | UPLC-MS $R_t$ [min], method | MS (ESI+, m/z) $(M + H)^+$ |
|---|---|---|---|---|
| 32b | 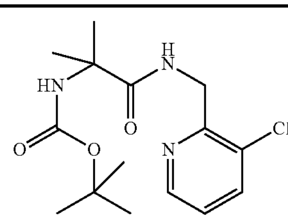 | (3-chloropyridin-2-yl)methanamine (1 g) HATU | 0.91 1 | 328 |
| 32c | 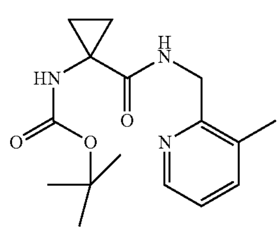 [SMILES: Cc1cccnc1CNC(=O)C1(NC(=O)OC(C)(C)C)CC1] | C-(3-Methyl-pyridin-2-yl)-methylamine (500 mg) Boc-1-amino-1-cyclopropanecarboxylic acid (823 mg) | 0.66 1 | 306 |

| Example | Structure | Reactant(s) Conditions | UPLC-MS $R_t$ [min], method | MS (ESI+, m/z) $(M + H)^+$ |
|---|---|---|---|---|
| 32d | 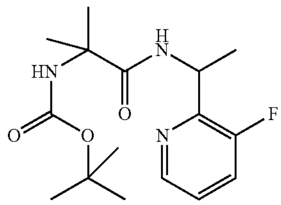 [SMILES: CC(NC(=O)C(C)(C)NC(=O)OC(C)(C)C)c1ncccc1F] | 1-(3-Fluoro-pyridin-2-yl)-ethylamine hydrochloride (5.8 g) HATU | 0.94 2 | 326 |
| 32e | 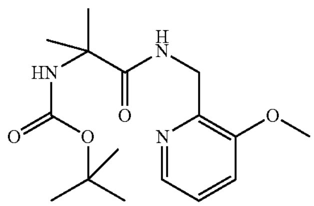 [SMILES: COc1cccnc1CNC(=O)C(C)(C)NC(=O)OC(C)(C)C] | C-(3-Methoxy-pyridin-2-yl)-methylamine dihydrochloride (1 g) HATU | 0.68 1 | 324 |
| 32f | 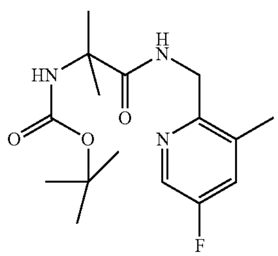 [SMILES: Cc1cc(F)cnc1CNC(=O)C(C)(C)NC(=O)OC(C)(C)C] | C-(5-fluoro-3-methyl-pyridin-2-yl)-methylamine (202 mg) HATU | 1.04 2 | 326 |
| 32g | 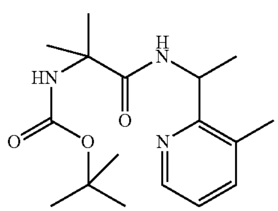 [SMILES: Cc1cccnc1C(C)NC(=O)C(C)(C)NC(=O)OC(C)(C)C] | 1-(3-methyl-2-pyridinyl)ethanamine (1 g) HATU 4 day reaction | 0.98 2 | 322 |
| 32h | 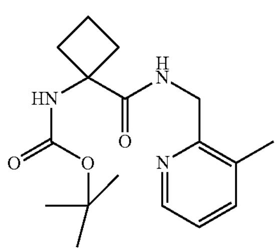 [SMILES: Cc1cccnc1CNC(=O)C1(NC(=O)OC(C)(C)C)CCC1] | C-(3-Methyl-pyridin-2-yl)-methylamine (500 mg) Boc-1-amino-1-cyclobutanecarboxylic acid (880 mg) overnight reaction | 0.90 2 | 320 |
| 32i | 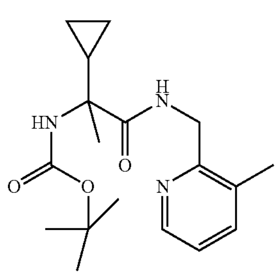 [SMILES: Cc1cccnc1CNC(=O)C(C)(NC(=O)OC(C)(C)C)C1CC1] | C-(3-Methyl-pyridin-2-yl)-methylamine (530 mg) 2-([(tert-butoxy)carbonyl]amino)-2-cyclopropylpropanoic acid (1.0 g) | 1.02 2 | 334 |

-continued

| Example | Structure | Reactant(s) Conditions | UPLC-MS $R_t$ [min], method | MS (ESI+, m/z) $(M + H)^+$ |
|---|---|---|---|---|
| 32j | 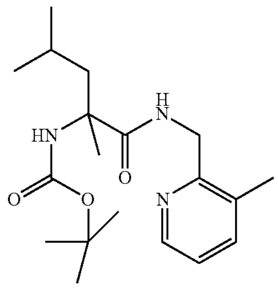 [SMILES: Cc1cccnc1CNC(=O)C(C)(CC(C)C)NC(=O)OC(C)(C)C] | C-(3-Methyl-pyridin-2-yl)-methylamine (483 mg) 2-tert-Butoxycarbonylamino-2,4-dimethyl-pentanoic acid (968 mg) | 1.20 2 | 350 |
| 32k | 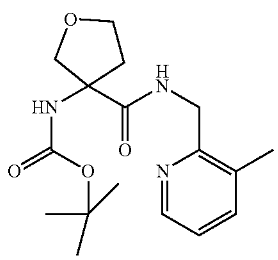 [SMILES: Cc1cccnc1CNC(=O)C1(NC(=O)OC(C)(C)C)CCOC1] | C-(3-Methyl-pyridin-2-yl)-methylamine (520 mg) 3-tert-Butoxycarbonylamino-tetrahydro-furan-3-carboxylic acid (990 mg) | 0.85 2 | 336 |
| 32l | 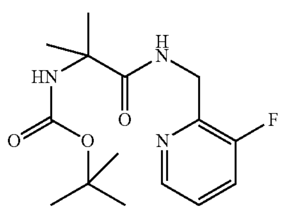 [SMILES: CC(C)(C)OC(=O)NC(C)(C)C(=O)NCc1ncccc1F] | 1-(3-fluoropyridin-2-yl)methanamine (1 g) | 0.82 2 | 312 |
| 32m | 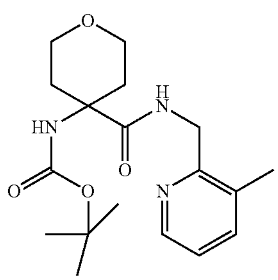 [SMILES: Cc1cccnc1CNC(=O)C1(NC(=O)OC(C)(C)C)CCOCC1] | C-(3-Methyl-pyridin-2-yl)-methylamine (470 mg) 4-N-Boc-amino-4-carboxytetrahydropyran (945 mg) 3 day reaction | 0.86 2 | 350 |
| 32n | 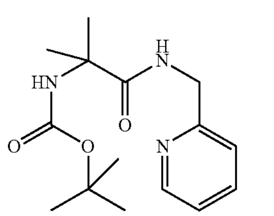 [SMILES: CC(C)(C)OC(=O)NC(C)(C)C(=O)NCc1ccccn1] | 2-(aminomethyl) pyridine (532 mg) | 0.79 2 | 294 |
| 32o | 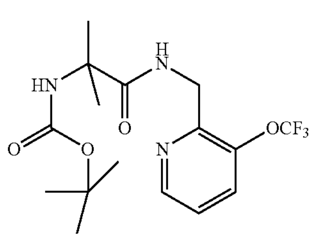 [SMILES: CC(C)(C)OC(=O)NC(C)(C)C(=O)NCc1ncccc1OC(F)(F)F] | C-(3-trifluoromethoxy-pyridin-2-yl)-methylamine (860 mg) | 1.09 2 | 378 |

-continued

| Example | Structure | Reactant(s) Conditions | UPLC-MS $R_t$ [min], method | MS (ESI+, m/z) $(M + H)^+$ |
|---|---|---|---|---|
| 32p | 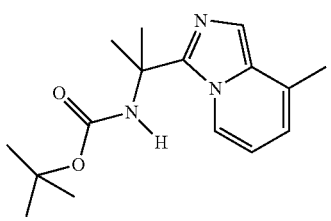 [SMILES: Cc1cccn2c(C(C)(C)NC(=O)OC(C)(C)C)ncc12] | C-(3-Methyl-pyridin-2-yl)-methylamine (1.94 g) Boc-Ala-OH (3.0 g) | 0.93 2 | 294 |

Example 33A

Example 32a (28.5 g, 92.8 mmol) is dissolved in DCM (360 mL) and cooled to 0° C., then Burgess reagent (20.1 g, 84.5 mmol) is added. The mixture is allowed to reach rt and stirred for 3 days. The reaction mixture is washed with water and brine. The organic layer is dried, filtered and evaporated under reduced pressure to give a residue that is purified by flash chromatography (eluent EtOAc/cyclohexane 30:70) to furnish the title compound (13.8 g, 51%).

UPLC-MS (Method 2): $R_t$=1.01 min

MS (ESI+): m/z=290 (M+H)$^+$

The following examples are synthesized in analogy to the preparation of example 33a. Products are purified where appropriate by flash chromatography (eluent: gradient of EtOAc in cyclohexame):

| Example | Structure | Reactant(s) Conditions | UPLC-MS $R_t$ [min], method | MS (ESI+, m/z) $(M + H)^+$ |
|---|---|---|---|---|
| 33b | 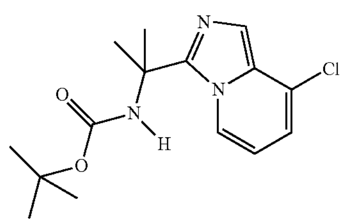 [SMILES: CC(C)(C)OC(=O)NC(C)(C)c1ncc2c(Cl)cccn12] | Example 32b (2.30 g, 7.02 mmol overnight reaction | 0.84 1 | 310 |
| 33c | 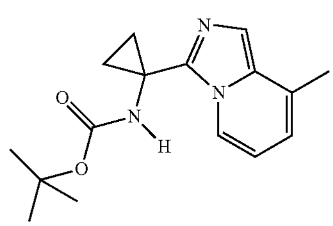 [SMILES: Cc1cccn2c(C3(NC(=O)OC(C)(C)C)CC3)ncc12] | Example 32c (0.77 g, 2.52 mmol) overnight reaction | $^1$H NMR (500 MHz, DMSO-d$_6$): (rotamers) δ 1.18 (br, m, 2H), 1.23 (br, m, 2H), 1.30 (br, s, 9H), 2.34 (s, 3H), 6.56 (ddd, J = 1.1, 2.0, 6.5 Hz, 1H), 6.63 (dd, J = 6.7 Hz, 1H), 7.22 (d, J = 0.6 Hz, 1H), 7.90 (br, s, 1H), 8.48 (br, d, J = 4.7 Hz, 1H) | |
| 33d | 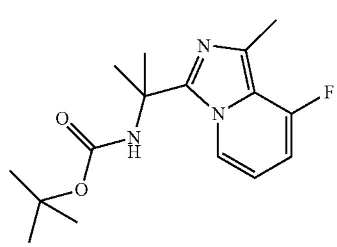 [SMILES: Cc1nc(C(C)(C)NC(=O)OC(C)(C)C)n2cccc(F)c12] | Example 32d (10 g, 30.73 mmol) overnight reaction | 1.54 2 | 308 |

-continued

| Example | Structure | Reactant(s) Conditions | UPLC-MS R$_t$ [min], method | MS (ESI+, m/z) (M + H)$^+$ |
|---|---|---|---|---|
| 33e | 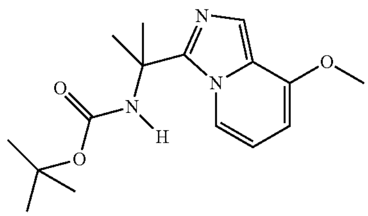 [SMILES: COc1cccn2c(C(C)(C)NC(=O)OC(C)(C)C)ncc12] | Example 32e (1.51 g, 4.67 mmol) overnight reaction | 0.77 1 | 306 |
| 33f | 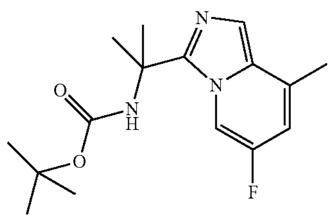 [SMILES: Cc1cc(F)cn2c(C(C)(C)NC(=O)OC(C)(C)C)ncc12] | Example 32f (102 mg, 0.31 mmol) overnight reaction | 1.11 2 | 308 |
| 33g | 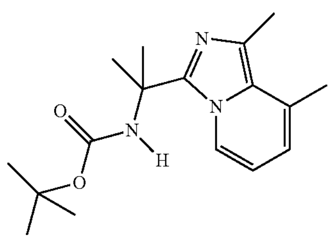 [SMILES: Cc1cccn2c(C(C)(C)NC(=O)OC(C)(C)C)nc(C)c12] | Example 32g (2.04 g, 6.33 mmol) overnight reaction | 1.05 2 | 304 |
| 33h | 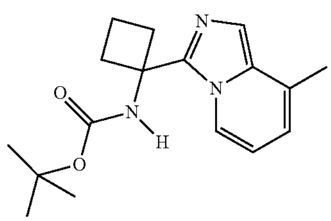 [SMILES: Cc1cccn2c(C3(NC(=O)OC(C)(C)C)CCC3)ncc12] | Example 32h (1.16 g, 3.63 mmol) overnight reaction | 1.12 2 | 302 |
| 33i | 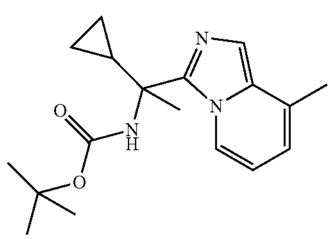 [SMILES: Cc1cccn2c(C(C)(NC(=O)OC(C)(C)C)C3CC3)ncc12] | Example 32i (1.40 g, 3.95 mmol) overnight reaction | 1.09 2 | 316 |
| 33j | 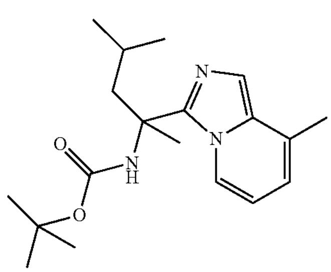 [SMILES: Cc1cccn2c(C(C)(CC(C)C)NC(=O)OC(C)(C)C)ncc12] | Example 32j (0.98 g, 2.80 mmol) overnight reaction | 1.25 2 | 332 |

| Example | Structure | Reactant(s) Conditions | UPLC-MS $R_t$ [min], method | MS (ESI+, m/z) $(M + H)^+$ |
|---|---|---|---|---|
| 33k | 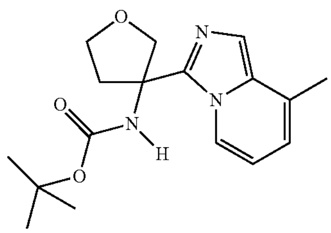 [SMILES: Cc1cccn2c(C3(NC(=O)OC(C)(C)C)CCOC3)ncc12] | Example 32k (0.92 g, 0.38 mmol) overnight reaction | 0.94 2 | 318 |
| 33l | 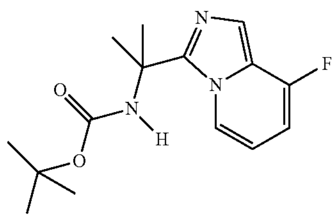 [SMILES: CC(C)(C)OC(=O)NC(C)(C)c1ncc2c(F)cccn12] | Example 32l (1.0 g, 3.21 mmol) | 0.97 2 | 294 |
| 33m | 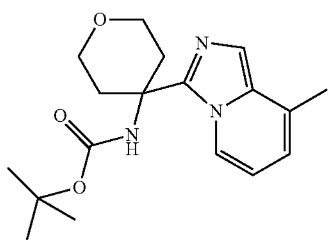 [SMILES: Cc1cccn2c(C3(NC(=O)OC(C)(C)C)CCOCC3)ncc12] | Example 32m (1.29 g, 3.69 mmol) | 0.94 2 | 332 |
| 33n | | Example 32n (685 mg, 2.33 mmol) | 0.91 2 | 276 |
| 33n | | Example 32n (685 mg, 2.33 mmol) | 0.91 2 | 276 |
| 33o | 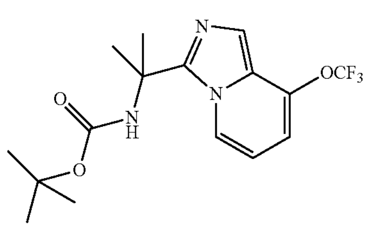 [SMILES: CC(C)(C)OC(=O)NC(C)(C)c1ncc2c(OC(F)(F)F)cccn12] | Example 32o (130 mg, 0.61 mmol) | 1.19 2 | 360 |

| Example | Structure | Reactant(s) Conditions | UPLC-MS $R_t$ [min], method | MS (ESI+, m/z) $(M + H)^+$ |
|---|---|---|---|---|
| 33p | 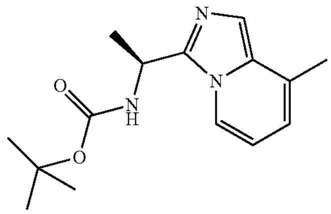 [SMILES: Cc1cccn2c([C@H](C)NC(=O)OC(C)(C)C)ncc12] | Example 32p (3.60 g, 12.3 mmol) | 1.11 2 | 276 |

Example 33q

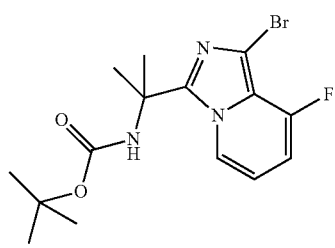 [SMILES: CC(C)(C)OC(=O)NC(C)(C)c1nc(Br)c2c(F)cccn12]

Example 33l (1.3 g, 4.43 mmol) is suspended in DCM (12 mL) and cooled to 0° C. N-bromosucciminide (0.83 g, 4.65 mmol) is added and the mixture stirred at 0° C. for 60 minutes. Saturated aqueous sodium thiosulfate solution is added, the mixture stirred for 30 minutes and the phases separated. The organic layer is evaporated under reduced pressure to give a residue that is purified by flash chromatography (eluent 0-50% ethyl acetate in cyclohexane) to furnish the title compound (600 mg, 36%).

UPLC-MS (Method 2): $R_t$=1.22 min
MS (ESI+): m/z=372/374 (M+H)$^+$

Example 33r

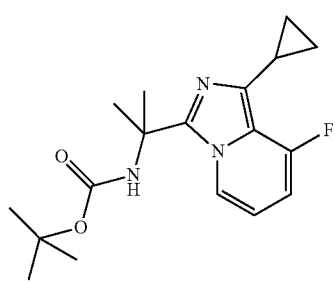 [SMILES: CC(C)(C)OC(=O)NC(C)(C)c1nc(C2CC2)c2c(F)cccn12]

Example 33q (600 mg, 1.61 mmol), potassium cyclopropyltrifluoroborate (477 mg, 3.22 mmol), Potassium triphosphate (1.20 mg, 5.64 mmol), tricyclohexylphosphine (90 mg, 0.32 mmol) and palladium (II) acetate (36 mg, 0.16 mmol) are suspended in a mixture of toluene (17 mL) and water (0.2 mL) in a microwave vial and degassed for 5 minutes with a flow of nitrogen gas. The mixture is heated under microwave irradiation for 2×5 hours at 120° C. then allowed to cool and diluted with ethyl acetate and water. The phases are separated, the organic phase filtered through decalite and the solvent removed under vacuum. The residue is purified by flash chromatography (0-20% ethyl acetate in cyclohexane) to give the title compound (170 mg, 30%).

UPLC-MS (Method 2): $R_t$=1.34 min
MS (ESI+): m/z=334 (M+H)$^+$

Example 33s

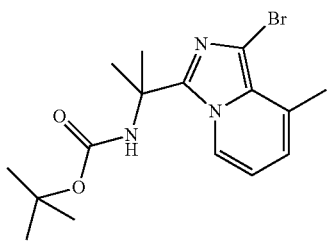 [SMILES: Cc1cccn2c(C(C)(C)NC(=O)OC(C)(C)C)nc(Br)c12]

Prepared in analogy to the method described for Example 33q using Example 33a (5.0 g, 17.3 mmol) as starting material.

UPLC-MS (Method 7a): $R_t$=4.73 min
MS (ESI+): m/z=368/370 (M+H)$^+$

Example 33t

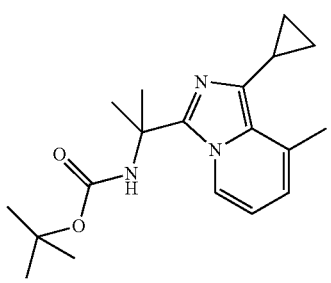 [SMILES: Cc1cccn2c(C(C)(C)NC(=O)OC(C)(C)C)nc(C3CC3)c12]

Prepared in analogy to the method described for Example 33r using Example 33s (250 mg, 0.68 mmol) as starting material.

UPLC-MS (Method 2): $R_t$=1.47 min
MS (ESI+): m/z=330 (M+H)$^+$

Example 33u

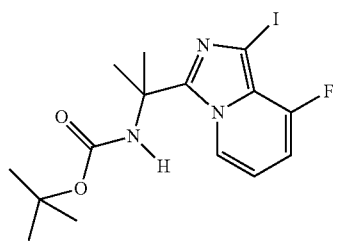 [SMILES: CC(C)(C)OC(=O)NC(C)(C)c1nc(I)c2c(F)cccn12]

Example 33l (200 mg, 0.68 mmol) is suspended in DCM (4 mL) and cooled to 0° C. N-iodosucciminide (153 mg, 0.68 mmol) is added and the mixture stirred at 0° C. for 30 minutes. 10% aqueous sodium thiosulfate solution is added, the mixture shaken and the phases separated. The organic layer is evaporated under reduced pressure to give a residue that is purified by flash chromatography (eluent 0-50% ethyl acetate in cyclohexane) to furnish the title compound (200 mg, 70%).

UPLC-MS (Method 2): $R_t$=1.17 min

MS (ESI+): m/z=420 (M+H)$^+$

Example 33v

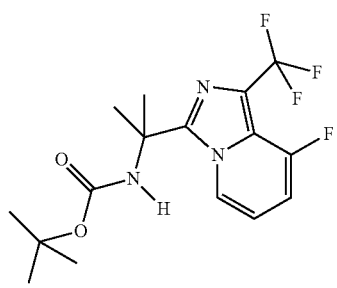 [SMILES: CC(C)(C)OC(=O)NC(C)(C)c1nc(C(F)(F)F)c2c(F)cccn12]

Example 33u (200 mg, 0.48 mmol), methyl 2,2-difluoro-2-(fluorosulfonyl)acetate (182 μL, 1.43 mmol) and copper (I)iodide (136 mg, 0.72 mmol) are suspended in N-methylpyrrolidinone (4 mL) and heated at 110° C. for 50 minutes. The mixture is cooled in ice, diluted with water and extracted with ethyl acetate. The organic layer is evaporated under reduced pressure to give a residue that is purified by flash chromatography (eluent 0-50% ethyl acetate in cyclohexane) to furnish the title compound (150 mg, 78%).

UPLC-MS (Method 12): $R_t$=3.68 min

MS (ESI+): m/z=462 (M+H)$^+$

Example 34A

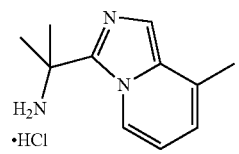

Example 33a (13.8 g, 47.7 mmol) is suspended in dry methanol (71 mL) and cooled to 0° C. 2M Hydrogen chloride in diethyl ether (236 mL, 472 mmol) is added and the mixture is stirred overnight. The solvent is evaporated and the residue is used without purification (10.7 g, 99%).

UPLC-MS (Method 2): $R_t$=0.81 min

MS (ESI+): m/z=174 (M-NH2)$^+$

The following examples are synthesized in analogy to the preparation of example 34a:

| Example | Structure | Reactant(s) Conditions | UPLC-MS $R_t$ [min], method | MS (ESI+, m/z) (M + H)$^+$ |
|---|---|---|---|---|
| 34b | 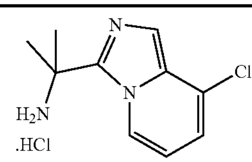 | Example 33b (448 mg, 1.45 mmol) 4M HCl in 1,4-dioxane, 1 hour | 0.67  1 | 210 |
| 34c | 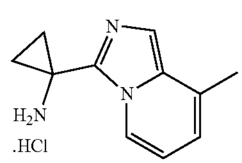 | Example 33c (570 mg, 1.98 mmol) 2M HCl in diethyl ether (9.75 mL), methanol (3 mL) Overnight reaction | 0.49  1 | 188 |
| 34d | 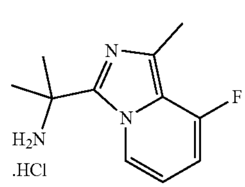 | Example 33d (110 mg, 0.30 mmol) 2M HCl in diethyl ether (10 mL, 1 hour | 0.93  2 | 192 (M − NH2)$^+$ |

| Example | Structure | Reactant(s) Conditions | UPLC-MS $R_t$ [min], method | MS (ESI+, m/z) $(M + H)^+$ |
|---|---|---|---|---|
| 34e | 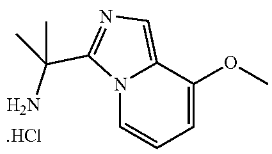 | Example 33e (150 mg, 0.49 mmol) 4M HCl in 1,4-dioxane, 1 hour | 0.62 1 | 189 (M − NH2)+ |
| 34f | 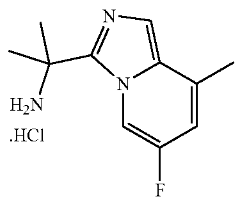 | Example 33f (24 mg, 0.08 mmol) 2M HCl in diethyl ether (2 mL), 4 hour reaction | 0.94 2 | 191 (M − NH2)+ |
| 34g | 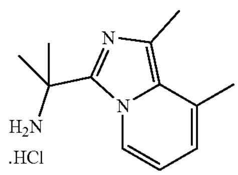 | Example 33g (300 mg, 0.99 mmol) 2M HCl in diethyl ether (5 mL), methanol (2 mL) Overnight reaction | 0.73 2 | 187 (M − NH2)+ |
| 34h | 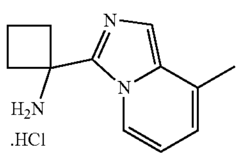 | Example 33h (588 mg, 1.95 mmol) 2M HCl in diethyl ether (9.75 mL), methanol (3 mL) Overnight reaction | 0.89 2 | 185 (M − NH2)+ |
| 34i | 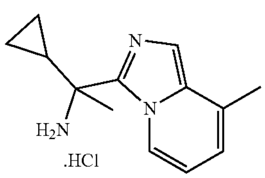 [SMILES: Cc1cccn2c(C(C)(N)C3CC3)ncc12 ; ".HCl"] | Example 33i (1.0 g, 3.17 mmol) 4M HCl in 1,4-dioxane, 1 hour | 0.68 2 | 199 (M − NH2)+ |
| 34j | 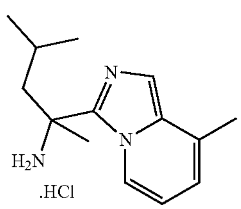 [SMILES: Cc1cccn2c(C(C)(N)CC(C)C)ncc12 ; ".HCl"] | Example 33j (469 mg, 1.41 mmol) 2M HCl in diethyl ether (7 mL), methanol (2 mL) Overnight reaction | 1.04 2 | 216 (M − NH2)+ |
| 34k | 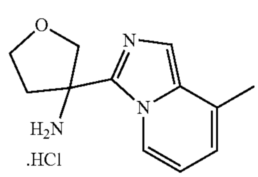 [SMILES: Cc1cccn2c(C3(N)CCOC3)ncc12 ; ".HCl"] | Example 33k (233 mg, 0.73 mmol) 2M HCl in diethyl ether (3.6 mL), methanol (3 mL) Overnight reaction | 0.73 2 | 201 (M − NH2)+ |
| 34l | 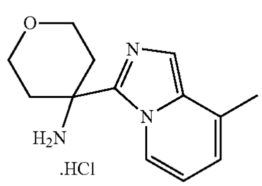 [SMILES: Cc1cccn2c(C3(N)CCOCC3)ncc12 ; ".HCl"] | Example 33m (300 mg, 0.91 mmol) 4M HCl in 1,4-dioxane, 1 hour | 0.76 1 | 215 (M − NH2)+ |

| Example | Structure | Reactant(s) Conditions | UPLC-MS R$_t$ [min], method | MS (ESI+, m/z) (M + H)$^+$ |
|---|---|---|---|---|
| 34m | 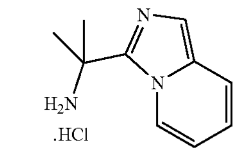 | Example 33n (258 mg, 0.94 mmol) 2M HCl in diethyl ether (3 mL), Diethyl ether (7 mL) 5 hours | 0.57 2 | 176 |
| 34n | 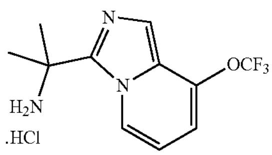 [SMILES: ".HCl" ; CC(C)(N)c1ncc2c(OC(F)(F)F)cccn12] | Example 33o (30 mg, 0.08 mmol) 2M HCl in diethyl ether (2 mL) | 1.03 2 | 243 (M − NH2)$^+$ |
| 34o | 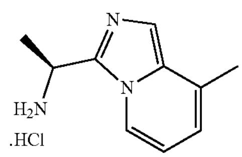 | Example 33p (2.4 g, 8.7 mmol) 2M HCl in diethyl ether (44 mL), methanol overnight reaction | 0.77 2 | 159 (M − NH2)$^+$ |
| 34p | 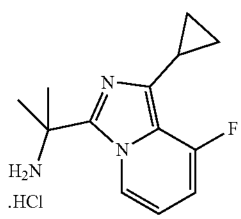 [SMILES: ".HCl" ; CC(C)(N)c1nc(C2CC2)c2c(F)cccn12] | Example 33r (170 mg, 0.51 mmol) 2M HCl in diethyl ether (10 mL), 1 hour | 1.14 2 | 218 (M − NH2)$^+$ |
| 34q | 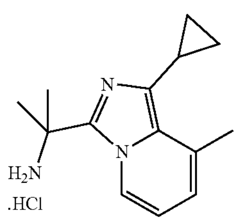 [SMILES: ".HCl" ; Cc1cccn2c(C(C)(C)N)nc(C3CC3)c12] | Example 33t (340 mg, 1.03 mmol) 2M HCl in diethyl ether (5 mL), methanol (5 mL) Overnight reaction | 1.07 2 | 230 |
| 34r | 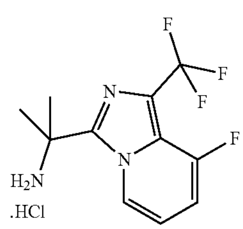 [SMILES: ".HCl" ; CC(C)(N)c1nc(C(F)(F)F)c2c(F)cccn12] | Example 33v (150 mg, 0.42 mmol) 4M HCl in 1,4-dioxane, Overnight reaction | 0.97 2 | 245 (M − NH2)$^+$ |

Example 35A

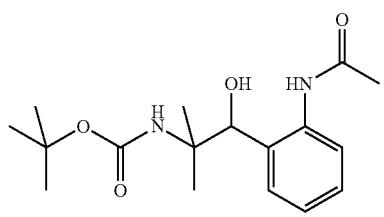 [SMILES: CC(=O)Nc1ccccc1C(O)C(C)(C)NC(=O)OC(C)(C)C]

2-Bromoacetanilide (1.68 g, 90% content, 7.06 mmol) is dissolved in dry THF (15 mL) and cooled to −78° C. under a nitrogen atmosphere. n-Butyllithium (2.5 M solution in hexane, 5.93 mL, 14.8 mmol) is added dropwise and the mixture stirred at −78° C. for 30 minutes. tert-Butyl 2-formylpropan-2-ylcarbamate (1.39 g, 7.42 mmol) in dry THF (10 mL) is added dropwise and the mixture stirred for 30 minutes at −78° C. then allowed to warm to −50° C. over 1 hour. Saturated aqueous ammonium chloride solution (20 mL) is added, the mixture allowed to warm to room temperature and the phases separated. The organic phase is washed with brine, dried and the solvent removed. The residue is purified by flash chromatography (Eluent 0-2% MeOH in DCM) to give the title product (370 mg, 16%).

UPLC-MS (Method 1): R$_t$=1.02 min

MS (ESI+): m/z=323 (M+H)$^+$

The following examples are synthesized in analogy to the preparation of example 35a:

| Example | Structure | Reactant(s) Conditions | UPLC-MS R$_t$ [min], method | MS (ESI+, m/z) (M + H)$^+$ |
|---|---|---|---|---|
| 35b | 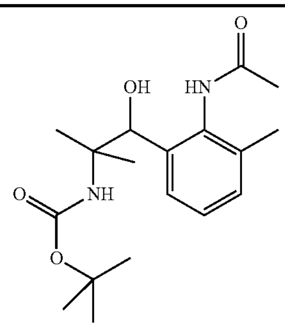 | N-(2-bromo-6-methylphenyl)-acetamide (3.70 g, 50% content, 8.11 mmol) Eluent for purification 0-100% EtOAc in cyclohexane | 0.96 Method 1 | 337 |
| 35c | 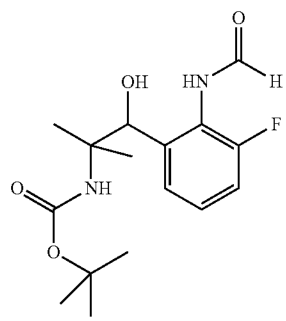 [SMILES: CC(C)(C)OC(=O)NC(C)(C)C(O)c1cccc(F)c1NC=O] | N-(2-bromo-6-fluorophenyl)-formamide (1.81 g, 8.30 mmol) Eluent for purification 0-40% EtOAc in cyclohexane | 1.01 Method 2 | 327 |
| 35d | 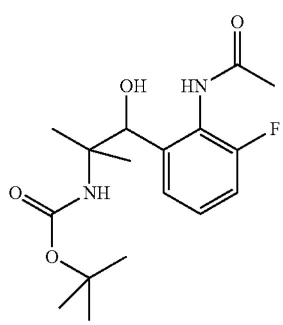 [SMILES: CC(=O)Nc1c(F)cccc1C(O)C(C)(C)NC(=O)OC(C)(C)C] | N-(2-bromo-6-fluorophenyl)-acetamide (6.0 g, 20.7 mmol) Eluent for purification 0-40% EtOAc in cyclohexane | 0.96 Method 2 | 341 |

Example 35a (210 mg, 0.65 mmol) is suspended in DCM and Dess Martin periodinane (304 mg, 0.72 mmol) is added. The mixture is stirred for 10 minutes and then shaken with 10% aqueous sodium thiosulfate solution and the phases separated. The organic phase is washed with saturated aqueous sodium bicarbonate solution, dried and the solvent removed to give the title product (208 mg, 100%).

UPLC-MS (Method 1): R$_t$=1.13 min

MS (ESI+): m/z=321 (M+H)$^+$

The following examples are synthesized in analogy to the preparation of example 36a:

Example 36A

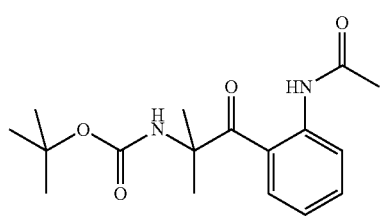 [SMILES: CC(=O)Nc1ccccc1C(=O)C(C)(C)NC(=O)OC(C)(C)C]

| Example | Structure | Reactant(s) Conditions | UPLC-MS $R_t$ [min], method | MS (ESI+, m/z) $(M + H)^+$ |
|---|---|---|---|---|
| 36b | 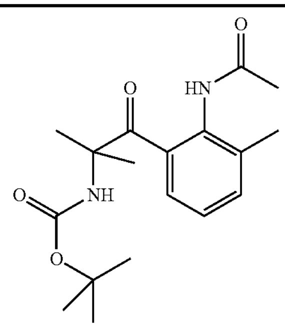 | Example 35b (356 mg, 85% content, 0.90 mmol), 4 hour reaction Purification by flash chromatography (eluent 50% EtOAc in cyclohexane | 1.05 1 | 335 |
| 36c | 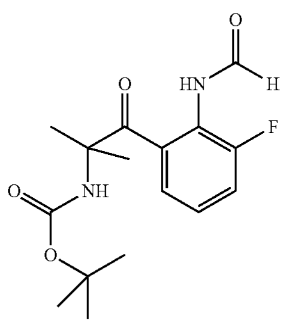 [SMILES: CC(C)(C)OC(=O)NC(C)(C)C(=O)c1cccc(F)c1NC=O] | Example 35c (724 mg), 4 hour reaction Purification by flash chromatography (eluent 0-50% EtOAc in cyclohexane | 1.06 2 | 325 |
| 36d | 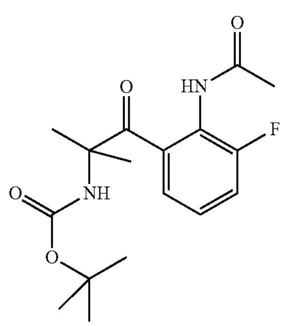 [SMILES: CC(=O)Nc1c(F)cccc1C(=O)C(C)(C)NC(=O)OC(C)(C)C] | Example 35d (350 mg), 4 hour reaction Purification by flash chromatography (eluent 0-50% EtOAc in cyclohexane | 1.17 2 | 339 |

Example 37A

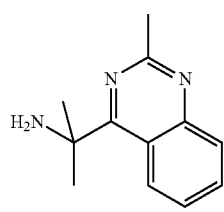

Example 36a (205 mg, 0.64 mmol) and ammonium chloride (300 mg, 5.58 mmol) are suspended in 7M ammonia in methanol (4 mL) and heated under microwave irradiation at 140° C. for 16 hours. The solvent is removed, the residue suspended in methanol and filtered to remove excess ammonium chloride then loaded onto a prewashed SCX cartridge, washed with water and methanol and eluted with 7M ammonia in methanol. The solvent is removed under vacuum to give the crude title product (106 mg).

UPLC-MS (Method 1): $R_t$=0.58 min

MS (ESI+): m/z=202 (M+H)$^+$

The following examples are synthesized in analogy to the preparation of example 37a:

| Example | Structure | Reactant(s) Conditions | UPLC-MS $R_t$ [min], method | MS (ESI+, m/z) $(M + H)^+$ |
|---|---|---|---|---|
| 37b | 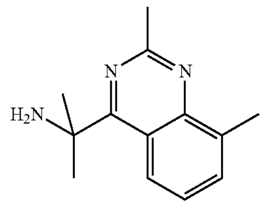 [SMILES: Cc1nc(C(C)(C)N)c2cccc(C)c2n1] | Example 36b (265 mg, 0.79 mmol), | 0.70 1 | 216 |
| 37c | 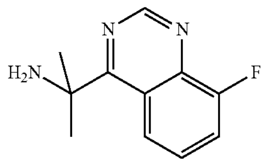 | Example 36c (580 mg, 1.79 mmol), | 0.75 2 | 206 |
| 37d | 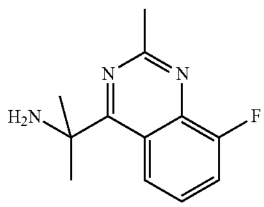 [SMILES: Cc1nc(C(C)(C)N)c2cccc(F)c2n1] | Example 36d (230 mg) | 0.55 2 | 220 |

Example 38A

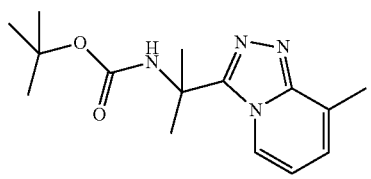 [SMILES: Cc1cccn2c(C(C)(C)NC(=O)OC(C)(C)C)nnc12]

Step 1:

Boc-AIB-OH (0.50 g, 2.44 mmol), 2-hydrazino-3-methylpyridine (1.0 g, 8.24 mmol), HATU (3.70 g, 9.73 mmol) and triethyl amine (2.48 mL, 17.8 mmol) are suspended in DCM and the mixture stirred overnight. The mixture is filtered, the solvent removed and the residue purified by flash chromatography (eluent 0-100% ethyl acetate in cyclohexane) to give impure hydrazide intermediate (800 mg) which is used directly in the following step.

Step 2:

The material from step 1 is suspended in dry DCM (20 ML) and polymer supported triphenylphosphine (3 mmol/g, 1.3 g. 3.9 mmol), trimethylsilylazide (520 µL, 3.9 mmol) and diethylazodicarboxylate (2.03 mL, 4.7 mmol) are added. The mixture is stirred overnight, filtered and the solvent removed. The residue is purified by flash chromatography (eluent 0-100% ethyl acetate in cyclohexane) to give the title product (Yield 180 mg).

UPLC-MS (Method 2): $R_t$=0.76 min

MS (ESI+): m/z=291 $(M+H)^+$

Example 39A

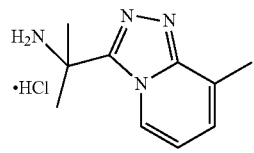

Example 38a (180 mg, 0.62 mmol) is suspended in 4M HCl in dioxane (4 ML) and stirred for 3 hours. The solvent is removed under vacuum to give the title product (150 mg, 90% content)

UPLC-MS (Method 2): $R_t$=0.49 min

MS (ESI+): m/z=191 $(M+H)^+$

Example 40A

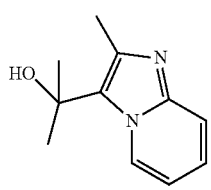

Ethyl 2-methylimidazo[1,2-a]pyridine-3-carboxylate (3.30 g, 16.1 mmol) is suspended in dry THF and cooled to −20° C. under nitrogen atmosphere. Methylmagnesium bromide (1.4 M in THF/toluene, 35 mL, 48.5 mmol) is added dropwise, the mixture allowed to warm to room temperature and stirred overnight. Saturated aqueous ammonium chloride solution is added and the mixture extracted with ethyl acetate. The organic extracts are dried and the solvent removed. The residue is purified by flash chromatography (eluent 0-100% EtOAc in cyclohexane) to give the title product (yield 1.20 g, 39%)

$^1$H NMR (500 MHz, DMSO-d$_6$): δ 1.64 (s, 6H), 2.44 (s, 3H), 5.40 (s, 1H), 6.82 (dd, 1H), 7.16 (dd, 1H), 7.43 (d, 1H), 8.84 (dd, 1H).

Example 41A

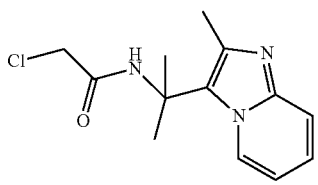 [SMILES: Cc1nc2ccccn2c1C(C)(C)NC(=O)CCl]

Example 40a (1.2 g, 6.31 mmol) is suspended in chloroacetonitrile (15 mL) and TFA (15 mL) and the mixture stirred overnight, The solvent is evaporated and the residue is purified by flash chromatography (eluent 0-10% MeOH in DCM) to give the title product (yield 0.5 g, 30%

UPLC-MS (Method 1): R$_t$=0.60 min
MS (ESI+): m/z=266 (M+H)$^+$

Example 42A

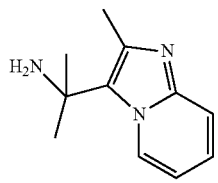

Example 41a (100 mg, 0.38 mmol) is suspended in 6M aqueous HCl (2 mL) and heated at 80° C. overnight, The mixture is loaded onto a prewashed SCX cartridge, washed with water and methanol and eluted with 7M NH3 in methanol. The solvent is removed to give the title product (yield 70 g, 98%).

$^1$H NMR (500 MHz, DMSO-d$_6$): δ 1.57 (s, 6H), 2.44 (s, 3H), 6.74 (dd, 1H), 7.08 (dd, 1H), 7.34 (d, 1H), 9.15 (dd, 1H). NH2 not observed.

Example 43A

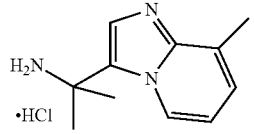

The title product is synthesised from ethyl 8-methylimidazo[1,2-a]pyridine-3-carboxylate (1.0 g, prepared in analogy to the procedure described in Bioorg. Med. Chem. Lett, 2012, 1870-1873), in analogy to the procedure described for the synthesis of Example 40a through to Example 42a. The product was isolated as a hydrochloride salt without purification (yield 110 mg).

UPLC-MS (Method 2): R$_t$=0.78 min
MS (ESI+): m/z=190 (M+H)$^+$

Example 44A

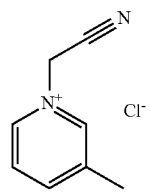

3-picoline (5.0 g, 53.7 mmol) is suspended in acetonitrile and chloroacetinitrile (6.76 mL, 107.4 mmol) is added. The mixture is stirred at room temperature for 4 hours and the precipitate is collected by filtration and dried under vacuum to give the title compound (7.0 g)

$^1$H NMR (500 MHz, DMSO-d$_6$): δ 2.53 (s, 3H), δ 6.04 (s, 2H), 8.16 (dd, J=6.0, 8.0 Hz, 1H), 8.58 (d, J=8.0, 1H), 9.09 (d, J=6.0 Hz, 1H), 9.17 (s, 1H).

Example 45A

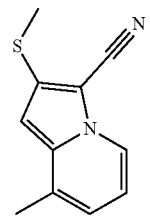

Example 44a (3.22 g, 19.1 mmol), 1-nitro-2,2-bis-metil-mercapto-etilene (3.16 g, 19.1 mmol) and triethylamine (3.30 mL, 38.2) are suspended in ethanol (40 mL) and refluxed overnight. The solvent is evaporated and the residue purified by flash chromatography (eluent 0-10% ethyl acetate in cyclohexane) to give the title compound (0.8 g)

UPLC-MS (Method 2): R$_t$=1.25 min
MS (ESI+): m/z=203 (M+H)$^+$

Example 46A

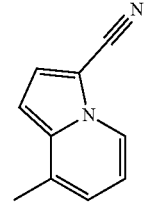

Example 45a (4.8 g, combined batches, 23.7 mmol) and excess raney nickel (approx. 20 g) are suspended in ethanol and stirred for 6 hours. The solvent is evaporated and the residue purified by flash chromatography (eluent 0-10% ethyl acetate in cyclohexane) to give the title compound (900 mg)

LC-MS (Method 7a): R$_t$=4.42 min
MS (ESI+): m/z=157 (M+H)$^+$

Example 47A

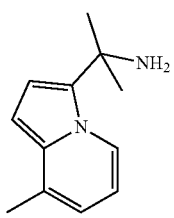

Cerium(III) chloride (7.89 g, 32 mmol) is heated under vacuum at 140° C. for 3 hours then cooled to room temperature under nitrogen atmosphere and dry THF (90 mL) are added. The mixture is stirred at room temperature overnight then cooled to −78° C. Methyl lithium LiCl complex (2 M in diethyl ether, 20 mL, 32 mmol) is added and the mixture stirred at −78° C. for 2 hours. Example 46a (500 mg, 3.2 mmol) in dry THF (5 mL) is added dropwise, the mixture stirred for 2 hours at −78° C. then saturated ammonium chloride solution is added followed by 32% aqueous ammonia. The mixture is warmed to room temperature, filtered through celite, washing with abundant DCM. The organic phase is washed with water, dried and the solvent removed to give a crude title compound (600 mg)

UPLC-MS (Method 2): $R_t$=1.12 min
MS (ESI+): m/z=172 (M-NH2)$^+$

Example 48A

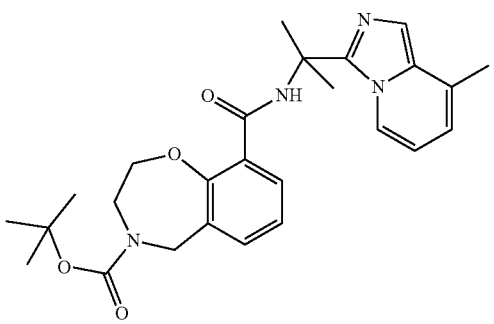 [SMILES: Cc1cccn2c(C(C)(C)NC(=O)c3cccc4c3OCCN(C(=O)OC(C)(C)C)C4)ncc12]

Example 34a (200 mg, 0.897 mmol), 2,3-dihydro-5H-benzo[f][1,4]oxazepine-4,9-dicarboxylic acid 4-tert-butyl ester (263 mg, 0.90 mmol, WO2008108445), HATU (337 mg, 0.89 mmol) and triethylamine (742 uL, 5.34 mmol) are suspended in dichloromethane (16 mL) and stirred at room temperature until UPLC-MS shows the reaction is complete. The mixture is washed with water and dilute aqueous sodium hydroxide solution, dried and the solvent evaporated. The residue was purified by flash chromatography (50% EtOAc in cyclohexane) to give the title compound (332 mg).

UPLC-MS (Method 2): $R_t$=1.22 min
MS (ESI+): m/z=465 (M+H)$^+$

The following examples are synthesized in analogy to the preparation of Example 48a:

| Example | Structure | Reactant(s) Conditions | HPLC-MS or UPLC-MS $R_t$ [min], method | MS (ESI+, m/z) (M + H)$^+$ |
|---|---|---|---|---|
| 48b | 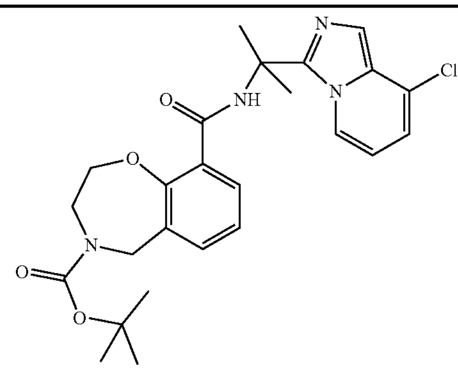 | Example 34b (80 mg, 0.31 mmol) Purified by flash chromatography (0-100% EtOAc in cyclohexane) | 1.06 1 | 485 |
| 48c | 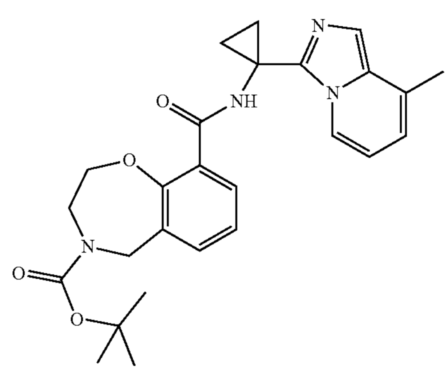 [SMILES: Cc1cccn2c(C3(NC(=O)c4cccc5c4OCCN(C(=O)OC(C)(C)C)C5)CC3)ncc12] | Example 34c (100 mg, 0.45 mmol) Purified by flash chromatography (0-100% EtOAc in cyclohexane) | 0.96 1 | 463 |

| Example | Structure | Reactant(s) Conditions | HPLC-MS or UPLC-MS R$_t$ [min], method | MS (ESI+, m/z) (M + H)$^+$ |
|---|---|---|---|---|
| 48d | 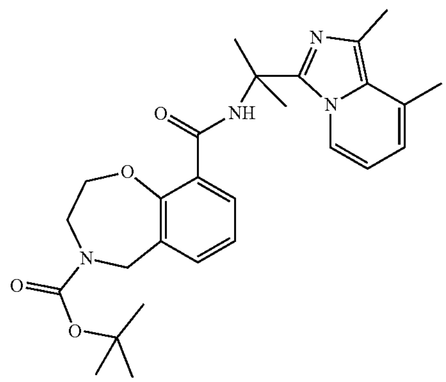 [SMILES: Cc1cccn2c(C(C)(C)NC(=O)c3cccc4c3OCCN(C(=O)OC(C)(C)C)C4)nc(C)c12] | Example 34d (24 mg, 0.08 mmol) No purification | 1.81 4a | 483 |
| 48e | 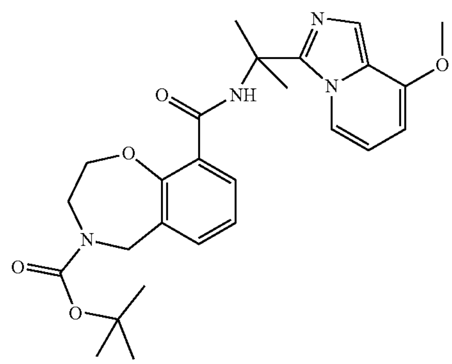 [SMILES: COc1cccn2c(C(C)(C)NC(=O)c3cccc4c3OCCN(C(=O)OC(C)(C)C)C4)ncc12] | Example 34e (45 mg) Purified by flash chromatography (0-100% EtOAc in cyclohexane) | 0.99 1 | 481 |
| 48f | 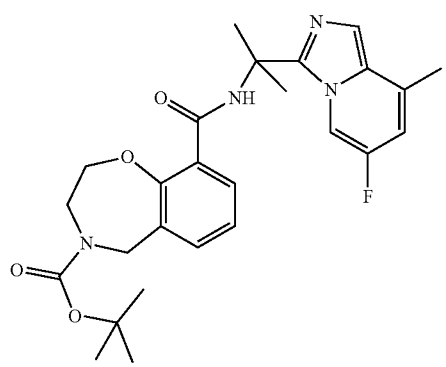 [SMILES: Cc1cc(F)cn2c(C(C)(C)NC(=O)c3cccc4c3OCCN(C(=O)OC(C)(C)C)C4)ncc12] | Example 34f (70 mg, 0.29 mmol) Purified by flash chromatography (0-50% EtOAc in cyclohexane) | 1.21 2 | 483 |
| 48g | 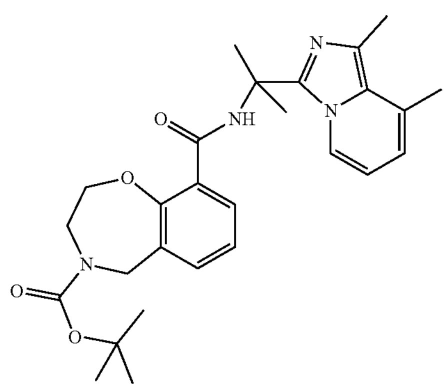 [SMILES: Cc1cccn2c(C(C)(C)NC(=O)c3cccc4c3OCCN(C(=O)OC(C)(C)C)C4)nc(C)c12] | Example 34g (117 mg, 0.49 mmol) Purified by flash chromatography (60% EtOAc in cyclohexane) | 1.22 2 | 479 |

-continued

| Example | Structure | Reactant(s) Conditions | HPLC-MS or UPLC-MS R_t [min], method | MS (ESI+, m/z) (M + H)+ |
|---|---|---|---|---|
| 48h | 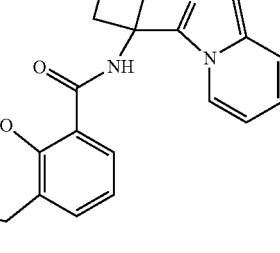 | Example 34h (100 mg, 0.42 mmol) Purified by flash chromatography (50% EtOAc in cyclohexane) | 1.25 2 | 477 |
| 48i | 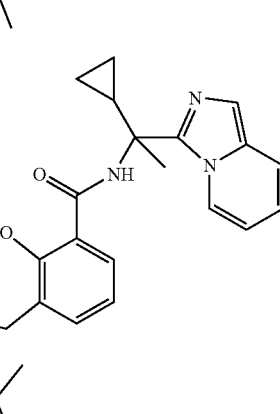 | Example 34i (116 mg, 0.40 mmol) Purified by flash chromatography (0-50% EtOAc in cyclohexane) | 1.26 2 | 491 |
| 48j | 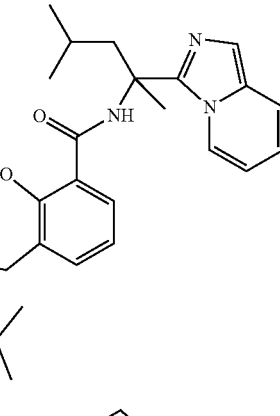 | Example 34j (100 mg, 0.37 mmol) Purified by flash chromatography (20% EtOAc in cyclohexane) | 1.43 2 | 507 |
| 48k | 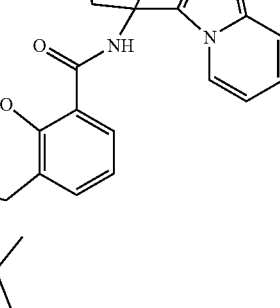 | Example 34k (60 mg, 0.24 mmol) Purified by flash chromatography (80% EtOAc in cyclohexane) | 1.12 2 | 493 |

-continued

| Example | Structure | Reactant(s) Conditions | HPLC-MS or UPLC-MS R_t [min], method | MS (ESI+, m/z) (M + H)+ |
|---|---|---|---|---|
| 48l | 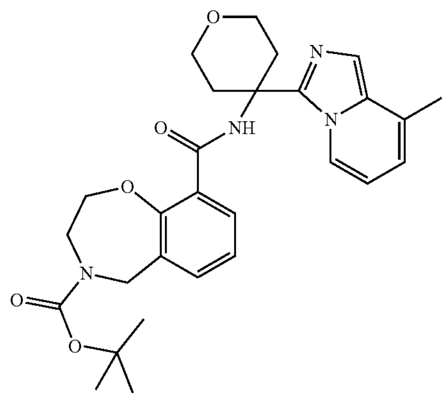 [SMILES: Cc1cccn2c(C3(NC(=O)c4cccc5c4OCCN(C(=O)OC(C)(C)C)C5)CCOCC3)ncc12] | Example 34l (100 mg, 0.37 mmol) Purified by flash chromatography (80% EtOAc in cyclohexane) | 1.12 2 | 507 |
| 48m | 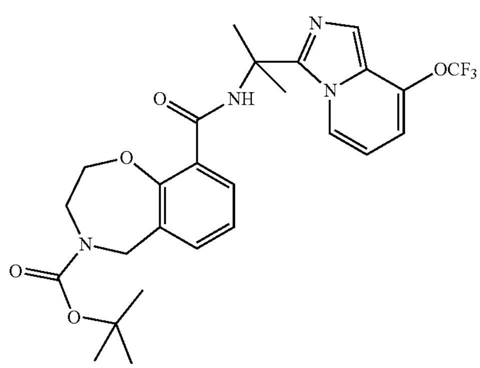 [SMILES: CC(C)(C)OC(=O)N1CCOc2c(cccc2C(=O)NC(C)(C)c2ncc3c(OC(F)(F)F)cccn23)C1] | Example 34n (25 mg, 0.08 mmol) Purified by flash chromatography (0-50% EtOAc in cyclohexane) | 1.31 2 | 535 |
| 48n | 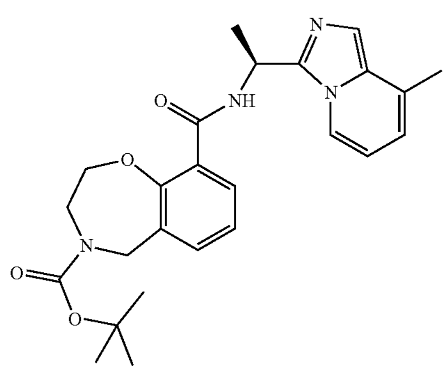 [SMILES: Cc1cccn2c([C@H](C)NC(=O)c3cccc4c3OCCN(C(=O)OC(C)(C)C)C4)ncc12] | Example 34o (100 mg, 0.47 mmol) Purified by flash chromatography (0-100% EtOAc in cyclohexane) | 4.21 12a | 451 |

-continued

| Example | Structure | Reactant(s) Conditions | HPLC-MS or UPLC-MS R_t [min], method | MS (ESI+, m/z) (M + H)+ |
|---|---|---|---|---|
| 48o | 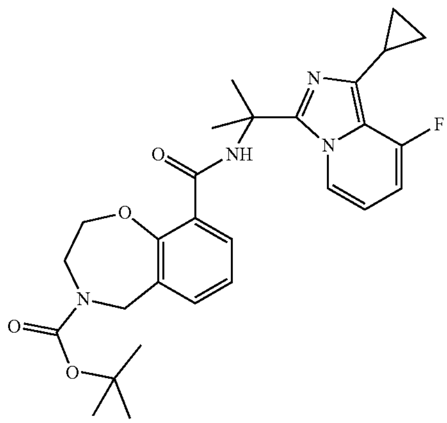 [SMILES: CC(C)(C)OC(=O)N1CCOc2c(cccc2C(=O)NC(C)(C)c2nc(C3CC3)c3c(F)cccn23)C1] | Example 34p (30 mg, 0.13 mmol) Purified by flash chromatography (0-30% EtOAc in cyclohexane) | 1.44 2 | 507 ESI neg [M − H]− |
| 48p | 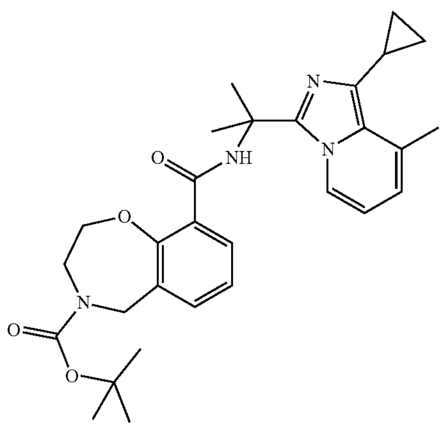 [SMILES: Cc1cccn2c(C(C)(C)NC(=O)c3cccc4c3OCCN(C(=O)OC(C)(C)C)C4)nc(C3CC3)c12] | Example 34q (66 mg, 0.22 mmol) Purified by flash chromatography (15% EtOAc in cyclohexane) | 1.48 2 | 505 |
| 48q | 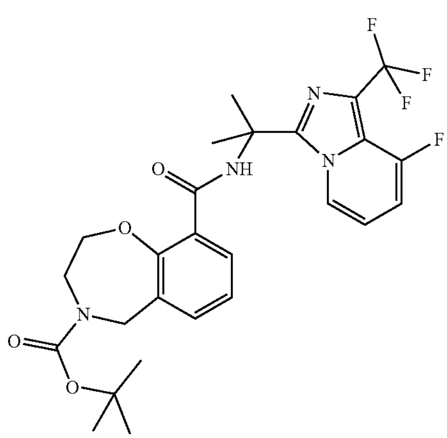 [SMILES: CC(C)(C)OC(=O)N1CCOc2c(cccc2C(=O)NC(C)(C)c2nc(C(F)(F)F)c3c(F)cccn23)C1] | Example 34r (30 mg, 0.10 mmol) Purified by flash chromatography (0-50% EtOAc in cyclohexane) | 1.32 2 | 537 |

-continued

| Example | Structure | Reactant(s) Conditions | HPLC-MS or UPLC-MS R$_t$ [min], method | MS (ESI+, m/z) (M + H)$^+$ |
|---|---|---|---|---|
| 48r | 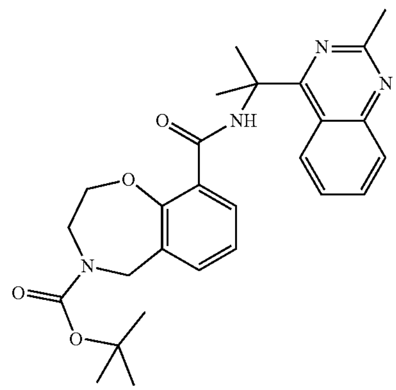 [SMILES: Cc1nc(C(C)(C)NC(=O)c2cccc3c2OCCN(C(=O)OC(C)(C)C)C3)c2ccccc2n1] | Example 37a (25 mg, 0.12 mmol) Purified by flash chromatography (0-3% MeOH in DCM) | 1.15 1 | 477 |
| 48s | 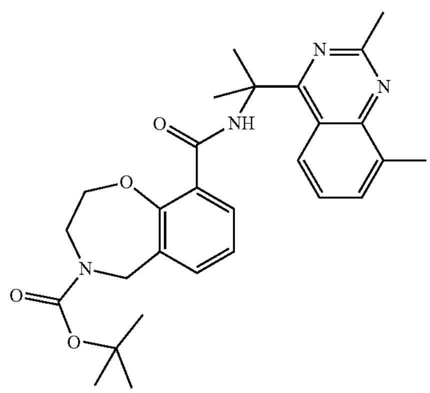 [SMILES: Cc1nc(C(C)(C)NC(=O)c2cccc3c2OCCN(C(=O)OC(C)(C)C)C3)c2cccc(C)c2n1] | Example 37b (50 mg, 0.22 mmol) Purified by flash chromatography (0-50% EtOAc in cyclohexane) | 1.36 1 | 491 |
| 48t | 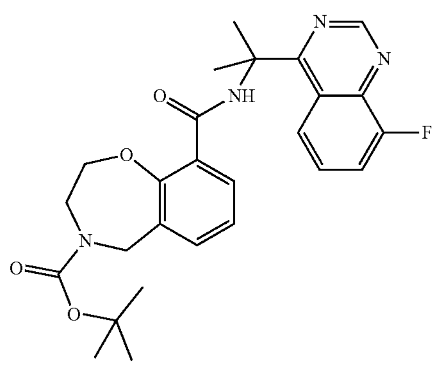 [SMILES: CC(C)(C)OC(=O)N1CCOc2c(cccc2C(=O)NC(C)(C)c2ncnc3c(F)cccc23)C1] | Example 37c (40 mg) No purification, crude product used directly in following reaction | 1.25 2 | 481 |
| 48u | 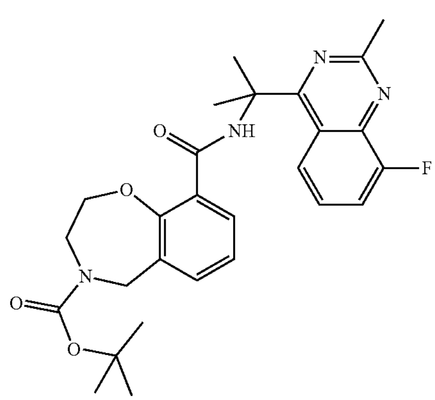 [SMILES: Cc1nc(C(C)(C)NC(=O)c2cccc3c2OCCN(C(=O)OC(C)(C)C)C3)c2cccc(F)c2n1] | Example 37d (25 mg) No purification, crude product used directly in following reaction | 1.29 2 | 495 |

-continued

| Example | Structure | Reactant(s) Conditions | HPLC-MS or UPLC-MS R$_t$ [min], method | MS (ESI+, m/z) (M + H)$^+$ |
|---|---|---|---|---|
| 48v | 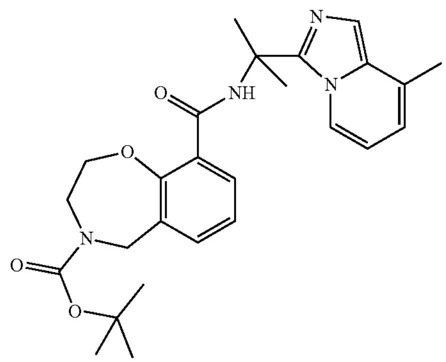 [SMILES: Cc1cccn2c(C(C)(C)NC(=O)c3cccc4c3OCCN(C(=O)OC(C)(C)C)C4)ncc12] | Example 39a (50 mg, 0.22 mmol) Purified by flash chromatography (0-5% MeOH in DCM) | 0.97 2 | 466 |
| 48w | 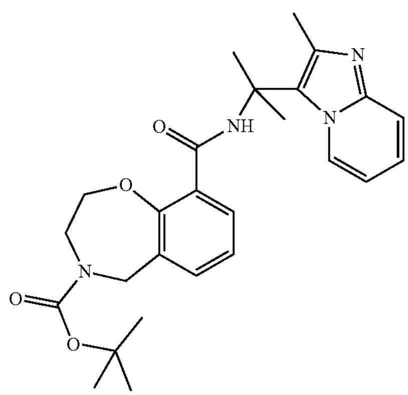 [SMILES: Cc1nc2ccccn2c1C(C)(C)NC(=O)c1cccc2c1OCCN(C(=O)OC(C)(C)C)C2] | Example 42a (55 mg, 0.29 mmol) Purified by flash chromatography (0-100% EtOAc in cyclohexane) | 0.91 1 | 465 |
| 48x | 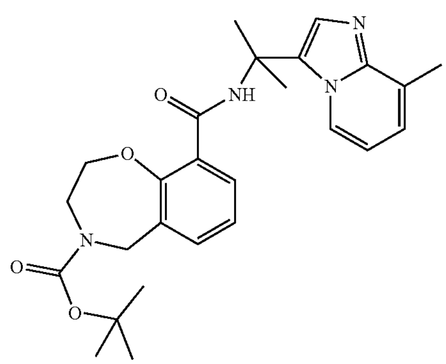 [SMILES: Cc1cccn2c(C(C)(C)NC(=O)c3cccc4c3OCCN(C(=O)OC(C)(C)C)C4)cnc12] | Example 43a (55 mg, 0.24 mmol) Purified by flash chromatography (0-5% MeOH in DCM) | 1.15 2 | 465 |
| 48y | 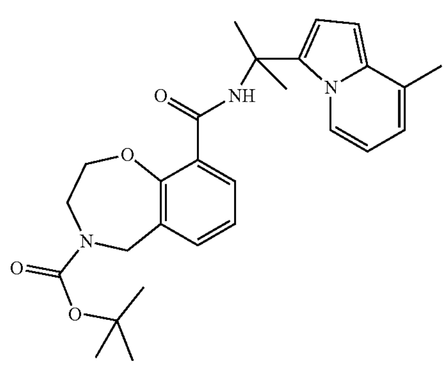 [SMILES: Cc1cccn2c(C(C)(C)NC(=O)c3cccc4c3OCCN(C(=O)OC(C)(C)C)C4)ccc12] | Example 47a (70 mg, 0.37 mmol) Purified by flash chromatography (0-50% EtOAc in cyclohexane) | 1.46 2 | 464 |

The following examples are synthesized in analogy to the preparation of Example 48a using Example 4a in place of 2,3-dihydro-5H-benzo[f][1,4]oxazepine-4,9-dicarboxylic acid 4-tert-butyl ester:

| Example | Structure | Reactant(s) Conditions | UPLC-MS R_t [min], method | MS (ESI+, m/z) (M + H)+ |
|---|---|---|---|---|
| 49a | 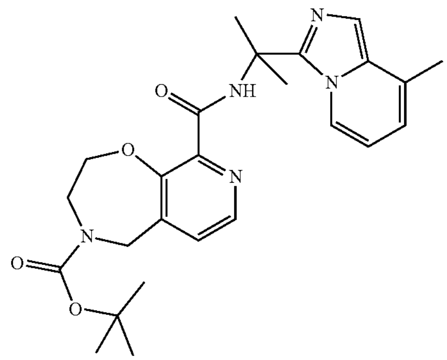 [SMILES: Cc1cccn2c(C(C)(C)NC(=O)c3nccc4c3OCCN(C(=O)OC(C)(C)C)C4)ncc12] | Example 34a (115 mg, 0.31 mmol) Purified by RP-HPLC | 1.01 2 | 466 |
| 49b | 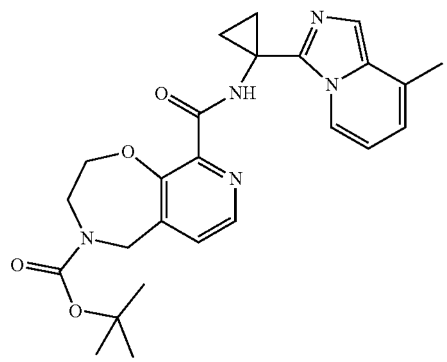 [SMILES: Cc1cccn2c(C3(NC(=O)c4nccc5c4OCCN(C(=O)OC(C)(C)C)C5)CC3)ncc12] | Example 34c (50 mg, 0.22 mmol) Purified by flash chromatography (0-100% EtOAc in cyclohexane) | 1.04 2 | 464 |
| 49c | 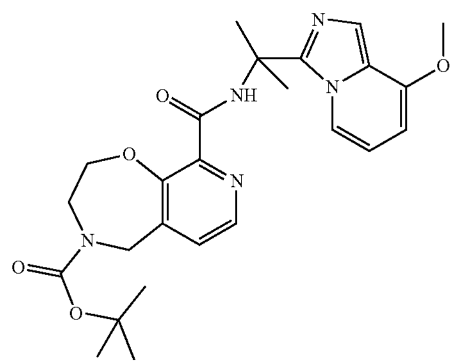 [SMILES: COc1cccn2c(C(C)(C)NC(=O)c3nccc4c3OCCN(C(=O)OC(C)(C)C)C4)ncc12] | Example 34e (70 mg, 0.29 mmol) Purified by flash chromatography (0-50% EtOAc in cyclohexane) | 0.98 2 | 482 |
| 49d | 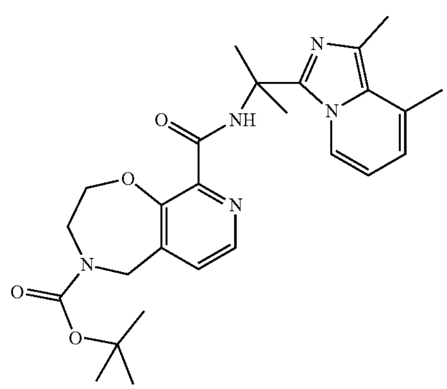 [SMILES: Cc1cccn2c(C(C)(C)NC(=O)c3nccc4c3OCCN(C(=O)OC(C)(C)C)C4)nc(C)c12] | Example 34g (163 mg, 0.68 mmol) Purified by RP-HPLC | 1.06 2 | 480 |

| Example | Structure | Reactant(s) Conditions | UPLC-MS $R_t$ [min], method | MS (ESI+, m/z) (M + H)+ |
|---|---|---|---|---|
| 49e | 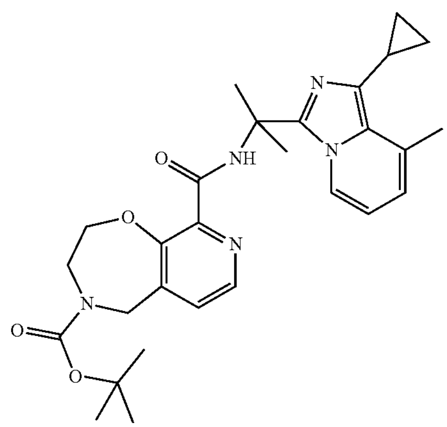 [SMILES: Cc1cccn2c(C(C)(C)NC(=O)c3nccc4c3OCCN(C(=O)OC(C)(C)C)C4)nc(C3CC3)c12] | Example 34q (70 mg, 0.37 mmol) Purified by flash chromatography (0-100% EtOAc in cyclohexane) | 1.29 2 | 506 |
| 49f | 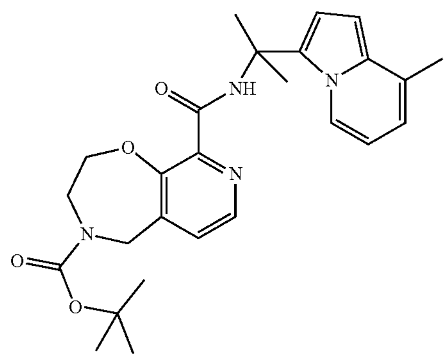 [SMILES: Cc1cccn2c(C(C)(C)NC(=O)c3nccc4c3OCCN(C(=O)OC(C)(C)C)C4)ccc12] | Example 47a (70 mg, 0.3 mmol) Purified by flash chromatography (0-50% EtOAc in cyclohexane) | 1.28 2 | 465 |

Example 50A

Example 51A

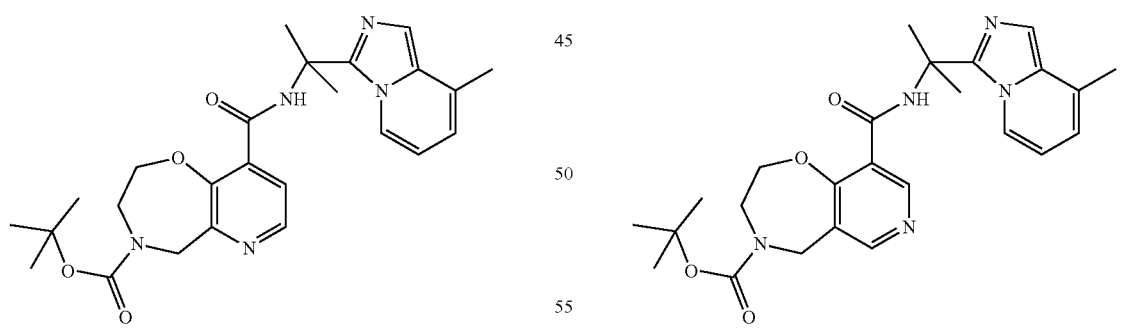

The title compound was prepared in analogy to Example 48a using Example 4b (59 mg, 0.20 mmol) in place of 2,3-dihydro-5H-benzo[f][1,4]oxazepine-4,9-dicarboxylic acid 4-tert-butyl ester. The crude product was used in the next step without purification (32 mg).

UPLC-MS (Method 2): $R_t$=1.04 min

MS (ESI+): m/z=466 (M+H)+

The title compound was prepared in analogy to Example 48a using Example 4c (65 mg, 0.22 mmol) in place of 2,3-dihydro-5H-benzo[f][1,4]oxazepine-4,9-dicarboxylic acid 4-tert-butyl ester. The product was purified by flash chromatography (5% MeOH in DCM) (69 mg).

UPLC-MS (Method 2): $R_t$=1.00 min

MS (ESI+): m/z=466 (M+H)+

EXEMPLARY EMBODIMENTS

Example 1

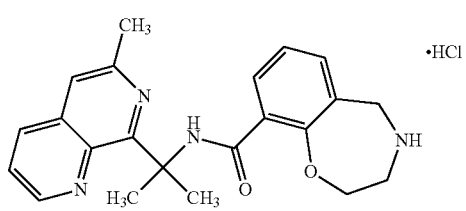 [SMILES: Cc1cc2cccnc2c(C(C)(C)NC(=O)c2cccc3c2OCCNC3)n1 ; Cl]

2,3-Dihydro-5H-benzo[f][1,4]oxazepine-4,9-dicarboxylic acid 4-tert-butyl ester (for the preparation, see WO2008108445) (3.2 mg, 0.011 mmol) is added to a solution of HATU (8 mg, 0.022 mmol) and DIPEA (6 µl, 0.035 mmol) in DMF (0.200 mL); then example 8 g (2 mg, 0.010 mmol) in DMF (0.200 mL) is added and stirring is continued for 18 h at rt. The reaction is filtered on a basic aluminum oxide pad, washed with DMF/MeOH 9:1 (600 µl) and then dried. The residue is diluted with dioxane 0.500 ml and 0.200 mL of 4N HCl solution in dioxane and stirring is continued overnight. Solvent is evaporated to give the title compound (1.1 mg, 27%).

UPLC-MS (Method 4a): $R_t$=1.57

MS (ESI+): m/z=377 (M+H)$^+$

The following examples are synthesized in analogy to the preparation of example 1:

Example 3

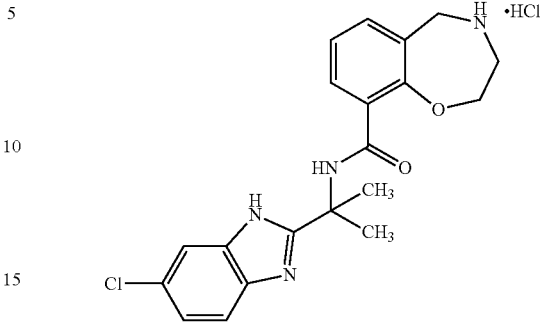

TEA (6 mL, 44.985 mmol) followed by TBTU (5.3 g, 16.511 mmol) are added to 4-chloro-o-phenylenediamine (2.1 g, 15.001 mmol) and α-(Boc-amino)isobutyric acid (3.3 g, 16.247 mmol) in THF (50 mL). After stirring for 3 d at rt, volatiles are evaporated under reduced pressure, the residue taken up in EtOAc, washed with 5% citric acid, 2M NaOH, dried over Na$_2$SO$_4$, filtered and evaporate under reduce pressure to give a residue that is purified by flash chromatography (eluent 50% EtOAc/cyclohexane) to furnish a mixture of adducts (4.2 g, 85%). Such mixture is heated at 60° C. overnight in acetic acid (35 mL). Volatiles are evaporated under reduced pressure to give a residue that is taken up in EtOAc, washed with 2M NaOH, dried over MgSO$_4$, filtered and evaporate under reduce pressure to give a residue. Such residue is suspended in DCM (25 mL) and treated with TFA (10 mL). Stirring is continued for 2 h. Volatiles are evaporated under reduced pressure and the resulting residue taken up with methyl tert-butyl ether,

| Example | Structure | Reactants | UPLC-MS $R_t$ [min], method | MS (ESI+, m/z) (M + H)$^+$ |
|---|---|---|---|---|
| 2 | | 2,3-Dihydro-5H-benzo[f][1,4]oxazepine-4,9-dicarboxylic acid 4-tert-butyl ester (3.2 mg, 0.011 mmol); 1-(1H-benzoimidazol-2-yl)-ethylamine dihydrochloride (2.3 mg, 0.010 mmol) | 1.01 4a | 337 | washed with 0.5 M HCl and evaporated under reduced pressure. The resulting mixture is taken up and evaporated twice with EtOH to give a residue (3.4 g). 2.5 mg of such residue (0.010 mmol) and DIPEA (3 µl, 0.018 mmol) in DMF (0.200 mL) are added to HATU (8 mg, 0.022 mmol), 2,3-dihydro-5H-benzo[f][1,4]oxazepine-4,9-dicarboxylic acid 4-tert-butyl ester (for the preparation, see WO2008108445) (3.2 mg, 0.011 mmol) and DIPEA (3 µl, 0.018 mmol) in DMF (0.200 mL) and stirring is continued overnight at rt. The reaction is filtered on a basic aluminum oxide pad, washed with DMF/MeOH 9:1 (600 µl) and then dried. The residue is diluted with dioxane 0.500 ml and 0.200 mL of 4N HCl solution in dioxane and stirring is continued overnight. Solvent is evaporated to give the title compound (4.2 mg, 100%).

UPLC-MS (Method 4a): $R_t$=1.25

MS (ESI+): m/z=385 (M+H)$^+$

The following examples are synthesized in analogy to the preparation of example 3:

| Example | Structure | Reactant | UPLC-MS $R_t$ [min], method | MS (ESI+, m/z) (M + H)$^+$ |
|---|---|---|---|---|
| 4 | ·HCl (structure shown) | 1-(Boc-amino)cyclopropanecarboxylic acid (0.5 g, 2.49 mmol); 2,3-Dihydro-5H-benzo[f][1,4]oxazepine-4,9-dicarboxylic acid 4-tert-butyl ester (3.2 mg, 0.011 mmol) | 1.19 4a | 383 |
| 5 | ·HCl (structure shown) | 3-((tert-butoxycarbonyl)amino)tetrahydrofuran-3-carboxylic acid (1.97 g, 8.5 mmol); 2,3-Dihydro-5H-benzo[f][1,4]oxazepine-4,9-dicarboxylic acid 4-tert-butyl ester (3.2 mg, 0.011 mmol) | 1.19 4a | 413 |

Example 6

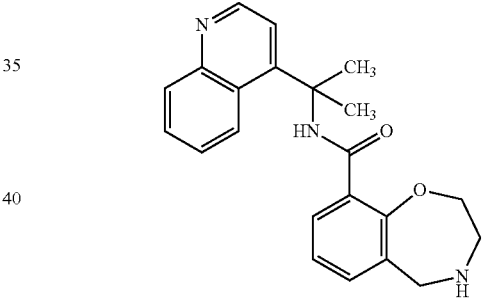

HATU (187 mg, 0.490 mmol) is added to 2,3-dihydro-5H-benzo[f][1,4]oxazepine-4,9-dicarboxylic acid 4-tert-butyl ester (for the preparation, see WO2008108445) (120 mg, 0.410 mmol), example 8i (84 mg, 0.450 mmol and DIPEA (250 µl, 1.430 mmol) in DMF (1 mL) and stirring is continued overnight at rt. The reaction is purified by preparative HPLC (stationary phase: Xbridge C18 5 µm 19×100 mm. Mobile phase: ACN/H$_2$O+NH$_4$HCO$_3$ 5 mM). Fractions containing the title compound are combined and lyophilised. The residue dissolved in MeOH (3 mL) is treated with HCl in ethyl ether (2M, 4 mL, 8 mmol). After overnight stirring, volatiles are evaporated under reduced pressure and the resulting residue redissolved in MeOH, then purified over a Waters CX 2 g cartridge, washed with MeOH and eluted with NH$_4$OH 3.5N solution in MeOH. Solvents are evaporated and the resulting residue redissolved in ACN/H$_2$O 1:1 and lyophilised to furnish the title compound (85 mg, 58%)

HPLC-MS (Method 11): $R_t$=1.98

MS (ESI+): m/z=362 (M+H)$^+$

The following examples are synthesized in analogy to the preparation of example 6:

| Example | Structure | Reactants | UPLC-MS R$_t$ [min], method | MS (ESI+, m/z) (M + H)$^+$ |
|---|---|---|---|---|
| 7 | 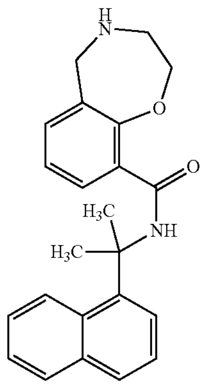 [SMILES: CC(C)(NC(=O)c1cccc2c1OCCNC2)c1cccc2ccccc12] | 2,3-Dihydro-5H-benzo[f][1,4]oxazepine-4,9-dicarboxylic acid 4-tert-butyl ester (29.3 mg, 0.100 mmol); 2-(naphthalen-1-yl)propan-2-amine (20.4 mg, 0.110 mmol) | 2.70 11 | 361 |

Example 8

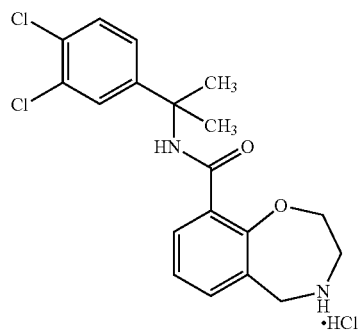 [SMILES: CC(C)(NC(=O)c1cccc2c1OCCNC2)c1ccc(Cl)c(Cl)c1 ; Cl]

HATU (45.6 mg, 0.120 mmol) is added to 2,3-dihydro-5H-benzo[f][1,4]oxazepine-4,9-dicarboxylic acid 4-tert-butyl ester (for the preparation, see WO2008108445) (29.3 mg, 0.100 mmol), 2-(3,4-dichlorophenyl)propan-2-amine (22.5 mg, 0.110 mmol and DIPEA (61 µl, 0.350 mmol) in DMF (1 mL) and stirring is continued overnight at rt. The reaction is purified by preparative HPLC (stationary phase: Xbridge C18 5 µm 19×100 mm. Mobile phase: ACN/H$_2$O+ NH$_4$HCO$_3$ 5 mM). Fractions containing the title compound are combined and lyophilised. The residue dissolved in dioxane (2 mL) is treated with HCl in dioxane (4M, 1 mL, 4 mmol). After overnight stirring, volatiles are evaporated under reduced pressure and the resulting residue redissolved in ACN/H$_2$O 1:1 (3 mL) and lyophilised to furnish the title compound (30 mg, 79%)

HPLC-MS (Method 4a): R$_t$=1.68

MS (ESI+): m/z=379 (M+H)$^+$

The following examples are synthesized in analogy to the preparation of example 8:

| Example | Structure | Reactant | UPLC-MS R$_t$ [min], method | MS (ESI+, m/z) (M + H)$^+$ |
|---|---|---|---|---|
| 9 | 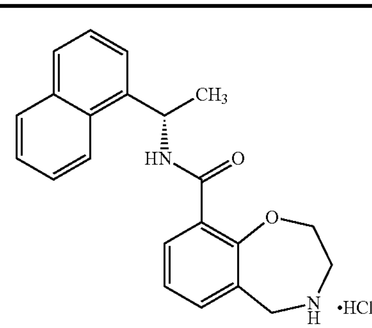 | (S)-(-)-1-(1-Naphthyl)ethyl-amine (18.8 mg, 0.110 mmol) | 1.51 4a | 347 |

-continued
| Example | Structure | Reactant | UPLC-MS $R_t$ [min], method | MS (ESI+, m/z) (M + H)+ |
|---|---|---|---|---|
| 10 | 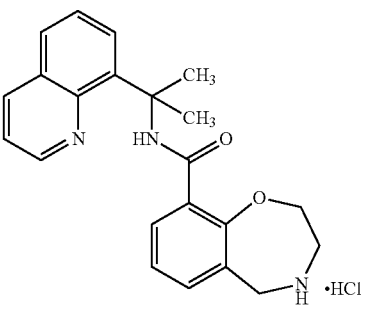 [SMILES: CC(C)(NC(=O)c1cccc2c1OCCNC2)c1cccc2cccnc12 ; Cl] | 2-(Quinolin-8-yl)propan-2-amine (24.5 mg, 0.110 mmol) | 1.49 4a | 362 |
| 11 | 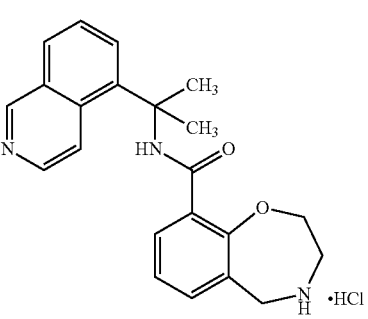 [SMILES: CC(C)(NC(=O)c1cccc2c1OCCNC2)c1cccc2cnccc12 ; Cl] | 2-(Isoquinolin-5-yl)propan-2-amine (24.5 mg, 0.110 mmol) | 1.12 4a | 362 |
| 12 | 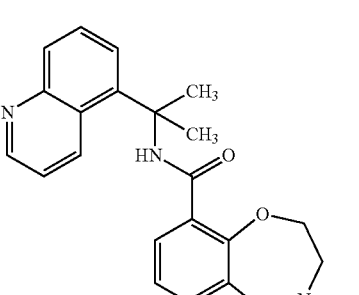 | 2-(Quinolin-5-yl)propan-2-amine (24.5 mg, 0.110 mmol) | 1.12 4a | 362 |
| 13 | 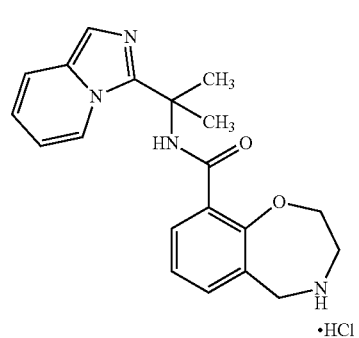 [SMILES: CC(C)(NC(=O)c1cccc2c1OCCNC2)c1ncc2ccccn12 ; Cl] | Example 34m (23.3 mg, 0.110 mmol) | 0.98 4a | 351 |

-continued

| Example | Structure | Reactant | UPLC-MS $R_t$ [min], method | MS (ESI+, m/z) $(M + H)^+$ |
|---|---|---|---|---|
| 14 | (4-(trifluoromethyl)pyridin-3-yloxy derivative) ·HCl | Example 5a (25.8 mg, 0.110 mmol) | 1.38 4a | 410 |
| 15 | (3-methylpyridin-2-yloxy derivative) ·HCl | Example 5b (19.8 mg, 0.110 mmol) | 1.43 4a | 356 |
| 16 | (4-fluorophenyl derivative) ·HCl | 1-(4-fluorophenyl)-1-methylethylamine (16.9 mg, 0.110 mmol) | 1.91 4a | 329 |
| 17 | (4-chlorophenyl derivative) ·HCl | 1-(4-chlorophenyl)-1-methylethylamine (18.7 mg, 0.110 mmol) | 2.08 4a | 345 |

Example 18

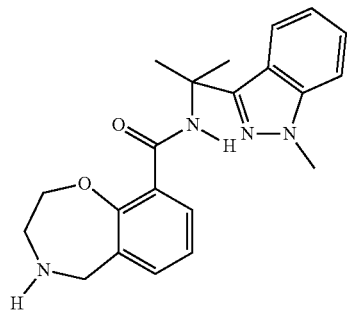 [SMILES: Cn1nc(C(C)(C)NC(=O)c2cccc3c2OCCNC3)c2ccccc21]

Example 9a (113 mg, 98% content, 0.238 mmol) is suspended in MeOH/Water 2:1 (2 mL/1 mL) and heated two times under microwaves irradation (150° C.), each time for 40 min. The reaction mixture is purified by preparative HPLC (stationary phase XTerra C18 OBD 5 μM 30×100 mm. Mobile phase: ACN/$H_2O$+$NH_4$COOH 5 mM). Fractions containing the title compound are combined and ACN is evaporated under reduced pressure. The aqueous layer is extracted with DCM, separated and the DCM is evaporated to furnish the title compound (78 mg, 90%).

HPLC-MS (Method 10): $R_t$=3.31 min

MS (ESI+): m/z=365 (M+H)$^+$

Example 19

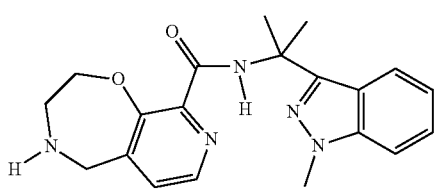 [SMILES: Cn1nc(C(C)(C)NC(=O)c2nccc3c2OCCNC3)c2ccccc21]

Hydrogen chloride 4M in dioxane (2 mL, 8.0 mmol) is added to example 9b (220 mg, 0.473 mmol) and stirring is continued for 2 h. The reaction mixture is cooled and basified by addition of methanolic ammonia. The resulting solids are filtered and volatiles are evaporated under reduced pressure to furnish the title compound (110 mg, 64%)

HPLC-MS (Method 7a): $R_t$=3.24 min

MS (APCI+): m/z=366 (M+H)$^+$

The following examples are synthesized in analogy to the preparation of example 19:

| Example | Structure | Reactant(s) | HPLC-MS $R_t$ [min], method | MS (ESI+ or APCI+, m/z) (M + H)$^+$ |
|---|---|---|---|---|
| 20 | 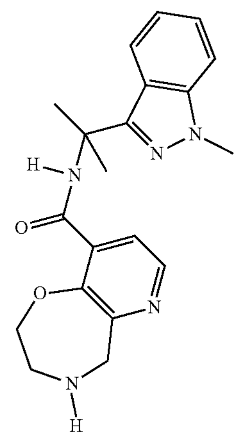 [SMILES: Cn1nc(C(C)(C)NC(=O)c2ccnc3c2OCCNC3)c2ccccc21] | Example 9c (150 mg, 0.322 mmol) | 1.92 11 | 366 |
| 21 | 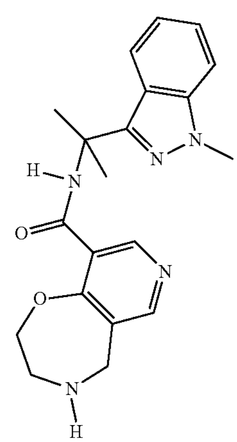 [SMILES: Cn1nc(C(C)(C)NC(=O)c2cncc3c2OCCNC3)c2ccccc21] | Example 9d (180 mg, 0.387 mmol) | 2.00 11 | 366 |
| 22 | 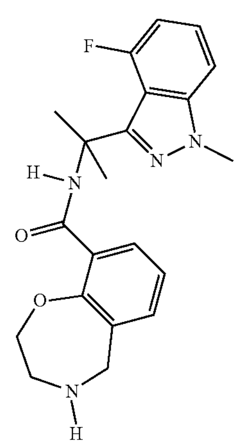 [SMILES: Cn1nc(C(C)(C)NC(=O)c2cccc3c2OCCNC3)c2c(F)cccc21] | Example 9e (90 mg, 42% content, 0.078 mmol) | 3.53 7a | 383 |

| Example | Structure | Reactant(s) | HPLC-MS R$_t$ [min], method | MS (ESI+ or APCI+, m/z) (M + H)$^+$ |
|---|---|---|---|---|
| 23 | 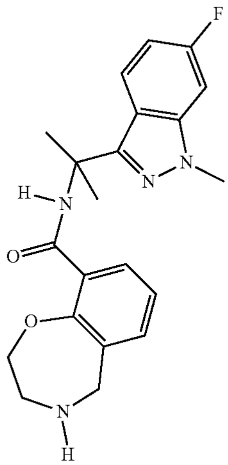 [SMILES: Cn1nc(C(C)(C)NC(=O)c2cccc3c2OCCNC3)c2ccc(F)cc21] | Example 9f (120 mg, 40% content, 0.099 mmol) | 3.52 7a | 383 |

Example 24

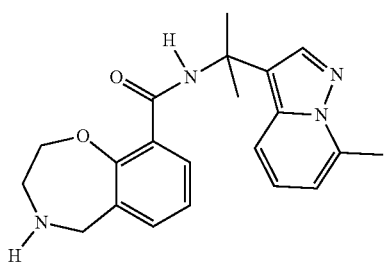 [SMILES: Cc1cccc2c(C(C)(C)NC(=O)c3cccc4c3OCCNC4)cnn12]

tert-Butyldimethylsilyl trifluoromethanesulfonate (126 µL, 0.547 mmol) is added to example 9 g (166 mg, 0.357 mmol) and 2,6-lutidine (83 µL, 0.715 mmol) in DCM (4.3 mL). After 1 h tert-butyldimethylsilyl trifluoromethanesulfonate (83 µL, 0.357 mmol) and 2,6-lutidine (54 µL, 0.465 mmol) are added to the reaction mixture. The reaction mixture is washed with saturated ammonium chloride and brine. The organic layer is separated and dried with a Phase separator cartridge and evaporated under vacuum to obtain a residue that is dissolved in THF (4.4 mL) at −30° C. and treated with tetrabutylammonium fluoride (1.0 M in THF, 379 µL, 0.379 mmol). After stirring 30 min at −30° C., volatiles are evaporated under reduced pressure and the resulting residue is purified by flash chromatography (eluent 0-10% MeOH+1% NH$_4$OH/DCM). Fractions containing the title compound are combined, volatiles are removed and the resulting residue is purified by preparative HPLC (stationary phase Xbridge C18 5 µm 19×100 mm. Mobile phase: ACN/H$_2$O+NH$_4$HCO$_3$ 5 mM). Fractions containing the title compound are combined and ACN is evaporated under reduced pressure. The aqueous layer is extracted with DCM, separated and the DCM is evaporated to furnish the title compound (4 mg, 3%).

HPLC-MS (Method 7a): R$_t$=3.47 min

MS (APCI+): m/z=365 (M+H)$^+$

The following example is synthesized in analogy to the preparation of example 19:

| Example | Structure | Reactant(s) | HPLC-MS R$_t$ [min], method | MS (APCI+, m/z) (M + H)$^+$ |
|---|---|---|---|---|
| 25 | 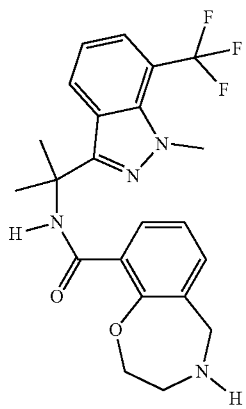 [SMILES: Cn1nc(C(C)(C)NC(=O)c2cccc3c2OCCNC3)c2cccc(C(F)(F)F)c21] | Example 9h (200 mg, 60% content, 0.225 mmol) | 4.12 7a | 433 |

The following example is synthesized in analogy to the preparation of example 18:

| Example | Structure | Reactant(s) | HPLC-MS R$_t$ [min], method | MS (APCI+, m/z) (M + H)$^+$ |
|---|---|---|---|---|
| 26 | 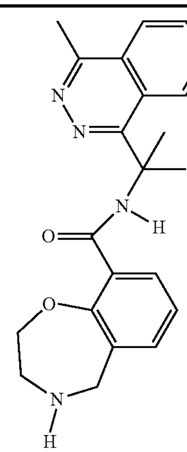 | Example 9i (55 mg, 0.115 mmol) | 2.90 7a | 377 |

The following example is synthesized in analogy to the preparation of example 19:

| Example | Structure | Reactant(s) | HPLC-MS $R_t$ [min], method | MS (ESI+, m/z) (M + H)+ |
|---|---|---|---|---|
| 27 | 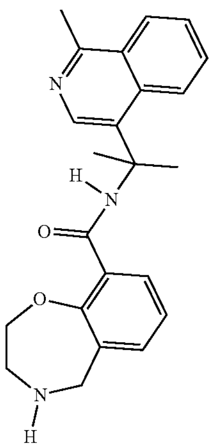 [SMILES: Cc1ncc(C(C)(C)NC(=O)c2cccc3c2OCCNC3)c2ccccc12] | Example 9j (25 mg, 0.053 mmol) | 2.17 11 | 376 |

The following example is synthesized in analogy to the preparation of example 18:

| Example | Structure | Reactant(s) | HPLC-MS $R_t$ [min], method | MS (ESI+, m/z) (M + H)+ |
|---|---|---|---|---|
| 28 | 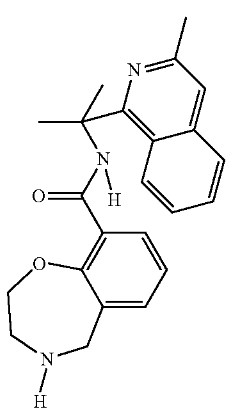 [SMILES: Cc1cc2ccccc2c(C(C)(C)NC(=O)c2cccc3c2OCCNC3)n1] | Example 9k (32 mg, 0.067 mmol) | 2.76 11 | 376 |

The following examples are synthesized in analogy to the preparation of example 19:

| Example | Structure | Reactant(s) | HPLC-MS $R_t$ [min], method | MS (ESI+ or APCI+, m/z) (M + H)+ |
|---|---|---|---|---|
| 29 | 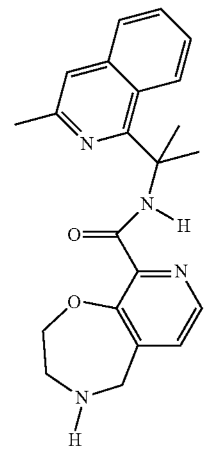 [SMILES: Cc1cc2ccccc2c(C(C)(C)NC(=O)c2nccc3c2OCCNC3)n1] | Example 9i (80 mg, 0.168 mmol) | 4.18 7a | 377 |
| 30 | 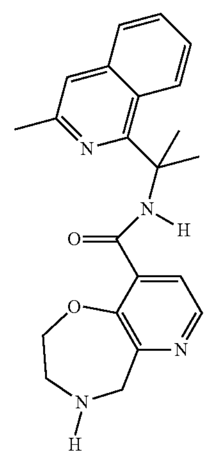 [SMILES: Cc1cc2ccccc2c(C(C)(C)NC(=O)c2ccnc3c2OCCNC3)n1] | Example 9m (40 mg, 0.084 mmol) | 4.13 7a | 377 |
| 31 | 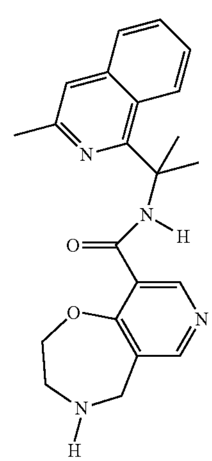 [SMILES: Cc1cc2ccccc2c(C(C)(C)NC(=O)c2cncc3c2OCCNC3)n1] | Example 9n (130 mg, 0.273 mmol) | 4.45 7a | 377 |

-continued

| Example | Structure | Reactant(s) | HPLC-MS $R_t$ [min], method | MS (ESI+ or APCI+, m/z) (M + H)+ |
|---|---|---|---|---|
| 32 | 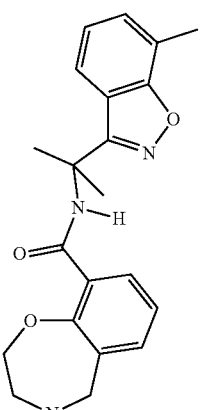 | Example 14a (130 mg, 85% content, 0.237 mmol) | 2.50 11 | 366 |

The following example is synthesized in analogy to the preparation of example 18:

| Example | Structure | Reactant(s) | HPLC-MS $R_t$ [min], method | MS (ESI+, m/z) (M + H)+ |
|---|---|---|---|---|
| 33 | 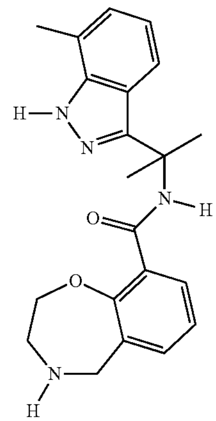 [SMILES: Cc1cccc2c(C(C)(C)NC(=O)c3cccc4c3OCCNC4)n[nH]c12] | Example 19b (76 mg, 80% content, 0.130 mmol) | 2.25 11 | 365 |

The following examples are synthesized in analogy to the preparation of example 19:

| Example | Structure | Reactant(s) | HPLC-MS $R_t$ [min], method | MS (ESI+ or APCI+, m/z) (M + H)+ |
|---|---|---|---|---|
| 34 | 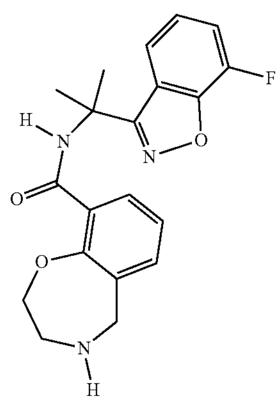 [SMILES: CC(C)(NC(=O)c1cccc2c1OCCNC2)c1noc2c(F)cccc12] | Example 24a (290 mg, 0.618 mmol) | 2.47 11 | 370 |
| 35 | 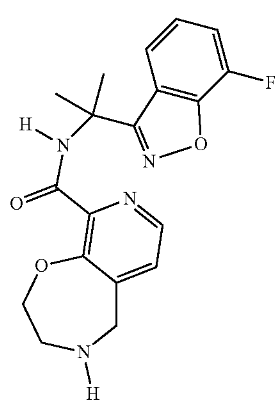 [SMILES: CC(C)(NC(=O)c1nccc2c1OCCNC2)c1noc2c(F)cccc12] | Example 24b (120 mg, 70% content, 0.179 mmol) | 3.32 7a | 371 |

-continued

| Example | Structure | Reactant(s) | HPLC-MS R$_t$ [min], method | MS (ESI+ or APCI+, m/z) (M + H)$^+$ |
|---|---|---|---|---|
| 36 | 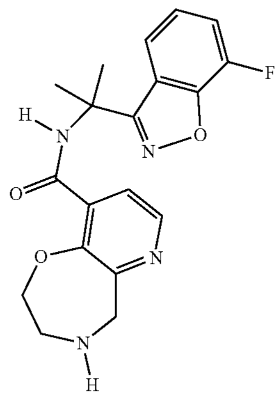 [SMILES: CC(C)(NC(=O)c1ccnc2c1OCCNC2)c1noc2c(F)cccc12] | Example 24c (20 mg, 0.043 mmol) | 3.30 7a | 371 |
| 37 | 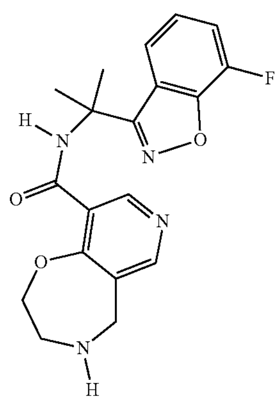 [SMILES: CC(C)(NC(=O)c1cncc2c1OCCNC2)c1noc2c(F)cccc12] | Example 24d (90 mg, 0.191 mmol) | 2.10 11 | 371 |
| 38 | 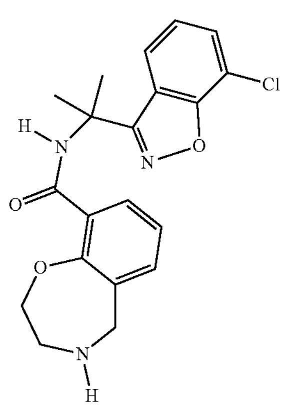 [SMILES: CC(C)(NC(=O)c1cccc2c1OCCNC2)c1noc2c(Cl)cccc12] | Example 24e (160 mg, 95% content, 0.313 mmol) | 4.00 7a | 386 |

The following examples are synthesized in analogy to the preparation of example 18:

| Example | Structure | Reactant(s) | HPLC-MS R$_t$ [min], method | MS (ESI+ or APCI+, m/z) (M + H)$^+$ |
|---|---|---|---|---|
| 39 | 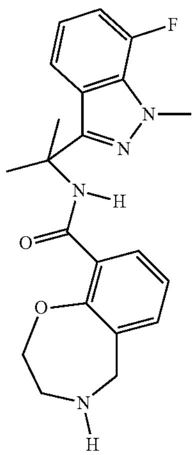 | Example 27a (129 mg, 0.267 mmol) | 2.48 11 | 383 |
| 40 | 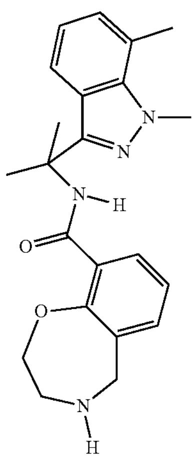 [SMILES: Cc1cccc2c(C(C)(C)NC(=O)c3cccc4c3OCCNC4)nn(C)c12] | Example 27b (55 mg, 92% content, 0.106 mmol) | 2.58 11 | 379 |
| 41 | 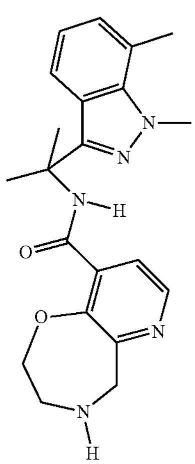 | Example 27c (90 mg, 0.188 mmol) | 3.55 7a | 380 |
| 42 | | Example 27d (75 mg, 84% content, 0.131 mmol) | 2.19 11 | 380 |

The following example is synthesized in analogy to the preparation of example 19:

| Example | Structure | Reactant(s) | HPLC-MS R$_t$ [min], method | MS (ESI+, m/z) (M + H)$^+$ |
|---|---|---|---|---|
| 43 | 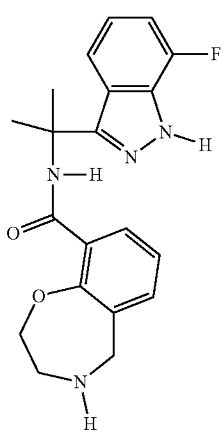 [SMILES: CC(C)(NC(=O)c1cccc2c1OCCNC2)c1n[nH]c2c(F)cccc12] | Example 27e (69 mg, 0.147 mmol) | 2.13 11 | 369 |

The following example is synthesized in analogy to the preparation of example 18:

| Example | Structure | Reactant(s) | HPLC-MS R$_t$ [min], method | MS (ESI+ or APCI+, m/z) (M + H)$^+$ |
|---|---|---|---|---|
| 44 | 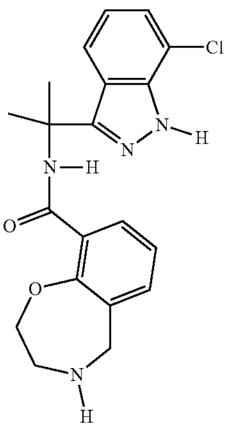 [SMILES: CC(C)(NC(=O)c1cccc2c1OCCNC2)c1n[nH]c2c(Cl)cccc12] | Example 27f (109 mg, 85% content, 0.191 mmol) | 3.60 7a | 385 |
| 45 | 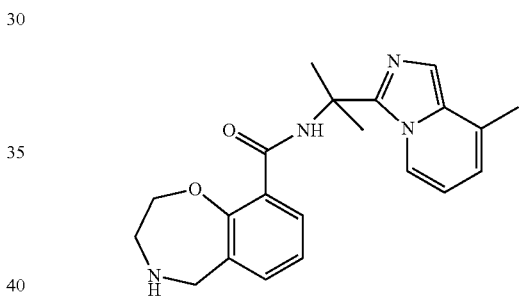 | Example 31a (120 mg, 0.252 mmol) | 3.24 7a | 377 |
| 46 | | Example 31b (110 mg, 0.238 mmol) | 1.92 11 | 363 |

Example 47

Example 48a (332 mg, 0.68 mmol) is suspended in diethyl ether and then hydrogen chloride 2M in ethyl ether (3.55 mL, 7.1 mmol) is added. The mixture is stirred until the Boc group has been completely removed and then the solvent is evaporated. The mixture is redissolved in methanol, loaded onto a prewashed SCX cartridge, washed with methanol and eluted with a solution of ammonia in methanol. The solvent is evaporated and the residue dried under vacuum. The residue is purified by preparative RP-HPLC to give the title compound (145 mg).

HPLC-MS (Method 7a): R$_t$=3.04 min

MS (APCI+): m/z=365 (M+H)$^+$

The following examples are synthesized in analogy to the preparation of example 95 using the acids and solvent (if used) described. RP-HPLC purification is not required unless specified:

| Example | Structure | Reactant, acid, solvent | HPLC-MS $R_t$ [min], method | MS (ESI+/ESI- or APCI+, m/z) |
|---|---|---|---|---|
| 48 | 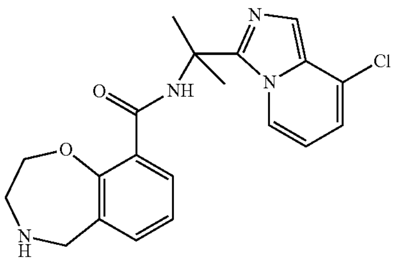 [SMILES: CC(C)(NC(=O)c1cccc2c1OCCNC2)c1ncc2c(Cl)cccn12] | Example 47b, (119 mg, 0.25 mmol), TFA (0.3 mL), DCM (3 mL) | 2.18 11 | 383 [M − H]⁻ |
| 49 | 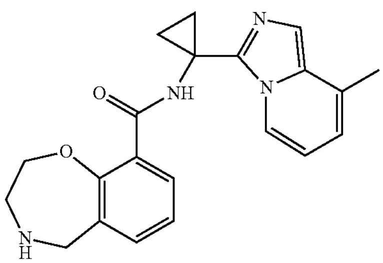 [SMILES: Cc1cccn2c(C3(NC(=O)c4cccc5c4OCCNC5)CC3)ncc12] | Example 48c (150 mg, 0.32 mmol) TFA (2 mL) | 3.20 7a | 363 [M + H]⁺ |
| 50 | 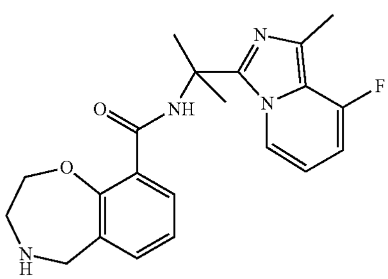 [SMILES: Cc1nc(C(C)(C)NC(=O)c2cccc3c2OCCNC3)n2cccc(F)c12] | Example 48d (40 mg, 0.08 mmol) TFA (0.3 mL), DCM (3 mL) Purification by RP-HPLC | 3.30 7a | 383 [M + H]⁺ |
| 51 | 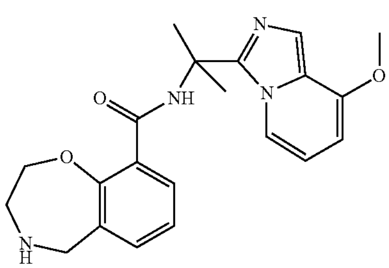 [SMILES: COc1cccn2c(C(C)(C)NC(=O)c3cccc4c3OCCNC4)ncc12] | Example 48e (69 mg, 0.14 mmol) TFA (0.3 mL), DCM (3 mL) | 2.02 11 | 381 [M + H]⁺ |
| 52 | 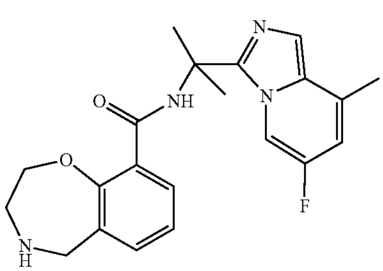 [SMILES: Cc1cc(F)cn2c(C(C)(C)NC(=O)c3cccc4c3OCCNC4)ncc12] | Example 48f (65 mg, 0.13 mmol) TFA (1 mL), DCM (5 mL) | 2.14 11 | 383 [M + H]⁺ |

| Example | Structure | Reactant, acid, solvent | HPLC-MS R$_t$ [min], method | MS (ESI+/ESI- or APCI+, m/z) |
|---|---|---|---|---|
| 53 | ·HCl | Example 48g (181 mg, 0.38 mmol) 2M HCl in ether (1.9 mL), MeOH (2 mL) No SCX | 2.71 12a | 379 [M + H]$^+$ |
| 54 | 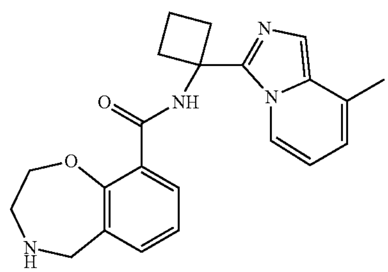 [SMILES: Cc1cccn2c(C3(NC(=O)c4cccc5c4OCCNC5)CCC3)ncc12] | Example 48h (65 mg, 0.13 mmol) 2M HCl in ether (2.1 mL), MeOH (3 mL) | 3.17 7a | 377 [M + H]$^+$ |
| 55 | 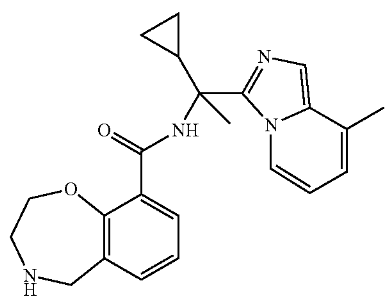 [SMILES: Cc1cccn2c(C(C)(NC(=O)c3cccc4c3OCCNC4)C3CC3)ncc12] | Example 48i (40 mg, 0.10 mmol) TFA (1 mL), DCM (5 mL) | 3.58 7a | 391 [M + H]$^+$ |
| 56 | 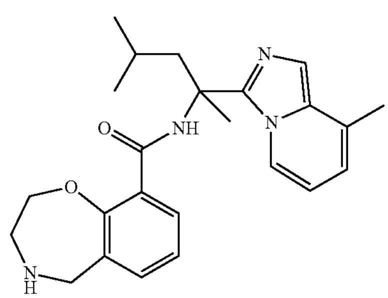 [SMILES: Cc1cccn2c(C(C)(CC(C)C)NC(=O)c3cccc4c3OCCNC4)ncc12] | Example 48j (174 mg, 0.34 mmol) TFA (1 mL), DCM (3 mL) | 2.63 11 | 407 [M + H]$^+$ |
| 57 | 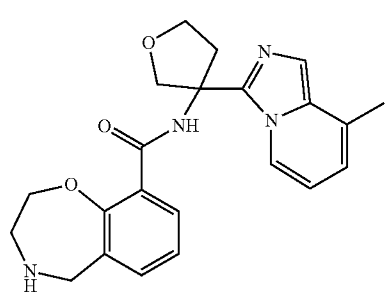 [SMILES: Cc1cccn2c(C3(NC(=O)c4cccc5c4OCCNC5)CCOC3)ncc12] | Example 48k (103 mg, 0.20 mmol) TFA (1 mL), DCM (3 mL) | 1.91 11 | 393 [M + H]$^+$ |

| Example | Structure | Reactant, acid, solvent | HPLC-MS R$_t$ [min], method | MS (ESI+/ESI– or APCI+, m/z) |
|---|---|---|---|---|
| 58 | 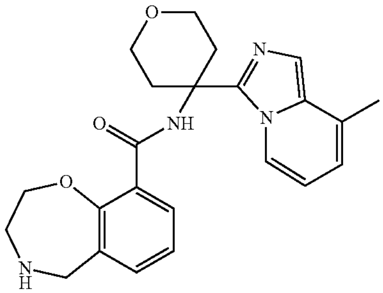 [SMILES: Cc1cccn2c(C3(NC(=O)c4cccc5c4OCCNC5)CCOCC3)ncc12] | Example 48l (160 mg, 0.32 mmol) TFA (1 mL), DCM (3 mL) | 1.97 11 | 407 [M + H]$^+$ |
| 59 | 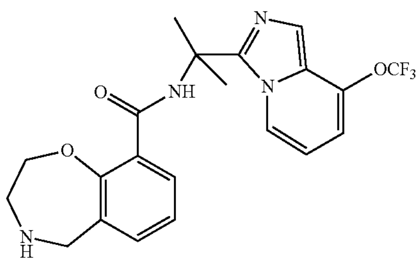 [SMILES: CC(C)(NC(=O)c1cccc2c1OCCNC2)c1ncc2c(OC(F)(F)F)cccn12] | Example 48m (30 mg, 0.05 mmol) TFA (2 mL), Purification by rP-HPLC | 3.63 7a | 435 [M + H]$^+$ |
| 60 | 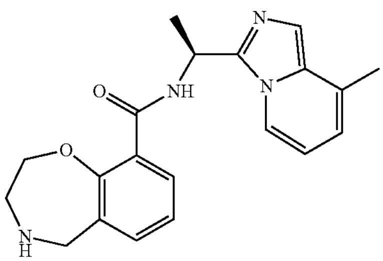 [SMILES: Cc1cccn2c([C@H](C)NC(=O)c3cccc4c3OCCNC4)ncc12] | Example 48n (170 mg, 0.38 mmol) TFA (1 mL), DCM (5 mL) | 3.63 7a | 351 [M + H]$^+$ |
| 61 | 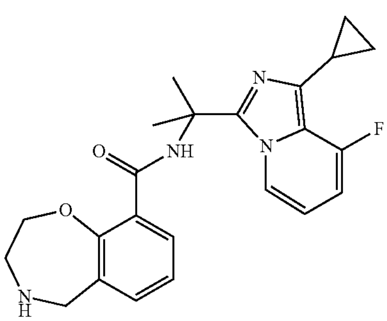 [SMILES: CC(C)(NC(=O)c1cccc2c1OCCNC2)c1nc(C2CC2)c2c(F)cccn12] | Example 48o (40 mg, 0.08 mmol) TFA (2 mL) | 2.88 11 | 409 [M + H]$^+$ |
| 62 | 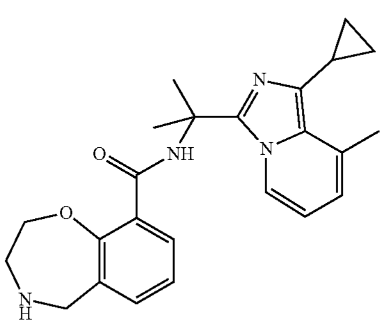 [SMILES: Cc1cccn2c(C(C)(C)NC(=O)c3cccc4c3OCCNC4)nc(C3CC3)c12] | Example 48p (63 mg, 0.12 mmol) 2M HCl in ether (0.6 mL), MeOH (4 mL) | 3.95 7a | 405 [M + H]$^+$ |

-continued

| Example | Structure | Reactant, acid, solvent | HPLC-MS R$_t$ [min], method | MS (ESI+/ESI- or APCI+, m/z) |
|---|---|---|---|---|
| 63 | 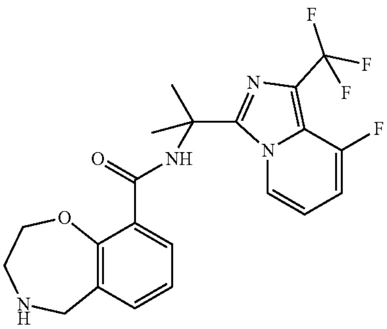 [SMILES: CC(C)(NC(=O)c1cccc2c1OCCNC2)c1nc(C(F)(F)F)c2c(F)cccn12] | Example 48q (16 mg, 0.03 mmol) 4M HCl in dioxane (5 mL), Purification by RP-HPLC | 2.69 11 | 435 [M − H]$^-$ |
| 64 | 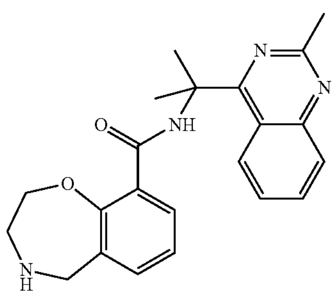 [SMILES: Cc1nc(C(C)(C)NC(=O)c2cccc3c2OCCNC3)c2ccccc2n1] | Example 48r (46 mg, 0.10 mmol) TFA (0.3 mL), DCM (3 mL) | 2.67 12a | 377 [M + H]$^+$ |
| 65 | 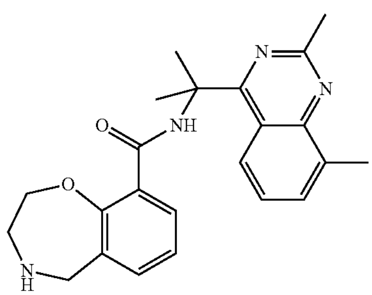 [SMILES: Cc1nc(C(C)(C)NC(=O)c2cccc3c2OCCNC3)c2cccc(C)c2n1] | Example 48s (50 mg, 0.10 mmol) TFA (2 mL) Purification by RP-HPLC | 3.89 7a | 391 [M + H]$^+$ |
| 66 | 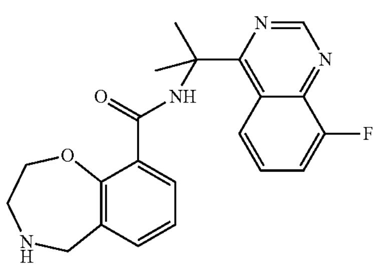 [SMILES: CC(C)(NC(=O)c1cccc2c1OCCNC2)c1ncnc2c(F)cccc12] | Example 48t (40 mg, 0.08 mmol) TFA (1 mL) DCM (5 mL) Purification by RP-HPLC | 2.82 7a | 381 [M + H]$^+$ |
| 67 | 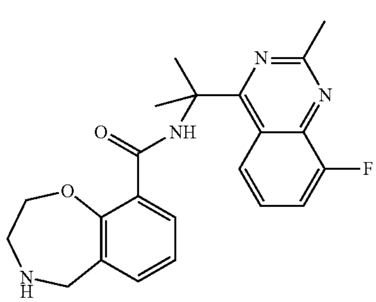 [SMILES: Cc1nc(C(C)(C)NC(=O)c2cccc3c2OCCNC3)c2cccc(F)c2n1] | Example 48u (40 mg, 0.08 mmol) TFA (1 mL) DCM (5 mL) Purification by RP-HPLC | 3.04 10 | 395 [M + H]$^+$ |

-continued

| Example | Structure | Reactant, acid, solvent | HPLC-MS R$_t$ [min], method | MS (ESI+/ESI– or APCI+, m/z) |
|---|---|---|---|---|
| 68 | 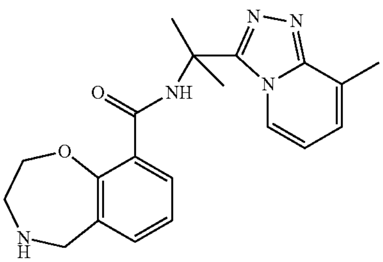 [SMILES: Cc1cccn2c(C(C)(C)NC(=O)c3cccc4c3OCCNC4)nnc12] | Example 48v (40 mg, 0.09 mmol) TFA (1 mL) | 1.60 11 | 364 [M – H]⁻ |
| 69 | 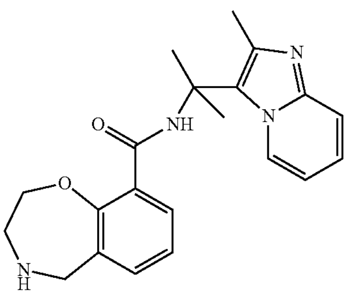 [SMILES: Cc1nc2ccccn2c1C(C)(C)NC(=O)c1cccc2c1OCCNC2] | Example 48v (60 mg, 0.13 mmol) TFA (2 mL) | 2.53 7a | 365 [M + H]⁺ |
| 70 | 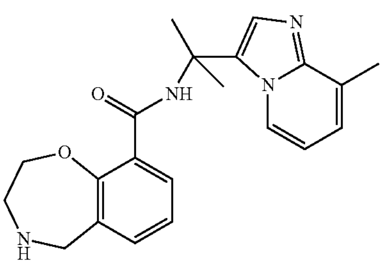 [SMILES: Cc1cccn2c(C(C)(C)NC(=O)c3cccc4c3OCCNC4)cnc12] | Example 48x (82 mg, 0.18 mmol) TFA (1 mL) DCM (5 mL) Purification by flash chromatography (0-10% MeOH in DCM) | 3.13 7a | 365 [M + H]⁺ |
| 71 | 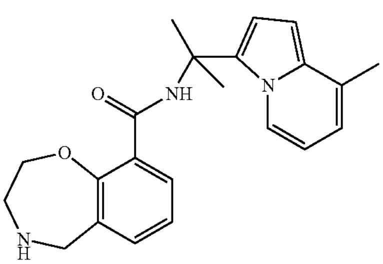 [SMILES: Cc1cccn2c(C(C)(C)NC(=O)c3cccc4c3OCCNC4)ccc12] | Example 48y (90 mg, 0.19 mmol) TFA (1 mL) DCM (5 mL) Purification by RP-HPLC | 4.17 7a | 364 [M + H]⁺ |
| 72 | 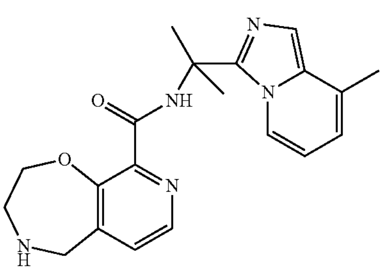 [SMILES: Cc1cccn2c(C(C)(C)NC(=O)c3nccc4c3OCCNC4)ncc12] | Example 49a (30 mg, 0.06 mmol) TFA (1 mL) DCM (5 mL) Purification by RP-HPLC | 2.92 7a | 366 [M + H]⁺ |

| Example | Structure | Reactant, acid, solvent | HPLC-MS R_t [min], method | MS (ESI+/ESI- or APCI+, m/z) |
|---|---|---|---|---|
| 73 | 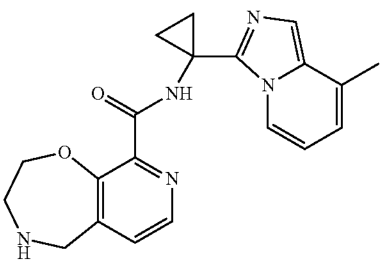 [SMILES: Cc1cccn2c(C3(NC(=O)c4nccc5c4OCCNC5)CC3)ncc12] | Example 49b (37 mg, 0.08 mmol) TFA (1 mL) DCM (5 mL) Purification by RP-HPLC | 1.70 11 | 364 [M + H]+ |
| 74 | 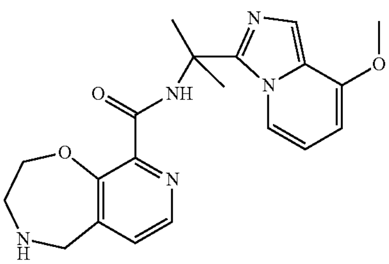 [SMILES: COc1cccn2c(C(C)(C)NC(=O)c3nccc4c3OCCNC4)ncc12] | Example 49c (30 mg, 0.06 mmol) TFA (1 mL) DCM (5 mL) | 1.58 11 | 382 [M + H]+ |
| 75 | 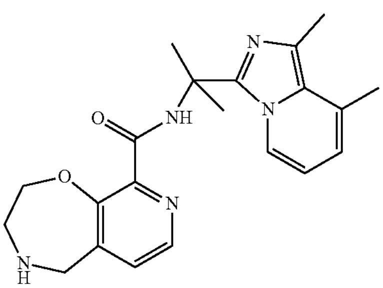 [SMILES: Cc1cccn2c(C(C)(C)NC(=O)c3nccc4c3OCCNC4)nc(C)c12] | Example 49d (46 mg, 0.10 mmol) TFA (1 mL) DCM (3 mL) | 2.05 11 | 380 [M + H]+ |
| 76 | 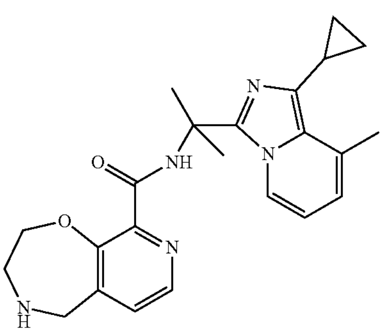 [SMILES: Cc1cccn2c(C(C)(C)NC(=O)c3nccc4c3OCCNC4)nc(C3CC3)c12] | Example 49e (37 mg, 0.07 mmol) TFA (1 mL) DCM (5 mL) Purification by RP-HPLC | 2.23 11 | 406 [M + H]+ |
| 77 | 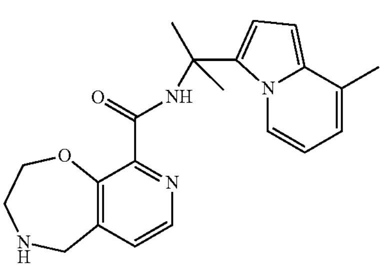 [SMILES: Cc1cccn2c(C(C)(C)NC(=O)c3nccc4c3OCCNC4)ccc12] | Example 49f (75 mg, 0.16 mmol) TFA (1 mL) DCM (5 mL) | 3.85 7a | 365 [M + H]+ |

| Example | Structure | Reactant, acid, solvent | HPLC-MS R$_t$ [min], method | MS (ESI+/ESI- or APCI+, m/z) |
|---|---|---|---|---|
| 78 | | Example 50a (32 mg) TFA (1 mL) DCM (5 mL) Purification by RP-HPLC | 1.69 11 | 366 [M + H]$^+$ |
| 78 | | Example 51a (69 mg, 0.15 mmol) TFA (1 mL) DCM (3 mL) | 1.72 11 | 366 [M + H]$^+$ | cAMP ASSAY

Method description for cAMP assay with human Somatostatin 4 receptor.

The activation of the SSTR4 receptor (Gi coupled) causes an inhibition of intracellular cAMP after stimulation with Forskolin, which can be quantifiable by use of a suitable assay Kit and an adequate plate reader. This technique is used to characterize pharmacological effects of the SSTR4 receptor agonists by use of hSSTR4 expressing H4 cells.

Description:

Compounds are dissolved and diluted in DMSO. The final test solution contains 1 DMSO. The cAMP standard (Lance cAMP 384 Kit; PerkinElmer, Cat #AD0264) is prepared in assay buffer (HBSS with 0.1% BSA, 5 mM HEPES, 0.5 M IBMX, pH 7.4) containing 1% DMSO and the cAMP standard curve is included at least on one plate. Cells are centrifuged and suspended in assay buffer (incl. 1:100 diluted Alexa antibody).

For the assay 5 μl of a cell suspension (approximately 5000 cells/well)—incl. Alexa antibody (diluted 1:100) are added into a 384 well MTP microtitre plate excepting one row or column (depending on the plate layout), which is reserved for the standard curve. Then 2 μl of compound sample is added as concentration response curve (e.g. 1e-5 M to 6e-10 M), usually in triplicates. Each assay contains incubations with vehicle controls instead of compound as controls for non-inhibited cAMP generation (100% CTL; 'high values') and incubations with 1 μM Somatosatin as controls for full inhibition and background (0% CTL; 'low values'). After approximately 10-15 min incubation time 3 μl Forskolin (dissolved in DMSO, final conc. 15 μM) is added. Then the plates are shaken briefly and incubated for 60 min at room temperature. After 60 min 10 μl of the detection mix is added into all wells followed by an additional incubation period of 1 h. The plates are read in a suitable plate reader.

The analysis of the data is based on the "ratio" of the time-resolved fluorescence measurements of donor and acceptor fluorophore (Ex: 320 nm; Em1: 665 nm; Em2: 615 nm; ratio 665/615). From this ratio, cAMP concentrations are calculated from standard curve and the EC50 is estimated by least square curve fit program.

Radioligand Binding Assays

Method description for binding assays with human Somatostatin receptors by use of CHO cell membranes expressing recombinant human SSTR1 or human SSTR2 or human SSTR3 or human SSTR4 or human SSTR5

Receptor binding assays refer to a technique in which labeled receptor ligands are used to detect binding to a receptor. In competition experiments test compounds, which are not labeled, compete with the binding side of a labeled ligand. The displacement of the labeled ligand by the test compound leads to a decreased signal.

Procedure:

For the binding experiments 200 μL of membrane homogenate from one of the following protein amounts is used: hSSTR1 (40 μg/well); hSSTR2 (25 μg/well); hSSTR3 (1.5 μg/well); hSSTR4 (0.5 μg/well); hSSTR5 (25 μg/well). The homogenate is incubated with 0.05 nM of radioligand ([3-125I-Tyr]-Somatostatin-(1-14)) in addition to increasing concentrations of a test compound or vehicle (100% binding) in a total volume of 250 μL using a Hepes buffer (10 mM, EDTA 1 mM, MgCl$_2$ 5 mM, pH7.6, BSA 0.5%, Bacitracin 0.003%, DMSO 1% for 180 min at room temperature. The incubation is terminated by filtration with ice cold NaCl 0.9% through polyethyleneimine treated (0.3%) GF/B glass fiber filters using a cell harvester. The protein-bound radioactivity is measured in a suitable reader. The non-specific binding is defined as radioactivity bound in the presence of 1 μM Somatostatin-14 during the incubation period.

The analysis of the concentration-binding curves is performed by computer-assisted nonlinear least square curve fitting method using the model of one receptor binding site.

Metabolic Stability

The metabolic stability of the compounds according to the invention may be investigated as follows:

The metabolic degradation of the test compound is assayed at 37° C. with pooled human liver microsomes. The final incubation volume of 100 μl per time point contains TRIS buffer pH 7.6 at room temperature (0.1 M), magnesium chloride (5 mM), microsomal protein (1 mg/mL) and the test compound at a final concentration of 1 μM. Following a short preincubation period at 37° C., the reactions are initiated by addition of beta-nicotinamide adenine dinucleotide phosphate, reduced form (NADPH, 1 mM), and terminated by transferring an aliquot into solvent after different time points. After centrifugation (10000 g, 5 min), an aliquot of the supernatant is assayed by LC-MS/MS for the amount of parent compound. The half-life is determined by the slope of the semi-logarithmic plot of the concentration-time profile.

Biological Activity

The agonstic activity of the above described examples is demonstrated by the data in Table 2. The EC50 values were obtained with the aid of the above decribed cAMP ASSAY.

TABLE 2

Agonistic activity of compounds of the present invention.

| Example | SSTR4 agonism EC50 [nM] |
|---|---|
| 1 | 58.1 |
| 2 | 302.0 |
| 3 | 45.1 |
| 4 | 342.5 |
| 5 | 750.5 |
| 6 | 8.4 |
| 7 | 1.4 |
| 8 | 22.3 |
| 9 | 2.8 |
| 10 | 42.1 |
| 11 | 423.0 |
| 12 | 98.4 |
| 13 | 14.3 |
| 14 | 132.2 |
| 15 | 28.1 |
| 16 | 33.0 |
| 17 | 8.2 |
| 18 | 4.4 |
| 19 | 14.6 |
| 20 | 17.5 |
| 21 | 35.5 |
| 22 | 8.0 |
| 23 | 0.9 |
| 24 | 4.4 |
| 25 | 6.8 |
| 26 | 2.5 |
| 27 | 0.6 |
| 28 | 4.2 |
| 29 | 19.9 |
| 30 | 19.0 |
| 31 | 37.0 |
| 32 | 2.8 |
| 33 | 0.8 |
| 34 | 18.2 |
| 35 | 349.5 |
| 36 | 380.5 |
| 37 | 1595.0 |
| 38 | 2.9 |
| 39 | 2.1 |
| 40 | 2.2 |
| 41 | 18.3 |
| 42 | 15.8 |
| 43 | 2.2 |
| 44 | 1.3 |
| 45 | 9.2 |
| 46 | 9.2 |

TABLE 2-continued

Agonistic activity of compounds of the present invention.

| Example | SSTR4 agonism EC50 [nM] |
|---|---|
| 47 | 2.0 |
| 48 | 1.7 |
| 49 | 1.5 |
| 50 | 2.0 |
| 51 | 4.3 |
| 52 | 8.7 |
| 53 | 1.6 |
| 54 | 15.2 |
| 55 | 133.7 |
| 56 | 1975.0 |
| 57 | 354.5 |
| 58 | 2485.0 |
| 59 | 30.5 |
| 60 | 94.4 |
| 61 | 6.3 |
| 62 | 4.0 |
| 63 | 32.3 |
| 64 | 22.3 |
| 65 | 21.4 |
| 66 | 30.0 |
| 67 | 75.0 |
| 68 | 37.9 |
| 69 | 17.6 |
| 70 | 11.3 |
| 71 | 2.9 |
| 72 | 13.6 |
| 73 | 39.3 |
| 74 | 106.0 |
| 75 | 10.4 |
| 76 | 145.0 |
| 77 | 22.6 |
| 78 | 33.6 |
| 79 | 31.3 |

Selectivity

Selectivity data was obtained with the aid of the above described radioligand binding assays.

TABLE 3

Selectivity of compounds of the present invention for SSTR4 over other SSTRs.

| Ex | SSTR4 binding Ki [nM] | SSTR1 binding Ki [nM] | SSTR2 binding Ki [nM] | SSTR3 binding Ki [nM] | SSTR5 binding Ki [nM] |
|---|---|---|---|---|---|
| 6 | 103.9 | 9010 | 9630 | 8710 | 9860 |
| 18 | 39.5 | 7820 | 9630 | 8710 | 9860 |
| 19 | 613.0 | 9450 | 9600 | 8620 | 9750 |
| 20 | 573.5 | 9450 | 9600 | 8620 | 9750 |
| 26 | 65.0 | 9450 | 9600 | 8620 | 9750 |
| 33 | 21.7 | 9450 | 9600 | 8620 | 9750 |
| 39 | 29.1 | 9010 | 9630 | 8710 | 9860 |
| 42 | 532.0 | 9450 | 9600 | 8620 | 9750 |
| 47 | 53.2 | 9010 | 9630 | 8710 | 9860 |

Stability

Stability data was obtained with the above described experimental procedure.

TABLE 4

Stability of compounds of the present invention in human liver microsomes.

| Example | Half-life $t_{1/2}$ [min] |
|---|---|
| 6 | 130 |
| 7 | 32 |

TABLE 4-continued

Stability of compounds of the present invention in human liver microsomes.

| Example | Half-life $t_{1/2}$ [min] |
|---|---|
| 8 | 4.4 |
| 9 | 19 |
| 13 | >130 |
| 17 | 14 |
| 18 | 73 |
| 19 | 130 |
| 20 | >130 |
| 22 | 42 |
| 23 | 67 |
| 24 | 110 |
| 26 | >130 |
| 27 | >130 |
| 28 | 30 |
| 29 | 27 |
| 32 | 54 |
| 33 | 99 |
| 38 | 35 |
| 39 | 51 |
| 40 | 31 |
| 41 | >130 |
| 42 | >130 |
| 43 | 87 |
| 44 | >130 |
| 45 | 110 |
| 46 | >130 |
| 47 | >130 |
| 48 | 85 |
| 49 | 93 |
| 50 | 83 |
| 51 | 130 |
| 53 | 72 |
| 61 | 45 |
| 62 | 32 |
| 64 | >130 |
| 70 | >130 |
| 71 | 11 |
| 72 | >130 |
| 75 | >130 |
| 78 | >130 |
| 79 | >130 |

The invention claimed is:

1. A compound of formula (I)

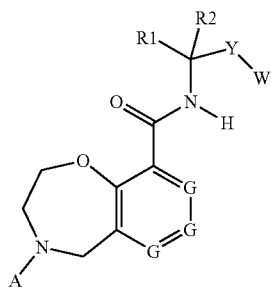

(I)

wherein
A is selected from the group $A^1$ consisting of
H and $C_{1-6}$-alkyl;
G is selected from the group $G^1$ consisting of CH and N, wherein up to two G are
N, the other(s) being CH;
$R^1$ and $R^2$ are independently selected from the group $R^{1.1}$, $R^{2.1}$ consisting of
H, $C_{1-6}$-alkyl and $C_{3-6}$-cycloalkyl, wherein at least one of $R^1$ or $R^2$ is $C_{1-6}$-alkyl or $C_{3-6}$-cycloalkyl, or wherein $R^1$ and $R^2$ together form a 2- to 5-membered alkylene-bridge incorporating 0 to 2 heteroatoms independently selected from the group consisting of N, O and S wherein the $C_{1-6}$-alkyl, the $C_{3-6}$-cycloalkyl or the alkylene-bridge is optionally substituted with halogens;

W is selected from the group $W^1$ consisting of a
mono- or bicyclic aryl, mono- or bicyclic heteroaryl, mono- or bicyclic heterocyclyl and mono- or bicyclic cycloalkyl,
wherein each of these ring systems are optionally substituted with one or more $R^3$, and wherein the heteroaryl comprises up to 4 heteroatoms and one or two 5- or 6-membered ring(s);

$R^3$ is independently selected from the group $R^3$ consisting of
$C_{1-6}$-alkyl, $C_{3-8}$-cycloalkyl, $C_{1-6}$-alkyl-O—, benzyl, halogen, HO—, NC-, mono- or bicyclic heteroaryl, and 5- or 6-membered monocyclic heterocyclyl containing one heteroatom selected from the group consisting of N, O and S(O)$_r$, wherein the heteroaryl contains up to 4 heteroatoms and one or two 5- or 6-membered ring(s), and r is 0, 1 or 2, wherein the $C_{1-6}$-alkyl, $C_{3-8}$-cycloalkyl, $C_{1-6}$-alkyl-O—, benzyl, heteroaryl and the heterocyclyl are optionally substituted with halogens, HO—, acetyl, $C_{1-6}$-alkyl-O—, oxo, $R^4$—S(O)$_2$—, with $R^4$ being aryl, $C_{3-6}$-cycloalkyl and/or $C_{1-6}$-alkyl;

Y is selected from the group $Y^1$ consisting of a bond and —CH$_2$O—;
or a salt thereof.

2. The compound according to claim 1, wherein A is H.

3. The compound according to claim 1, wherein
W is selected from the group consisting of a
mono- or bicyclic aryl, a mono- or bicyclic heteroaryl and a mono- or bicyclic heterocyclyl,
wherein each of these ring systems are optionally substituted with one or more $R^3$, and wherein the heteroaryl comprises up to 4 heteroatoms and one or two 5- or 6-membered ring(s).

4. The compound according to claim 1, wherein
W is selected from the group consisting of

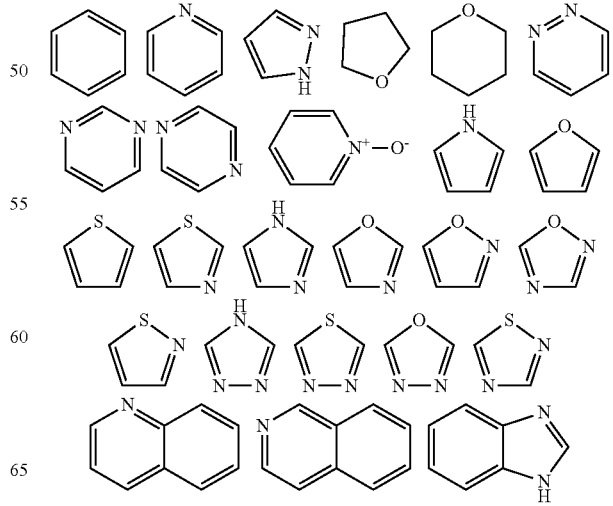

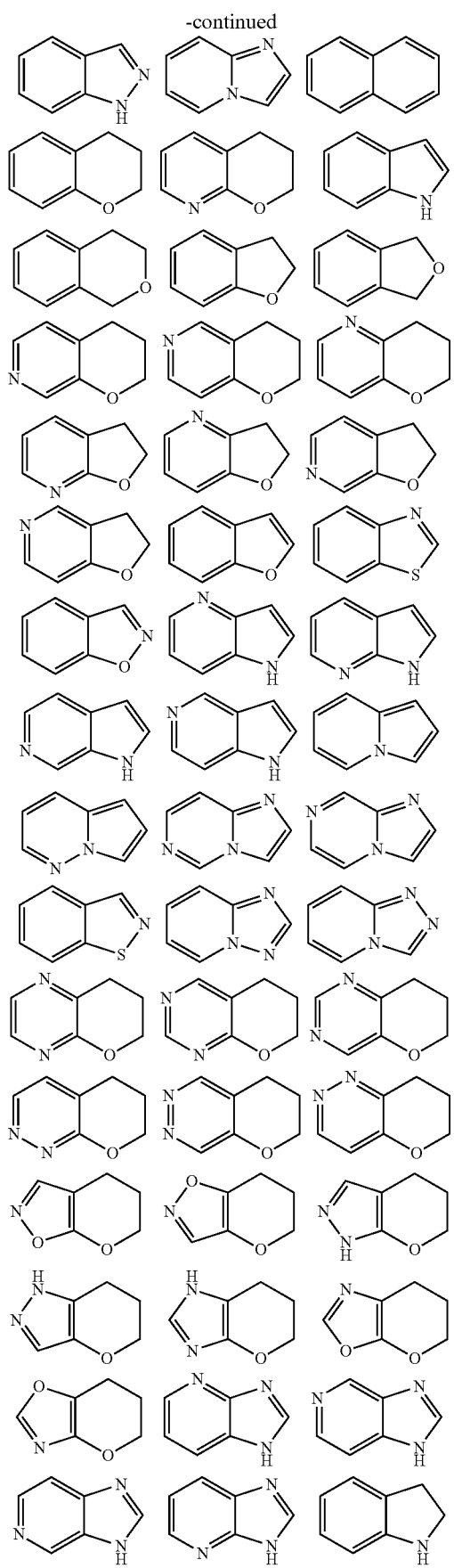
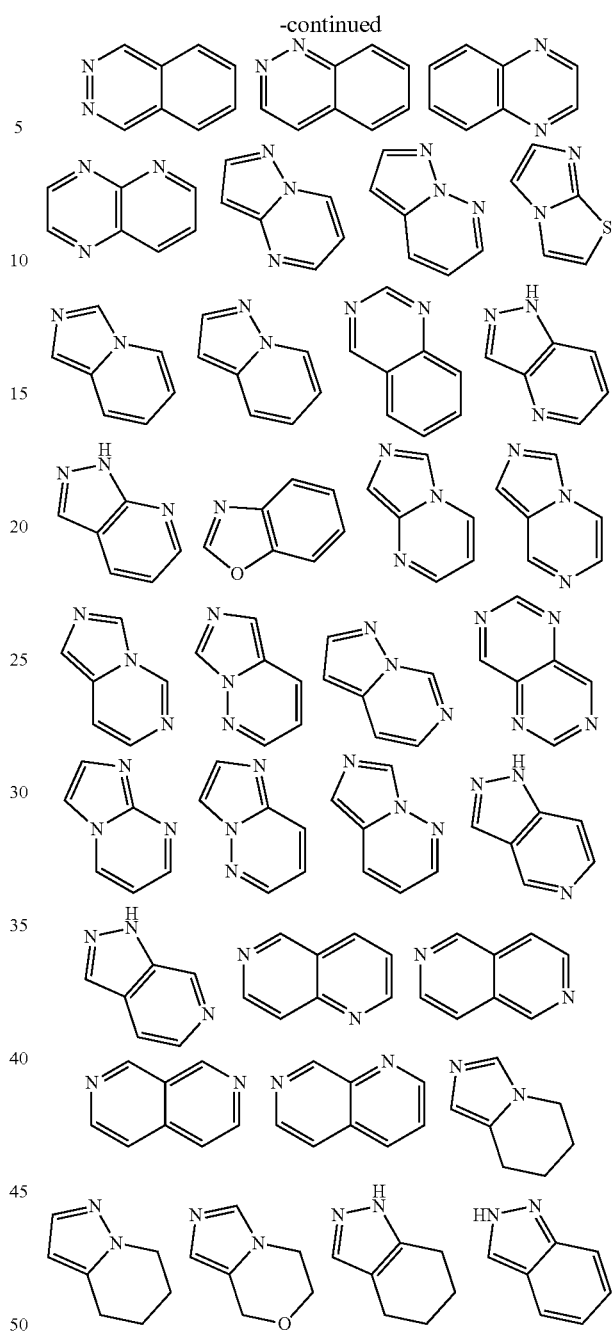
wherein each of these ring systems are optionally substituted with one or more $R^3$.
5. The compound according to claim 1, wherein W is selected from the group consisting of
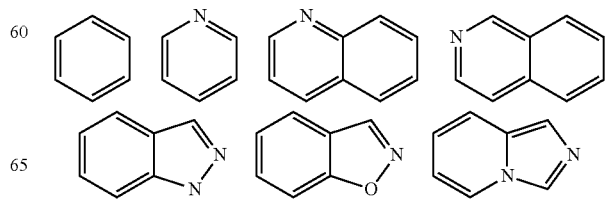

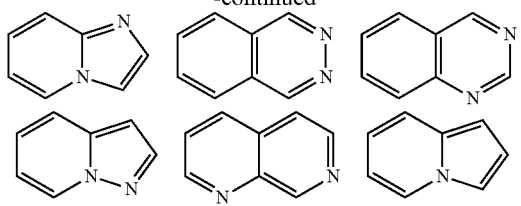

wherein each of these ring systems are optionally substituted with one to three R³.

6. The compound according to claim 1, wherein G is CH or N, wherein up to one G is N, the others being CH.

7. The compound according to claim 1, wherein R³ is selected from the group consisting of
$C_{1-3}$-alkyl, $C_{3-6}$-cycloalkyl, $C_{1-3}$-alkyl-O—, halogen, and NC—,
wherein, when in case R³ is connected to N-atoms of W, R³ is selected from the group consisting of $C_{1-3}$-alkyl and $C_{3-6}$-cycloalkyl,
wherein the $C_{1-3}$-alkyl, $C_{3-6}$-cycloalkyl, and the $C_{1-3}$-alkyl-O-substituents are optionally substituted with halogens.

8. The compound according to claim 1, wherein R³ is selected from the group consisting of
$H_3C$—, F— and $F_3C$—,
wherein, when R³ is connected to N-atoms of W, R³ is $H_3C$—.

9. The compound according to claim 1, wherein R¹ and R² are independently selected from the group consisting of
$C_{1-6}$-alkyl and $C_{3-6}$-cycloalkyl, or wherein R¹ and R² together form a 2- to 5-membered alkylene-bridge incorporating 0 to 2 heteroatoms independently selected from the group consisting of N, O and S,
wherein the $C_{1-6}$-alkyl, the $C_{3-6}$-cycloalkyl or the alkylene-bridge is optionally substituted with halogens.

10. The compound according to claim 1, wherein R¹ and R² are both $H_3C$—.

11. The compound according to claim 1, wherein Y is a bond.

12. A compound according to claim 1, wherein the compound is selected from the group consisting of:

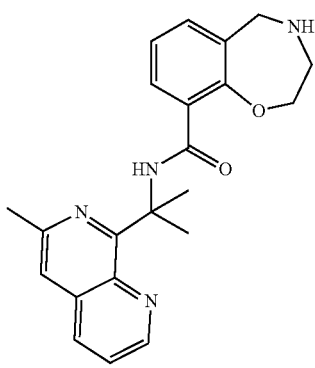

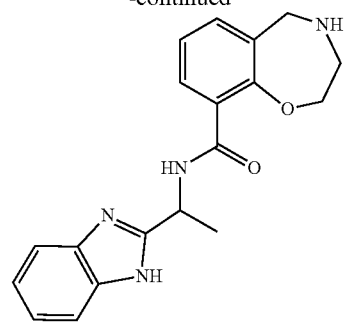

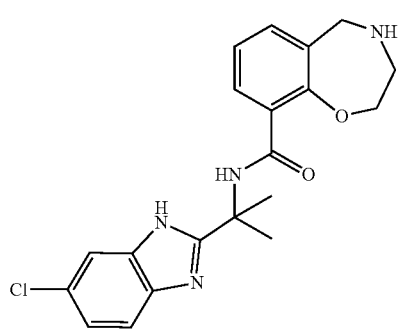

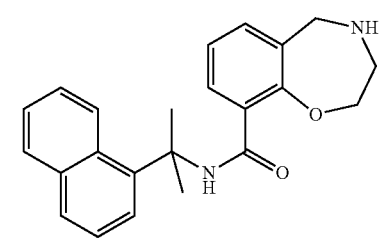

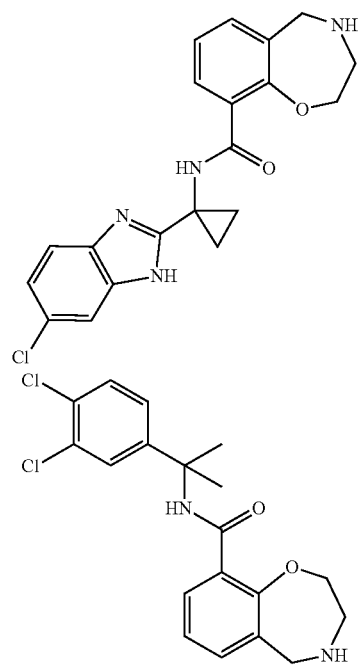

209
-continued
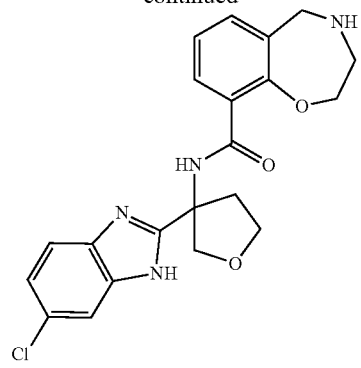
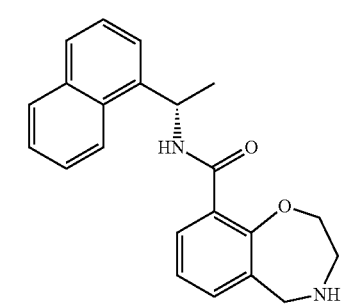
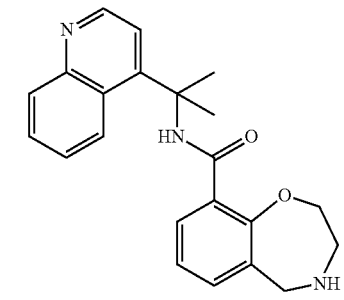
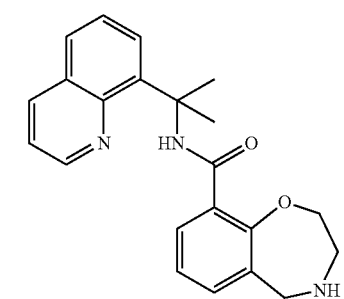
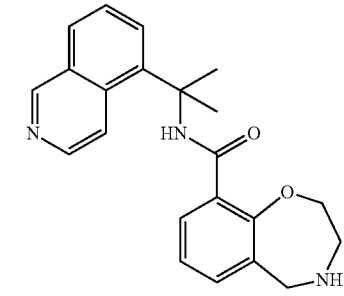
210
-continued
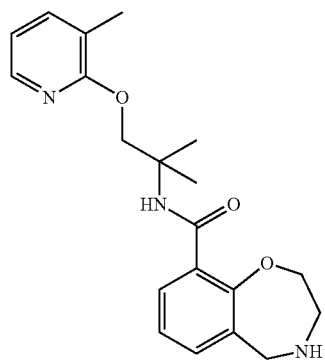
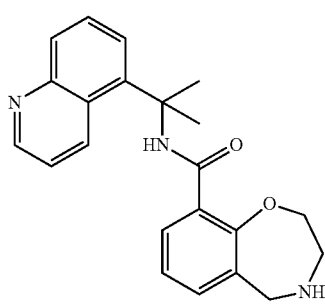
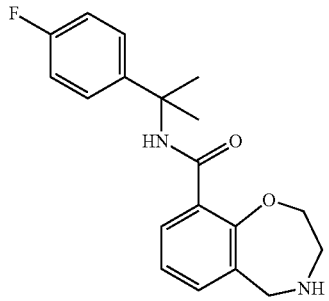
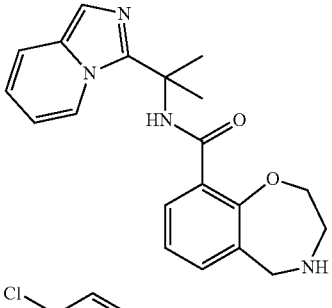
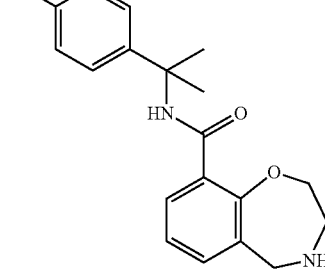

211
-continued
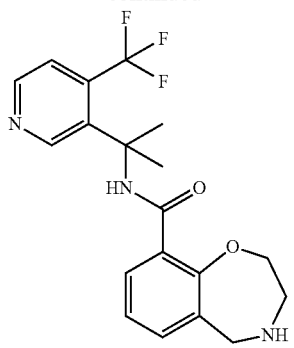
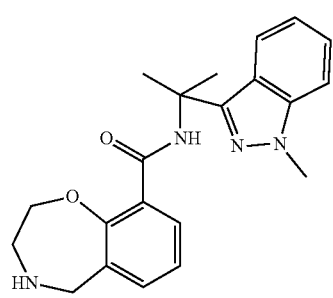
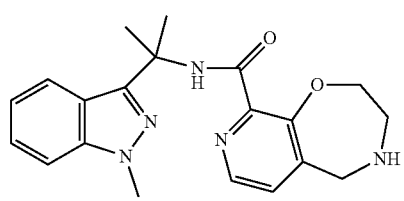
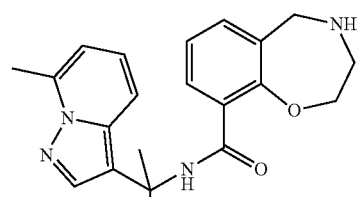
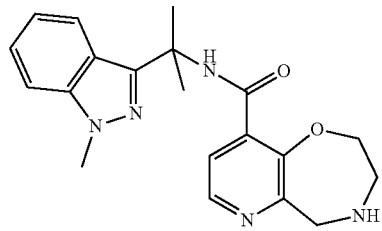
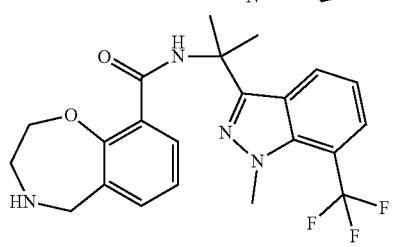
212
-continued
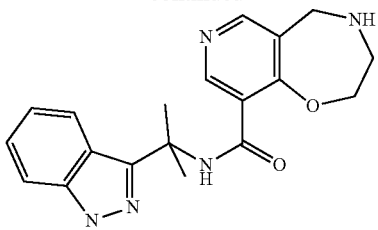
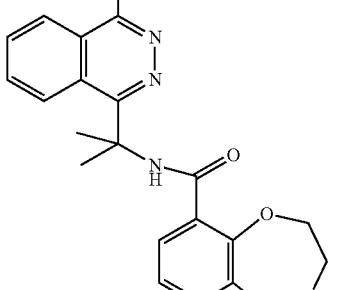
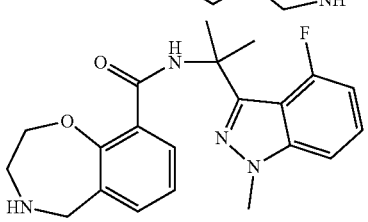
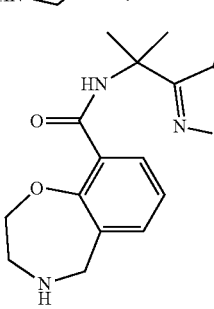
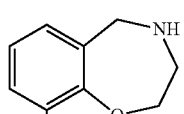
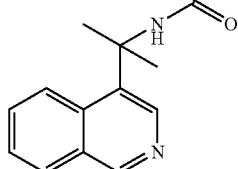
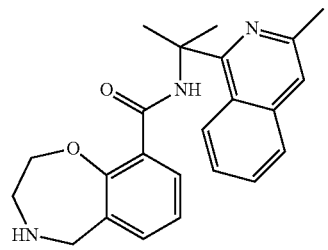

213
-continued
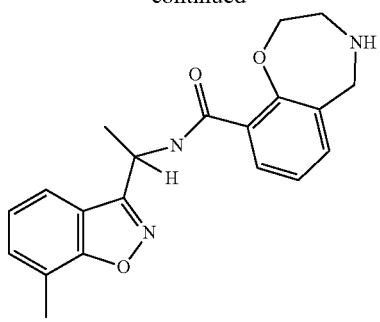
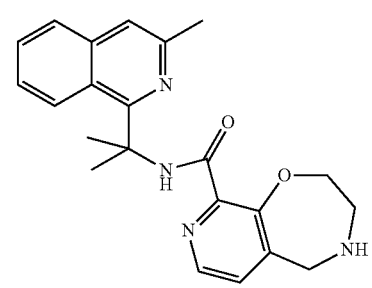
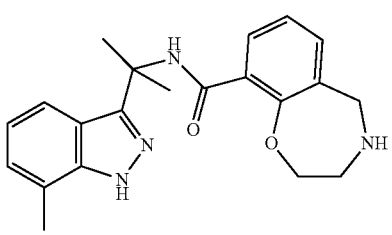
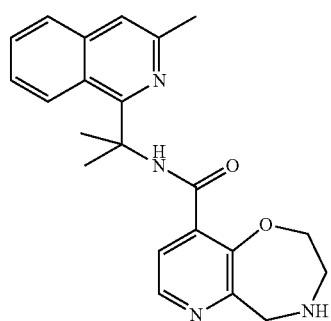
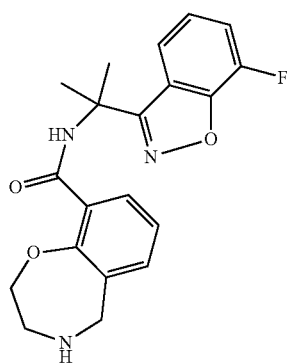
214
-continued
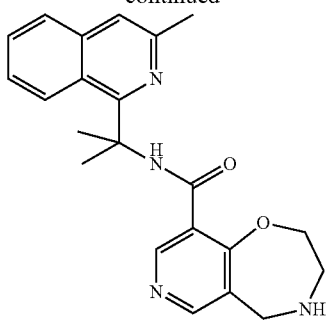
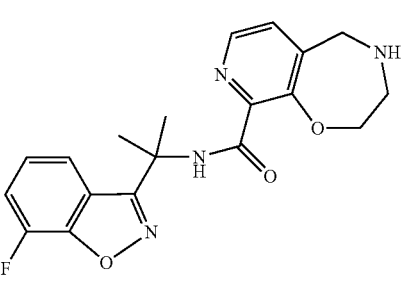
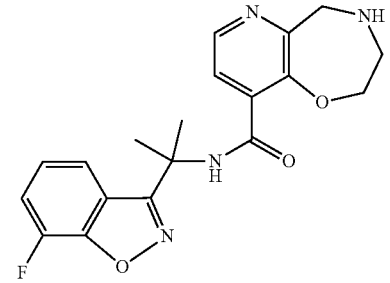
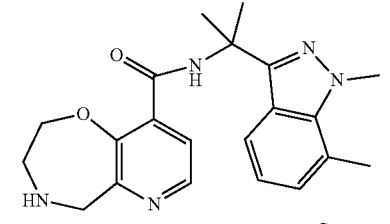
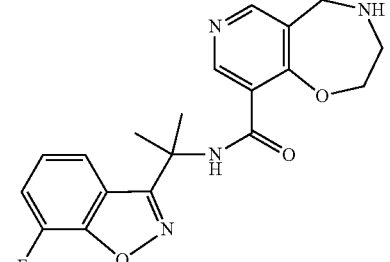
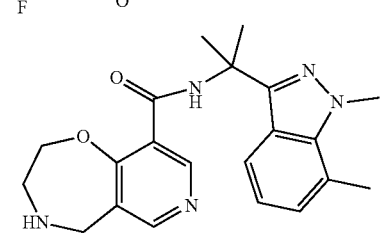

215
-continued
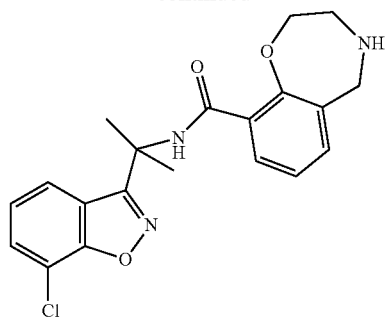
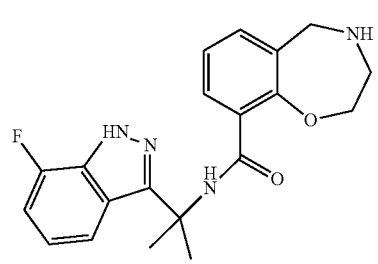
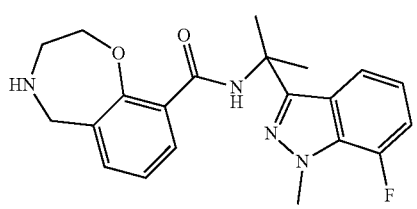
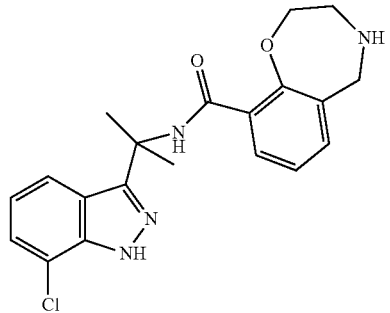
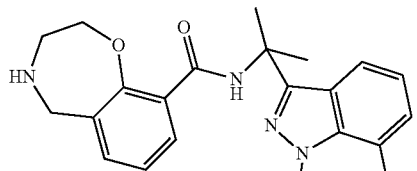
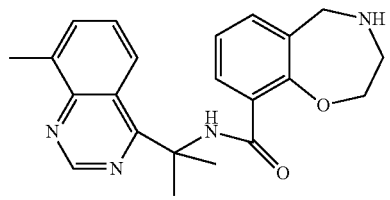
216
-continued
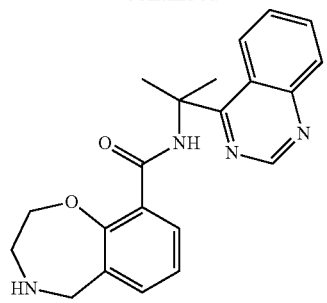
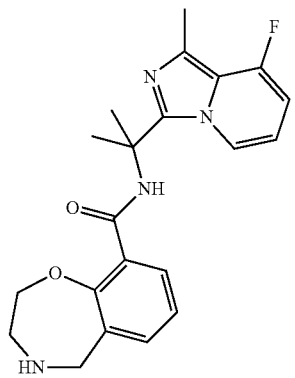
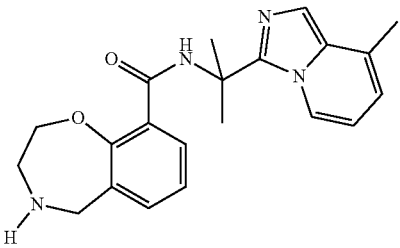
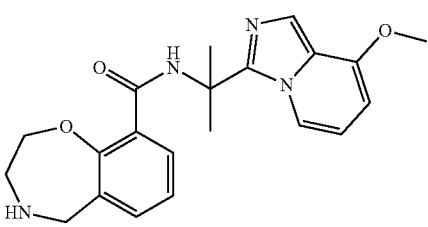
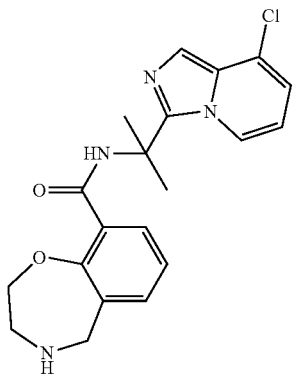

-continued
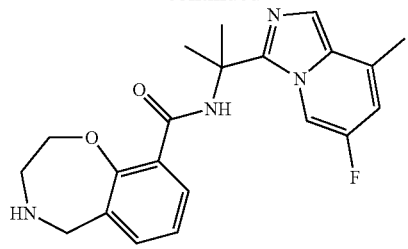
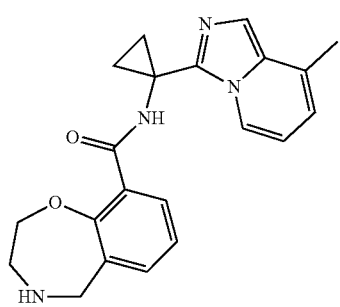
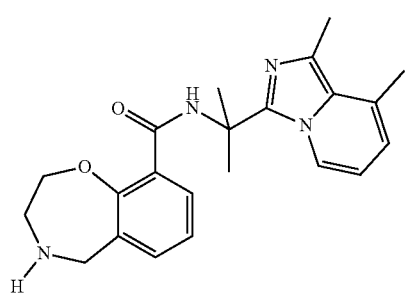
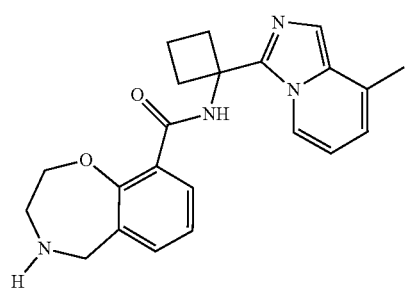
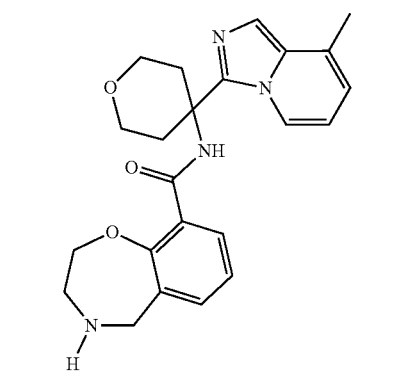
-continued
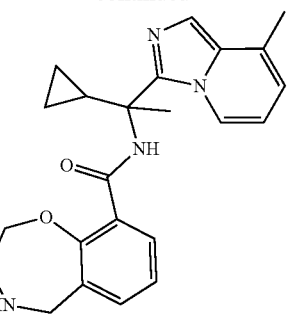
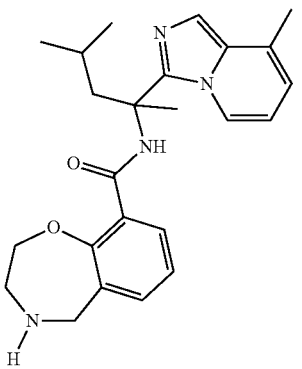
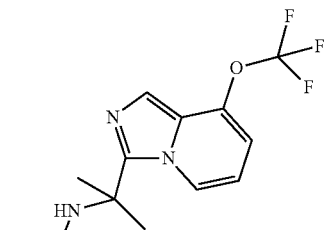
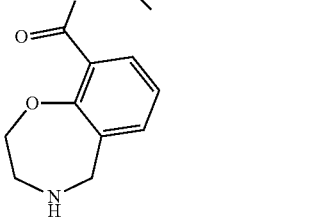
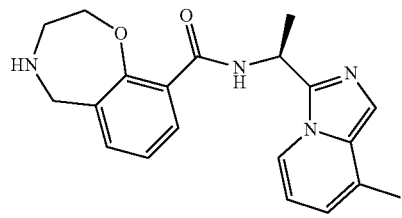
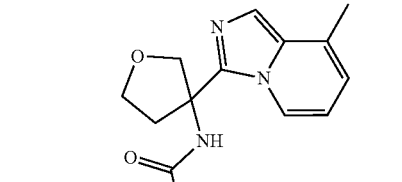

-continued
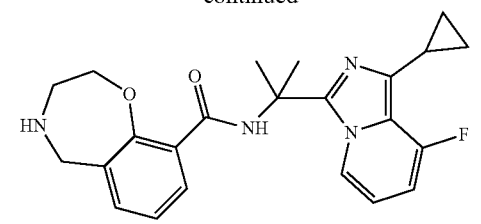
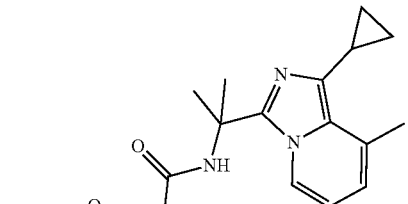
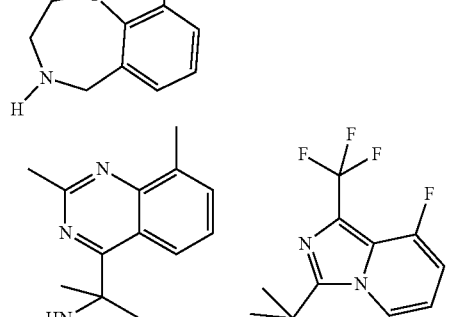
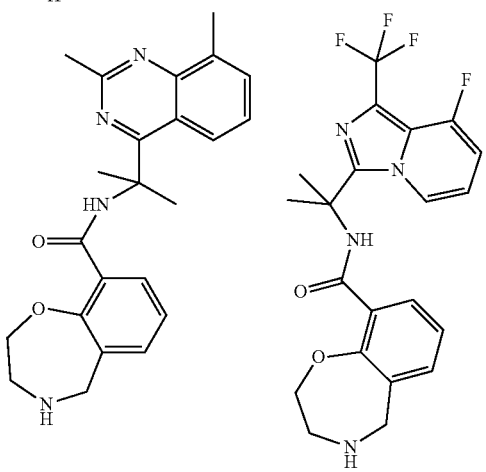
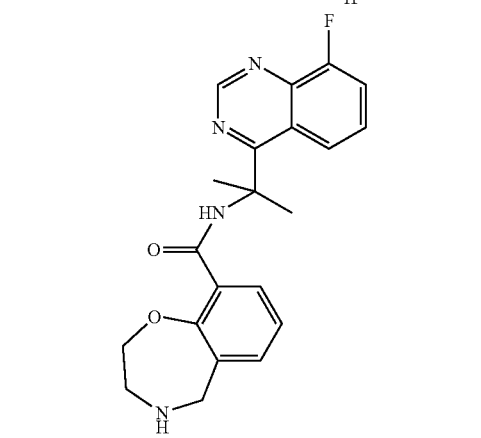
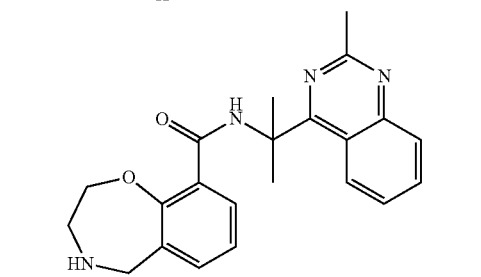
-continued
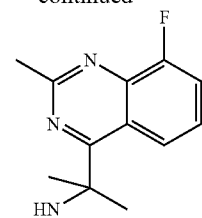
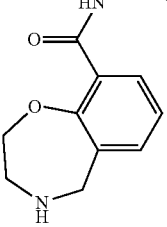
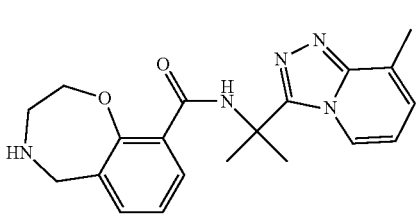
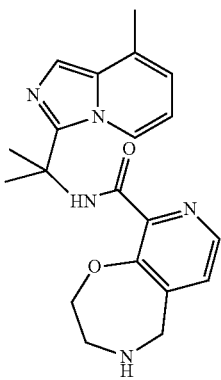
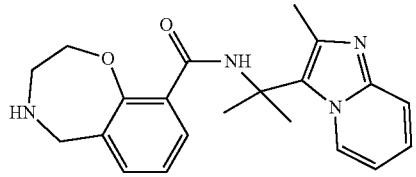
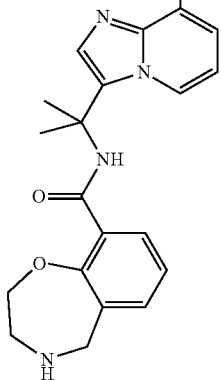

-continued

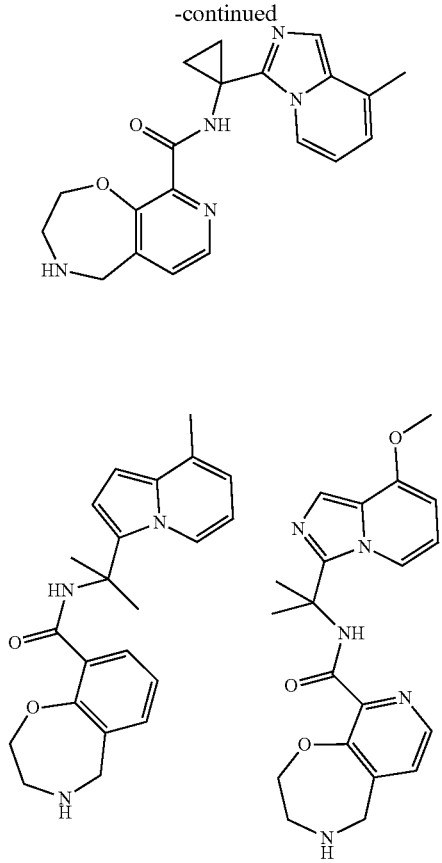

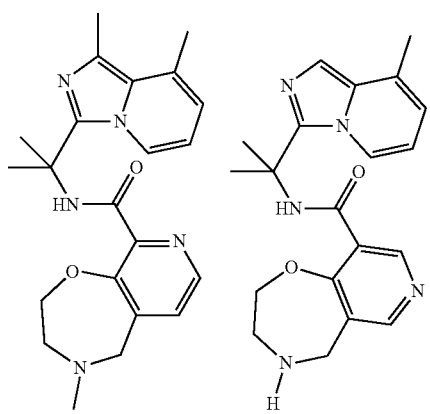

-continued

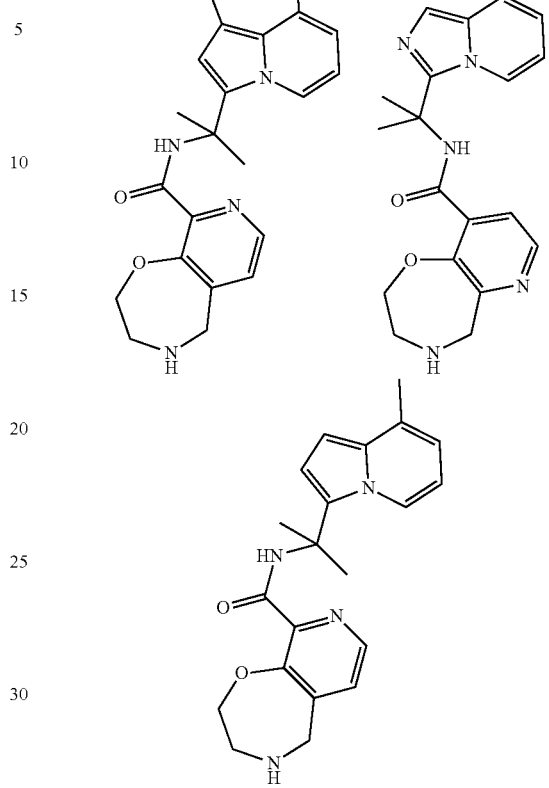

or a salt thereof.

13. A method of treating a SSTR4-mediated disease comprising administering a compound according to, wherein treatment is effected by inhibiting SSTR4 claim 1, or a pharmaceutically acceptable salt thereof, to a patient in need thereof.

14. Pharmaceutical compositions containing at least one compound according to claim 1 or a pharmaceutically acceptable salt thereof together with one or more pharmaceutically acceptable carrier.

15. A method for the treatment of pain, selected from acute pain, neuropathic peripheral pain, chronic pain or osteoarthritis, which comprises administering to a human a therapeutically effective amount of a compound according to claim 1, a pharmaceutically acceptable salt thereof or a pharmaceutical composition thereof.

* * * * *